(12) United States Patent
Moore

(10) Patent No.: US 8,768,731 B2
(45) Date of Patent: Jul. 1, 2014

(54) SYNDICATING ULTRASOUND ECHO DATA IN A HEALTHCARE ENVIRONMENT

(75) Inventor: James F. Moore, Lincoln, MA (US)

(73) Assignee: Newsilike Media Group, Inc., Cambridge, MA (US)

( * ) Notice: Subject to any disclaimer, the term of this patent is extended or adjusted under 35 U.S.C. 154(b) by 45 days.

(21) Appl. No.: 11/615,161

(22) Filed: Dec. 22, 2006

(65) Prior Publication Data

US 2007/0106751 A1 May 10, 2007

Related U.S. Application Data

(63) Continuation of application No. 11/346,587, filed on Feb. 1, 2006, which is a continuation of application No. 11/223,826, filed on Sep. 10, 2005, now Pat. No. 8,200,775.

(60) Provisional application No. 60/649,311, filed on Feb. 1, 2005, provisional application No. 60/649,312, filed on Feb. 1, 2005, provisional application No. 60/649,504, filed on Feb. 2, 2005, provisional application No. 60/649,502, filed on Feb. 2, 2005, provisional application No. 60/657,840, filed on Mar. 1, 2005, provisional application No. 60/594,298, filed on Mar. 26, 2005, provisional application No. 60/594,416, filed on Apr. 6, 2005, provisional application No. 60/669,666, filed on Apr. 8, 2005, provisional application No. 60/594,456, filed on Apr. 10, 2005, provisional application No. 60/594,478, filed on Apr. 12, 2005, provisional application No. 60/673,661, filed on Apr. 20, 2005, provisional application No. 60/680,879, filed on May 13, 2005, provisional application No. 60/684,092, filed on May (Continued)

(51) Int. Cl.
*G06Q 40/00* (2012.01)
*G06Q 50/00* (2012.01)
*G06F 19/00* (2011.01)
*G06Q 50/24* (2012.01)

(52) U.S. Cl.
CPC .............. *G06F 19/322* (2013.01); *G06Q 50/24* (2013.01)
USPC ............................................................ 705/4

(58) Field of Classification Search
None
See application file for complete search history.

(56) References Cited

U.S. PATENT DOCUMENTS

| | | | |
|---|---|---|---|
| 5,664,109 A | 9/1997 | Johnson et al. | |
| 5,758,095 A | 5/1998 | Albaum et al. | |

(Continued)

FOREIGN PATENT DOCUMENTS

| | | |
|---|---|---|
| DE | 226868 | 9/1984 |
| DE | 4434369 A1 | 3/1996 |

(Continued)

OTHER PUBLICATIONS

Definition: Dicom introduction. www.sph.sc.edu/comd/roden/dicom.html.*

(Continued)

*Primary Examiner* — Neal Sereboff
(74) *Attorney, Agent, or Firm* — GTC Law Group LLP & Affiliates

(57) ABSTRACT

Disclosed herein are systems and methods for syndication and management of structured and unstructured data to assist institutional healthcare delivery, healthcare providers' practices, healthcare providers' group practices, collaborative academic research and decision making in healthcare, including through the utilization of medical devices and healthcare pools.

24 Claims, 34 Drawing Sheets

Related U.S. Application Data 23, 2005, provisional application No. 60/685,904, filed on May 31, 2005, provisional application No. 60/686,630, filed on Jun. 2, 2005, provisional application No. 60/688,826, filed on Jun. 9, 2005, provisional application No. 60/694,080, filed on Jun. 24, 2005, provisional application No. 60/695,029, filed on Jun. 28, 2005, provisional application No. 60/699,631, filed on Jul. 15, 2005, provisional application No. 60/700,122, filed on Jul. 18, 2005, provisional application No. 60/702,467, filed on Jul. 26, 2005, provisional application No. 60/703,688, filed on Jul. 29, 2005, provisional application No. 60/703,535, filed on Jul. 29, 2005, provisional application No. 60/703,544, filed on Jul. 29, 2005, provisional application No. 60/709,683, filed on Aug. 19, 2005, provisional application No. 60/719,073, filed on Sep. 21, 2005, provisional application No. 60/719,283, filed on Sep. 21, 2005, provisional application No. 60/719,284, filed on Sep. 21, 2005, provisional application No. 60/720,250, filed on Sep. 22, 2005, provisional application No. 60/721,803, filed on Sep. 28, 2005, provisional application No. 60/722,021, filed on Sep. 29, 2005, provisional application No. 60/724,956, filed on Oct. 7, 2005, provisional application No. 60/725,166, filed on Oct. 7, 2005, provisional application No. 60/726,542, filed on Oct. 14, 2005, provisional application No. 60/726,731, filed on Oct. 14, 2005, provisional application No. 60/726,727, filed on Oct. 14, 2005, provisional application No. 60/734,187, filed on Nov. 6, 2005, provisional application No. 60/734,156, filed on Nov. 6, 2005, provisional application No. 60/735,712, filed on Nov. 11, 2005, provisional application No. 60/741,770, filed on Dec. 1, 2005, provisional application No. 60/741,958, filed on Dec. 2, 2005, provisional application No. 60/742,975, filed on Dec. 6, 2005, provisional application No. 60/749,757, filed on Dec. 13, 2005, provisional application No. 60/750,291, filed on Dec. 14, 2005, provisional application No. 60/751,254, filed on Dec. 15, 2005, provisional application No. 60/751,249, filed on Dec. 16, 2005, provisional application No. 60/753,959, filed on Dec. 23, 2005, provisional application No. 60/756,774, filed on Jan. 6, 2006, provisional application No. 60/759,483, filed on Jan. 16, 2006.

(56) References Cited

U.S. PATENT DOCUMENTS

| | | | |
|---|---|---|---|
| 5,784,635 | A | 7/1998 | McCallum |
| 5,845,255 | A | 12/1998 | Mayaud |
| 5,930,764 | A | 7/1999 | Melchione et al. |
| 5,931,946 | A | 8/1999 | Terada et al. |
| 5,933,136 | A | 8/1999 | Brown |
| 6,022,315 | A | 2/2000 | Iliff |
| 6,029,195 | A | 2/2000 | Herz |
| 6,070,189 | A | 5/2000 | Bender et al. |
| 6,131,085 | A | 10/2000 | Rossides |
| 6,163,774 | A | 12/2000 | Lore et al. |
| 6,199,082 | B1 | 3/2001 | Ferrel et al. |
| 6,233,618 | B1 | 5/2001 | Shannon |
| 6,253,210 | B1 | 6/2001 | Smith et al. |
| 6,311,194 | B1 | 10/2001 | Sheth et al. |
| 6,442,333 | B1 | 8/2002 | Izawa |
| 6,484,182 | B1 | 11/2002 | Dunphy et al. |
| 6,551,243 | B2 | 4/2003 | Bocionek et al. |
| 6,598,161 | B1 | 7/2003 | Kluttz et al. |
| 6,678,764 | B2 * | 1/2004 | Parvulescu et al. ............ 710/65 |
| 6,693,947 | B1 | 2/2004 | Schroeder |
| 6,734,886 | B1 | 5/2004 | Hagan et al. |
| 6,804,656 | B1 | 10/2004 | Rosenfeld et al. |
| 6,904,461 | B1 | 6/2005 | Randhava et al. |
| 6,931,532 | B1 | 8/2005 | Davis et al. |
| 6,954,532 | B1 | 10/2005 | Handley et al. |
| 6,961,858 | B2 | 11/2005 | Fransdonk |
| 6,993,522 | B2 | 1/2006 | Chen et al. |
| 7,010,681 | B1 | 3/2006 | Fletcher et al. |
| 7,020,635 | B2 | 3/2006 | Hamilton et al. |
| 7,058,710 | B2 | 6/2006 | McCall et al. |
| 7,072,934 | B2 | 7/2006 | Helgeson et al. |
| 7,080,049 | B2 | 7/2006 | Truitt et al. |
| 7,090,128 | B2 | 8/2006 | Farley et al. |
| 7,107,462 | B2 | 9/2006 | Fransdonk |
| 7,117,504 | B2 | 10/2006 | Smith et al. |
| 7,127,328 | B2 | 10/2006 | Ransom |
| 7,142,691 | B2 | 11/2006 | Levy |
| 7,146,415 | B1 | 12/2006 | Doi et al. |
| 7,149,813 | B2 | 12/2006 | Flanagin et al. |
| 7,150,045 | B2 | 12/2006 | Koelle et al. |
| 7,188,144 | B2 | 3/2007 | Fuisz |
| 7,269,664 | B2 | 9/2007 | Hutsch et al. |
| 7,296,077 | B2 | 11/2007 | Harmon et al. |
| 7,302,567 | B2 | 11/2007 | Hearn et al. |
| 7,308,477 | B1 | 12/2007 | Gress et al. |
| 7,406,427 | B1 | 7/2008 | Guyan et al. |
| 7,412,534 | B2 | 8/2008 | Tsang et al. |
| 7,421,155 | B2 | 9/2008 | King et al. |
| 7,451,147 | B1 | 11/2008 | Kao et al. |
| 7,472,349 | B1 | 12/2008 | Srivastava et al. |
| 7,519,591 | B2 | 4/2009 | Landi et al. |
| 7,565,410 | B2 | 7/2009 | Stickler |
| 7,584,208 | B2 | 9/2009 | Spivack et al. |
| 7,587,502 | B2 | 9/2009 | Crawford et al. |
| 7,620,606 | B2 | 11/2009 | Gentry et al. |
| 7,711,586 | B2 | 5/2010 | Aggarwal et al. |
| 7,904,367 | B2 | 3/2011 | Chung et al. |
| 7,949,666 | B2 | 5/2011 | Wolff et al. |
| 7,953,725 | B2 | 5/2011 | Burris et al. |
| 8,010,282 | B2 | 8/2011 | Barry et al. |
| 8,140,482 | B2 | 3/2012 | Moore |
| 8,200,700 | B2 | 6/2012 | Moore et al. |
| 8,200,775 | B2 | 6/2012 | Moore |
| 8,316,005 | B2 | 11/2012 | Moore |
| 8,347,088 | B2 | 1/2013 | Moore et al. |
| 8,566,115 | B2 | 10/2013 | Moore |
| 2001/0016851 | A1 | 8/2001 | Gramsamer et al. |
| 2001/0051881 | A1 * | 12/2001 | Filler ............................. 705/3 |
| 2001/0052933 | A1 | 12/2001 | Nybo et al. |
| 2001/0056359 | A1 | 12/2001 | Abreu |
| 2002/0010616 | A1 | 1/2002 | Itzhaki |
| 2002/0010764 | A1 | 1/2002 | Spicer |
| 2002/0029157 | A1 | 3/2002 | Marchosky |
| 2002/0032742 | A1 | 3/2002 | Anderson |
| 2002/0038316 | A1 | 3/2002 | Onyon et al. |
| 2002/0049614 | A1 | 4/2002 | Rice et al. |
| 2002/0059049 | A1 * | 5/2002 | Bradbury et al. ............... 703/11 |
| 2002/0059399 | A1 | 5/2002 | Learmonth |
| 2002/0091734 | A1 | 7/2002 | Redlich et al. |
| 2002/0138467 | A1 | 9/2002 | Jacobson et al. |
| 2002/0143742 | A1 | 10/2002 | Nonomura et al. |
| 2002/0143819 | A1 | 10/2002 | Han et al. |
| 2002/0152210 | A1 | 10/2002 | Johnson et al. |
| 2002/0152318 | A1 | 10/2002 | Menon et al. |
| 2002/0154178 | A1 | 10/2002 | Barnett et al. |
| 2002/0157023 | A1 | 10/2002 | Callahan et al. |
| 2002/0188522 | A1 | 12/2002 | McCall et al. |
| 2003/0046434 | A1 | 3/2003 | Flanagin et al. |
| 2003/0050801 | A1 | 3/2003 | Ries et al. |
| 2003/0055818 | A1 | 3/2003 | Faybishenko et al. |
| 2003/0055825 | A1 | 3/2003 | Chen et al. |
| 2003/0061404 | A1 | 3/2003 | Atwal et al. |
| 2003/0069751 | A1 | 4/2003 | Lichtenstein et al. |
| 2003/0074352 | A1 | 4/2003 | Raboczi et al. |
| 2003/0088544 | A1 | 5/2003 | Kan et al. |
| 2003/0088784 | A1 | 5/2003 | Ginter et al. |
| 2003/0126120 | A1 | 7/2003 | Faybishenko et al. |
| 2003/0217047 | A1 | 11/2003 | Marchisio |
| 2003/0225718 | A1 | 12/2003 | Shmulevich et al. |

(56) References Cited

U.S. PATENT DOCUMENTS

| | | |
|---|---|---|
| 2003/0229692 A1 | 12/2003 | Vo |
| 2004/0002966 A1 | 1/2004 | Perkowski |
| 2004/0034550 A1 | 2/2004 | Menschik et al. |
| 2004/0054675 A1 | 3/2004 | Li |
| 2004/0054722 A1 | 3/2004 | Defloor et al. |
| 2004/0064428 A1 | 4/2004 | Larkin et al. |
| 2004/0073661 A1 | 4/2004 | Eibach et al. |
| 2004/0078231 A1 | 4/2004 | Wilkes et al. |
| 2004/0078236 A1 | 4/2004 | Stoodley et al. |
| 2004/0093412 A1 | 5/2004 | Chen et al. |
| 2004/0133580 A1 | 7/2004 | Liu et al. |
| 2004/0139317 A1 | 7/2004 | Fronberg |
| 2004/0139327 A1 | 7/2004 | Brown et al. |
| 2004/0143623 A1 | 7/2004 | Fukui et al. |
| 2004/0172423 A1 | 9/2004 | Kaasten et al. |
| 2004/0181679 A1 | 9/2004 | Dettinger et al. |
| 2004/0199765 A1 | 10/2004 | Kohane et al. |
| 2004/0207659 A1 | 10/2004 | Goodman et al. |
| 2004/0221226 A1 | 11/2004 | Lin et al. |
| 2004/0224674 A1 | 11/2004 | O'Farrell et al. |
| 2004/0230674 A1 | 11/2004 | Pourheidari et al. |
| 2004/0254816 A1 | 12/2004 | Myers |
| 2004/0260767 A1 | 12/2004 | Kedem et al. |
| 2004/0267610 A1 | 12/2004 | Gossett et al. |
| 2005/0027567 A1 | 2/2005 | Taha |
| 2005/0027871 A1 | 2/2005 | Bradley et al. |
| 2005/0038717 A1 | 2/2005 | McQueen, III et al. |
| 2005/0055308 A1 * | 3/2005 | Meyer et al. ................. 705/38 |
| 2005/0108057 A1 | 5/2005 | Cohen et al. |
| 2005/0117527 A1 | 6/2005 | Williams et al. |
| 2005/0120300 A1 | 6/2005 | Schwager et al. |
| 2005/0132048 A1 | 6/2005 | Kogan et al. |
| 2005/0160065 A1 | 7/2005 | Seeman |
| 2005/0165615 A1 | 7/2005 | Minar |
| 2005/0198021 A1 | 9/2005 | Wilcox et al. |
| 2005/0203917 A1 | 9/2005 | Freeberg et al. |
| 2005/0216315 A1 | 9/2005 | Andersson |
| 2005/0234740 A1 | 10/2005 | Krishnan et al. |
| 2005/0262340 A1 | 11/2005 | Rabb |
| 2005/0267973 A1 | 12/2005 | Carlson et al. |
| 2005/0289468 A1 | 12/2005 | Kahn et al. |
| 2006/0004691 A1 | 1/2006 | Sifry |
| 2006/0004764 A1 | 1/2006 | Kurhekar et al. |
| 2006/0010251 A1 | 1/2006 | Mrsic-flogel et al. |
| 2006/0053156 A1 | 3/2006 | Kaushansky et al. |
| 2006/0059208 A1 | 3/2006 | Chen et al. |
| 2006/0064320 A1 | 3/2006 | Postrel |
| 2006/0064326 A1 | 3/2006 | Tucker |
| 2006/0073812 A1 | 4/2006 | Punaganti Venkata et al. |
| 2006/0074980 A1 | 4/2006 | Sarkar |
| 2006/0075426 A1 | 4/2006 | Koch et al. |
| 2006/0080166 A1 | 4/2006 | Takahashi |
| 2006/0085412 A1 * | 4/2006 | Johnson et al. ................. 707/4 |
| 2006/0085788 A1 | 4/2006 | Amir et al. |
| 2006/0095507 A1 * | 5/2006 | Watson ................. 709/203 |
| 2006/0095628 A1 | 5/2006 | Ludwig et al. |
| 2006/0101035 A1 | 5/2006 | Mustakallio et al. |
| 2006/0106655 A1 | 5/2006 | Lettovsky et al. |
| 2006/0106748 A1 | 5/2006 | Chafle et al. |
| 2006/0111938 A1 | 5/2006 | Vitiello |
| 2006/0112076 A1 | 5/2006 | Burris et al. |
| 2006/0136259 A1 | 6/2006 | Weiner et al. |
| 2006/0149591 A1 | 7/2006 | Hanf et al. |
| 2006/0155698 A1 | 7/2006 | Vayssiere |
| 2006/0167860 A1 | 7/2006 | Eliashberg et al. |
| 2006/0173985 A1 | 8/2006 | Moore |
| 2006/0178910 A1 | 8/2006 | Eisenberger et al. |
| 2006/0178918 A1 | 8/2006 | Mikurak |
| 2006/0184617 A1 | 8/2006 | Nicholas et al. |
| 2006/0188327 A1 | 8/2006 | Moon |
| 2006/0200380 A1 | 9/2006 | Ho et al. |
| 2006/0200478 A1 | 9/2006 | Pasztor et al. |
| 2006/0221076 A1 | 10/2006 | Takahashi et al. |
| 2006/0229911 A1 | 10/2006 | Gropper et al. |
| 2006/0230011 A1 | 10/2006 | Tuttle et al. |
| 2006/0230021 A1 * | 10/2006 | Diab et al. ................. 707/3 |
| 2006/0230221 A1 | 10/2006 | Hsu et al. |
| 2006/0247961 A1 | 11/2006 | Klemow |
| 2006/0265489 A1 | 11/2006 | Moore |
| 2006/0265508 A1 | 11/2006 | Angel et al. |
| 2006/0288011 A1 | 12/2006 | Gandhi et al. |
| 2006/0288329 A1 | 12/2006 | Gandhi et al. |
| 2007/0011665 A1 | 1/2007 | Gandhi et al. |
| 2007/0011710 A1 | 1/2007 | Chiu |
| 2007/0027710 A1 | 2/2007 | Mohr |
| 2007/0038712 A1 | 2/2007 | Affronti et al. |
| 2007/0050446 A1 | 3/2007 | Moore |
| 2007/0061266 A1 | 3/2007 | Moore et al. |
| 2007/0061393 A1 | 3/2007 | Moore et al. |
| 2007/0061487 A1 | 3/2007 | Moore et al. |
| 2007/0073934 A1 | 3/2007 | Rogers |
| 2007/0079237 A1 | 4/2007 | Abrams et al. |
| 2007/0081550 A1 | 4/2007 | Moore |
| 2007/0088807 A1 | 4/2007 | Moore |
| 2007/0094156 A1 | 4/2007 | Isaacs |
| 2007/0094350 A1 | 4/2007 | Moore |
| 2007/0094365 A1 | 4/2007 | Nussey et al. |
| 2007/0094389 A1 | 4/2007 | Nussey et al. |
| 2007/0100959 A1 | 5/2007 | Eichstaedt et al. |
| 2007/0106536 A1 | 5/2007 | Moore |
| 2007/0106537 A1 | 5/2007 | Moore |
| 2007/0106649 A1 | 5/2007 | Moore |
| 2007/0106650 A1 | 5/2007 | Moore |
| 2007/0106750 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0130457 A1 | 6/2007 | Kamat et al. |
| 2007/0139182 A1 | 6/2007 | O'Connor et al. |
| 2007/0143215 A1 | 6/2007 | Willems |
| 2007/0150482 A1 | 6/2007 | Taylor et al. |
| 2007/0156809 A1 | 7/2007 | Dickinson et al. |
| 2007/0168461 A1 | 7/2007 | Moore |
| 2007/0207782 A1 | 9/2007 | Tran |
| 2007/0220016 A1 | 9/2007 | Estrada et al. |
| 2007/0225047 A1 | 9/2007 | Bakos |
| 2007/0245020 A1 | 10/2007 | Ott, IV |
| 2008/0005086 A1 | 1/2008 | Moore |
| 2008/0040151 A1 | 2/2008 | Moore |
| 2008/0046369 A1 | 2/2008 | Wood |
| 2008/0046437 A1 | 2/2008 | Wood |
| 2008/0046471 A1 | 2/2008 | Moore et al. |
| 2008/0052162 A1 | 2/2008 | Wood |
| 2008/0052343 A1 | 2/2008 | Wood |
| 2008/0126178 A1 | 5/2008 | Moore |
| 2008/0126476 A1 | 5/2008 | Nicholas et al. |
| 2008/0141126 A1 | 6/2008 | Johnson et al. |
| 2008/0195483 A1 | 8/2008 | Moore |
| 2008/0244091 A1 | 10/2008 | Moore et al. |
| 2009/0172773 A1 | 7/2009 | Moore |
| 2012/0150813 A1 | 6/2012 | Moore |
| 2013/0104251 A1 | 4/2013 | Moore |
| 2013/0291060 A1 | 10/2013 | Moore |

FOREIGN PATENT DOCUMENTS

| | | |
|---|---|---|
| EP | 0504774 A2 | 12/1992 |
| GB | 901723 A | 7/1962 |
| JP | 06347169 A | 12/1994 |
| JP | 09145249 A | 6/1997 |
| WO | WO-8304161 A1 | 12/1983 |
| WO | WO-03077558 A2 | 9/2003 |
| WO | WO-2004015742 A2 | 2/2004 |
| WO | WO-2006083958 A2 | 8/2006 |
| WO | WO-2007011917 A2 | 1/2007 |
| WO | WO-2007130865 A2 | 11/2007 |
| WO | WO-2007137145 A2 | 11/2007 |
| WO | WO-2008036464 A2 | 3/2008 |

(56) References Cited

OTHER PUBLICATIONS

Definition Metadata, Webster's New World Computer Dictionary, 2003.*
PS Oct. 3, 2004 Digital Imaging and Communications (DICOM) part 10, National Electronics Manufactures Association.*
Gawlick, Dieter et al., "Using the Oracle Database as a Declarative RSS Hub", *International Conference on Management of Data*, Proceedings of the 2006 ACM SIGMOD international conference on Management of data,(2006),722.
USPTO, "U.S. Appl. No. 11/458,092, Non-Final Office Action mailed Jun. 9, 2008", OARN,23 pgs.
Appnel, T. "RSS: The Web Services We Already Have", (Jan. 22, 2003).
Maurer, L. "U.S. Appl. No. 09/584,318 (Appendix)".
USPTO, ""U.S. Appl. No. 11/615,030 Non Final Office Action mailed Jan. 23, 2008"", (Jan. 23, 2008),all.
Wood, Charlie "Introducing Spanning Feed Builder for AppExchange", http://www.spanningpartners.com/2006/07/introducing_spa.html, (Jul. 2, 2006).
Wood, Charlie "Blog of Subscribe Your Calendar to Your Salesforce.com Events", http://globelogger.com/item.php?id=660, (May 12, 2006).
Wood, Charlie "Subscribe Your Calendar to Your Salesforce.com Events", http://www.spanningpartners.com/2006/05/subscribe_your_.html, (May 12, 2006).
Wood, Charlie "RSS-Enabled AppExchange Applications", http://www.spanningpartners.com/2006/05/spanning_partne_1.html, (May 30, 2006).
Wood, Charlie "Latest Spanning Salesforce Release", http://www.spanningpartners.com/2006/04/latest_spanning.html, (Apr. 5, 2006).
Wood, Charlie "New Spanning Salesforce Feeds and Features", http://globelogger.com/item.php?id=606, (Mar. 14, 2006).
Wood, Charlie "On Creating Real Business Value with RSS", http://www.spanningpartners.com/2006/02/on_creating_rea.html, (Feb. 23, 2006).
Wood, Charlie "Spanning Salesforce 2.0 is Live", http://qlobelogger.com/item.php?id=466, (Aug. 28, 2005).
Wood, Charlie "Introducing Spanning Salesforce 2.0", http://www.spanningpartners.com/2005/08/introducing_spa.html, (Aug. 28, 2005).
Wood, Charlie "Adoption Using RSS to Track Sales Leads", http://globelogger.com/item.php?id=285, (Jan. 28, 2005).
Wood, Charlie "Adoption Salesforce.com via RSS", http://globelogger.com/item.php?id=294, (Feb. 6, 2005).
Wood, Charlie "Spanning Salesforce Goes Public", http://globelogger.com/item.php?id=285, (Jul. 17, 2005).
Krill, Paul "Microsoft to demo CRM-RSS", http://weblog.infoworld.com/techwatch/archives/003933.html, (Sep. 7, 2005).
"Customer, Roget's II the New Thesaurus", Boston: Houghton Mifflin. Credo Reference. [online][retrieved on Jul. 10, 2011], 2003, 1 page.
"Drugs and Herbs", WebMD Health—Drug, available at Indexhttp://web.archive.org/web/20051101101459/http://www.webmd.com/drugs/index-drugs.aspx,, (accessed online Jul. 11, 2011), Nov. 2005, 45 pages.
"Outline Processor Markup Language, OPML 1.0 Specification", available at http://www.opml.org/spec, (accessed online Jul. 5, 2011), 6 pages.
Definition, "Serve", Chambers 21st Century Dictionary. London: Chambers Harrap. Credo Reference [online][retrieved on Jul. 10, 2011], 2001, 1 page.
Definition, "Service", Chambers 21st Century Dictionary. London: Chambers Harrap. Credo Reference. [online][retrieved on Jul. 10, 2011], 2001, 1 page.
"W3Schools Online Web Tutorials", 2002, pp. 3-5.
Definition, "application programming interface" Computer Dictionary, 5th Edition, Microsoft Press, Redmond, WA, May 1, 2002, pp. 33.

Definition, "graphical user interface" Computer Dictionary, 5th Edition, Microsoft Press, Redmond, WA, May 1, 2002, pp. 239.
Definition, "interface" Computer Dictionary, 5th Edition, Microsoft Press, Redmond, WA, May 1, 2002, pp. 279-280.
FEMA, "FEMA: Federal Disaster Declarations RSS", FEMA.gov, available at http://web.archive.org/web/20050413031904/http://fema.gov/news . . . , (accessed online Dec. 29, 2010), 1 page.
FEMA, "FEMA: News Releases", available at web.archive.org/web/20050403173625/www.fema.gov/news/recentnews_rss.fema, (accessed online Jul. 5, 2011), Apr. 3, 2005, 2 pages.
FEMA, "FEMA: RSS(Really Simple Syndication)", available at web.archive.org/web/20050416033644/http://www.fema.gov/help/rss.shtm, (accessed online Jul. 5, 2011), Apr. 16, 2005, 2 pages.
Hammond et al., "The Role of RSS in Science Publishing", D-Lib Magazine, vol. 10, No. 12, Dec. 2004, pp. 1-17.
Kifer et al., "Database Systems: An Application-Oriented Approach", Second Edition, Boston, MA: Pearson Education Inc., 2005, pp. 1151-1152.
Lewin, James, "An Introduction to RSS news feeds: Using open formats for content syndication", available at http://www.opensourcetutorials.com/tutorials/Server-Side-Coding/Perl/perl-rss-news-feed/page1.html, (accessed online Jul. 5, 2011), Apr. 5, 2004, 11 pages.
Lund, Ben, "Using Urchin, Notes for Webmasters", Urchin version 0.8, 2003, 8 pages.
Marshall, James, "Http Made Really Easy", A Practical Guide to Writing Clients and Servers, available at http:www.jmarshall.com/easy/http/, (accessed online Jul. 12, 2011), Aug. 15, 1997, 21 pages.
Nakano et al., "A proposal of RSS WebCrawler model of product information", IEEE, Proceedings of the 2005 International Conference on Active Media Technology, May 2005, pp. 147-151.
OAISS, "UDDI Version 2.04 API Specification", UDDI Spec TC, available at http://www.uddi.org/pubs/ProgrammersAPI-V2.04-Published_20020719.htm, accessed online Jul. 5, 2011, Jul. 19, 2002, pp. 1-66.
Pande, Nitin, "System.xml.xmlSerializer" as found on the EggHeadCafe.Com website, http://www.eggheadcafe.com/articles/system.xml.xmlserialization.asp, (accessed online Nov. 5, 2012), Dec. 8, 2004, 4 pages.
International Application Serial No. PCT/US2006/003544, International Search Report mailed, Sep. 17, 2008, 3 pages.
International Application Serial No. PCT/US2006/003544, Written Opinion mailed, Sep. 17, 2008, 3 pages.
International Application Serial No. PCT/US2006/003544, International Preliminary Report on Patentability mailed, Sep. 17, 2008, 7 pages.
International Application Serial No. PCT/US2006/027794, International Search Report mailed, Nov. 26, 2007, 3 pages.
International Application Serial No. PCT/US2006/027794, Written Opinion mailed, Nov. 26, 2007, 6 pages.
International Application Serial No. PCT/US2006/027794, International Preliminary Report on Patentability Issued, Jan. 16, 2008, 7 pages.
International Application Serial No. PCT/US2006/034944, International Search Report mailed, Mar. 19, 2007, 5 pages.
International Application Serial No. PCT/US2006/034944, Written Opinion mailed, Mar. 19, 2007, 7 pages.
International Application Serial No. PCT/US2006/034944, International Preliminary Report on Patentability Issued, Mar. 11, 2008, 8 pages.
International Application Serial No. PCT/US2007/067643, International Search Report mailed, Jun. 30, 2008, 1 page.
International Application Serial No. PCT/US2007/067643, Written Opinion mailed, Jun. 20, 2008, 5 pages.
International Application Serial No. PCT/US2007/067643, International Preliminary Report on Patentability Issued, Nov. 4, 2008, 6 pages.
International Application Serial No. PCT/US2007/069195, International Search Report mailed, Sep. 2, 2008, 3 pages.
International Application Serial No. PCT/US2007/069195, Written Opinion mailed, Sep. 2, 2008, 5 pages.

(56) References Cited

OTHER PUBLICATIONS

International Application Serial No. PCT/US2007/069195, International Preliminary Report on Patentability Issued, Nov. 18, 2008, 6 pages.
International Application Serial No. PCT/US2007/074475, International Search Report mailed, Jun. 30, 2008, 1 page.
International Application Serial No. PCT/US2007/074475, Written Opinion mailed, Jun. 30, 2008, 3 pages.
International Application Serial No. PCT/US2007/074475, International Preliminary Report on Patentability Issued, Jan. 27, 2009, 4 pages.
Pilgrim, Mark, "How to consume RSS safely", available at http://diveintomark.org/archives/2003/06/12/how_to_consume_rss_safely , (accessed on Jul. 5, 2011), 2003, pp. 1-28.
Ponnekanti et al., "SWORD: A Developer Toolkit for Web Service Composition", available at http://www2002.org/CDROM/alternate/786/, (accessed online Jul. 5, 2011), 2002, pp. 1-22.
Roszkowski et al., "A Distributed Architecture for Resource Discovery Using Metadata", D-Lib Magazine, Jun. 1998, pp. 1-11.
Scheier, Bruce, "Applied Cryptography: Protocols, Algorithms, and Source Code in C", John Wiley & Sons, Inc., Second Edition, 1996, pp. 584-587.
sourceforge.net, "Urchin RSS Aggregator, version 0.92", available at http://urchin.sourceforge.net/index.html, accessed online Jun. 2, 2009, 2004, pp. 1-5.
Stal, Michael, "Web Services: Beyond Component Based Computing Seeking a Better Solution to the Application Integration Problem", Communications of the ACM, vol. 45, No. 10, Oct. 2002, pp. 71-76.
W3C, "RDF Primer", W3C Recommendation, available at http://www.w3.org/TR/rdf-syntax/, (accessed online Jul. 5, 2011), Feb. 10, 2004, pp. 1-73.
W3C, "XML Encryption Syntax and Processing" W3C Recommendation, available at: http://www.w3.org/TR/xmlenc-core/, (accessed online Nov. 5, 2012), Dec. 10, 2002, pp. 46 pages.
Winer, Dave, "OPML(Outline Processor Markup Language) About PAGE", available at http://ww.opml.org/about, (accessed online Jul. 5, 2011 ), Nov. 7, 2000, 2 pages.

* cited by examiner

FIG. 8

HOME SEARCH FEEDS USER PROFILE MANAGE FEEDS MANAGE FILTERS LOGOUT

Username: mcadam
First Name: Nick
Last Name: Caramello
E-mail: ncaramello@gmail.com
Password:
Retype Password:
Default Maximum Age of feeds (Hours): 24
Default Number of Posts per Feed: 5
Show Post Description: ☑
Use Most Common Category: ☐
Show Site to Public: ☐
Feed Display Mode: By Category Save WHAT'S HOT
All Politics
Left Wing Politics
Right Wing Politics
Technology
Law
The Market NEWS THEY LIKE
John Palfrey
Law

FIG. 9

SYNDICATING ULTRASOUND ECHO DATA IN A HEALTHCARE ENVIRONMENT

CROSS-REFERENCE TO RELATED APPLICATIONS

This application is a continuation of U.S. patent application Ser. No. 11/346,587 filed in Feb. 1, 2006, which is a continuation-in-part of U.S. patent application Ser. No. 11/223,826, filed on Sep. 10, 2005, each of which is incorporated by reference in its entirety.

This application also claims the benefit of the following commonly owned U.S. Provisional Applications, either directly or through one or more of the above utility applications, or both. Each of the following and foregoing applications is incorporated by reference in its entirety.

Ser. No. 60/649,311, filed on Feb. 1, 2005, and entitled DATA STREAM MANAGEMENT.

Ser. No. 60/649,312, filed on Feb. 1, 2005, and entitled DATA STREAM MANAGEMENT SOFTWARE.

Ser. No. 60/649,504, filed on Feb. 2, 2005, and entitled RSS MEDIA PROCESSING SYSTEMS.

Ser. No. 60/649,502, filed on Feb. 2, 2005, and entitled SEMANTIC PROCESSING.

Ser. No. 60/657,840, filed on Mar. 1, 2005, and entitled USER INTERFACES AND WORKFLOWS FOR USE WITH DATA STREAM MANAGEMENT SYSTEMS.

Ser. No. 60/594,298, filed on Mar. 26, 2005, and entitled USES OF METADATA IN A STRUCTURED DATA FEED ENVIRONMENT.

Ser. No. 60/594,416, filed on Apr. 6, 2005, and entitled DATA STREAM MANAGEMENT.

Ser. No. 60/669,666, filed on Apr. 8, 2005, and entitled DATA STREAM MANAGEMENT.

Ser. No. 60/594,456, filed on Apr. 10, 2005, and entitled FUNCTIONAL SEARCH OUTLINES.

Ser. No. 60/594,478, filed on Apr. 12, 2005, and entitled DATA STREAM MANAGEMENT.

Ser. No. 60/673,661, filed on Apr. 20, 2005, and entitled DATA STREAM MANAGEMENT.

Ser. No. 60/680,879, filed on May 13, 2005, and entitled DATA STREAM SECURITY SYSTEMS.

Ser. No. 60/684,092, filed on May 23, 2005, and entitled FUNCTIONAL SEARCH OUTLINES.

Ser. No. 60/685,904, filed on May 31, 2005, and entitled WIRELESS DELIVERY OF RSS CONTENT.

Ser. No. 60/686,630, filed on Jun. 2, 2005, and entitled DATA STREAM ADVERTISING.

Ser. No. 60/688,826, filed on Jun. 9, 2005, and entitled USES OF OUTLINES AND STRUCTURED DATA.

Ser. No. 60/694,080, filed on Jun. 24, 2005, and entitled USES OF LISTS, OUTLINES AND STRUCTURED DATA.

Ser. No. 60/695,029, filed on Jun. 28, 2005, and entitled EVALUATION OF DATA FEED CONTENT.

Ser. No. 60/699,631, filed on Jul. 15, 2005, and entitled OPML SEARCH ENGINES AND SUPERSERVICES.

Ser. No. 60/700,122, filed on Jul. 18, 2005, and entitled WEB SUPERSERVICES.

Ser. No. 60/702,467, filed on Jul. 26, 2005, and entitled VERTICAL MARKETS AND FEATURES FOR ENHANCED WEB SYSTEMS.

Ser. No. 60/703,688, filed on Jul. 29, 2005, and entitled OPML SYSTEMS.

Ser. No. 60/703,535, filed on Jul. 29, 2005, and entitled OPML CONVERTER.

Ser. No. 60/703,544, filed on Jul. 29, 2005, and entitled OPML SEARCH ENGINE.

Ser. No. 60/709,683, filed on Aug. 19, 2005, and entitled USER INTERFACES FOR OPML SEARCH ENGINES.

Ser. No. 60/719,073, filed on Sep. 21, 2005, and entitled WEB SUPERSERVICES.

Ser. No. 60/719,283, filed on Sep. 21, 2005, and entitled HEALTH CARE INFORMATION MANAGEMENT.

Ser. No. 60/719,284, filed on Sep. 21, 2005, and entitled OPML ROUTERS.

Ser. No. 60/720,250, filed on Sep. 22, 2005, and entitled BEHAVIORAL METADATA IN SYNDICATION AND STRUCTURED DATA ENVIRONMENTS.

Ser. No. 60/721,803, filed on Sep. 28, 2005, and entitled WEB SUPERSERVICES.

Ser. No. 60/722,021, filed on Sep. 29, 2005, and entitled INFORMATION POOLS.

Ser. No. 60/724,956, filed on Oct. 7, 2005, and entitled HEATH CARE INFORMATION MANAGEMENT.

Ser. No. 60/725,166, filed on Oct. 7, 2005, and entitled COMPUTER PROGRAMS FOR SEARCH, MANAGEMENT, AND USE OF OUTLINES.

Ser. No. 60/726,542, filed on Oct. 14, 2005, and entitled RSS ENABLED DEVICES.

Ser. No. 60/726,731, filed on Oct. 14, 2005, and entitled SEMICONDUCTER-BASED SYNCIDATION AND OUTLINING.

Ser. No. 60/726,727, filed on Oct. 14, 2005, and entitled SYNDICATION FILTERS.

Ser. No. 60/734,187, filed on Nov. 6, 2005, and entitled OPML SYSTEMS.

Ser. No. 60/734,156, filed on Nov. 6, 2005, and entitled NOTIFICATION SERVICES FOR USE WITH OUTLINING AND SYNDICATION.

Ser. No. 60/735,712, filed on Nov. 11, 2005, and entitled OPML PROCESSING MODULES AND SYSTEMS.

Ser. No. 60/741,770, filed on Dec. 1, 2005, and entitled NAVIGATION AND MANIPULATION OF DISTRIBUTED CONTENT.

Ser. No. 60/741,958, filed on Dec. 2, 2005, and entitled DATABASES USING OPML-BASED CONTENT POOLS AND SYNDICATED CONTENT.

Ser. No. 60/742,975, filed on Dec. 6, 2005, and entitled SYNDICATED DATA IN MEDICAL DECISION MAKING.

Ser. No. 60/749,757, filed on Dec. 13, 2005, and entitled AN ENTERPRISE PLATFORM FOR ENHANCED SYNDICATION.

Ser. No. 60/750,291, filed on Dec. 14, 2005, and entitled CREATING AND MANAGING VIEWS OF SYNDICATED INFORMATION.

Ser. No. 60/751,254, filed on Dec. 15, 2005, and entitled SYNDICATED TELECOMMUNICATION SERVICES.

Ser. No. 60/751,249, filed on Dec. 16, 2005, and entitled USE OF SYNDICATED DATA WITHIN INSTITUTIONAL HEALTHCARE PRACTICES.

Ser. No. 60/753,959, filed on Dec. 23, 2005, and entitled METHODS AND SYSTEMS FOR CREATING AND MANAGING VIEWS OF SYNDICATED INFORMATION VIA A COMMUNICATIONS NETWORK.

Ser. No. 60/756,774, filed on Jan. 6, 2006, and entitled COMPOSITE SERVICE VISUALIZATION TOOLS.

Ser. No. 60/759,483, filed on Jan. 16, 2006, and entitled USE OF SYNDICATED DATA WITHIN HEALTHCARE PROVIDER AND GROUP PRACTICES.

BACKGROUND

1. Field of Invention

The invention relates to hardware, software and electronic service components and systems to provide large-scale, reliable, and secure foundations for distributed databases and content management systems, combining unstructured and structured data, and allowing post-input reorganization to achieve a high degree of flexibility.

2. Description of Related Art

One can envision highly distributed databases capable of managing simultaneous participation by billions of users, and highly distributed content management systems coordinating the contributions of billions, routinely integrating the contributions of both people and machines, and spanning multiple organizations, firms, and the globe itself. One can imagine flexible systems, where data is input in unstructured as well as structured forms, and subsequent users can access and present the data in flexible, evolving forms not anticipated at the point of data entry. Massively parallel processing—envisioned as occurring inside one machine or cluster of machines—was once the premier challenge facing the database and content management community. The new challenge, in our view, is massively parallel, and flexible, participation of billions.

In order to accomplish this, the world will need a new "business ecosystem." Advances in information technology often show three related themes that may be thought of as analogous to the biological processes of expansion of and species succession in natural ecosystems. First, non-expert end-users will be empowered to solve problems. Second, technology platforms will be created that modularize technology contributions into niches. The niche contributions interrelate with each other through standard protocols and interfaces that are made "open" to technologists and the general public, so that tens, hundreds, and sometimes millions of innovators can contribute to the resulting business ecosystem, each according to his or her choice, creativity and competence. In turn new niches will be established, opened-up, and will bring in further new contributors and contributions.

As the business ecosystem expands, some specific technological components will become critical enablers to the continuing advance of the whole. Issues of flexibility, scale, reliability, and security will become vital to the community. These vital components, for example microprocessors, storage controllers, and network devices in the personal computer ecosystem, will require systematic application of research and development, capital investment, and coordination with industry partners in order that the whole ecosystem can progress. If the world is to make real the vision of the flexible participation of billions, there are a number of core components and systems that have not been invented, and will need to be invented.

The flexible participation of billions has been presaged by blogging—that is, the act of individuals creating Web sites and adding to them more or less daily. By dramatically increasing production and sharing of Web-based content, the blogging movement now produces a virtual river of content—available continuously and with global circulation. Just as word processing empowered millions to create their own documents, blogging software has made it relatively easy for millions to produce their own Web sites and keep them continually updated. By the promotion of a simple underlying standard for sharing text and other media, blogging has popularized the "syndication" or passing on of content borrowed from others—extending the reach of any given blogger and further increasing the total quantity of information in circulation.

A number of companies have emerged as niche players targeting various aspects of large-scale distributed databases, content management, and group participation. For example, some companies such as FeedDemon, NewsGator, myYahoo (Yahoo), and Bloglines have focused on client-side aggregation and presentation. Companies such as Technorati, Google, and Feedster have focused on the complementary services of searching for data feeds of interest. Other companies have focused on technologies for providing syndicated data streams such as SixApart, Drupal, TypePad, Flickr, Picasa (Google), and Blogger (Google). Other companies have positioned themselves as content providers, including new companies such as Engadget, Weblogs Inc., Topix.net, and MySpace, as well as established media companies such as the New York Times and BBC. Of course, various generic Internet technologies are also relevant to the rapidly growing weblog data flow, such as BitTorrent or Akamai's EdgePlatform.

While offering significant advancement in terms of experiences such as sharing news, music, videos and other items, as well as enabling players of games to interact with each other individually and in groups, the value chain is weak, fragmented, and closed to interoperability among contributors in many areas. The value chain will benefit from both improved contributions in specific functions or niches, as well as a more comprehensive overall vision of a possible "flexible participations of billions" ecosystem, additional niches (layers and modules) of functionality, recast functionality among modules, rationalization of protocols and interfaces among modules, and custom combinations of functions that establish end-to-end solutions for specific purposes. For example, available services are weak in presentation, search, signal, and network routing. Aggregators that centralize content use display formats that are widely criticized, despite a general agreement among users that they improve over conventional search engine displays. Storage of most blog content is in proprietary, isolated data sets controlled by blog service operators, and the data cannot be easily restructured or even moved from one provider to another. In their current form, services fail to provide enterprise-class features such as security, privacy, data integrity, and quality of service.

There remains a vital need for components and services that explicitly address the challenge of enabling the "flexible participation of billions" and that are capable of levels of scale, reliability, security and flexibility as yet unrealized and perhaps unimagined. There is a need for a new global business ecosystem, within which innovation by millions of people will be embraced, in order to meet the challenge. In order to stimulate the formation and rapid evolution of such a business ecosystem, there will have to be systematic development of general purpose software, systems and protocols specifically engineered to enable the flexible participation of billions. There also remains a need for such an infrastructure in the health care industry.

SUMMARY OF THE INVENTION

Disclosed herein are systems and methods for syndication and management of structured and unstructured data to assist institutional healthcare delivery, healthcare providers' practices, healthcare providers' group practices, collaborative academic research and decision making in healthcare, including through the utilization of medical devices and healthcare pools.

In one aspect, a method and system disclosed herein includes the handling of health care information based at least in part on providing a user interface that is adapted to receive and handle information that is syndicated from a plurality of pools of information, the pools including at least one pool of health care information.

In embodiments, the syndicated information may be secured by a security facility. The security facility may protect information according to a pool-specific security protocol.

In embodiments, the syndicated information may be structured into a hierarchy. The hierarchy may be defined using OPML. The hierarchy may be defined according to what pools are accessed by what portion of the hierarchy. The hierarchy may define conditions for aggregating information from the pools. In embodiments, the pools may be stored with protocols for using the information in the pools. The pools may be stored with conditions for access of the pools. The pools may include patient record data that is de-identified.

In embodiments, a portion of the syndicated information may be published by a healthcare device.

In embodiments, the pools may contain information selected from a group including, but not limited to, medical instruments, x-ray equipment, MRI equipment, other forms of medical imaging equipment, blood work data, genetic information, medical exam information, medical device information, information from emergency rooms, information from medical labs, diet information, exercise information, metabolic information, medical history information, age information, gender information, behavior information, race information, or information from other systems related to the healthcare and or medical field.

In one aspect, a method and system disclosed herein includes involving the handling of health care based at least in part on disposing health care information into a plurality of pools of information, and syndicating the information from at least one of the plurality of pools. In embodiments, syndicating the information may involve a dynamic generation of syndicated content that may further involve processing a request to convert information into syndicated information. The step of processing the request may involve a security check.

In embodiments, the syndicated information may be secured by a security facility. The security facility may protect information according to a pool-specific security protocol.

In embodiments, the syndicated information may be structured into a hierarchy. The hierarchy may be defined using OPML. The hierarchy may be defined according to what pools are accessed by what portion of the hierarchy. The hierarchy may define conditions for aggregating information from the pools. In embodiments, the pools may be stored with protocols for using the information in the pools. The pools may be stored with conditions for access of the pools. The pools may include patient record data that is de-identified.

In embodiments, a portion of the syndicated information may be published by a healthcare device.

In embodiments, the pools may contain information selected from a group including, but not limited to, medical instruments, x-ray equipment, MRI equipment, other forms of medical imaging equipment, blood work data, genetic information, medical exam information, medical device information, information from emergency rooms, information from medical labs, diet information, exercise information, metabolic information, medical history information, age information, gender information, behavior information, race information, or information from other systems related to the healthcare and or medical field.

In one aspect, a method and system disclosed herein includes the handling of healthcare information based at least in part on configuring a healthcare device to subscribe to a data fee of healthcare information. In embodiments, the data feed may be adapted to collect healthcare information with is in RSS format, OPML format, or other formats.

In embodiments, the device may be selected from a device group including, but not limited to, anesthesiology devices, cardiovascular devices, clinical chemistry devices, clinical toxicology devices, dental devices, ear nose and throat devices, gastroenterology devices, urology devices, general surgery devices, plastic surgery devices, general hospital devices, personal use devices, hematology devices, pathology devices, immunology devices, mammography devices, neurological devices, obstetrical devices, gynecological devices, ophthalmic devices, physical medicine devices, radiology devices, clinical chemistry testing devices, clinical toxicology testing devices, immunology testing devices, and microbiology testing devices.

In embodiments, the healthcare device may be a medical device, medical instrument, handheld medical device, a device associated with an operating room, a device configured to display an electronic medical record, a device configured to run a healthcare software application, and the like.

In embodiments, the healthcare device may subscribe to the syndicated data feed wirelessly.

In embodiments, the healthcare device may be associated with a hospital environment, used to examine a health condition, and or used to measure an environmental condition of a healthcare environment.

In embodiments, the syndicated information may originate from a plurality of separate pools of information. The information may be structured into a hierarchy. The hierarchy may defined by using OPML.

In embodiments, the information may be secured. The information may be associated with a security facility. The security facility may secure the information according to a data pool-specific security protocol.

In one aspect, a method and system disclosed herein includes the handling of healthcare information based at least in part on configuring a healthcare device to syndicate information that is periodically handled by the device. In embodiments, the step of syndicating the healthcare information may comprise receiving information and formatting the information in a syndication format, such as RSS, OPML, or other formats.

In embodiments, the device may be selected from a device group including, but not limited to, anesthesiology devices, cardiovascular devices, clinical chemistry devices, clinical toxicology devices, dental devices, ear nose and throat devices, gastroenterology devices, urology devices, general surgery devices, plastic surgery devices, general hospital devices, personal use devices, hematology devices, pathology devices, immunology devices, mammography devices, neurological devices, obstetrical devices, gynecological devices, ophthalmic devices, physical medicine devices, radiology devices, clinical chemistry testing devices, clinical toxicology testing devices, immunology testing devices, and microbiology testing devices.

In embodiments, the healthcare device may be a medical device, medical instrument, handheld medical device, a device associated with an operating room, a device configured to display an electronic medical record, a device configured to run a healthcare software application, and the like.

In embodiments, the step of syndicating the information may comprise publication of the information. The information may be published to a data pool, a secured data pool, and the like. The information may be secured. The information may be associated with a security facility. The security facility may secure the information according to a data pool-specific security protocol.

In embodiments, the healthcare device may publish the syndicated information wirelessly.

In embodiments, the healthcare device may be associated with a hospital environment, used to examine a health condition, and or used to measure an environmental condition of a healthcare environment.

In embodiments, the syndicated information may originate from a plurality of separate pools of information. The information may be structured into a hierarchy. The hierarchy may defined by using OPML.

Each aspect of the foregoing may be embodied in one or more of a client-side application, a server-side application, one or more semiconductor devices, a computer program product embodied in a computer readable medium, a web service, a services-oriented architecture service, an applet, or an application, either alone or in combination. Further, each of the foregoing systems may also, or instead, be embodied in a method, or in a computer program product embodied in a computer readable medium that, when executing on one or more computers, performs the steps of such a method.

The terms "feed", "data feed", "data stream" and the like, as well as the S-definition described further herein, as used herein, are intended to refer interchangeably to syndicated data feeds and/or descriptions of such feeds. While RSS is one popular example of a syndicated data feed, any other source of news or other items may be used with the systems described herein, such as the outlining markup language, OPML, and these terms should be given the broadest possible meaning unless a narrow sense is explicitly provided or clear from the context. Similarly, terms such as "item", "news item", and "post", as well as the S-messages described further herein, are intended to refer to items within a data feed, and may contain text and/or binary data encoding any digital media including still or moving images, audio, application-specific file formats, and so on.

The term "syndication" is intended to refer to publication, republication, or other distribution of content using any suitable technology, including RSS and any extensions or modifications thereto, as well as any other publish-subscribe or similar technology that may be suitably adapted to the methods and systems described herein. "Syndicated" is intended to describe content in syndication.

BRIEF DESCRIPTION OF THE FIGURES

The foregoing and other objects and advantages of the invention will be appreciated more fully from the following further description thereof, with reference to the accompanying drawings, wherein:

FIG. 8 shows a user interface for a syndication system.

FIG. 9 shows a user interface for a syndication system.

DETAILED DESCRIPTION

Various embodiments of the present invention are described below, including certain embodiments relating particularly to RSS feeds and other syndicated data streams. It should be appreciated, however, that the present invention is not limited to any particular protocol for data feeds and that the various embodiments discussed explicitly herein are primarily for purposes of illustration. Thus, the term syndication generally, and references to RSS specifically, should be understood to include, for example, RDF, RSS v 0.90, 0.91, 0.9x, 1.0, and 2.0, variously attributable to Netscape, UserLand Software, and other individuals and organizations, as well as Atom from the AtomEnabled Alliance, and any other similar formats, as well as non-conventional syndication formats that can be adapted for syndication, such as OPML. Still more generally, while RSS technology is described, and RSS terminology is used extensively throughout, it will be appreciated that the various concepts discussed herein may be usefully employed in a variety of other contexts. For example, various privacy and identity techniques described herein could be usefully combined with HTML Web content rather than RSS-based XML data. Similarly, some of the branding and advertising techniques described herein may be usefully combined with list servers, bulletin boards, or other Internet news sources. Thus, it will be understood that the embodiments described herein are provided by way of example only and are not intended to limit the scope of the inventive concepts disclosed herein.

Figure 1:
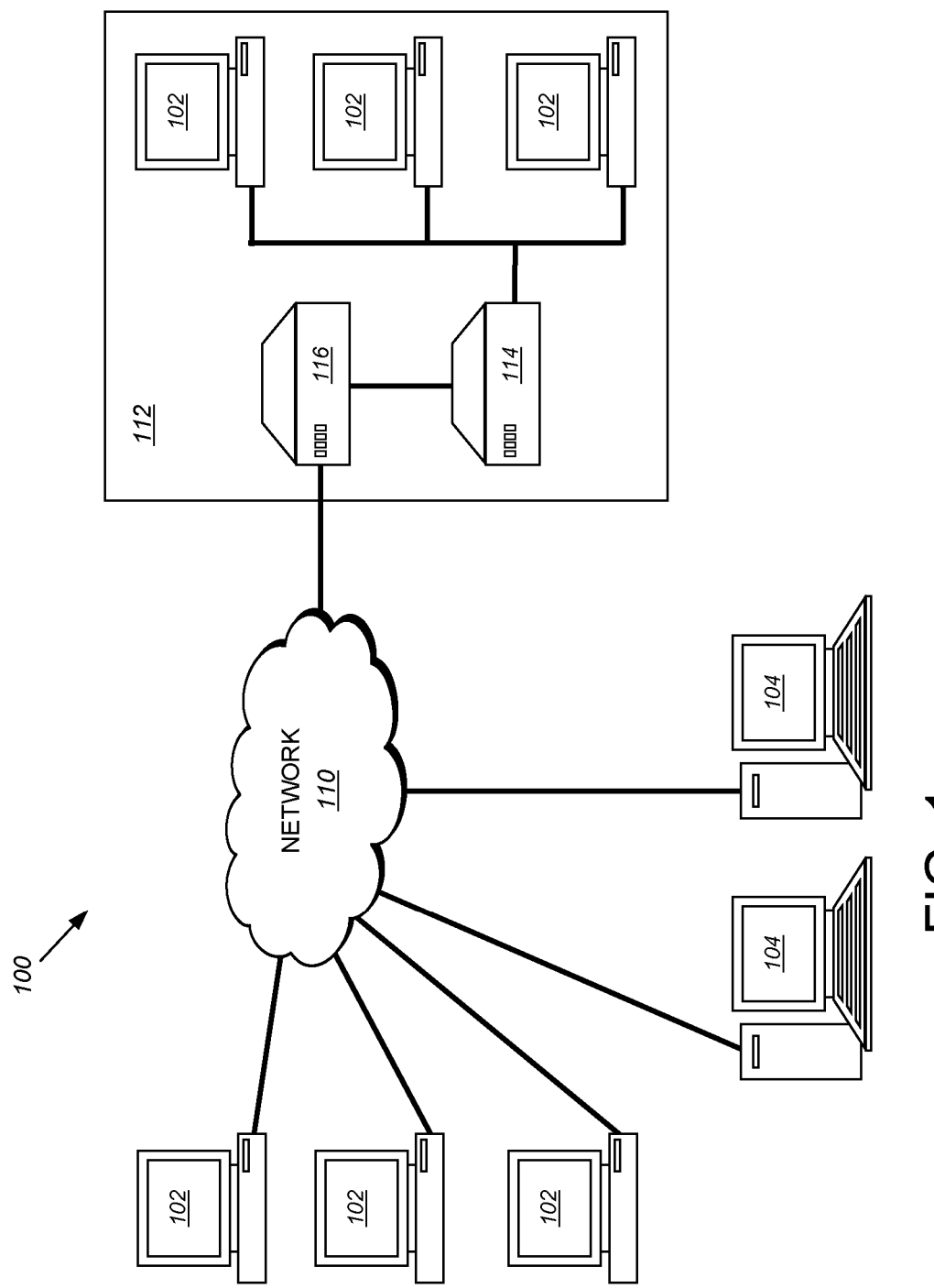
FIG. 1 shows a network that may be used with the systems described herein.

FIG. 1 shows a network for providing a syndicated data stream such as an RSS stream. Short for Really Simple Syndication, RDF (Resource Description Framework) Site Summary or Rich Site Summary, RSS is an XML format for syndicating Web content. A Web site operator who wants to allow other sites to publish some of the Web site's content may create an RSS document and register the document with an RSS publisher. The published or "syndicated" content can then be presented on a different site, or through an aggregator or other system, directly at a client device. Syndicated content may include such data as news feeds, events listings, news stories, headlines, project updates, and excerpts from discussion forums or even corporate information. While RSS content often includes text, other data may also be syndicated, typically in binary form, such as images, audio, and so forth. The systems described herein may use all such forms of data feed. In one embodiment, the XML/RSS feed itself may be converted to binary in order to conserve communications bandwidth. This may employ, for example, Microsoft's DINE specification for binary information or any other suitable binary format.

As shown in FIG. 1, a network 100 may include a plurality of clients 102 and servers 104 connected via an internetwork 110. Any number of clients 102 and servers 104 may participate in such a system 100. The system may further include one or more local area networks ("LAN") 112 interconnecting clients 102 through a hub 114 (in, for example, a peer network such as a wired or wireless Ethernet network) or a local area network server 114 (in, for example, a client-server network). The LAN 112 may be connected to the internetwork 110 through a gateway 116, which provides security to the LAN 112 and ensures operating compatibility between the LAN 112 and the internetwork 110. Any data network may be used as the internetwork 110 and the LAN 112.

In one aspect of the systems described herein, a device within the internetwork 110 such as a router or, on an enterprise level, a gateway or other network edge or switching device, may cache popular data feeds to reduce redundant traffic through the internetwork 110. In other network enhancements, clients 102 may be enlisted to coordinate sharing of data feeds using techniques such as those employed in a BitTorrent peer-to-peer network. In the systems described herein, these and other techniques generally may be employed to improve performance of an RSS or other data feed network.

In one embodiment, the internetwork 110 is the Internet, and the World Wide Web provides a system for interconnecting clients 102 and servers 104 in a communicating relationship through the Internet 110. The internetwork 110 may also, or instead, include a cable network, and at least one of the clients 102 may be a set-top box, cable-ready game console, or the like. The internetwork 110 may include other networks, such as satellite networks, the Public Switched Telephone Network, WiFi networks, WiMax networks, cellular networks, and any other public, private, or dedicated networks that might be used to interconnect devices for transfer of data.

An exemplary client 102 may include a processor, a memory (e.g. RAM), a bus which couples the processor and the memory, a mass storage device (e.g. a magnetic hard disk or an optical storage disk) coupled to the processor and the memory through an I/O controller, and a network interface coupled to the processor and the memory, such as a modem, digital subscriber line ("DSL") card, cable modem, network interface card, wireless network card, or other interface device capable of wired, fiber optic, or wireless data communications. One example of such a client 102 is a personal computer equipped with an operating system such as Microsoft Windows XP, UNIX, or Linux, along with software support for Internet communication protocols. The personal computer may also include a browser program, such as Microsoft Internet Explorer, Netscape Navigator, or FireFox, to provide a user interface for access to the internetwork 110. Although the personal computer is a typical client 102, the client 102 may also be a workstation, mobile computer, Web phone, VOIP device, television set-top box, interactive kiosk, personal digital assistant, wireless electronic mail device, or other device capable of communicating over the Internet. As used herein, the term "client" is intended to refer to any of the above-described clients 102 or other client devices, and the term "browser" is intended to refer to any of the above browser programs or other software or firmware providing a user interface for navigating an internetwork 110 such as the Internet.

An exemplary server 104 includes a processor, a memory (e.g. RAM), a bus which couples the processor and the memory, a mass storage device (e.g. a magnetic or optical disk) coupled to the processor and the memory through an I/O controller, and a network interface coupled to the processor and the memory. Servers may be clustered together to handle more client traffic and may include separate servers for different functions such as a database server, an application server, and a Web presentation server. Such servers may further include one or more mass storage devices such as a disk farm or a redundant array of independent disk ("RAID") system for additional storage and data integrity. Read-only devices, such as compact disk drives and digital versatile disk drives, may also be connected to the servers. Suitable servers and mass storage devices are manufactured by, for example, Compaq, IBM, and Sun Microsystems. Generally, a server 104 may operate as a source of content and provide any associated back-end processing, while a client 102 is a consumer of content provided by the server 104. However, it should be appreciated that many of the devices described above may be configured to respond to remote requests, thus operating as a server, and the devices described as servers 104 may operate as clients of remote data sources. In contemporary peer-to-peer networks and environments such as RSS environments, the distinction between clients and servers blurs. Accordingly, as used herein, the term "server" as used herein is generally intended to refer to any of the above-described servers 104, or any other device that may be used to provide content such as RSS feeds in a networked environment.

In one aspect, a client 102 or server 104 as described herein may provide OPML-specific functionality or, more generally, functionality to support a system using outlining grammar or markup language with processing, storage, search, routing, and the like.

For example, the network 100 may include an OPML or RSS router. While the following discussion details routing of OPML content, it will be understood that the system described may also, or instead, be employed for RSS or any other outlined or syndicated content. The network 100 may include a plurality of clients 102 that are OPML users and a number of servers 104 that are OPML sources connected via an internetwork 110. Any number of clients 102 and servers 104 may participate in such a network 100. A device within the internetwork 110 such as a router or, on an enterprise level, a gateway or other network edge or switching device, may cache popular data feeds to reduce redundant traffic through the internetwork 110. In other network enhancements, clients 102 may be enlisted to coordinate sharing of data feeds using techniques such as those employed in a BitTorrent peer-to-peer network. In the systems described herein, these and other techniques generally may be employed to improve performance of an OPML data network.

A router generally may be understood as a computer networking device that forwards data packets across an internetwork through a process known as routing. A router may act as a junction between two networks, transferring data packets between them and validating that information is sent to the correct location. Routing most typically is associated with Internet Protocol (IP); however, specialized routers exist for routing particular types of data, such as ADSL routers for asynchronously routing signals across digital subscriber lines. An OPML router may route data across an internetwork, such as the Internet, which may include data in OPML format. In particular, the OPML router may be configured to route data in response to or in correspondence with the structure or the content of an OPML document; that is, various species of OPML router may be provided that correspond to user-developed outline structures in OPML. For example, a financial services OPML outline may correspond to a financial services OPML router that is configured to route financial services data packets among constituent networks of one or more financial services institutions.

An OPML router may use a configuration table, also known as a routing table, to determine the appropriate route for sending a packet, including an OPML data packet. The configuration table may include information on which connections lead to particular groups of addresses, connection priorities, and rules for handling routine and special types of network traffic. In embodiments, the configuration table is dynamically configurable in correspondence to the incoming structure of an OPML data packet; that is, an OPML structure may be provided that includes routing instructions that are automatically executed by the OPML router. In other embodiments, a configuration table is configured to route particular portions of an OPML-structured document to particular addresses. In embodiments an OPML router includes rules that can be triggered by OPML content, such as rules for prioritizing nodes, rules for routing OPML content to particular locations, and the like. The rules may be triggered by the structure of an OPML document, the title, or one or more content items within the OPML document.

In the process of transferring data between networks, an OPML router may perform translations of various protocols between the two networks, including, for example, translating data from one data format to another, such as taking RSS input data and outputting data in another format. In embodiments the OPML router may also protect networks from one another by preventing the traffic on one from unnecessarily spilling over to the other, or it may perform a security function by using rules that limit the access that computers from outside the network may have to computers inside the network. The security rules may be triggered by the content of the OPML document, the structure of an OPML document, or other features, such as the author, title, or the like. For example, an OPML router may include an authentication facility that requires an OPML document to contain a password, a particular structure, an embedded code, or the like in order to be routed to a particular place. Such a security feature can protect networks from each other and can be used to enable features such as version control.

OPML routers may be deployed in various network contexts and locations. An OPML edge router may connect OPML clients to the Internet. An OPML core router may serve solely to transmit OPML and other data among other routers. Data traveling over the Internet, whether in the form of a Web page, a downloaded file or an e-mail message, travels over a packet-switching network. In this system, the data in a message or file is broken up into packages approximately 1,500 bytes long. Each of these packages has a "wrapper" that includes information on the sender's address, the receiver's address, the package's place in the entire message, and how the receiving computer can be sure that the package arrived intact. Each data package, called a packet, is then sent off to its destination via the best available route. In embodiments, the OPML router determines the best available route taking into account the structure of the OPML document, including the need to maintain associations among packets. A selected route may be taken by all packets in the message or only a single packet in a message. By packaging data in this manner, a network can continuously balance the data load on its equipment. For example, if one component of a network is overloaded or malfunctioning, data packets may be routed for processing on other network equipment that has a lighter data load and/or is properly working. An OPML router may also route OPML content according to semantic structure. For example, an OPML router configured to handle medical records may route X-Rays to an expert in reading X-Rays while routing insurance information to another department of a hospital.

Routers may reconfigure the paths that data packets take because they look at the information surrounding the data packet and can communicate with each other about line conditions within the network, such as delays in receiving and sending data and the overall traffic load on a network. An OPML router may communicate with other OPML routers to determine, for example, whether the entire structure of an OPML document was preserved or whether recipients of a particular component in fact received the routed component. Again, the OPML document itself may include a structure for routing it. A router may also locate preferential sources for OPML content using caching and other techniques. Thus, for example, where an OPML document includes content from an external reference, the external reference may be a better source for that portion of the OPML document based upon an analysis of, e.g., network congestion, geographic proximity, and the like.

An OPML router may use a subnet mask to determine the proper routing for a data packet. The subnet mask may employ a model similar to IP addressing. This tells the OPML router that all messages in which the sender and receiver have an address sharing the first three groups of numbers are on the same network and shouldn't be sent out to another network. For example, if a computer at address 15.57.31.40 sends a request to the computer at 15.57.31.52, the router will match the first three groups in the IP addresses (15.57.31) and keep the packet on the local network. OPML routers may be programmed to understand the most common network protocols. This programming may include information regarding the format of addresses, the format of OPML documents, the number of bytes in the basic package of data sent out over the network, and the method which insures all the packages reach their destination and get reassembled, including into the structure of an OPML document, if desired.

There are two major routing algorithms in common use: global routing algorithms and decentralized routing algorithms. In decentralized routing algorithms, each router has information about the routers to which it is directly connected but does not know about every router in the network. These algorithms are also known as DV (distance vector) algorithms. In global routing algorithms, every router has complete information about all other routers in the network and the traffic status of the network. These algorithms are also known as LS (link state) algorithms. In LS algorithms, every router identifies the routers that are physically connected to them and obtains their IP addresses. When a router starts working, it first sends a "HELLO" packet over the network. Each router that receives this packet replies with a message that contains its IP address. All routers in the network measure the delay time (or any other important parameters of the network, such as average traffic) for its neighboring routers within the network. In order to do this, the routers send echo packets over the network. Every router that receives these packets replies with an echo reply packet. By dividing round trip time by two, routers can compute the delay time. This delay time includes both transmission and processing times (i.e., the time it takes the packets to reach the destination and the time it takes the receiver to process them and reply). Because of this inter-router communication, each OPML router within the network knows the structure and status of the network and can use this information to select the best route between two nodes of a network.

The selection of the best available route between two nodes on a network may be done using an algorithm, such as the Dijkstra shortest path algorithm. In this algorithm, an OPML router, based on information that has been collected from other OPML routers, builds a graph of the network. This graph shows the location of OPML routers in the network and their links to each other. Every link is labeled with a number called the weight or cost. This number is a function of delay time, average traffic, and sometimes simply the number of disparate links between nodes. For example, if there are two links between a node and a destination, the OPML router chooses the link with the lowest weight.

Closely related to the function of OPML routers, OPML switches may provide another network component that improves data transmission speed in a network. OPML switches may allow different nodes (a network connection point, typically a computer) of a network to communicate directly with one another in a smooth and efficient manner. Switches that provide a separate connection for each node in a company's internal network are called LAN switches. Essentially, a LAN switch creates a series of instant networks that contain only the two devices communicating with each other at that particular moment. An OPML switch may be configured to route data based on the OPML structure of that data.

In one embodiment, an OPML router may be a one-armed router used to route packets in a virtual LAN environment. In the case of a one-armed router, the multiple attachments to different networks are all over the same physical link. OPML routers may also function as an Internet gateway (e.g., for small networks in homes and offices), such as where an Internet connection is an always-on broadband connection like cable modem or DSL.

The network 100 may also, or instead, include an OPML server, as described in greater detail below. OPML, which may, for example, be encapsulated within an RSS data feed, may contain one or more RSS channel identifiers or items, or may be a separate document, has the general format shown in the OPML specification hosted at www.opml.org/spec, the entire contents of which is incorporated herein by reference. The structure generally includes OPML delimiters, general authorship and creation data, formatting/viewing data (if any), and a series of outline entries according to a knowledge structure devised by the author.

An OPML server may be provided for manipulating OPML content. The OPML server may provide services and content to clients 102 using, for example, a Web interface, an API, an XML processing interface, an RSS feed, an OPML renderer, and the like.

The OPML server may, for example, provide a search engine service to visitors. Output from the OPML server may be an OPML file, an HTML file, or any other file suitable for rendering to a client device or subsequent processing. The file may, for example, have a name that explicitly contains the search query from which it was created in order to facilitate redistribution, modification, recreation, synchronization, updating, and storage of the OPML file. A user may also manipulate the file, such as by adding or removing outline elements representing individual search results, or by reprioritizing or otherwise reorganizing the results, and the user may optionally store the revised search as a new OPML file. Thus in one aspect the OPML server may create new, original OPML content based upon user queries submitted thereto. In a sense, this function is analogous to the function of aggregators in an RSS syndication system, where new content may be dynamically created from a variety of different sources and republished in a structured form.

The OPML server may, more generally, provide a front-end for an OPML database that stores OPML content. The OPML database may store OMPL data in a number of forms, such as by casting the OPML structure into a corresponding relational database where each OPML file is encapsulated as one or more records. The OPML database may also store links to external OPML content or may traverse OPML content through any number of layers and store data, files, and the like externally referenced in OPML documents. Thus, for example, where an OPML file references an external OPML file, that external OPML file may be retrieved by the database and parsed and stored. The external OPML file may, in turn, reference other external OPML files that may be similarly processed to construct, within the database, an entire OPML tree. The OMPL database may also, or instead, store OPML files as simple text or in any number of formats optimized for searching (such as a number of well-known techniques used by large scale search engines Google, AltaVista, and the like), or for OPML processing, or for any other purpose(s). The OPML database may provide coherency for formation of an OPML network among an array of clients 102 and servers 104, where content within the network 100 is structured according to user-created OPML outlines.

The OPML server may provide a number of functions or services related to OPML content. For example, the OPML server may permit a user to publish OPML content, either at a hosted site or locally from a user's computer. The OPML server may provide a ping service for monitoring updates of OPML content. The OPML server may provide a validation service to validate content according to the OPML specification. The OPML server may provide a search service or function which may permit searching against a database of OPML content, or it may provide user-configurable spidering capabilities to search for OPML content across a wide area network. The OPML server may provide an interface for browsing (or more generally, navigating) and/or reading OPML content. The OPML server may provide tools for creating, editing, and/or managing OPML content.

The OPML server may provide a number of complementary functions or services to support OPML-based transactions, content management, and the like. In one aspect, a renderer or converter may be provided to convert between a structured format such as OPML and a presentation format such as PowerPoint and display the respective forms. While the converter may be used with OPML and PowerPoint, it should be understood that the converter may be usefully employed with a variety of other structured, hierarchical, or outlined formats and a variety of presentation formats or programs. For example, the presentation format may include Portable Document Format, Flash Animation, electronic books, a variety of Open Source alternatives to PowerPoint (e.g., OpenOffice.org's Presenter, KDE's KPresenter, HTML Slidy, and so forth), whether or not they are PowerPoint compatible. The structured format may include OPML, an MS Word outline, simple text, or any other structured content, as well as files associated with leaf nodes thereof, such as audio, visual, moving picture, text, spreadsheet, chart, table, graphic, or any other format, any of which may be rendered in association with the structured format and/or converted between a structured format and a presentation format It will also be understood that the converter may be deployed on a client device for local manipulation, processing, and/or republication of content.

The OPML database may, for example, operate through the OPML server to generate, monitor, and/or control spiders that locate OPML content. A spider may, upon identification of a valid OPML file, retrieve the file and process it into the database. A spider may also process an OPML file to identify external references, systematically traversing an entire OPML tree. A spider may be coordinated using known techniques to identify redundant references within a hierarchy. A spider may also differentiate processing according to, e.g., structure, content, location, file types, metadata, and the like. The user interface described below may also include one or more tools for configuring spiders, including a front end for generating initial queries, displaying results, and tagging results with any suitable metadata.

By way of example, and not of limitation, medical records may be stored as OPML files, either within the database or in a distributed fashion among numerous locations across the OPML network. Thus, for example, assorted X-Ray data may be maintained in one location, MRI data in another location, patient biographical data in another location, and clinical notes in another location. These data may be entirely decoupled from individual patients (thus offering a degree of security/privacy) and optionally may include references to other content, such as directories of other types of data, directories of readers or interpretive metadata for understanding or viewing records, and the like. Separately, OPML files may be created to provide structure to the distributed data. For example, a CT Scan OPML master record may index the locations of all CT Scan records, which may be useful, for example, for studies or research relating to aggregated CT Scan data. This type of horizontal structure may be captured in one or more OPML records which may themselves be hierarchical. Thus, for example, one OPML file may identify participating hospitals by external reference to OPML records for those hospitals. Each hospital may provide a top-level OPML file that identifies OPML records that are available, which may in turn identify all CT Scan records maintained at that hospital. The CT Scan master record may traverse the individual hospital OPML records to provide a flattened list of CT Scan records available in the system. As another example, an OPML file may identify medical data for a particular patient. This OPML file may traverse records of any number of different hospitals or other medical institutions, or it may directly identify particular records where, for example, concerns about confidentiality cause institutions to strip any personally identifying data from records. For certain applications, it may be desirable to have a central registry of data so that records such as patient data are not inadvertently lost due to, for example, data migration within a particular hospital.

Thus in one embodiment there is generally disclosed herein a pull-based data management system in which atomic units of data are passively maintained at any number of network-accessible locations, while structure is imposed on the data through atomic units of relationship that may be arbitrarily defined through OPML or other grammars. The source data may be selectively pulled and organized according to user-defined OPML definitions. The OPML server and OPML database may enable such a system by providing a repository for organization and search of source data in the OPML network. Traversing OPML trees to fully scope an outline composed of a number of nested OPML outlines may be performed by a client 102 or may be performed by the OPML server, either upon request from a client 102 for a particular outline or continually in a manner that insures integrity of external reference links.

In another aspect, there is disclosed herein a link maintenance system for use in an OPML network. In general, a link maintenance system may function to insure integrity of external references contained within OPML files. Broken links, which may result for example from deletion or migration of source content, may be identified and addressed in a number of ways. For example, a search can be performed using the OPML server and OPML database for all OPML files including a reference to the missing target. Additionally, the OPML server and/or OPML database may include a registry of content sources including an e-mail contact manager/administrator of outside sources. Notification of the broken link including a reference to the content may be sent to all owners of content. Optionally, the OPML server may automatically modify content to delete or replace the reference, assuming the OPML server has authorization to access such content. The OPML server may contact the owner of the missing content. The message to the owner may include a request to provide an alternative link which may be forwarded to owners of all content that references the missing content. If the referenced subject matter has been fully indexed by the OPML server and/or OPML database, the content may itself be reconstructed and a replacement link to the location of the reconstructed content provided. Various combinations of reconstruction and notification, such as those above, may be applied to maintain the integrity of links in OPML source files indexed in the database. In various embodiments the links may be continuously verified and updated, or the links may be updated only when an OPML document with a broken link is requested by a client 102 and processed or traversed by the client 102 or the OPML server in response.

The OPML server may provide a client-accessible user interface to view items in a data stream or OMPL outline. The user interface may be presented, for example, through a Web page viewed using a Web browser or through an outliner or outline viewer specifically adapted to display OPML content. In general, an RSS or OPML file may be converted to HTML for display at a Web browser of a client 102. For example, the source file on a server 104 may be converted to HTML using a Server-Side Include ("SSI") to bring the content into a template by iterating through the XML/RSS internal structure. The resulting HTML may be viewed at a client 102 or posted to a different server 104 along with other items. The output may also, or instead, be provided in OPML form for viewing through an OPML renderer. Thus, feeds and items may be generally mixed, shared, forwarded, and the like in a variety of formats.

Again it is noted that specific references to OPML and RSS above are not intended to be limiting and more generally should be understood as references to any outlining, syndication, or other grammar suitable for use with the systems described herein.

Focusing now on the internetwork 110, one embodiment is the Internet. The structure of the Internet 110 is well known to those of ordinary skill in the art and includes a network backbone with networks branching from the backbone. These branches, in turn, have networks branching from them and so on. The backbone and branches are connected by routers, bridges, switches, and other switching elements that operate to direct data through the internetwork 110. For a more detailed description of the structure and operation of the Internet 110, one may refer to "The Internet Complete Reference," by Harley Hahn and Rick Stout, published by McGraw-Hill, 1994. However, one may practice the present invention on a wide variety of communication networks. For example, the internetwork 110 can include interactive television networks, telephone networks, wireless voice or data transmission systems, two-way cable systems, customized computer networks, Asynchronous Transfer Mode networks, and so on. Clients 102 may access the internetwork 110 through an Internet Service Provider ("ISP", not shown) or through a dedicated DSL service, ISDN leased lines, T1 lines, OC3 lines, digital satellite service, cable modem service, or any other connection, or through an ISP providing same.

In its present deployment as the Internet, the internetwork 110 includes a worldwide computer network that communicates using the well-defined Transmission Control Protocol ("TCP") and Internet Protocol ("IP") to provide transport and network services. Computer systems that are directly connected to the Internet 110 each have a unique IP address. The IP address consists of four one-byte numbers (although a planned expansion to sixteen bytes is underway with IPv6). To simplify Internet addressing, the Domain Name System ("DNS") was created. The DNS allows users to access Internet resources with a simpler alphanumeric naming system. A DNS name consists of a series of alphanumeric names separated by periods. When a domain name is used, the computer accesses a DNS server to obtain the explicit four-byte IP address. It will be appreciated that other internetworks 110 may be used with the invention. For example, the internetwork 110 may be a wide-area network, a local area network, a campus area network, or corporate area network. The internetwork 110 may be any other network used to communicate data, such as a cable broadcast network.

To further define the resources on the Internet 110, the Uniform Resource Locator system was created. A Uniform Resource Locator ("URL") is a descriptor that specifically defines a protocol for an Internet resource along with its location. URLs have the following format:
protocol://domain.address/path-name
in which the domain address and path-name provide a location for a resource, and the protocol defines the type of protocol used to access the resource. It will be appreciated that, in the context of this paragraph only, the term "resource" is used in the conventional sense of RFC 1738 to refer to a document, image, or the like available on the Web. Web documents are identified by the protocol "http" which indicates that the hypertext transfer protocol should be used to access the document. Other common protocols include "ftp" (file transmission protocol), "mailto" (send electronic mail), "file" (local file), and "telnet." The domain.address defines the domain name address of the computer on which the resource is located. Finally, the path-name defines a directory path within the file system of the server that identifies the resource. As used herein, the term "IP address" is intended to refer to the four-byte Internet Protocol address (or the expanded address provided by IPv6), and the term "Web address" is intended to refer to a domain name address, along with any resource identifier and path name appropriate to identify a particular Web resource. The term "address," when used alone, may refer to either a Web address or an IP address.

In an exemplary embodiment, a browser, executing on one of the clients 102, retrieves a Web document at an address from one of the servers 104 via the internetwork 110 and displays the Web document on a viewing device, e.g., a screen. A user can retrieve and view the Web document by entering, or selecting a link to, a URL in the browser. The browser then sends an http request to the server 104 that has the Web document associated with the URL. The server 104 responds to the http request by sending the requested Web document to the client 102. The Web document is an HTTP object that includes plain text (ASCII) conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHML"), and the Standard Generalized Markup Language ("SGML").

Each Web document usually contains hyperlinks to other Web documents. The browser displays the Web document on the screen for the user, and the hyperlinks to other Web documents are emphasized in some fashion such that the user can identify and select each hyperlink. To enhance functionality, a server 104 may execute programs associated with Web documents using programming or scripting languages, such as Perl, C, C++, C#, or Java, or a Common Gateway Interface ("CGI") script to access applications on the server. A server 104 may also use server-side scripting languages such as ColdFusion from MacroMedia or PHP. These programs and languages may perform "back-end" functions such as order processing, database management, and content searching. A Web document may also contain, or include references to, small client-side applications, or applets, that are transferred from the server 104 to the client 102 along with a Web document and are executed locally by the client 102. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, animated media such as Flash media, and sound formats such as MP3 and MIDI. These media formats, along with a growing variety of proprietary media formats, may be used to enrich a user's interactive and audio-visual experience as each Web document is presented through the browser. The term "page" as used herein is intended to refer to the Web document described above as well as any of the above-described functional or multimedia content associated with the Web document.

In general operation, a server 104 may provide a data stream to a client 102. In an exemplary embodiment, the data stream may be a syndicated data stream such as RSS, an XML grammar for sharing data through the Web. An RSS-enabled server may include an RSS file with a title and description of items to be syndicated. As with simple HTML documents, the RSS file may be hand-coded or computer-generated. The first line of an RSS file may contain an XML declaration of the form:

<?xml version="1.0"?>

While not strictly required, this declaration may improve version compatibility. The next item in an RSS file may be a Document Type Declaration ("DTD") that identifies the file as an RSS document:

<!DOCTYPE rss PUBLIC "-//Netscape Communications//DTD RSS 0.91//EN" "http://my.netscape.com/publish/formats/rss-0.91.dtd">

The RSS element is the root or top-level element of an RSS file. The RSS element must specify the version attribute (in this example, version 0.91). It may also contain an encoding attribute (the default is UTF-8):

<rss version="0.91" encoding="ISO_8859-1">

The root element is the top-level element that contains the rest of an XML document. An RSS element may contain a channel with a title (the name of the channel), description (short description of the channel), link (HTML link to the channel Web site), language (language encoding of the channel, such as en-us for U.S. English), and one or more item elements. A channel may also contain the following optional elements:

rating—an independent content rating, such as a PICS rating
copyright—copyright notice information
pubDate—date the channel was published
lastBuildDate—date the RSS was last updated
docs—additional information about the channel
managingeditor—channel's managing editor
webMaster—channel Webmaster
image—channel image
textinput—allows a user to send an HTML form text input string to a URL
skipHours—the hours that an aggregator should not collect the RSS file
skipDays—the weekdays that an aggregator should not collect the RSS file A channel may contain an image or logo. In RSS, the image element contains the image title and the URL of the image itself. The image element may also include the following optional elements: a link (a URL that the image links to), a width, a height, and a description (additional text displayed with the image). There may also be a text input element for an HTML text field. The text input element may include a title (label for a submit button), description, name, and link (to send input). The link may enable richer functionality, such as allowing a user to submit search terms, send electronic mail, or perform any other text-based function.

Once defined in this manner, a channel may contain a number of items, although some services (e.g., Netscape Netcenter) may limit the number. In general, the "item" elements provide headlines and summaries of the content to be shared. New items may be added, either manually or automatically (such as through a script), by appending them to the RSS file.

Figure 2:
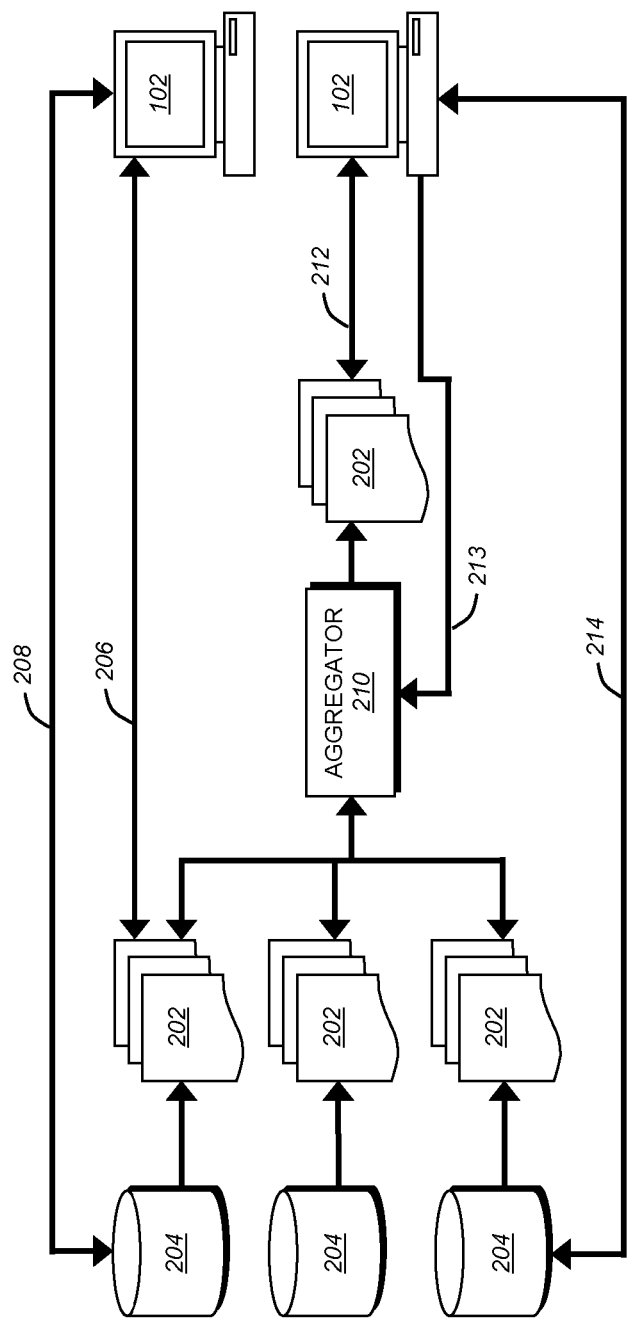
FIG. 2 shows a system for using and aggregating data feeds.

FIG. 2 depicts a system for using and aggregating data feeds or other syndicated content. In general, data feeds 202, such as RSS source files, are generated from a content source 204 and made available for use or review by clients 102 through a network.

The content source 204 may provide any electronic content including newspaper articles; Web magazine articles; academic papers; government documents such as court opinions, administrative rulings, regulation updates, or the like; opinions; editorials; product reviews; movie reviews; financial or market analysis; current events; bulletins; and the like. The content may include text, formatting, layout, graphics, audio files, image files, movie files, word processing files, spreadsheet files, presentation files, electronic documents, HTML files, executable files, scripts, multi-media, relational databases, data from relational databases and/or any other content type or combination of types suitable for syndication through a network. The content source 204 may be any commercial media provider(s) such as newspapers, news services (e.g., Reuters or Bloomberg), or individual journalists such as syndicated columnists. The content source 204 may also be from commercial entities such as corporations, non-profit corporations, charities, religious organizations, social organizations, or the like, as well as from individuals with no affiliation to any of the foregoing. The content source 204 may be edited, as with news items, or automated, as with data feeds 202 such as stock tickers, sports scores, weather conditions, and so on. While written text is commonly used in data feeds 202, it will be appreciated that any digital media may be binary encoded and included in an item of a data feed 202 such as RSS. For example, data feeds 202 may include audio, moving pictures, still pictures, executable files, application-specific files (e.g., word processing documents or spreadsheets), and the like. It should also be understood that, while a content source 204 may generally be understood as a well defined source of items for a data feed, the content source 204 may be more widely distributed or subjectively gathered by a user preparing a data feed 202. For example, an individual user interested in automotive mechanics may regularly read a number of related magazines and regularly attend trade shows. This information may be processed on an ad hoc basis by the individual and placed into a data feed 202 for review and use by others. Thus it will be understood that the data stream systems described herein may have broad commercial use, as well as non-commercial, educational, and mixed uses.

As described generally above, the data feed 202 may include, for each item of content, summary information such as a title, synopsis or abstract (or a teaser, for more marketing oriented materials), and a link to the underlying content. Thus as depicted in FIG. 2, when a client 102 accesses a data feed 202, as depicted by an arrow 206, the client 102 may then display the summary information for each item in a user interface. A client 102 may, in response to user input such as clicking on a title of an item in the user interface, retrieve the underlying item from the content source 204 as indicated by an arrow 208. In the bi-directional communication depicted by the arrow 208, the client 102 may also identify the specific data feed 202 through which the item was identified, which may be useful for tracking distribution channels, customer behavior, affiliate referral fees, and so forth. It should be appreciated that an RSS data feed 202 may be presented to a client 102 as an RSS file (in XML format) that the client 102 locally converts to HTML for viewing through a Web browser, or the data feed 202 may be converted to HTML at a Web site that responds to HTTP requests from a client 102 and responds with an HTML-formatted data feed.

A related concept is the so-called "permalink" that provides a permanent URL reference to a source document that may be provided from, for example, a dynamically generated Web site or a document repository served from a relational database behind a Web server. While there is no official standard for permalink syntax or usage, they are widely used in conjunction with data feeds. Permalinks typically consist of a string of characters which represent the date and time of posting, and some (system dependent) identifier (which includes a base URL, and often identifies the author, subscriber, or department which initially authored the item). If an item is changed, renamed, or moved, its permalink remains unaltered. If an item is deleted altogether, its permalink cannot be reused. Permalinks are exploited in a number of applications including link tracing and link track back in Weblogs and references to specific Weblog entries in RSS or Atom syndication streams. Permalinks are supported in most modern weblogging and content syndication software systems, including Movable Type, LiveJournal, and Blogger.

RSS provides a standard format for the delivery of content through data feeds. This makes it relatively straightforward for a content provider to distribute content broadly and for an affiliate to receive and process content from multiple sources. It will be appreciated that other RSS-compliant and/or non-RSS-compliant feeds may be syndicated as that term is used herein and as is described in greater detail below. As noted above, the actual content may not be distributed directly, only the headlines, which means that users will ultimately access the content source 204 if they're interested in a story. It is also possible to distribute the item of content directly through RSS, though this approach may compromise some of the advantages of network efficiency (items are not copied and distributed in their entirety) and referral tracking. Traffic to a Web site that hosts a content source 204 can increase in response to distribution of data feeds 202.

Although not depicted, a single content source 204 may also have multiple data feeds 202. These may be organized topically or according to target clients 102. Thus, the same content may have data feeds 202 for electronic mailing lists, PDAs, cell phones, and set-top boxes. For example, a content provider may decide to offer headlines in a PDA-friendly format, or it may create a weekly email newsletter describing what's new on a Web site.

Data feeds 202 in a standard format provide for significant flexibility in how content is organized and distributed. An aggregator 210, for example, may be provided that periodically updates data from a plurality of data feeds 202. In general, an aggregator 210 may make many data feeds 202 available as a single source. As a significant advantage, this intermediate point in the content distribution chain may also be used to customize feeds, and presentation thereof, as well as to filter items within feeds and provide any other administrative services to assist with syndication, distribution, and review of content.

As will be described in greater detail below, the aggregator 210 may filter, prioritize, or otherwise process the aggregated data feeds. A single processed data feed 202 may then be provided to a client 102 as depicted by an arrow 212. The client 102 may request periodic updates from the data feed 202 created by the aggregator 210 as also indicated by an arrow 212. As indicated by an arrow 213, the client 102 may also configure the aggregator 210 such as by adding data streams 202, removing data streams 202, searching for new data streams 202, explicitly filtering or prioritizing items from the data streams 202, or designating personal preferences or profile data that the aggregator 210 may apply to generate the aggregated data feed 202. When an item of interest is presented in the user interface of the client 102, a user may select a link to the item, causing the client 102 to retrieve the item from the associated content source 204 as indicated by an arrow 214. The aggregator 210 may present the data feed 202 as a static web page that is updated only upon an explicit request from the client 102, or the aggregator 210 may push updates to a client 102 using either HTTP or related Web browser technologies, or by updates through some other channel, such as e-mail updates. It will also be appreciated that, while the aggregator 210 is illustrated as separate from the client 102, the aggregator 210 may be realized as a primarily client-side technology, where software executing on the client 102 assumes responsibility for directly accessing a number of data feeds 202 and aggregating/filtering results from those feeds 202.

It will be appreciated that a user search for feeds will be improved by the availability of well organized databases. While a number of Weblogs provide local search functionality, and a number of aggregator services provide lists of available data feeds, there remains a need for a consumer-level searchable database of feed content. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

The advent of commonly available data feeds 202, such as RSS feeds, along with tools such as aggregators 210, enables new modes of communication. In one common use, a user may, through a client 102, post aggregated feeds 202 to a Weblog. The information posted on a Weblog may include an aggregated feed 202, one or more data feeds 202 that are sources for the aggregated feed 202, and any personal, political, technical, or editorial comments that are significant to the author. As such, all participants in an RSS network may become authors or sources of content, as well as consumers.

Figure 3:
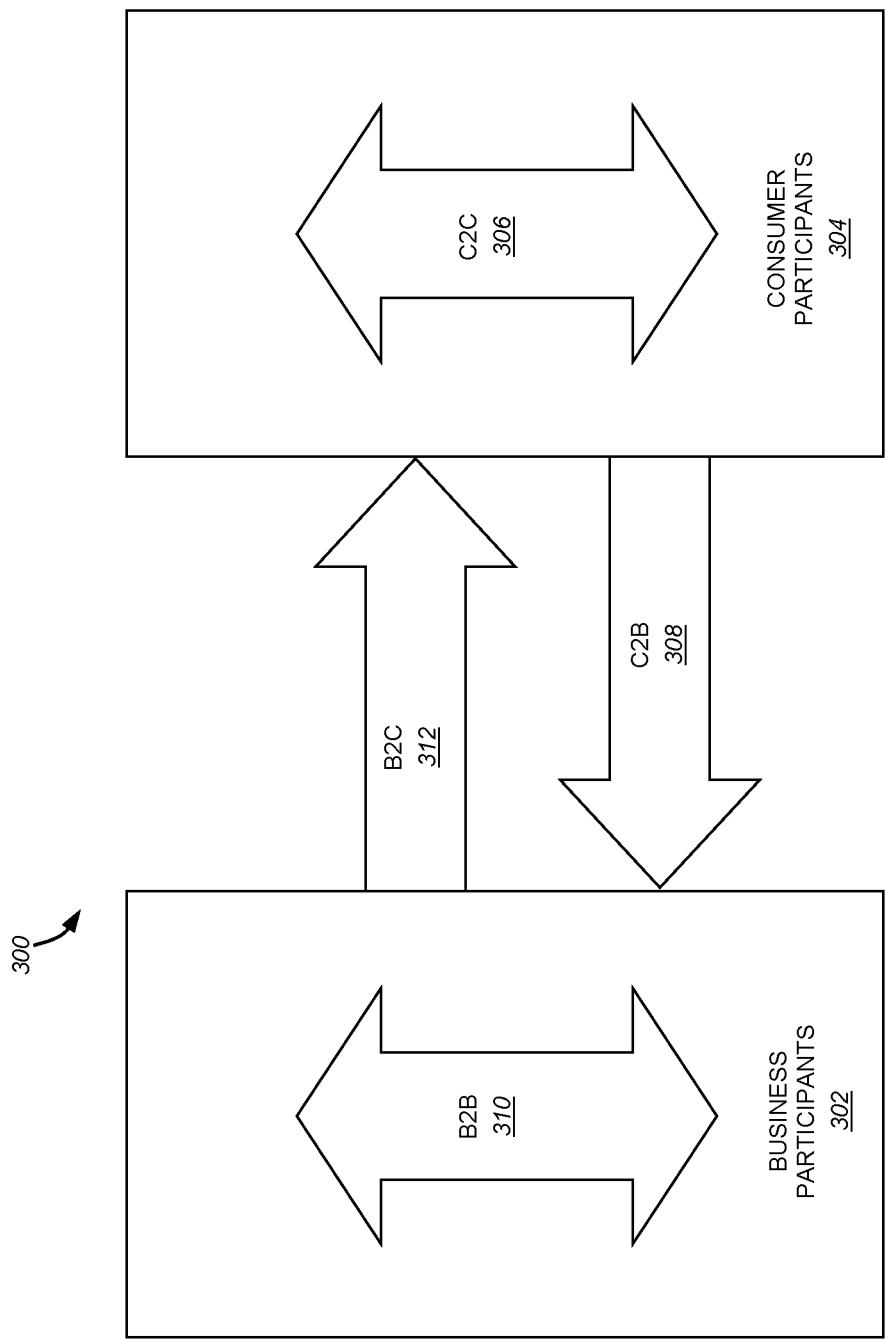
FIG. 3 depicts markets for syndicated content.

FIG. 3 depicts certain aspects of the markets for data feeds. This generally depicts characteristics that can be present in a number of different markets in which the systems described herein may be usefully deployed. Market 300 for data feeds 302 such as RSS may be understood as including four main models for information exchange among business participants in the commercial space 302 and individuals in the consumer space 304. As large, established companies such as Yahoo, Google, and Microsoft adopt and integrate RSS technologies, these markets should grow significantly.

At present, the consumer-to-consumer market model 306 consists primarily of millions of individual bloggers, mostly communicating with each other. This includes non-commercial Weblogs where individuals aggregate data feeds 302 from a variety of sources and include editorial commentary or other information. In general, a source in this space is an individual presenting aggregated feeds 302 in a Web site with some common theme or themes of interest to the author, such as history, sports, science, technology, politics, literature, art, music, and so forth. However, there are no strict requirements that any one or more themes be followed, and the Weblog may simply reflect an ad hoc selection of topics that the author finds interesting. Weblogs in this space gain popularity according to the content provided, with readership (and associated RSS subscriptions or registrations) rising or falling according to general interest.

The consumer-to-business model or segment 308 brings together consumers who are interested in a particular topic, typically a topic with a corresponding commercial market, such as automobiles, mortgages, financial services, home repair, hobbies, and the like. A topic may be still more refined, such as antique automobiles, or antique American automobiles; however, the corresponding participation of commercial participants may depend on the scope of the market. Thus, a large number of financial service providers could be expected to subscribe to an RSS data feed for general consumers of financial services; however, a smaller number of commercial subscribers might be expected for derivative currency hedge instruments among Pacific Rim country currencies. In general, consumer-to-business uses may provide consumers with concerns, interests, and preferences in a particular market with a forum that will be followed by corresponding commercial interests. In addition, by participating in this RSS network, businesses may also address consumer interests in a more direct and personal way, as distinguished from the business-to-consumer segment 312 discussed below. At the same time, it will be appreciated that the distinction between these segments 308, 312 need not be an absolute one, and a synthesis of these two communication channels may result in a greater dialogue between commercial and individual actors, to their collective and mutual benefit. Thus, for example, with a suitably configured aggregated feed 302 and associated Web presentation, an automobile manufacturer could design a new minivan or SUV in cooperation with the automobile-buying public in a manner that addresses previously unknown purchasing preferences of consumers. Additionally, since the community of participants is likely to be highly focused, this segment 308 may offer significant opportunities for revenue from targeted advertising.

The business-to-business segment 310 does not appear to be commonly used, although in the methods and systems described herein syndication may substitute for electronic mail and other forms of corporate and business-to-business communication, such as time management, inventory, supply chain, manufacturing, and customer relations information flow.

The business-to-consumer segment 312 includes an extension of traditional media companies that can add data feed capabilities to their online presence. This includes news companies in print media, radio, television media, and Internet media, including, by way of example and not limitation, the New York Times, the Washington Post, the Wall Street Journal, Forbes, Time, Business Week, CSPAN, ESPN, The Weather Channel, CNBC, CNET, Bloomberg, Reuters, and so on. This may also include non-news related media that nonetheless periodically update content, such as movie studios, network television, cable television, and so on. In addition, other companies that serve consumers may also usefully employ data feed systems, including companies ranging from catalogue companies such as Land's End to consumer electronics retailers such as Best Buy. In this context, a syndication platform such as enhanced RSS offers a reliable distribution channel for advertising new products and special offers to presumably interested consumers. These and other applications may be realized using the data feed technology described herein.

All such entity-to-entity communications described above may be improved through enhanced syndication systems as generally described herein. It will be appreciated that one obstacle to expanded use across all of these markets is the absence in the primary technology, RSS, of enterprise-class features such as security, authentication, conditional access data repositories, and rich metadata, to name a few. In one aspect, the systems described herein bring many of these features to RSS-like systems to provide secure, scalable syndication systems.

It should be clear that, while the term "aggregator" is used to label aspects of the systems disclosed herein, those systems include significant useful and advantageous functionality that is not present in any aggregator in the prior art, and as such the term should be interpreted broadly to optionally include all of the functions and techniques described below, rather than narrowly in the sense that it is currently used in the art. Although broader in meaning, the aggregator and interface described below may operate, for example, from one of the servers 104 described above with reference to FIG. 1 and may cooperate with other participants and content sources in the manner depicted for the aggregator 210 described in FIG. 2.

It will be appreciated that the components described herein correspond generally to various areas of functionality for a data feed system. However, in various embodiments, other components may be added, or certain components may be removed or combined with other components. For example, the aggregator described herein may cooperate with an n-tier architecture for a more general purpose Web server or with a relational database or other back end systems not specifically depicted herein to store and access data. Similarly, the systems described herein may include FTP servers, e-mail servers, PSTN interfaces, and other physical connections and protocols for various other functions that may be usefully combined with the aggregator to enhance functionality. Any number of such combinations and variations may be employed consistent with the systems described herein and are intended to fall within the scope of the present disclosure.

It will also be appreciated that a wide range of software and hardware platforms may be used to deploy the systems described herein. Generally, the system components may be realized in hardware, software, or some combination of these. The components may be realized in one or more microprocessors, microcontrollers, embedded microcontrollers, programmable digital signal processors or other programmable devices, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The components may also, or instead, include one or more application specific integrated circuits (ASICs), dedicated semiconductor devices, programmable gate arrays, programmable array logic devices, or any other device that may be configured to process electronic signals.

Any combination of the above circuits and components, whether packaged discretely, as a chip, as a chip set, or as a die, may be suitably adapted to use with the systems described herein. It will further be appreciated that the above components may be realized as computer executable code created using a structured programming language such as C, an object oriented programming language such as C++, or any other high-level or low-level programming language that may be compiled or interpreted to run on one of the above devices, as well as heterogeneous combinations of processors, processor architectures, or combinations of different hardware and software.

Figure 4:
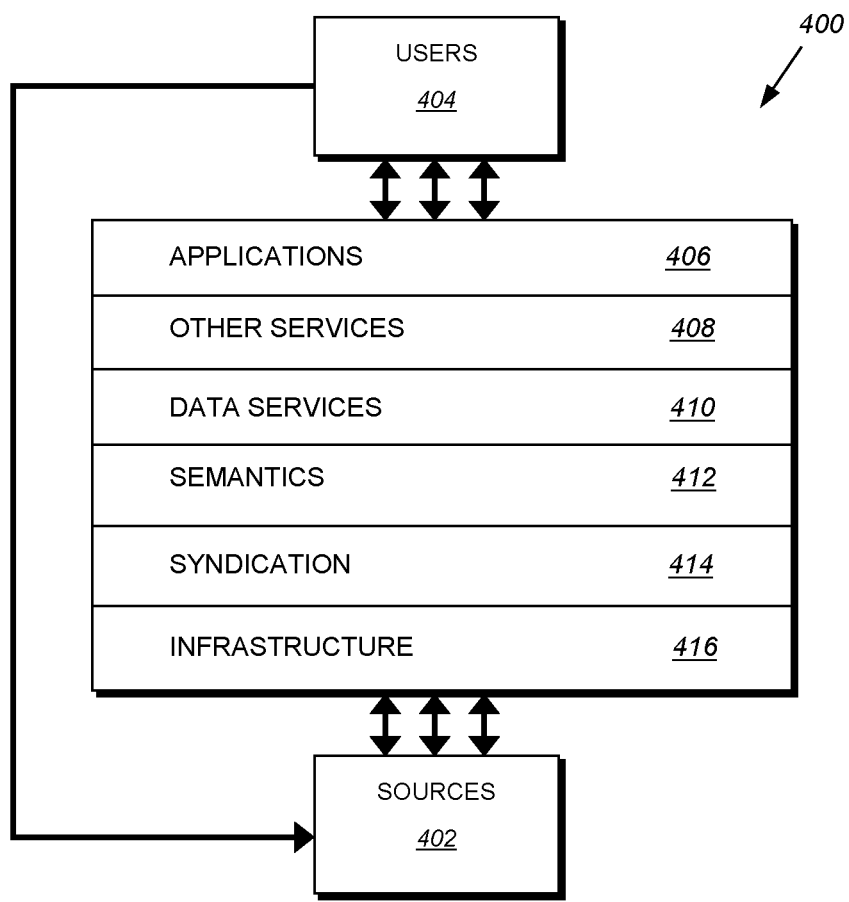
FIG. 4 depicts a conceptual framework for syndicated communications.

FIG. 4 depicts a conceptual framework for syndicated communications. In a syndication system 400, a plurality of sources 402, which may be for example any of the content sources 204 described above, are published to a plurality of users 404, which may be users of any of the clients 102 described above. Users 404 may include individuals, consumers, business entities, government entities, workgroups, and other categories of users 404. Access to the sources 402 by the users 404 may be through layers of devices, services, and systems (which may be analogous to or actually embodied in a protocol stack) in which various layers are responsible for discrete functions or services, as depicted generally in FIG. 4. However, it will be appreciated that each layer of FIG. 4 may instead be provided as one or more non-layered services. This may include, for example, deployment as services in a Services Oriented Architecture or other Web-based or similar environment where individual services may be located and called from remote locations. This may also, or instead, include deployment in a fixed architecture where a specific collection of services or functions, such as atomic functions, is deployed either locally or in a distributed manner and accessible through a syntax such as an instruction set. The functions within the conceptual framework may also be deployed within a web application framework such as Ruby on Rails or any other open source or proprietary application framework. Thus, numerous architectures and variations are possible for deploying the functions and operations described herein, and all such arrangements are intended to fall within the scope of this disclosure.

At the same time, it should be understood that the number, arrangement, and functions of the layers may be varied in a number of ways within a syndication system 400; in particular, depending on the characteristics of the sources, the needs of the users 404 and the features desired for particular applications, a number of improved configurations for syndication systems 404 may be established, representing favorable combinations and sub-combinations of layers depicted in FIG. 4. The layers may provide services such as, for example, services related to applications 406, other services 408 (including relating to processing), services related to data 410, services related to semantics of content 412, syndication services 414, and services related to infrastructure 416. More generally, all of the services and functions described below, either individual or in combinations, as well as other services not specifically mentioned, may be incorporated into an enhanced syndication system as described herein. It should be understood that any of the services depicted in the layers of FIG. 4 may be embodied in hardware, software, firmware, or a combination thereof; for example, a service may be embodied in software as a web service, according to a services oriented architecture. Alternatively, without limitation, a service may be a client-side or server-side application or take any of the forms described herein and in the documents incorporated by reference herein. In one embodiment, one or more layers may be embodied in a dedicated semiconductor device, such as an ASIC, that is configured to enable syndication.

Services related to applications 406 may be embodied, for example, in a client-side application (including commercially available applications such as a word processor, spreadsheet, presentation software, database system, task management system, supply chain management system, inventory management system, human resources management system, user interface system, operating system, graphics system, computer game, electronic mail system, calendar system, media player, and the like), a remote application or service, an application layer of an enhanced syndication services protocol stack, a web service, a service oriented architecture service, a Java applet, or a combination of these. Applications 406 may include, for example, a user interface, social networking, vertical market applications, media viewers, transaction processing, alerts, event-action pairs, analysis, and so forth. Applications 406 may also accommodate vertical market uses of other aspects of the system 400 by integrating various aspects of, for example, security, interfaces, databases, syndication, and the like. Examples of vertical markets include financial services, health care, electronic commerce, communications, advertising, sales, marketing, supply chain management, retail, accounting, professional services, and so forth. In one aspect, the applications 406 may include social networking tools to support functions such as sharing and pooling of syndicated content, content filters, content sources, content commentary, and the like, as well as formation of groups, affiliations, and the like. Social networking tools may support dynamic creation of communities and moderation of dialogues within communities, while providing individual participants with any desired level of anonymity. Social networking tools may also, or instead, evaluate popularity of feeds or items in a syndication network or permit user annotation, evaluation, or categorization. A user interface from the application may also complement other services layers. For example, an application may provide a user interface that interprets semantic content to determine one or more display characteristics for associated items of syndicated content.

Other services 408 may include any other services not specifically identified herein that may be usefully employed within an enhanced syndication system. For example, content from the sources 402 may be formatted for display through a formatting service that interprets various types of data and determines an arrangement and format suitable for display. This may also include services that are specifically identified, which may be modified, enhanced, or adapted to different uses through the other services 408. Other services 408 may support one or more value added services. For example, a security service may provide for secure communications among users or from users to sources. An identity service may provide verification of user or source identities, such as by reference to a trusted third party. An authentication service may receive user credentials and control access to various sources 402 or other services 408 within the system. A financial transaction service may execute financial transactions among users 404 or between users 404 and sources 402. Any service amenable to computer implementation may be deployed as one or more other services 408, either alone or in combination with services from other elements of the system 400.

Data services 410 may be embodied, for example, in a client-side application, a remote application or service, an application layer of an enhanced syndication services protocol stack, as application services deployed, for example, in the services oriented architecture described below, or a combination of these. Data services 410 may include, for example, search, query, view, extract, or any other database functions. Data services 410 may also, or instead, include data quality functions such as data cleansing, deduplication, and the like. Data services 410 may also, or instead, include transformation functions for transforming data between data repositories or among presentation formats. Thus, for example, data may be transformed from entries in a relational database, or items within an OPML outline, into a presentation format such as MS Word, MS Excel, or MS PowerPoint. Similarly, data may be transformed from a source such as an OPML outline into a structured database. Data services 410 may also, or instead, include syndication-specific functions such as searching of data feeds, or items within data feeds, or filtering items for relevance from within selected feeds, or clustering groups of searches and/or filters for republication as an aggregated and/or filtered content source 402. In one aspect, a data service 410 as described herein provides a repository of historical data feeds, which may be combined with other services for user-configurable publication of aggregated, filtered, and/or annotated feeds. More generally, data services 410 may include any functions associated with data including storing, manipulating, retrieving, transforming, verifying, authenticating, formatting, reformatting, tagging, linking, hyperlinking, reporting, viewing, and so forth. A search engine deployed within the data services 410 may permit searching of data feeds or, with a content database as described herein, searching or filtering of content within data feeds from sources 402. Data services 410 may be adapted for use with databases such as commercially available databases from Oracle, Microsoft, IBM, and/or open source databases such as MySQL AB or PostgreSQL.

In one aspect, data services 410 may include services for searching and displaying collections of OPML or other XML-based documents. This may include a collection of user interface tools for finding, building, viewing, exploring, and traversing a knowledge structure inherent or embedded in a collection of interrelated or cross-linked documents. Such a system has particular utility, for example, in creating a structured knowledge directory of OPML structures derived from an exploration of relationships among individual outlined OPML documents and the nodes thereof (such as end nodes that do not link to further content). In one embodiment, the navigation and building of knowledge structures may advantageously be initiated from any point within a knowledge structure, such as an arbitrarily selected OPML document within a tree. A user interface including the tools described generally above may allow a user to restrict a search to specific content types, such as RSS, podcasts (which may be recognized, e.g., by presence of RSS with an MP3 or WAV attachment) or other OPML links within the corpus of OPML files searched. The interface may be supported by a searchable database of OPML content, which may in turn be fed by one or more OPML spiders that seek to continually update content either generally or within a specific domain (i.e., an enterprise, a top-level domain name, a computer, or any other domain that can be defined for operation of a spider. The OPML generated by an OPML search engine may also be searchable, permitting, e.g., recovery of lost links to OPML content.

It will be appreciated that by storing an entire knowledge structure (or entire portions thereof), the tree structure may be navigated in either direction. That is, a tree may be navigated downward in a hierarchy (which is possible with conventional outlines) as well as upward in a hierarchy (which is not supported directly by OPML). Upward navigation becomes possible with reference to a stored version of the knowledge structure, and the navigation system may include techniques for resolving upward references (e.g. where two different OPML documents refer to the same object) using explicit user selections, pre-programmed preferences, or other selection criteria, as well as combinations thereof.

Data services 410 may include access to a database management system (DBMS). In one aspect, the DBMS may provide management of syndicated content. In another aspect, the DBMS may support a virtual database of distributed data. The DBMS may allow a user, such as a human or an automatic computer program, to perform operations on a data feed, references to the data feed, metadata associated with the data feed, and the like. Thus in one aspect, a DBMS is provided for syndicated content. Operations on the data managed by the DBMS may be expressed in accordance with a query language, such as SQL, XQuery, or any other database query language. In some embodiments, the query language may be employed to describe operations on a data feed, on an aggregate of data feeds, or on a distributed set of data feeds. It should be appreciated that the data feeds may be structured according to RSS, OPML, or any other syndicated data format. In another aspect, content such as OPML content may describe a relationship among distributed data, and the data services 410 may provide a virtual DBMS interface to the distributed data. Thus, there is disclosed herein an OPML-based database wherein data relationships are encoded in OPML and data are stored as content distributed among resources referenced by the OPML.

The data services 410 may include database transactions. Each database transaction may include an atomic set of reads and/or writes to the database. The transaction mechanism for the database transactions may support concurrent and/or conditional access to the data in the database. Conditional access may support privacy, security, data integrity, and the like within the database. The transaction mechanism may allow a plurality of users to concurrently read, write, create, delete, perform a query, or perform any other operation supported by the DMBS against an RSS feed or OPML file, either of which may be supported by the data in the database or support a database infrastructure. In one aspect, the transaction mechanism may avoid or resolve conflicting operations and maintain the consistency of the database. The transaction mechanism may be adapted to support availability, scalability, mobility, serializability, and/or convergence of a DBMS. The transaction mechanism may also, or instead, support version control or revision control. The DBMS may additionally or alternatively provide methods and systems for providing access control, record locking, conflict resolution, avoidance of list updates, avoidance of system delusion, avoidance of scaleup pitfall, and the like.

The data services 410 may provide an interface to a DBMS that functions as a content source by publishing or transmitting a data feed to a client. The DBMS may additionally or alternatively perform as a client by accessing or receiving a data feed from a content source. The DBMS may perform as an aggregator of feeds. The DBMS may provide a syndication service. The DBMS may perform as an element in a service-oriented architecture. The DBMS may accept and/or provide data that are formatted according to XML, OPML, HTML, RSS, or any other markup language.

Semantics 412, or semantic processing, may include any functions or services associated with the meaning of content from the sources 402 and may be embodied, for example, in a client-side application, a remote application or service, an application layer of an enhanced syndication services protocol stack, as application services deployed, for example, in the services oriented architecture described below, or a combination of these. Semantics 412 may include, for example, interrelating content into a knowledge structure using, for example, OPML, adding metadata or enriching current metadata, interpreting or translating content, and so forth. Semantics 412 may also include parsing content, either linguistically for substantive or grammatical analysis, or programmatically for generation of executable events. Semantics 412 may include labeling data feeds and items within feeds, either automatically or manually. This may also include interpretation of labels or other metadata, and automated metadata enrichment. Semantics 412 may also provide a semantic hierarchy for categorizing content according to user-specified constraints or against a fixed dictionary or knowledge structure. Generally, any function relating to the categorization, interpretation, or labeling of content may be performed within a semantic layer, which may be used, for example, by users 404 to interpret content or by sources 402 to self-identify content. Categorization may be based on one or more factors, such as popularity, explicit user categorization, interpretation or analysis of textual, graphical, or other content, relationship to other items (such as through an outline or other hierarchical description), content type (e.g., file type), content metadata (e.g., author, source, distribution channel, time of publication, etc.) and so forth. Currently available tools for semantic processing include OPML, dictionaries, thesauruses, and metadata tagging. Current tools also include an array of linguistic analysis tools which may be deployed as a semantic service or used by a semantic service. These and other tools may be employed to evaluate semantic content of an item, including the body and metadata thereof, and to add or modify semantic information accordingly.

It will be understood that, while OPML is one specific outlining grammar, any similar grammar, whether XML-based, ASCII-based, or the like, may be employed, provided it offers a manner for explicitly identifying hierarchies and/or relationships among items within a document and/or among documents. Where the grammar is XML-based, it is referred to herein as an outlining markup language.

Semantics 412 may be deployed, for example, as a semantic service associated with a syndication platform or service. The semantic service may be, for example, a web service, a service in a services oriented architecture, a layer of a protocol stack, a client-side or server-side application, or any of the other technologies described herein, as well as various combinations of these. The semantic service may offer a variety of forms of automated, semi-automated, or manual semantic analysis of items of syndicated content, including feeds or channels that provide such items. The semantic service may operate in one or more ways with syndicated content. In one aspect, the semantic service may operate on metadata within the syndicated content, as generally noted above. The semantic service may also, or instead, store metadata independent from the syndicated content, such as in a database, which may be publicly accessible or privately used by a value-added semantic service provider or the like. The semantic service may also or instead specify relationships among items of syndicated content using an outlining service such as OPML. In general, an outlining service, outlining markup language, outlining syntax, or the like, provides a structured grammar for specifying relationships such as hierarchical relationships among items of content. The relationship may, for example, be a tree or other hierarchical structure that may be self-defined by a number of discrete relationships among individual items within the tree. Any number of such outlines may be provided in an outline-based semantic service.

By way of an example of use of a semantic service, a plurality of items of syndicated content, such as news items relating to a corporate entity, may be aggregated for presentation as a data feed. Other content, such as stored data items, may be associated with the data feed using an outline markup language so that an outline provided by the semantic service includes current events relating to a corporate entity, along with timely data from a suitable data source such as stock quotes, bond prices, or any other financial instrument data (e.g., privately held securities, stock options, futures contracts), and also publicly available data such as SEC filings including quarterly reports, annual reports, or other event reports. All of these data sources may be collected for a company using an outline that structures the aggregated data and provides pointers to a current source of data where the data might change (such as stock quotes or SEC filings). Thus an outline may provide a fixed, structured, and current view of the corporate entity where data from different sources changes with widely varying frequencies. Of course other content, such as message boards, discussion groups, and the like may be incorporated into the outline, along with relatively stable content such as a web site URL for the entity.

Syndication 414 may include any functions or services associated with a publish-subscribe environment and may be embodied, for example, in a client-side application, a remote application or service, an application layer of an enhanced syndication services protocol stack, as application services deployed, for example, in the services oriented architecture described below, or a combination of these. Syndication 412 may include syndication specific functions such as publication, subscription, aggregation, republication, and, more generally, management of syndication information (e.g., source, date, author, and the like). One commonly employed syndication system is RSS, although it will be appreciated from the remaining disclosure that a wide array of enhanced syndication services may provided in cooperation with, or separate from, an RSS infrastructure.

Infrastructure 416 may include any low level functions associated with enhanced syndication services and may be embodied, for example, in a client-side application, a remote application or service, an application layer of an enhanced syndication services protocol stack, as application services deployed, for example, in the services oriented architecture described below, or a combination of these. Infrastructure 416 may support, for example, security, authentication, traffic management, logging, pinging, communications, reporting, time and date services, and the like.

In one embodiment, the infrastructure 416 may include a communications interface adapted for wireless delivery of RSS content. RSS content is typically developed for viewing by a conventional, full-sized computer screen; however, users increasingly view web content, including RSS feeds, using wireless devices, such as cellular phones, Personal Digital Assistants ("PDAs"), wireless electronic mail devices such as Blackberrys, and the like. In many cases content that is suitable for a normal computer screen is not appropriate for a small screen; for example, the amount of text that can be read on the screen is reduced. Accordingly, embodiments of the invention include formatting RSS feeds for wireless devices. In particular, embodiments of the invention include methods and systems for providing content to a user, including taking a feed of RSS content, determining a user interface format for a wireless device, and reformatting the RSS content for the user interface for the wireless device. In embodiments the content may be dynamically reformatted based on the type of wireless device.

In embodiments, tags from an RSS feed can be used to feed a template, such as an XML-enabled template, that further modifies the RSS feed based on the nature of a wireless device. For example, the abstract of an RSS feed can be delivered in a shortened format, such as identifying and delivering the first sentence of the abstract. An RSS feed can also be broken up into sub-segments, and a user can be provided with a link within the feed for requesting additional sub-segments, or additional portions of the feed, thus permitting a user to control content delivery where, for example, the user has a bandwidth-constrained or display-constrained device. In embodiments the link may be interactive and may be activated or manipulated by a user with a control such as a button, thumbpad, touchscreen, dial button, or stylus.

In embodiments an RSS feed may further comprise inserting a phone number into the feed, wherein interacting with the phone number on a cellular phone or other telecommunications-capable device initiates a telephone call. The telephone call could be to a content source, so as to allow a user to hear a voice rendition of the content of the RSS feed, to hear related content, such as programming related to the RSS feed, to initiate a transaction, such as related to the content of the RSS feed, to request a particular type of additional information, to allow the user to subscribe to the feed, or the like.

In embodiments the RSS feed may include a time-related component, such as a schedule for the delivery of additional content. In embodiments the time-related component may be fed to a calendar, task list, or related facility, thus setting an appointment related to the time-related component in a user's electronic calendar, such as on a handheld device or on a conventional personal computer or laptop computer.

In embodiments an RSS feed may be provided with a separate layer of security that is associated with a security facility of a wireless device. For example, an RSS feed may be encrypted so that it may only be read by a specific type of wireless device, a specific wireless device, or on a specific wireless device only after entry of a password that is issued to a known user of that wireless device. In embodiments security may be associated with a location facility of the wireless device (such as GPS, cellular triangulation, or the like), so as to allow a user to access an RSS feed only if the user is physically located in a particular place. For example, a user attending a live concert or other event might be permitted to view an RSS feed about the concert, but other users might be excluded from that content, creating a secure new media channel for event attendees.

In embodiments a user interface for a wireless or handheld device may be customized to include menus that specifically relate to RSS content. For example, an interface may be provided with a separate RSS menu icon, drop down selection, or the like for allowing a user to place such a device in an RSS mode. Within an RSS mode, initiated by an RSS menu option, a user may be provided with options to take actions related to RSS, such as subscribing to feeds, selecting feeds from a set of feeds, prioritizing feeds, selecting feeds as favorites, or the like. In embodiments, an RSS mode may include a menu item for each of (or a subset of) the components of the RSS schema. For example, a menu icon, drop down item, or the like may allow a user to select and view the title of an RSS feed, the abstract, text, the authors, or other content. In embodiments the user interface of a wireless or handheld device may have an RSS search icon, menu, or screen that returns RSS results in response to entry of a keyword. In embodiments results may be returned that include commercial and non-commercial result sets, which may be distinguished on the screen, such as by screen location, by an icon that identifies them as such, or by another indicator of the distinction, such as color, font, underlining, italics, boldface type, highlighting, or the like.

Thus, in embodiments an RSS-customized user interface for a wireless handheld device is provided.

In another aspect, the infrastructure 416 may include improved pinging systems. The only current form of network service in an RSS environment is a primitive system of "pings", such as those provided by weblogs.com, that permit users to track changes and updates to content. When a producer updates its RSS output file, a message is sent to a central file server. When consumers want to know if there are updated RSS outputs from particular sources they go to the central file and see if there is a recent message from the producer of choice, rather than retrieving the RSS source directly. When new content is available, the consumer may send an electronic request directly to the producer's output file and read the contents into the consumers local files, archive, or repository. The infrastructure 416 for an enhanced syndication system may provide improved pinging systems. For example, a central server may be secure. In such a system, each request for a ping may carry an encryption-based key for the requestor. Responses to that requestor, which may be verified, for example with reference to a trusted third party, or using some other technique, may be time bound with constraints on start times, stop times, frequency, quotas, or the like. In another embodiment, the requester may simply use a unique identification number. Pings may be subscription based, so that a for-fee pinger may be used more frequently than a free pinger. Thus there is disclosed herein a secure pinger for use in an RSS system. Also disclosed herein is a managed pinger, which may limit ping responses according to subscription levels, frequency, or any other suitable criteria.

The infrastructure 416 may more generally provide traffic management services including but not limited to real time monitoring of message latency, traffic and congestion, and packet quality across a network of end-to-end RSS exchanges and relationships. This may include real time monitoring of special traffic problems such as denial of service attacks or overload of network capabilities. Another service may be Quality-of-Service management that provides a publisher with the ability to manage time of sending of signaling messages for pingers, time of availability of the signaled-about messages, and unique identifiers which apply to the signaling message and the signaled-about message or messages. This may also include quality of service attributes for the signaled-about message or messages and criteria for selecting end user computers that are to be treated to particular levels of end-to-end quality of service. This may be, for example, a commercial service in which users pay for higher levels of QoS.

It will be generally appreciated that the arrangement of layers and interfaces may vary; however, in one embodiment syndication 414 may communicate directly with sources 402 while the applications 406 may communicate directly with users 404. Thus, in one aspect, the systems described herein enable enhanced syndication systems by providing a consistent framework for consumption and republication of content by users 404. In general, existing technologies such as RSS provide adequate syndication services, but additional elements of a syndication system 400, such as social networking and semantic content management, have been provided only incrementally and only on an ad hoc basis from specific service providers. The functions and services described above may be realized through, for example, the services oriented architecture described below with reference to FIG. 5 and/or any of the markup languages described below with reference to FIG. 6.

In one example a model of an end-to-end content syndication system for, e.g., RSS, OPML, or other content, may include the following elements: convert, structure, store, spider, pool, search, filter, cluster, route, and run. Conversion may transform data (bi-directionally) between application-specific or database-specific formats and the syndication or outlining format. Structure may be derived from the content, such as a knowledge structure inherent in interrelated OPML outlines, or metadata contained in RSS tags. Storage may occur locally on a user device or at a remote repository. Spiders may be employed to search repositories and local data on user devices, to the extent that it is made publicly available or actively published. Pools of data may be formed at central repositories or archives. Searches may be conducted across one or more pools of data. Filters may be employed to select specific data feeds, items within a data feed, or elements of an OPML tree structure. Specific items or OPML tree branches may be clustered based upon explicit search criteria, inferences from metadata or content, or community rankings or commentary. Routing may permit combinations among content from various content sources using, e.g., web services or superservices. Such combinations may be run to generate corresponding displays of results. Other similar or different combinations of elements from the broad categories above may be devised according to various value chains or other conceptual models of syndication services.

More generally, well-defined interfaces between a collection of discrete modules for an established value chain may permit independent development, improvement, adaptation, and/or customization of modules by end users or commercial entities. This may include configurations of features within a module (which might be usefully shared with others, for example), as well as functional changes to underlying software.

For example, an author may wish to use any one or more of a number of environments to create content for syndication. By providing a module with a standardized interface to RSS posting, converters may be created for that module to convert between application formats and an RSS-ready format. This may free contributors to create content in any desired format and, with suitable converters, readily transform the content into RSS-ready material. Thus disparate applications such as Microsoft Word, Excel, and Outlook may be used to generate content, with the author leveraging off features of those applications (such as spell checking, grammar checking, calculation capabilities, scheduling capabilities, and so on). The content may then be converted into RSS material and published to an RSS feed. As a significant advantage, users may work in an environment in which they are comfortable and simply obtain needed converters to supply content to the RSS network. As a result, contributors may be able to more efficiently produce source material of higher quality. Tagging tools may also be incorporated into this module (or some author module) to provide any degree of automation and standardization desired by an author for categorization of content.

As another example, appropriate characterization of RSS material remains a constantly growing problem. However, if tagging occurs at a known and predictable point in the RSS chain, e.g., within a specific module, then any number of useful applications may be constructed within, or in communication with, that module to assist with tagging. For example, all untagged RSS posts may be extracted from feeds and pooled at a commonly accessible location where one or more people may resolve tagging issues. Or the module may automatically resolve tagging recommendations contributed by readers of the item. Different rules may be constructed for different streams of data, according to editorial demands or community preferences. In short, maintaining a separate tagging module, or fixing the tagging function at a particular module within the chain, permits a wide array of tagging functions which may be coordinated with other aspects of the RSS chain.

In another aspect, a well-defined organization of modules permits improved synchronization or coordination of different elements of the modules in the RSS chain. Thus for example centralized aggregators may be provided to improve usability or to improve the tagging of content with metadata, where a combination of lack of standards and constantly evolving topics has frustrated attempts to normalize tagging vocabulary. By explicitly separating tagging from content, visibility of tagging behavior may be improved and yield better tag selection by content authors. Similarly, search techniques (mapping and exploration) may be fully separated from indexing (pre-processing) to permit independent improvements in each.

A well-established "backplane" or other communications system for cooperating RSS modules (or other data feeds) may enable a number of business processes or enterprise applications, particularly if coupled with identity/security/role management, which may be incorporated into the backplane, or various modules connected thereto, to control access to data feeds.

For example, a document management system may be provided using an enhanced RSS system. Large companies, particularly document intensive companies such as professional services firms, including accounting firms, law firms, consulting firms, and financial services firms, employ sophisticated document management systems that provide unique identifiers and metadata for each new document created by employees. Each new document may also, for example, be added to an RSS feed. This may occur at any identifiable point during the document's life, such as when first stored, when mailed, when printed, or at any other time. By viewing the RSS feed with, for example, topical filters, an individual may filter the stream of new documents for items of interest. Thus, for example, a partner at a law firm may remain continuously updated on all external correspondence relating to SEC Regulation FD, compliance with Sarbanes Oxley, or any other matter of interest. Alternatively, a partner may wish to see all documents relating to a certain client. Similarly, a manager at a brokerage house may wish to monitor all trades of more than a certain number of shares for a certain stock. Or an accountant may wish to see all internal memoranda relating to revisions to depreciation allowances in the federal tax code. An enhanced RSS system may provide any number of different perspectives on newly created content within an organization.

Other enterprise-wide applications may be created. For example, a hospital may place all prescriptions written by physicians at the hospital into an RSS feed. This data may be viewed and analyzed to obtain a chronological view of treatment.

In one aspect, functions within the conceptual framework may include a group of atomic functions which may be accessed with a corresponding syntax. Arrangements of such calls into higher-level, more complex operations, may also be expressed in a file such as an OPML file, an XML file, or any other suitable grammar. Effectively, these groups of instructions may form programmatic expressions which may be stored for publication, re-use, and combination with other programmatic expressions. Data for these programmatic expressions may be separately stored in another physical location, in a separate partition at a location of the instructions, or together with the instructions. In one aspect, OPML may provide a grammar for expression of functional relationships, and RSS may provide a grammar for data. Thus the same complex operation may be re-executed against different data sets or against data in a syndicated feed that periodically updates. Thus, in one aspect, an architecture is provided for microprocessor-styled programming across distributed data and instructions.

Figure 5:
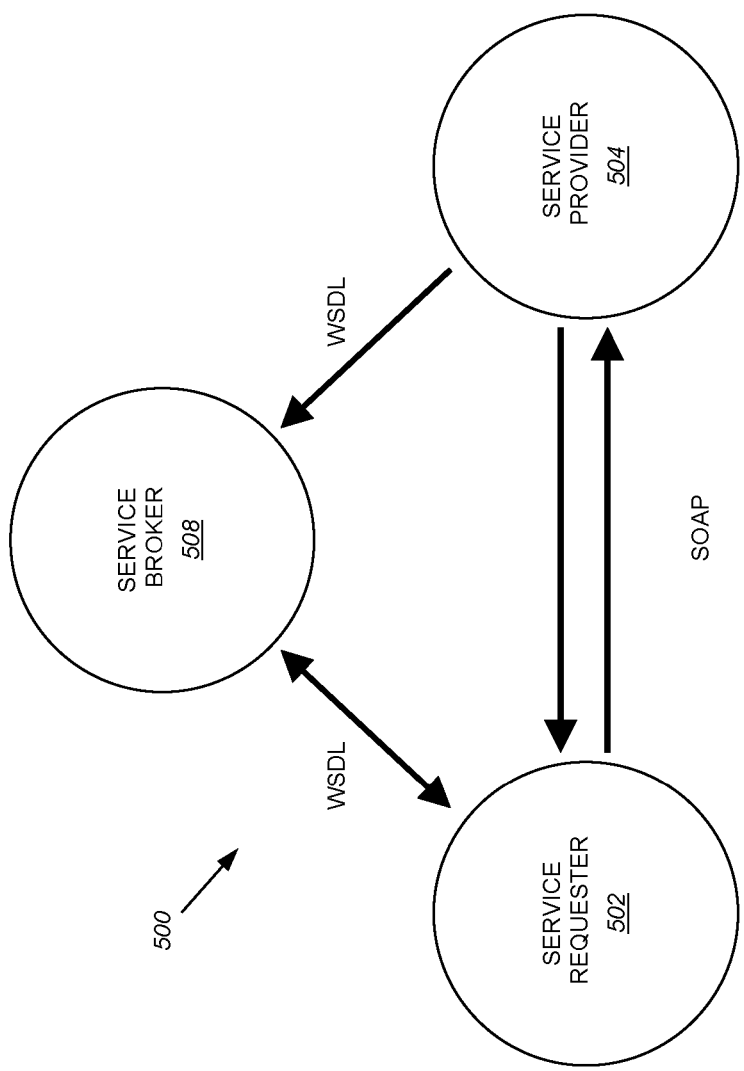
FIG. 5 depicts a system for delivering services in a syndication system.

FIG. 5 depicts a system for delivering services in a syndication system. As depicted, one technology for delivering services within the conceptual framework above is a service-oriented architecture. A service-oriented architecture ("SOA") 500 may include a service requester 502, a service provider 504, and a service broker 508.

In general, the service requester 502, which may be any of the clients 102 described above, discovers services and receives service descriptions through an exchange with the service broker 508 using a suitable syntax such as the Web Services Description Language ("WSDL"). The service provider 504 publishes service descriptions to the service broker 508, also using a syntax such as WSDL. The service requester 502 uses a service through communications with the service provider 504, using a transport protocol such as Simple Object Access Protocol ("SOAP"). An SOA 500 may include any number of requesters 502, brokers 508, and providers 504. Additionally, a number of protocols and standards may be employed to orchestrate the deployment of services in an SOA 500. In a web services embodiment, the Web service protocol stack is employed to define, locate, implement, and interact with Web services. In general, this includes four main areas: service transport, XML messaging, service description, and service discovery. Service transport transports messages among network applications using protocols such as HyperText Transport Protocol ("HTTP"), File Transfer Protocol ("FTP"), Simple Mail Transfer Protocol ("SMTP"), and more recently the Blocks Extensible Exchange Protocol ("BEEP"). XML messaging encodes messages in a common XML format using, for example, XML-RPC, SOAP, and REST. The service description is used to describe the public interface for services, typically using WSDL as noted above. Service discovery may use WSDL, along with Universal Description, Discovery, and Integration ("UDDI"), which provides a platform independent, XML-based registry for public Internet listings.

An SOA 500 architecture may be used, for example, in an enhanced syndication system to relate metadata in an item of content to services that are available from the registry. Thus, for example, a publicly available registry may provide, among other things, a number of viewers for graphical images. An RSS item may refer to an image source, such as an MRI image in a medical record from a hospital, and may specify a viewer for the source image that is available through the registry. In operation, a client with appropriate permission to view the image (also as managed, e.g., through the metadata for the enhanced syndication system), may retrieve the appropriate viewer service from the registry and apply the viewer to view the source image. In this example, viewers may be freely provided or may be licensed and made available through the registry on a fee per use basis or some other licensing terms. Similarly, the image source may be made available in various resolutions, each available under a different fee structure. In other embodiments, textual sources may be available in various forms ranging from a title and biographical data to an abstract to the full text of the source. Thus the SOA platform may be used to resell content from an RSS archive, using viewer or access privilege services made available through the registry. Other aspects such as identity and affiliation, as well as verification of these, may be made available as services in the SOA 500.

Figure 6:
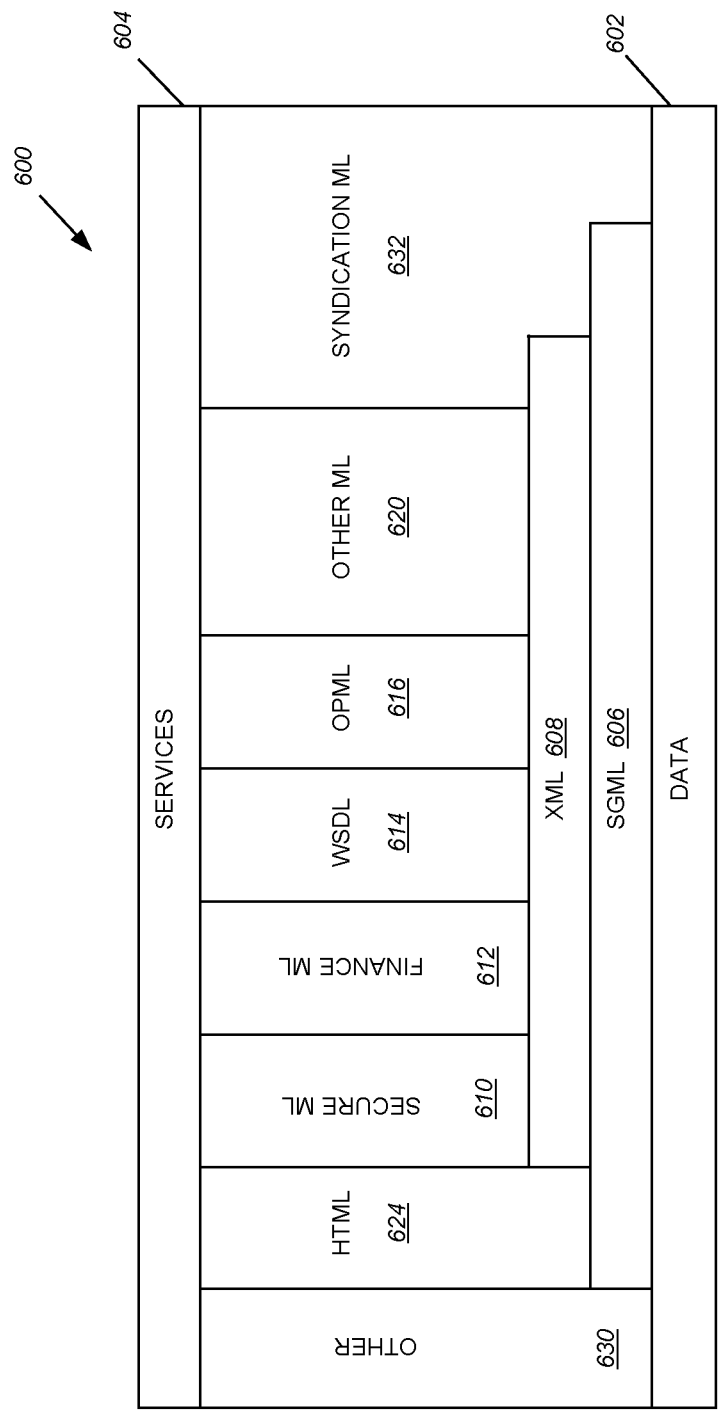
FIG. 6 shows an XML environment for syndication systems.

FIG. 6 shows an XML environment for syndication systems. As represented in FIG. 6, an XML environment 600 includes data 602, which may be any of the content sources or other data sources described above that interacts with services 604, which may execute on a client 102, a server 104, or any other entity within a network.

Services 604, which may be, for example, any of the services described above with reference to FIG. 4, may employ a variety of standards, protocols, and programming languages to interact meaningfully with the data 602. This includes, for example, the use of programming tools that permit program logic to be deployed in, e.g., Java, Windows, Perl, PHP, C/C++, and so on. This also includes parsing, processing, and database access using, e.g., data binding (mapping XML components into native formats of various programming languages), Document Object Model ("DOM", a programming interface for manipulation of XML/HTML as program objects), Simple API for XML ("SAX", another API for XML documents), XSL (a stylesheet expression language), XSL Transformations ("XSLT", a language for transforming XML documents into other XML documents), XML Path Language ("XPATH", a language for referring to parts of XML documents), XSL Formatting Objects ("XSL-FO", an XML vocabulary for formatting semantics), and a variety of tools for queries and other access to commercial databases. Further, presentation may be provided using, e.g., XHTML, CSS/XSL-FO, SMIL, WSUI, and a host of other presentation tools. Services 604 may also employ various other XML-oriented tools for messaging, metadata, and web services, including SOAP, XML-RPC, RDF, UDDI, WSDL, and the like. Other specifications, such as the Voice eXtensible Markup Language (VoiceXML), Security Services Markup Language (S2ML), and OASIS Security Assertion Markup Language (SAML), provide special purpose grammars for specific functions. In general, these tools in various combinations permit a relatively arbitrary deployment of functions as services on top of content, structured using XML grammars.

The services 604 may interact with data 602 through one or more established grammars, such as a secure markup language 610, a finance markup language 612, WSDL 614, the Outline Programming Markup Language ("OPML") 616, or other markup languages 620 based upon XML 608, which is a species of the Standard Generalized Markup Language ("SGML") 606. The interaction may be also, or instead, through non-XML grammars such as HTML 624 (which is a species of SGML) or other formats 630. More generally, a wide array of XML schemas has been devised for industry-specific and application-specific environments. For example, XML.org lists the following vertical industries with registered XML schemas, including the number of registered schemas in parentheses, all of which may be usefully combined with the systems described herein, and are hereby incorporated by reference in their entirety: Accounting (14), Advertising (6), Aerospace (20), Agriculture (3), Arts/Entertainment (24), Astronomy (14), Automotive (14), Banking (10), Biology (9), Business Reporting (2), Business Services (3), Catalogs (9), Chemistry (4), Computer (9), Construction (8), Consulting (20), Customer Relation (8), Customs (2), Databases (11), E-Commerce (60), EDI (18), ERP (4), Economics (2), Education (51), Energy/Utilities (35), Environmental (1), Financial Service (53), Food Services (3), Geography (5), Healthcare (25), Human Resources (23), Industrial Control (5), Insurance (6), Internet/Web (35), Legal (10), Literature (14), Manufacturing (8), Marketing/PR (1), Math/Data, Mining (10), Multimedia (26), News (12), Other Industry (12), Professional Service (6), Public Service (5), Publishing/Print (28), Real Estate (16), Religion, Retail (6), Robotics/AI (5), Science (64), Security (4), Social Sciences (4), Software (129), Supply Chain (23), Telecommunications (26), Translation (7), Transportation (10), Travel (4), Waste Management, Weather (6), Wholesale, and XML Technologies (238).

Syndication services, described in more detail below, may operate in an XML environment through a syndication markup language 632, which may support syndication-specific functions through a corresponding data structure. One example of a currently used syndication markup language 632 is RSS. However, it will be appreciated that a syndication markup language ("SML") as described herein may include any structure suitable for syndication, including RSS, RSS with extensions (RSS+), RSS without certain elements (RSS−), RSS with variations to elements (RSS'), or various combinations of these (e.g., RSS'−, RSS'+). Furthermore, an SML 632 may incorporate features from other markup languages, such as a financial markup language 612 and/or a secure markup language 610, or may be used in cooperation with these other markup languages 620. More generally, various combinations of XML schemas may be employed to provide syndication with enhanced services as described herein in an XML environment. It will be noted from the position of SML 632 in the XML environment that SML 632 may be XML-based, SGML-based, or employ some other grammar for services 604 related to syndication. All such variations to the syndication markup language 632 as may be usefully employed with the systems described herein are intended to fall within the scope of this disclosure and may be used in a syndication system as that term is used herein.

According to the foregoing, there is disclosed herein an enhanced syndication system. In one aspect, the enhanced syndication system permits semantic manipulation of syndicated content. In another aspect, the enhanced syndication system offers a social networking interface which permits various user interactions without a need to directly access underlying syndication technologies and the details thereof. In another aspect, a wide variety of additional services may be deployed in combination with syndicated content to enable new uses of syndicated content. In another aspect, persistence may be provided to transient syndicated content by the provision of a database or archive of data feeds, and particularly the content of data feeds, which may be searched, filtered, or otherwise investigated and manipulated in a syndication network. Such a use of a syndication system with a persistent archive of data feeds and items therein is now described in greater detail.

The syndication markup language 632, or the syndication markup language 632 in combination with other supporting markup languages and other grammars including but not limited to RSS, OPML, XML and/or any other definition, grammar, syntax, or format, either fixed or extensible, all as described in more detail below, may support syndication-related communications and functions. Syndication communications may generally occur through an internetwork between a subscriber and a publisher, with various searching, filtering, sorting, archiving, modifying, and/or outlining of information as described herein.

Two widely known message definitions for syndicated communications are RSS 2.0 (RSS) and the Atom Syndication Format Draft Version 9 (Atom, as submitted to the IETF on Jun. 7, 2005 in the form of an Internet-Draft). A syndication message definition, as used herein, will be understood to include these definitions as well as variations, modifications, extensions, simplifications, and the like as described generally herein. Thus, a syndication message definition will be understood to include the various XML specifications and other grammars described herein and may support corresponding functions and capabilities that may or may not include the conventional publish-subscribe operations of syndication. A syndication definition may be described in terms of XML or any other suitable standardized or proprietary format. XML, for example, is a widely accepted standard of the Internet community that may conveniently offer a human-readable and machine-readable format. Alternatively, the syndication definition may be described according to another syntax and/or formal grammar.

For purposes of establishing a general vocabulary, and not by way of limitation, components of syndicated communications are now described in greater detail.

A message instance, or message, may conform to a message definition, which may be an abstract, typed definition. The abstract, typed definition may be expressed, for example, in terms of an XML schema, which may without limitation comprise XML's built-in Document Type Definition (DTD), XML Schema, RELAX NG, and so forth. In some cases, information may lend itself to representation as a set of message instances, which may be atomic, and may be ordered and/or may naturally occur as a series. It should be appreciated that the information may change over time and that any change in the information may naturally be associated with a change in a particular message instance and/or a change in the set of message instances. A data feed or data stream may include a set of messages. In an RSS environment, a message instance may be referred to as an entry. In an OPML environment, the message instance may be referred to as a list. More generally, a message may include any elements of the syndication message definition noted above. Thus, it will be appreciated that the terms "list," "outline," "message," "item," and the like may be used interchangeably in the description of enhanced syndication systems herein. All such meanings are intended to fall within the scope of this disclosure unless a more specific meaning is expressly indicated or clear from the context. A channel definition may provide metadata associated with a data feed, and a subscription request may include a URI or other metadata identifying a data feed and/or data feed location. The location may without limitation comprise a network address, indication of a network protocol, path, virtual path, filename, and any other suitable identifying information.

A syndication message definition may include any or all of the elements of the following standards and drafts, all of which are hereby incorporated in their entirety by reference: RSS 2.0; Atom Syndication Format as presented in the IETF Internet-Draft Version 9 of the Atom Syndication Format; OPML 1.0; XML Signature Syntax (as published in the W3C Recommendation of 12 Feb. 2002); the XML Encryption Syntax (as published in the W3C Recommendation of 10 Dec. 2002); and the Common Markup for Micropayment per-fee-links (as published in the W3C Working Draft of 25 Aug. 1999). In summary, these elements, which are described in detail in the above documents, may include the following: channel, title, link, description, language, copyright, managing editor (managingEditor), Web master (webmaster), publication date (pubDate), last build date (lastBuildDate), category, generator, documentation URL (docs), cloud, time to live (ttl), image, rating, text input (textInput), skip hours (skipHours), skip days (skipDays), item, author, comments, enclosure, globally unique identifier (guid), source, name, URI, email, feed, entry, content, contributor, generator, icon, id, logo, published, rights, source, subtitle, updated, opml, head, date created (dateCreated), date modified (dateModified), owner name (ownerName), owner e-mail (ownerEmail), expansion state (expansionState), vertical scroll state (vertScrollState), window top (windowTop), window left (windowLeft), window bottom (windowBottom), window right (windowRight), head, body, outline, signature (Signature), signature value (SignatureValue), signed information (SignedInfo), canonicalization method (CanonicalizationMethod), signature method (SignatureMethod), reference (Reference), transforms (Transforms), digest method (DigestMethod), digest value (DigestValue), key information (KeyInfo), key value (KeyValue), DSA key value (DSAKeyvalue), RSA key value (RSAKeyValue), retrieval method (RetrievalMethod), X509 data (X509Data), PGP Data (PGPData), SPKI Data (SPKIData), management data (MgmtData), object (Object), manifest (Manifest), signature properties (SignatureProperties), encrypted type (EncryptedType), encryption method (EncryptionMethod), cipher data (CipherData), cipher reference (CipherReference), encrypted data (EncryptedData), encrypted key (EncryptedKey), reference list (ReferenceList), encryption properties (EncryptionProperties), price, text link (textlink), image link (imagelink), request URL (request URL), payment system (paymentsystem), buyer identification (buyerid), base URL (baseurl), long description (longdesc), merchant name (merchantname), duration, expiration, target, base language (hreflang), type, access key (accesskey), character set (charset), external metadata (ExtData), and external data parameter (ExtDataParm).

A syndication definition may also include elements pertaining to medical devices, crawlers, digital rights management, change logs, route traces, permanent links (also known as permalinks), time, video, devices, social networking, vertical markets, downstream processing, and other operations associated with Internet-based syndication. The additional elements may, without limitation, comprise the following: clinical note (ClinicalNote), biochemistry result (BiochemistryResult), DICOM compliant MRI image (DCMRI), keywords (Keywords), license (License), change log (ChangeLog), route trace (RouteTrace), permalink (Permalink), time (Time), shopping cart (ShoppingCart), video (Video), device (Device), friend (Friend), market (Market), downstream processing directive (DPDirective), set of associated files (FileSet), revision history (RevisionHistory), revision (Revision), branch (Branch), merge (Merge), trunk (Trunk), and symbolic revision (SymbolicRevision). Generally, in embodiments, the names of the elements may be case insensitive.

For example, the contents of the clinical note element may without limitation comprise a note written by a clinician, such as a referral letter from a primary care physician to a specialist. The contents of the biochemistry result element may without limitation comprise indicia of total cholesterol, LDL cholesterol, HDL cholesterol, and/or triglycerides. The contents of the DICOM compliant MRI image element may without limitation comprise an image file in the DICOM format. The content of the keyword element may without limitation comprise a word and/or phrase associated with the content contained in the message, wherein the word and/or phrase may be processed by a Web crawler. The content of the license element may without limitation comprise a URL that may refer to a Web page containing a description of a license under which the message is available. The content of the change log element may without limitation comprise a change log. The content of the route trace element may without limitation comprise a list of the computers through which the message has passed, such as a list of "received:" headers analogous to those commonly appended to an e-mail message as it travels from sender to receiver through one or more SMTP servers. The content of the permalink element may without limitation comprise a permalink, such as an unchanging URL. The content of the time element may without limitation comprise a time, which may be represented according to RFC 868. The content of the shopping cart element may without limitation comprise a representation of a shopping cart, such as XML data that may comprise elements representative of quantity, item, item description, weight, and unit price. The content of the video element may without limitation comprise a MPEG-4 encoded video file. The content of the device element may without limitation comprise a name of a computing facility. The content of the friend element may without limitation comprise a name of a friend associated with an author of an entry. The content of the market element may without limitation comprise a name of a market. The content of the downstream processing directive element may without limitation comprise a textual string representative of a processing step, such as and without limitation "Archive This," that ought to be carried out by a recipient of a message.

Thus, in general a syndication definition as that term is used herein describes a message format that enables Internet-syndication operations, as well as other complementary or separate operations. A message, as that term is used herein, may be associated with a feature of RSS, may be associated with a feature of Atom, may be associated with a feature of OPML, may be associated with a micropayment, may be associated with electronic commerce, may be associated with a representation of medical information, may be associated with the representation of public information, may be associated with the representation of private information, may be associated with the representation of protected information, may be associated with a tag for a crawler, may be associated with versioning and/or a change log, may be associated with a digital signature, may be associated with basic authentication, may be associated with digest authentication, may associated with encryption, may be associated with a license term, may be associated with a route trace, may be associated with a permalink, may be associated with an enclosure or file attachment, may be associated with an indication of time or a timestamp, may be associated with e-commerce, may be associated with searching, may be associated with filtering, may be associated with clustering, may be associated with a database, may be associated with security, may be associated with video, may be associated with a device, may be associated with a user interface, may be associated with a rule, may be associated with non-syndication technologies, may be associated with social networking, may be associated with a vertical market, may be associated with downstream processing, may be associated with semantic processing, and/or may be associated with a source.

A message as described herein may include, consist of, or be evaluated by one or more rules or expressions (referred to collectively in the following discussion as expressions) that provide descriptions of how a message should be processed. In this context, the message may contain data in addition to expressions or may refer to an external source for data. The expression may be asserted in a variety of syntaxes and may be executable and/or interpretable by a machine. For example, an expression may have a form such as that associated with the Lisp programming language. Although an expression may commonly be represented as what may be understood as a "Lisp-like expression" or "Lisp list"—for example, (a (b c))—this particular representation is not necessary. An expression may defined recursively and may include flow control, branching, conditional statements, loops, and any other aspects of structured, object oriented, aspect oriented, or other programming languages. For example and without limitation, it should be appreciated that information encoded as SGML or any species thereof (such as and without limitation, XML, HTML, OPML, RSS, and so forth) may easily be represented as a Lisp-like expression and vice versa. Likewise, data atoms, such as and without limitation a text string, a URL, a URI, a filename, and/or a pathname may naturally be represented as a Lisp-like expression and vice versa. Again, by way of illustration and not limitation, any representation of encoded information that can be reduced to a Lisp-like expression may be an expression as that term is used herein.

An expression may, without limitation, express the following: a data atom, a data structure, an algorithm, a style sheet, a specification, an entry, a list, an outline, a channel definition, a channel, an Internet feed, a message, metadata, a URI, a URL, a subscription, a subscription request, a network address, an indication of a network protocol, a path, a virtual path, a filename, a syntax, a syntax defining an S-expression, a set, a relation, a function, a graph, a tree, a counting algorithm, a probabilistic algorithm, a randomized algorithm, a geometric distribution, a binomial distribution, a heap, a heapsort algorithm, a priority queue, a quicksort algorithm, a counting sort algorithm, a radix sort algorithm, a bucket sort algorithm, a median, an order statistic, a selection algorithm, a stack, a queue, a linked list, a pointer, an object, a rooted tree, a hash table, a direct-address table, a hash function, an open addressing algorithm, a binary search tree, a binary search tree insertion algorithm, a binary search tree deletion algorithm, a randomly built binary search tree, a red-black tree, a red-black tree rotation algorithm, a red-black tree insertion algorithm, a red-black tree deletion algorithm, a dynamic order statistic, an interval tree, a dynamic programming algorithm, a matrix, a matrix-chain multiplication algorithm, a longest common subsequence, a polygon, a polygon triangulation, an optimal polygon triangulation, an optional polygon triangulation algorithm, a greedy algorithm, a Huffman code, a Huffman coding algorithm, an amortized analysis algorithm, an aggregate method algorithm, an accounting method algorithm, a potential method algorithm, a dynamic table, a b-tree, a b-tree algorithm (such as and without limitation search, create, split, insert, nonfull, delete), a binomial heap, a binomial tree, a binomial heap algorithm (such as and without limitation create, minimum, link, union, insert, extract minimum, decrease key, delete), a Fibonacci heap, a mergeable heap, a mergeable heap algorithm (such as and without limitation make heap, insert, minimum, extract minimum, and union), a disjoint set, a disjoint set algorithm, a cyclic graph, an acyclic graph, a directed graph, an undirected graph, a sparse graph, a breadth-first search algorithm, a depth-first search algorithm, a topological sort algorithm, a minimum spanning tree, a Kruskal algorithm, a Prim algorithm, a single-source shortest path, Dijkstra's algorithm, a Bellman-Ford algorithm, an all-pairs shortest path, a matrix, a matrix multiplication algorithm, the Floyd-Warshall algorithm, Johnson's algorithm, a flow network, the Ford-Fulkerson method, a maximum bipartite matching algorithm, a preflow-push algorithm, a lift-to-front algorithm, a sorting network, an arithmetic circuit, an algorithm for a parallel computer, a matrix operation, a polynomial, a fast Fourier transform, a number-theoretic algorithm, a string matching algorithm, a computational geometry algorithm, an algorithm in complexity class P, an algorithm in complexity class NP, and/or an approximation algorithm.

In one aspect, a message processor as described herein may include a hardware and/or software platform for evaluating messages according to any of the expressions described above. The message processor may reside, for example, on the server computer or client computer as described above. The processing may without limitation include the steps of read, evaluate, execute, interpret, apply, store, and/or print. The machine for processing an expression may comprise software and/or hardware. The machine may be designed to process a particular representation of an expression, such as and without limitation SGML or any species thereof. Alternatively, the machine may be a metacircular evaluator capable of processing any arbitrary representation of an S-expression as specified in a representation of an expression.

Generally, a message may include or be an expression. In other embodiments, the expression evaluation process may itself be syndicated. In such an embodiment, interpretations (i.e., evaluations) of a message may vary according to a particular evaluation expression, even where the underlying message remains constant, such as by filtering, concatenating, supplementing, sorting, or otherwise processing elements of the message or a plurality of messages. Different evaluation expressions may be made available as syndicated content using the syndication techniques described generally herein.

The message may specify presentation (e.g., display) parameters, or include expressions or other elements characterizing a conversion into one or more presentation formats.

In embodiments, the message may include an OPML file with an outline of content, such as and without limitation a table of contents; an index; a subject and associated talking points, wherein the talking points may or may not be bulleted; an image; a flowchart; a spreadsheet; a chart; a diagram; a figure; or any combination thereof. A conversion facility, which may include any of the clients or servers described above, may receive the message and convert it to a specified presentation format, which may include any proprietary or open format suitable for presentation. This may include without limitation a Microsoft PowerPoint file, a Microsoft Word file, a PDF file, an HTML file, a rich text file, or any other file comprising both a representation of content and a representation of a presentation of the content. The representation of content may comprise a sequence of text, an image, a movie clip, an audio clip, or any other embodiment of content. The representation of the presentation of the content may include characteristics such as a font, a font size, a style, an emphasis, a de-emphasis, a page-relative position, a screen-relative position, an abstract position, an orientation, a scale, a font color, a background color, a foreground color, an indication of opacity, a skin, a style, a look and feel, or any other embodiment of presentation, as well as combinations of any or all of the foregoing. In a corresponding method, a message may be received and processed, and a corresponding output file may be created, that represents a presentation format of the received message. In various aspects, the message may include an OPML file with references to external data. During processing, this data may be located and additionally processed as necessary or desired for incorporation into the output file.

In one embodiment, the system may include an OPML to PowerPoint converter that traverses one or more OPML outlines and converts the OPML outline into a Microsoft PowerPoint presentation having a structure representative of the structure embodied in the outline. This may include, for example, one or more introductory slides with title, author, creation date, and other information. This may also include one or more slides summarizing the contents of the entire PowerPoint document based upon the top level contents of the outline in the OPML document. Sub-categories may be similarly previewed in the PowerPoint document with slides that list all elements of an outline at one hierarchical level, followed by a number of slides addressing each element in greater detail. Additionally, items such as graphics, charts, tables, audio clips, word documents, and the like that are contained on leaf nodes of the OPML outline may be rendered within the PowerPoint slides to capture some or all of the multi-media content represented within the OPML outline. Similarly, the system may convert a PowerPoint presentation into an OPML outline and may either employ the explicitly outlined structure of the PowerPoint presentation or infer structure from the arrangement or titles of slides within the PowerPoint document.

Figure 7:
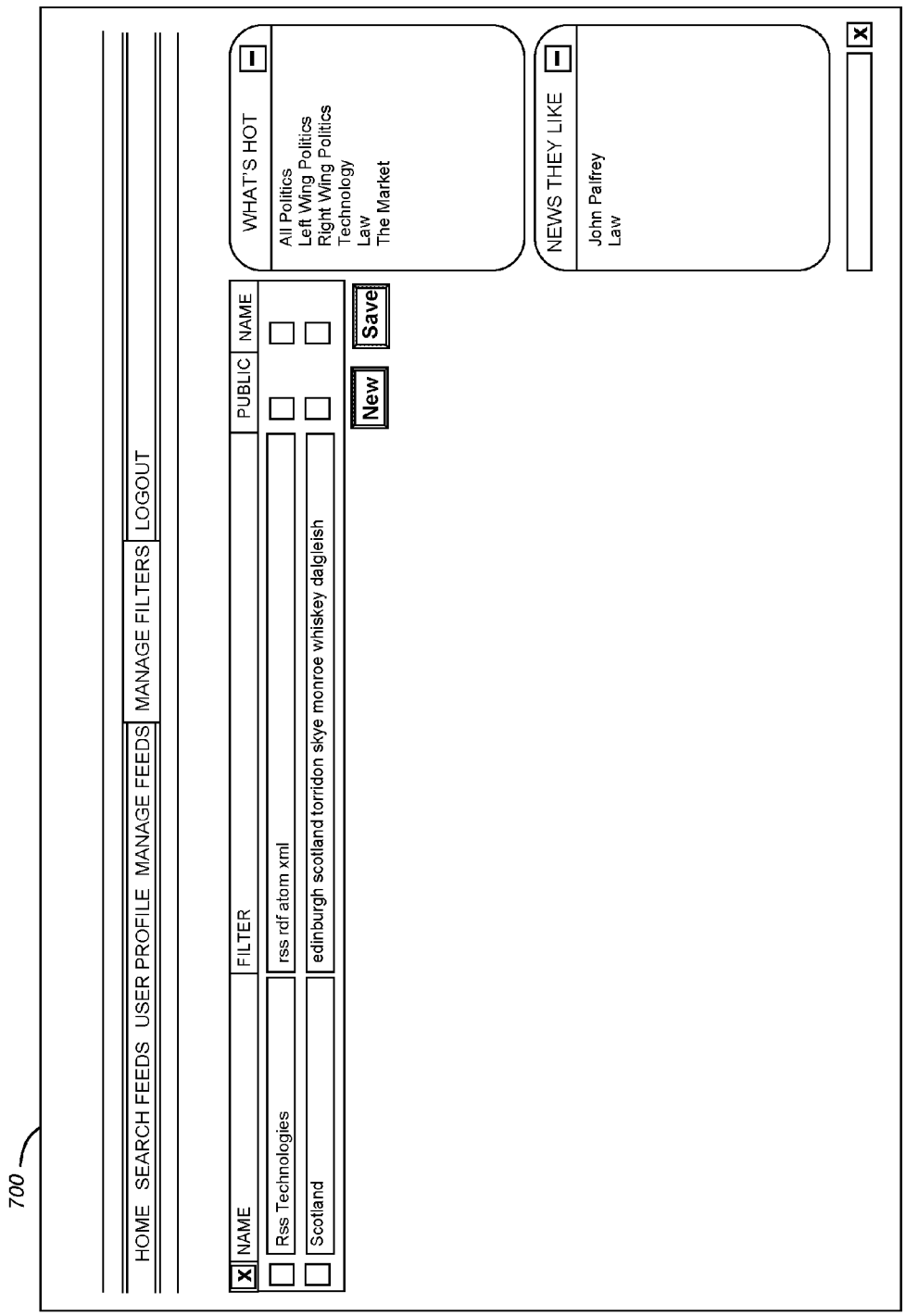
FIG. 7 shows a user interface for a syndication system.

FIG. 7 shows a user interface 700 for data feed management. More particularly, FIG. 7 depicts a manage filters page in which a user can create, edit, and share filters. The page may include navigation buttons and a "What's Hot" and a "News They Like" workspace. In addition, the page may provide a list of available filters. New filters may be created, and rules for each filter may be defined using, for example, Boolean or other operators on defined fields for data feeds or on full text of items within data fields. In order to promote community activity, each filter may be made public for others to use, and the rules and other structure of each filter may also be optionally shared for others to inspect. As a significant advantage over existing systems, these filters may be applied in real time to RSS data feeds or other data feeds to narrow the universe of items that is displayed to a user.

In one aspect, the systems described herein may be used to scan historical feed data and locate relevant data feeds. For example, filters may be applied to historical feed data to identify feeds of interest to a user. For example, by searching for words such as "optical" and "surgery" in a universe of medical feeds, a user may locate feeds relevant to optical laser surgery regardless of how those feeds are labeled or characterized by other users or content providers. In another complementary application, numerous filters may be tested against known relevant feeds, with a filter selected according to the results. This process may be iterative, where a user may design a filter, test it against relevant feeds, apply to other feeds to locate new relevant feeds, and repeat. Thus, while real-time or near real time filtering is one aspect of the systems described herein, the filtering technology may be used with historical data to improve the yield of relevant material for virtually any topic of interest.

Another advantage of filtering historical data is the ability to capture transient discussions and topics that are not currently of interest. Thus, a user interested in the 1996 U.S. Presidential campaign may find little relevant material on current data feeds but may find a high amount of relevant data in the time period immediately preceding the subsequent 2000 campaign. Similarly, an arbitrary topic such as Egyptian history may have been widely discussed at some time in the past, while receiving very little attention today. The application of filters to historical feeds may provide search functionality similar to structured searching of static Web content. Thus there is disclosed herein a time or chronology oriented search tool for searching the contents of one or more sequential data feeds.

In another aspect, the filters may be applied to a wide array of feeds, such as news sources, to build a real-time magazine dedicated to a particular topic. The results may be further parsed into categories by source. For example, for diabetes related filters, the results may be parsed into groups such as medical and research journals, patient commentaries, medical practitioner Weblogs, and so forth. The resulting aggregated data feed may also be combined with a readers' forum, editor's overview, highlights of current developments, and so forth, each of which may be an additional data feed for use, for example, in a Web-based, real-time, magazine or a new aggregated data feed.

In general, the filter may apply any known rules for discriminating text or other media to identified data feeds. For example, rules may be provided for determining the presence or absence of any word or groups of words. Wild card characters and word stems may also be used in filters. In addition, if-then rules or other logical collections of rules may be used. Proximity may be used in filters, where the number of words between two related words is factored into the filtering process. Weighting may be applied so that certain words, groups of words, or filter rules are applied with different weight toward the ultimate determination of whether to filter a particular item. External references from an item, e.g., links to other external content (either the existence of links, or the domain or other aspects thereof) may be used to filter incoming items of a data feed. External links to a data feed or data item may also be used, so as to determine relevance by looking at the number of users who have linked to an item. This process may be expanded to measure the relevance of each link by examining the number of additional links produced by the linking entity. In other words, if someone links to a reference and that user has no other links, this may be less relevant than someone who links to the reference and has one hundred other links. This type of linking analysis system is provided, for example, by Technorati.

Filters may apply semantic analysis to determine or approximate the tone, content, or other aspects of an item by analyzing words and word patterns therein. Filters may also examine the source of an item, such as whether it is from a .com top-level domain or an .edu top-level domain. The significance of a source designation as either increasing or decreasing the likelihood of passing through the filter may, of course, depend on the type of filter. Additionally, synonyms for search terms or criteria may be automatically generated and applied alongside user specified filter criteria.

Metadata may be used to measure relevance. Data feeds and data items may be tagged with either subject matter codes or descriptive words and phrases to indicate content. Tags may be provided by an external trusted authority, such as an editorial board, or provided by an author of each item or provider of each data feed. These and any other rules capable of expression through a user interface may be applied to items or posts in data feeds to locate content of interest to a particular user.

As noted above, a user may also share data feeds, aggregated data feeds, and/or filters with others. Thus, in general, there is provided herein a real-time data mining method for use with data feeds such as RSS feeds. Through the intelligent filtering enabled by this data feed management system, automatically updating information montages tailored to specific topics or users may be created that include any number of different perspectives from one to one hundred to one thousand or more. These real-time montages may be adapted to any number of distinct customer segments of any size, as well as to business vertical market applications.

In another aspect, filters may provide a gating technology for subsequent action. For example, when a number of items are identified meeting a particular filter criterion, specific, automated actions may be taken in response. For example, filter results, or some predetermined number of filter results, may trigger a responsive action such as displaying an alert on a user's monitor, posting the results on a Weblog, e-mailing the results to others, tagging the results with certain metadata, or signaling for user intervention to review the results and status. Thus, for example, when a filter produces four results, an e-mail containing the results may be transmitted to a user with embedded links to the source material.

Figure 8:
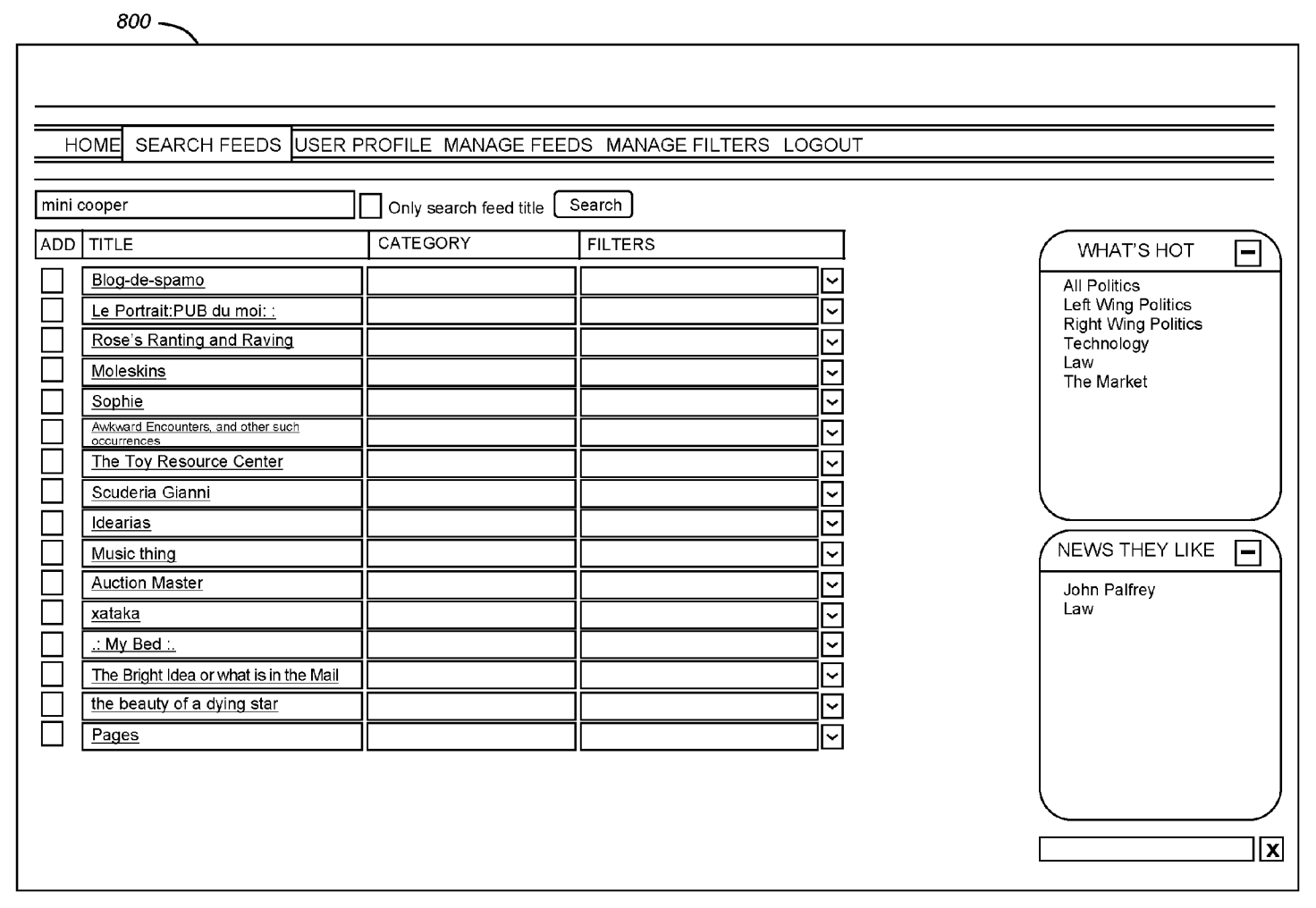

FIG. 8 shows a user interface 800 for data feed management. More particularly, FIG. 8 depicts a search feeds page in which a user can search for additional data feeds to monitor. The page may include navigation buttons and a "What's Hot" and a "News They Like" workspace. In addition, the page may include a text input field for user input of one or more search terms. There may also be one or more checkboxes or other controls for additional search parameters. For example, a user may select whether to search titles only, other information in the description of the feed, or individual items or postings in the feed. The search itself may also be stored, so that new searches for the same subject matter optionally will not include feeds that a user has already reviewed and rejected. Alternatively, the search may be persistent, so that the request search continues to execute against a database of feeds and posts as new feeds and new posts are added. Thus a user may leave the search and return to the search at a later time to review changes in results. The results for a search may be presented in the user interface along with a number of user controls for appropriately placing the feed within the user's feed environment. For example, a user may provide a new, user-assigned category to a feed or select from one or more of the user's pre-existing categories. The user may also specify one or more filters, either pre-built or custom-built by the user, to apply to items in the data feed once it is added. After a feed has been added, the user may review items passing through the assigned filter, if any, in the home page discussed above.

It will be appreciated that search results will be improved by the availability of well organized databases. While a number of Weblogs provide local search functionality, and a number of aggregator services provide lists of available data feeds, there does not presently exist a consumer-level searchable database of feed contents, at least nothing equivalent to what Google or Altavista provide for the Web. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

One useful parameter that may be included for searching is age. That is, the age of a feed, the age of posts within a feed, and any other frequency data may be integrated into the database for use in structured user searches (and the filters discussed in reference to FIG. 7).

As a further advantage, data may be retrieved from other aggregators and data feeds on a well-defined schedule. In addition to providing a very current view of data streams, this approach prevents certain inconsistencies that occur with currently used aggregators. For example, even for aggregator sites that push notification of updates to subscribers, there may be inconsistencies between source data and data feed data if the source data is modified. While it is possible to renew notification when source material is updated, this is not universally implemented in aggregators or Weblog software commonly employed by end users. Thus an aggregator may extract data from another aggregator that has not been updated. At the same time, an aggregator or data source may prevent repeated access from the same location (e.g., IP address). By accessing all of this data on a regular schedule (that is acceptable to the respective data sources and aggregators) and storing the results locally, the server described herein may maintain a current and accurate view of data feeds. Additionally, feeds may be automatically added by searching and monitoring in real time, in a manner analogous to Web bots used by search engines for static content.

In another aspect, a method of selling data feed services is disclosed herein. In this method, RSS data which is actually static content in files may be serialized for distribution according to some time base or time standard such as one item every sixty seconds or every five minutes. In addition, data may be filtered to select one item of highest priority at each transmission interval. In another configuration, one update of all items may be pushed to subscribers every hour or on some other schedule in an effective batch mode. Optionally, a protocol may be established between the server and clients that provides real time notification of new items. A revenue model may be constructed around the serialized data in which users pay increasing subscription rates for increasing timeliness, with premium subscribers receiving nearly instantaneous updates. Thus in one aspect, a data feed system is modified to provide time-based data feeds to end users. This may be particularly useful for time sensitive information such as sports scores or stock prices. In another embodiment, the end-user feed may adhere to an RSS or other data feed standard but nonetheless use a tightly controlled feed schedule that is known to both the source and recipient of the data to create a virtual time based data feed.

FIG. 9 shows a user interface 900 for data feed management. More particularly, FIG. 9 depicts a user profile page in which a user can search for additional data feeds to monitor. The page may include navigation buttons and a "What's Hot" and a "News They Like" workspaces. In addition, the page may include text entry boxes, check boxes, and other controls, along with a save button for saving profile data. Text entry items may include, for example, a first name, last name, e-mail address, password (and retype password), and a default maximum age of feeds (e.g., in hours) and a default minimum and/or maximum number of posts per feed for controlling a user display thereof, such as in the home page. Checkboxes may provide for selection of certain features. For example, a user may choose to have post descriptions displayed, a user may make his home page or features thereof public, a user may choose to use common categories provided by the system, and a user may choose among one or more pre-defined or user configured display modes for feeds.

Additional profile information, such as user interests, preferences, and biographical data may also be optionally provided. This data and other user profile data may be used to target advertising associated with data feed sites or content. Thus a data feed management system is described herein in which ads are delivered that are of value to customers. In addition to self-signaling through profile data, the system may apply customer-filtering, behavioral analysis, or any other analytic tools, as applied to the user's feed selection and displayed posts, to select appropriate advertisements for that user. The revenues from advertisements may be shared in a number of ways and may include shares of revenue to, for example, the operator of the data feed management system, an intermediary that places an ad that results in a sale, and/or individual or institutional content providers who contributed to the relevant data feed audience.

In another aspect of the systems described herein, feeds, posts, and/or filters may be clustered and shared in a number of ways as described above. Particular configurations may be branded and sold as a value-added service. Thus, for example, Warren Buffet's data feed selection and filtering may be of great interest to investors, bankers, and financiers. These selections may be sold to users who wish to see data feeds in the same manner as Warren Buffet. Similarly, someone may be interested in the writings and readings of Martha Stewart, Bill Clinton, Bill O'Reilly, Bill Gates, or Bill Belichick. Any of these individuals may brand and resell their selection of data feeds and design and use of filters. Similarly, commercial, political, or other institutional entities may present an official RSS feed identity. This may be provided for free for promotional purposes, such as promotion of a political party in a campaign or promotion of a seasonal sale event by a retailer. Similarly, topical selections may be promoted by trade groups or individuals. For example, a biotech or patent filter may be promoted by a patent law firm. In these applications, the service sold or promoted may include either the filters and selections themselves, which an end user may then modify or use as desired, or an aggregated feed of results from the filters and selections without identification of the underlying criteria. Access to such an aggregated feed may be controlled through password based protection to a resulting Weblog or using the identity-based RSS technology described above.

In one embodiment, a user may, either for a fee as described above, or for free, such as among a group of friends or interest-based community of bloggers, share not just search results but rules for finding those search results. In another application of this technology, a buddy list or other community may share aggregator configurations and other data. In another application of this, a recommendation engine may identify popular and successful search and filtering criteria that match a particular use profile.

In one aspect, there is described herein a systematic approach to managing data feeds in an integrated, and possibly Web-based, user interface. In a first step, the user may process feeds, including for example searching for, analyzing and selecting feeds. In a second step, a user may process posts within a feed, such as by filtering the posts as described above. In a third step, the aggregated and filtered results may be displayed to the user. This systematic approach also readily accommodates subsequent processing of the resulting items, such as by branding the technique for locating those items or by permitting sharing of the technique, both of which are described above. Additional processing steps may also include, for example, aggregating results into an aggregated feed or any of the other processing steps identified in the foregoing detailed description.

A number of enhanced syndication systems providing security are now described in greater detail. While a number of examples of RSS are provided as embodiments of a secure syndication system, it will be appreciated that RDF, Atom, or any other syndication language, or OPML or other structured grammar, including more generally the S-definition set out above, may be advantageously employed within a secure syndication framework as set forth herein.

Security may impact a number of features of a syndication system. For example, a data stream system may use identity assignment and/or encryption and/or identity authentication and/or decryption by public and private encryption keys for RSS items and similar structured data sets and data streams. The system may include notification of delivery as well as interpretation of delivery success, failure, notification of possible compromise of the end-to-end security system, non-repudiation, and so on. The identity assignment and encryption as well as the authentication and decryption as well as the notification and interpretation may occur at any or multiple points in the electronic communication process, some of which are illustrated and described below. A secure RSS system may be advantageously employed in a number of areas including, but not limited to, general business, health care, and financial services. Encryption may be employed in a number of ways within an RSS system, including encryption and/or authentication of the primary message, notification to a sender or third party of receipt of messages, interpretation of delivery method, and processing of an RSS item during delivery.

In item-level encryption of the primary message, an item from an RSS source or similar source may be assigned an identifier (which may be secure, such as a digital signature) and/or encrypted with a key (such as a private key in a Public Key Infrastructure (PKI)) and transmitted to a recipient, who may use a corresponding public key associated with a particular source to authenticate or decrypt the communication. A public key may be sent to the recipient simultaneously or in advance by a third party or collected by the recipient from a third-party source such as a public network location provided by the source or a trusted third party. In other embodiments, an intended recipient may provide a public key to a sender, so that the sender (which may be a content source, aggregator, or other RSS participant) may encrypt data in a manner that may only be decrypted by the intended recipient. In this type of exchange, the intended recipient's public key may similarly be published to a public web location, e-mailed directly from the recipient, or provided by a trusted third party.

In tag-level encryption of fields of data delimited within a message, similar encryption techniques may be employed. By using tag-level encryption, security may be controlled for specific elements of a message and may vary from field to field within a single message. Tag-level encryption may be usefully employed, for example, within a medical records context. In a medical environment (and in numerous other environments), it may be appropriate to treat different components of, e.g., a medical record, in different ways. Thus, while a medical record of an event may include information from numerous sources, it may be useful to compose the medical record from various atomic data types, each having unique security and other characteristics associated with its source. Thus, the medical record may include treatment objects, device objects, radiology objects, people objects, billing objects, insurance objects, diagnosis objects, and so forth. Each object may carry its own encryption keys and/or security features so that the entire medical record may be composed and distributed without regard to security for individual elements.

In a notification system, a secondary or meta return message may be triggered by receipt, authentication, and/or decryption of the primary message by a recipient and sent by the recipient to the message originator, or to a third party, to provide reliable notification of receipt.

In interpretation of delivery information, a sender or trusted intermediary may monitor the return message(s) and compare these with a list of expected return messages (based for example on the list of previously or recently sent messages). This comparison information may be interpreted to provide information as to whether a communication was successful and, in the case of communication to more than one recipient, to determine how many and what percentage of communications were successful. The receipt of return messages that do not match the list of expected messages may be used to determine that fraudulent messages are being sent to recipients, perhaps using a duplicate of an authentic private key, and that the security service may have been compromised.

In another aspect, a series of encryption keys may be used by the source and various aggregators or other intermediaries in order to track distribution of items through an RSS network. This tracking may either use notification and interpretation as described herein or may simply reside in the finally distributed item, which will require a specific order of keys to properly decrypt some or all of the item. If this system is being used primarily for tracking, rather than security, encryption and decryption information may be embedded directly into the RSS item, either in one of the current fields or in a new field for carrying distribution channel information (e.g., <DISTRIBUTION> . . . </DISTRIBUTION>.

In another aspect, the message may be processed at any point during distribution. For example, the communication process may include many stages of processing from the initial generation of a message through its ultimate receipt. Any two or more stages may be engaged in identity assignment and/or encryption as well as the authentication and/or decryption as well as notification and/or interpretation. These stages may include but are not limited to message generation software such as word-processors or blog software, message conversion software for producing an RSS version of a message and putting it into a file open to the Internet, relay by a messaging service such as one that might host message generation and RSS conversion software for many producers, relay by a proxy server or other caching server, relay by a notification server whose major function is notifying potential recipients to "pull" a message from a source, and services for message receiving and aggregating and filtering multiple messages, message display to recipients, and message forwarding to further recipients.

In another aspect, a message may include one or more digital signatures, which may be authenticated with reference to, for example, the message contents, or a hash or other digest thereof, in combination with a public key for the purported author. Conversely, a recipient of a digitally signed item may verify authenticity with reference to the message contents, or a hash or other digest version thereof, in combination with a private key of the recipient.

FIG. 11 shows a data pool environment. The environment 1000 may include a number of users 1002 in a user community 1004, a network 1006 such as the internetwork described above, a number of pools 1010 of data, and a pool management infrastructure 1012.

In general, the pools 1010 may be physically deployed on any data storage resource accessible through the network 1006. This may include, for example, a database, web server, FTP file, peer-to-peer file sharing resource, secure database, RSS channel, or any other technology platform and system(s) suitable for receiving, storing, and transmitting data. It will be understood that, in various embodiments, each pool may be a logically and/or physically separate storage location, permitting either distributed management of common data (e.g., for purposes of security, redundancy, or the like) or centralization of distributed data (e.g., for more efficient processing).

While a pool may be realized as, for example, a conventional RSS channel that receives and publishes items, other pools may collect and present data in more complex ways. For example, the pool management infrastructure 1012 may include a pool server or other system that either physically or logically sits between the user community 1004 and the pools 1010 and brokers interactions. The infrastructure 1012 may control access to the pools through a security system that includes, for example, any of the security features or systems described herein. In one embodiment, the infrastructure 1012 may include a firewall, router, switch, or similar device that physically resides between the pools 1010 and the user community 1004. The pools 1010 may also, or instead, be partially or completely encrypted. The infrastructure 1012 may also provide attention management by tracking user interactions with various pools and/or data within pools. In one aspect, the infrastructure 1012 may provide anonymity either to users 1002 accessing the pools 1010, or to the pools 1010 or sources of data therein. In another aspect, the infrastructure 1012 may provide formatting functions. As with anonymity, formatting may operate in either direction, i.e., by formatting user requests in a manner suitable for presentation to the pools (or that creates a logical appearance of pools to differently structured underlying data sources) or by formatting any responsive output from a pool. In one aspect, the infrastructure may provide a dynamic content system that provides different views of pools according to a user type, user identity, or the like. In another aspect, the infrastructure 1012 may provide search capabilities including structured searching and/or spidering for content within the pools 1010. It will be understood that, while depicted as a single, centralized server, the pool management infrastructure 1012 may include any number of servers and/or other network devices or systems that cooperate and/or operate autonomously to create a data pool environment for users 1002 in a community 1004.

The community 1004 may include any user or group of users 1002 that access data in pools 1012 either by providing data to the pools, extracting data from the pools, or both. This may include social groups, professional groups, commercial entities, and so forth.

Using a pool management infrastructure 1012, sources of data may be treated as populations and managed as an integrated but evolving ecology or topology, so that new forms of data can be added to the ecology continually, so that sets of data in particular forms can be added to and/or modified, and so that uses of data and combinations of data can be continually invented and implemented within the ecology without reworking the existing structure and applications.

In one example, the pool management infrastructure 1012 may enable secure management of a pool system and any associated data, data formats and pool enclosures. The infrastructure may, for example, provide an administrative dashboard that includes an administrative interface to a secure access control system, an administrative interface to a Common Vulnerabilities and Exposures system, and an administrative interface to the update notification, availability, and spider system (provided by vendor). The infrastructure 1012 may also, or instead, include an administrative interface for configuring the data converter and router systems to put data into pools, controls for a spider to control extraction, and search/filter/cluster and routing to pools and web services. It may also include interfaces for directing web services to take input directly from particular pools, to take input from the spider and other routing machines, and to output service results to particular pools and services in particular formats.

The pool data storage format may be XML, RSS, OPML, Atom, RDF or any other data format. Pool content may be managed using a file directory system maintained by an operating system such as Linux, Unix, and Microsoft Windows. Pool content, including enclosures to pool items, may be provided by a client-side central data store for XML, RSS, and related formats included in the Microsoft Vista operating system for personal computers.

Sources of data for pools may include any source(s) of digital data. For example, in a medical context, sources may include machines such as x-ray, MRE, PET, CT, and other medical imaging devices, as well as blood diagnostic, inventory management, ordering, scheduling, billing, human output-fed programs such as notes on medical record diagnostic forms, and/or process-fed outputs such as the result of a cross-functional medical second opinion process. In an enterprise, suitable sources may include document management systems, electronic mail systems, instant messaging systems, billing systems, accounting systems, human resources systems, computer/network traffic management systems, and so forth.

These sources may also or instead output data to the data pools in a common format such as XML, RSS, OPML, Atom, RDF, or any other common format. Data sources may also send their customary outputs through a format converter that outputs a common format and a data pool router that directs the output to an appropriate data pool or pools.

In one aspect, data pools may be viewed as folders open to inspection or, more formally, reading and writing by a spider or other search mechanism. A spider may, for example, use remote web service calls to poll each pool (or a pool interface provided by the pool management infrastructure) to determine if a given pool is accessible or if it has had any changes to its contents, and to read and write pool content. A spider may be deployed to monitor and manage a total topology of pools and any data contained therein.

Spiders may collect information from pools and enable the shared management of information across pools by allowing diverse information to be retrieved, assembled, and analyzed in order to, for example, create a virtual medical record by combining data elements that are held in different pools of diagnostic test results, physician notes, and the results of processes. Pools also may be accessed for quality control, for example to review x-ray's and diagnostic findings for a random sample of patients, in order to ascertain the quality of diagnosis.

Pools may employ a variety of security measures to achieve conditional access, privacy, security, and the like. Access to pools can be controlled for individuals (e.g., according to identity or role), spiders, web services, and so forth. Access control may be implemented, for example, using third party products such as Cisco Secure Access Server or Microsoft Products such as Windows Active Directory or the Windows Server Network Access Protection (NAP) policy enforcement platform built into the Microsoft Windows Vista and Windows Server operating systems.

CVE, or Common Vulnerabilities and Exposures, analysis and remediation is a process through which network assets are analyzed to determine vulnerability to hacking, data theft, unauthorized access and the like. The US government, in cooperation with The MITRE Corporation ("MITRE") and computer software and hardware vendors, monitors and inventories vulnerabilities and exposures. A number of companies provide software, hardware, and consulting services to identify and address these risks on a network such as an enterprise or corporate network. In an enterprise pool management system, CVE may be applied to data pools and any supporting infrastructure. Pools using conditional access and security systems such as those that assure compliance with HIPPA health data protection standards may be assessed using CVE techniques. In addition to identifying common vulnerabilities and threats, a security system may accommodate automated or semi-automated interventions to secure data pools and infrastructure. In one embodiment, CVE-enabled security for pools may be provided with suitable adaptations to commercially available products and services, such as the NetClarity Auditor Enterprise system.

In general syndicated data, outlined data, or, more generally, any structured or unstructured data may be stored in "pools", which provides a useful conceptual model for interaction with syndicated content and other data, as well as a specific term to refer to data sources and/or repositories that interact with the systems described herein. Aspects of the present invention relate to pooling syndicated information. Pools may contain information relating to information that was found in data streams. A pool may represent, for example, information from one or more data streams at particular times or from particular sources. For example, a financial market may produce a stream of data relating to trades made during a trading session, and a pool of data extracted from the stream may be created for subsequent use. As another example, medical information may be produced by a medical device, and the medical device information may be pushed into a data stream. The medical information from the data stream may be extracted from the stream and placed in a pool. As another example, all information related to a particular topic, person, entity, or the like may be acquired from a range of different data streams and placed into a corresponding pool.

Pools of data can be merged with other pools of data to form larger pools (e.g. to combine things of like file type, semantic meaning, subject matter, etc.). In embodiments, pools may be drained, and in doing so new data streams may be created. An example would be streaming a series of offers to sell goods (or services, securities, etc.) at a given price, out of a pool of such offers. In embodiments, the data stream may be buffered until relevant decision points are achieved.

In embodiments, a filter may be associated with a pool of data. A pool of data may be created from unfiltered data (e.g. an unfiltered data stream), and then over time the pool can be run through filters to produce a cleaner/more relevant pool of data. The filter could be a semantic filter, a collaborative filter, a logical filter, or a human filter (such as a community that validates the presence of content in the pool). E.g., a pool could contain "good movies" that are monitored by a community.

In embodiments, pools may be linked to other pools, so that one pool spills into the other (e.g., a pool of data that takes input from another pool upon occurrence of an event, such as availability of a resource for processing, for example, when a resource becomes available to process an incoming message requesting help from a software help desk and is handed into a pool of similar requests for handling by someone who is responsible for that type of request). Pools of data can evaporate (that is, data items can be made to expire from the pool), either based on age or based on the right conditions (e.g., if a price of a security drops low enough, then limit orders may be triggered; if time passes, an option can expire, etc.). Pools may be filled by different sources (a main source, as well as secondary sources or streams that augment the main source streams).

An aspect of the systems described herein relates to the filtering of contents such as syndicated feeds and the like. Syndication content filters may be used in connection with hardware, software, firmware, in a chip set or in another configuration. In embodiments, a user may publish or subscribe to a syndication feed on his desktop system or mobile communication facility (e.g. PDA, cellular phone and the like), and the syndication feed may be filtered through a syndication filter. In embodiments, the syndication filter is a mechanism adapted to define the syndication feed. For example, a device may be set to collect certain feeds through a hardware enabled syndication filter.

Figure 11A:
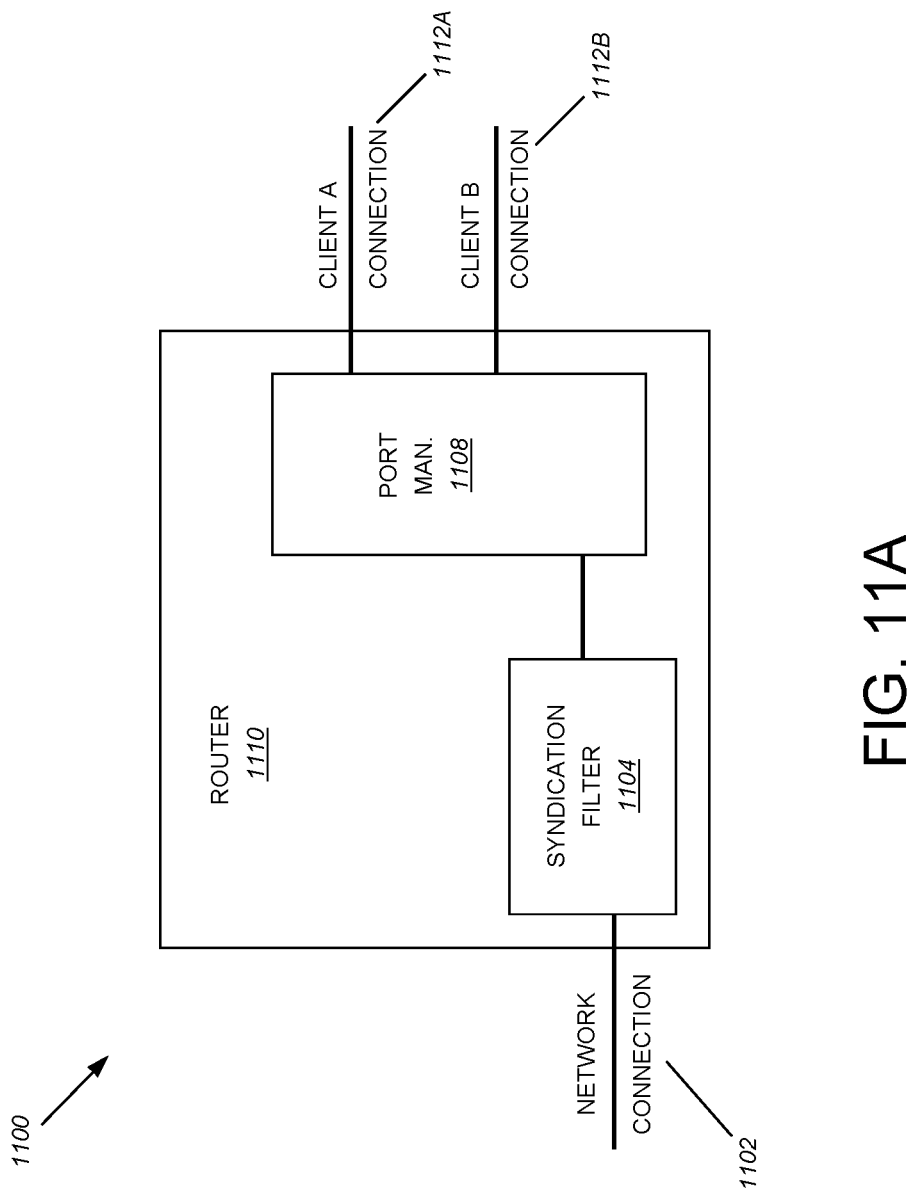
FIGS. 11A and 11B show embodiments of filters for syndicated content.

FIG. 11A illustrates a filter 1104 implemented in a hardware application 1100. The filter 1104 may be, for example, a syndication filter that operates on syndicated content such as data feeds. A router 1110 may be adapted to receive network information through a network connection 1102. The network connection 1102 may provide data received from a network, either directly or indirectly, to the filter 1104. The filter 1104 may be implemented through software, hardware, firmware, or other configurations, or some combination of these. The filter 1104 may be adapted to analyze network information received or transmitted through the network connection 1102 and perform filtering, direction, routing, or other manipulation of the data. For example, the syndication filter may analyze the data from the network connection and determine that certain data are related to a data feed that is not permitted (e.g. it may be a feed known for containing a virus, spyware, malware, or other undesirable content), and the non-permitted data may be extracted, removed, deleted, erased, logged, directed to a file, or otherwise manipulated. Information that is received on the network connection 1102 that is not determined as data requiring filtering may be passed to a port management facility 1108 in the router 1110. The port management facility 1108 may pass information to client A 1112A or client B 1112B based on an IP address or any other source or destination address, or other information.

Figure 11B:
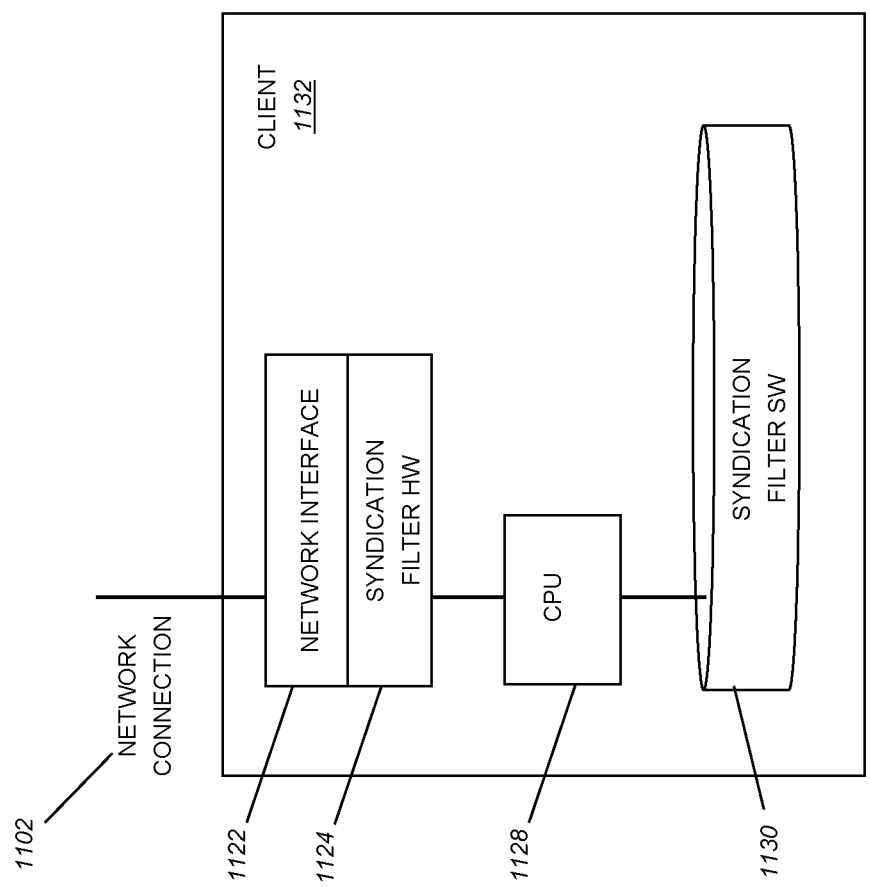

FIG. 11B illustrates a client facility 1132 with a hardware syndication filter 1124 and a software syndication filter 1130. The client facility 1132 may receive network information through a network connection 1102. The network information or data may be received by a network card 1122 (e.g. an Ethernet card, a Network Interface Card, or other communications interface) or the like. The network card 1122 may be associated with a syndication filter hardware facility 1124. The syndication hardware facility 1124 may perform functions similar to those described in connection with the filter 1104 of FIG. 11A, for example. The syndication filter hardware facility 1124 may perform filtering functions autonomously or in connection with another facility (e.g. software syndication filter facility 1130). The hardware syndication filter 1124 may operate in connection with dedicated hardware, software, and/or firmware. In embodiments, the hardware syndication filter 1124 is adapted to filter content in syndication feeds and the like. For example, the client device 1132 may be set to receive a syndication feed, and the feed may be received on the network connection 1102. The feed may include a virus, malware, spyware, or other undesired content, and the syndication filter hardware 1124 may strip or otherwise manipulate the undesired content from the syndication feed. The remaining portions of the syndication feed may be passed to other client hardware such as a central processing unit ("CPU") 1128. In embodiments, associated feed data such as enclosures, attachments, and the like may also be processed by the hardware syndication filter 1124.

The client 1132 may also or instead include a software based syndication filter 1130. The software syndication filter 1130 may execute as a background process associated with network traffic or be integrated into an operating system or an application executing on the CPU 1128, and it may run from volatile or non-volatile memory (not shown) associated with the client 1132. The software syndication filter 1130 may provide, for example, the functions of the hardware syndication filter 1124 or syndication filter 1104 described above. The CPU 1128 may call a software syndication filter routine from the data repository in the process of monitoring a syndication feed. For example, in the process of receiving a syndication feed, the CPU may call the routine to monitor, analyze, manipulate, or otherwise interact with the feed.

Figure 12:
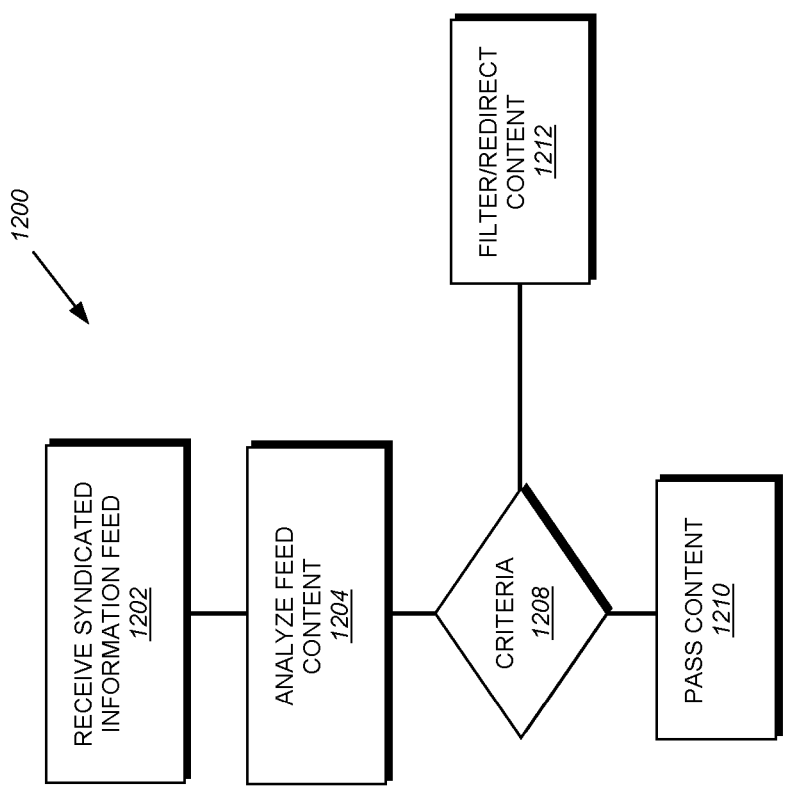
FIG. 12 shows a method for filtering syndicated content.

FIG. 12 illustrates a method for filtering syndicated data 1200. The method may involve receiving a syndicated information feed 1202, analyzing the feed 1204, and applying criteria 1208 to the feed to determine a filtering action. The analysis may be accomplished through hardware, software, firmware, or other solution (e.g. as described in connection with FIGS. 11A, 11B and 12). The analysis may be rule-based, look-up based, heuristic, algorithmic, semantic, or may employ any other suitable techniques for analyzing content. The criteria 1208 may also be applied through a hardware solution, a software solution, a firmware solution, or any other technique, or any combination of these. The criteria applied to the analysis may be algorithm-based, table-based, or it may use other criteria for determining whether the content should be filtered. For example, a table of known viruses may be used in a process of matching information extracted from the feed to determine if the feed, or portions thereof, includes known viruses, virus parameters, or indications of a virus. The filter may apply rules or the like based upon, e.g., content, source, destination, semantic content, user criteria, and so forth. Following the application of a criterion 1208, the content may be filtered (e.g. deleted) and/or redirected (e.g. placed in a folder adapted to hold filtered content for later review, deletion, and/or manipulation) 1212, or the content may be passed on for further processing, such as formatting and presentation to a user through a client.

Filters may operate on various data types within syndicated messages. Syndicated data feeds (e.g. RSS or syndicated OPML) may contain device configuration settings, images, video, data, broadcast rating information, and the like. Syndicated feeds may be available in or contain many different formats (e.g. tables, databases, documents, multimedia, web content formats, metadata, electronic mail, and so forth), and they may contain information from a variety of sources such as electronic mail, online content, or web content. A feed may contain various types of information for signal type filters such as radio and TV broadcast content/rating, security information, and the like. The feed, or messages within a feed, may include data for suitably enabled devices to change a mode of operation, using different modes to suit different content, client devices, and so forth. In an organization, users on different IP addresses may desire different information content from the same source; a hardware device may have a syndication filter incorporated to automatically filter and/or sort the syndicated data to the proper IP address(es). Syndication applications may be capable of automatically performing an analysis on received feeds to filter IP/URL addresses, viruses, attached files in email, weblog feeds, email/instant messages, web content, phone calls, TV channels, or various analog and digital signals. A filter may apply different rules to different types of enclosures or attachments. Thus, for example, a filter may apply a first set of rules to MP3 attachments, a second set of rules to OPML attachments, a third set of rules to metadata, and a fourth set of rules to textual content within a message.

In general, a filter may operate to pass certain information and/or block certain information. In a data feed environment, filters may employ a variety of techniques to filter a feed. The filter may operate on various aspects of the feed. This may include, for example, textual content, metadata, attachments, external references (either from an item or to an item), and so forth. A filter may employ rules, algorithms, look-up tables, keywords, Boolean expressions, heuristics, and the like. A filter may operate on specific fields within an item, such as source, name, date, title, and so forth. Numerous devices may incorporate syndication filtering as described generally above. A number of non-limiting examples are provided below. Some of these examples show a device that implements filtering of syndicated content. Other examples show conventional filters that send or receive filter-related data in a syndicated format. Various combinations and modifications of the examples and these general principles will be apparent to one of ordinary skill in the art and are intended to fall within the scope of this disclosure.

Filtering may be embedded into a network router. Network routers may have syndication filter capability incorporated into the network router firmware or may have a syndication-capable chip or chip set incorporated into at least one of the network router processors or circuit boards. The syndication-capable network router may be able to recognize that a received file is a syndication data feed and may make routing decisions based on the syndication data feed contents. The syndication-capable network router may be able to route data to IP addresses on a network based on the syndication data or information contained in the header and body of a network packet or by information in the syndication feed. The syndication feeds may originate from IP addresses within the router network or may be received from outside the router network, such as from the internet. For example, if a number of users received financial data from a common syndication source but the different users were interested in different parts of the financial data, the syndication-capable router may route portions of the syndicated data according to user criteria. Thus, for example, the router may handle data from a syndicated source of mortgage data by routing trading data for secondary mortgage markets to one user (e.g., a bond fund manager), current mortgage rates to a second user (e.g., a consumer), and mortgage qualification data to a third user (e.g., a retail bank).

The syndication-capable network router may be able to route syndication data feeds for at least one of personal data, financial data, medical data, enterprise data, or business data. The syndication-capable router may be capable of routing syndication data feeds to a particular IP address on the network based on the syndication data contained in the feed. In an embodiment, the syndication-capable network router may be able to filter spam, adware, or email by comparing an originating IP or URL to known spam, adware, or email addresses or to look for key words within the incoming packets. The syndication-capable network router may be able to filter, block, route, or permit at least one of online information sources such as news, newspapers, web magazines, academic papers, government court opinions, administrative rulings, regulation updates, opinions, editorials, product reviews, movie reviews, financial or market analyses, discussions of current events, internet media, and advertisements by IP address, URL, syndication content, or packet heading. The syndication-capable network router may be able to filter, block, route, or permit at least one of internet based web pages, weblogs, websites, and web popups by IP address, URL, syndication content, or packet heading.

The syndication-capable network router may be adapted to filter, block, route, or permit at least one of network packet traffic, IP address, MAC address, and VoIP network packets based on originating source, destination address, or syndication content of the packet. The syndication-capable network router may be adapted to filter, block, route, or permit packets based on at least one of a syndication digital signature, syndication password or key, and syndication identity certificate of the packets.

Filtering may be embedded into a firewall. A software or hardware firewall may incorporate syndication filtering. The firewall may be adapted to recognize syndicated content and further adapted to filter, block, or permit the syndicated content according to filter parameters. Filter parameters may be configured through an administrative interface to the firewall, such as a web-based user interface. The syndication-capable firewall may be adapted to filter, block, or permit at least one of personal data, financial data, medical data, enterprise data, or business data based on the syndication application, syndication incoming port, syndication incoming IP, syndication IP address, or syndication content. The syndication-capable firewall may be adapted to filter or block at least one of spam, adware, or email addresses based on a syndication source IP address, a syndication source URL, or content. The syndication-capable firewall may be adapted to filter or block at least one of internet based news, newspapers, web magazines, academic papers, government court opinions, administrative rulings, regulation updates, opinions, editorials, product reviews, movie reviews, financial or market analyses, discussions of current events, internet media, and advertisements by syndication IP address, syndication URL, syndication application, syndication port, syndication content, or syndication heading. The syndication-capable firewall may be adapted to filter or block at least one of internet based web pages, weblogs, websites, and web popups by syndication IP address, syndication URL, syndication application, syndication port, syndication content, or syndication heading. The syndication-capable firewall may be adapted to filter or block network packet traffic or IP addresses based on originating or destination syndication address.

Filtering may be embedded in a virus protection application. The virus protection application may incorporate syndication filtering capabilities. The syndication-capable virus protection application may inspect attachments or enclosures to syndicated content or may analyze the syndicated content itself for malicious instructions or the like. The syndication-capable virus protection application may be adapted to identify, filter, and/or block viral syndication content and/or attachments in one or more of personal data, financial data, medical data, enterprise data, or business data, electronic mail, internet based online news, newspapers, web magazines, academic papers, government court opinions, administrative rulings, regulation updates, opinions, editorials, product reviews, movie reviews, financial or market analyses, discussions of current events, internet media, advertisements, web pages, weblogs, and websites based on known syndication virus content.

A filter may be deployed as a syndication attachment or enclosure filter. This filter may be adapted to locate other syndicated content or sources of content. RSS data feeds, for example, may contain content or attachments that contain additional syndication data. A syndication attachment file filter may scan messages from a syndicated data feed for attachments that may contain other syndication data in which a user has interest. For example, a medical data feed may have information that a user is interested in but may also contain an attachment with additional medical information. The syndication attachment file filter may be able to determine if the attachment contains information that may be of interest to the user and either keep or omit the attachment from the received data feed. The filter may filter syndication attachments using at least one of personal data, financial data, medical data, enterprise data, or business data based on syndication content. The filter may filter attachments to other media types. For example, the filter may scan electronic mail for syndication attachments and apply various filtering rules to any such attachments. As another example, the filter may scan the content of a word processing document for references to syndication sources and/or messages.

A filter may operate locally or remotely. For example, a client device may filter a weblog, or collection of weblogs, or aggregator output to remove items that are not of interest. In another aspect, a remote weblog reader may filter content and transmit the filter output to a client device. A weblog filter may filter feeds according to at least one of personal data, financial data, medical data, enterprise data, or business data based on user defined syndication content. The weblog filter may filter feeds according to source using, such as, for example, filters based on internet based online news, newspapers, web magazines, academic papers, government court opinions, administrative rulings, regulation updates, opinions, editorials, product reviews, movie reviews, financial or market analyses, discussions of current events, internet media, and advertisements.

Websites may broadcast syndication data files that may contain a brief description of the content of the website. A syndication web content filter may be able to read the syndication data file content to block access to a certain site based on any user defined feature. For example, a parent wanting to block a certain type of websites from a child may be able to define the type of site to block. The parent may define key words, phrases, ratings, and so forth to look for in the syndication data file. The filter may block web sites according to one or more of personal data, financial data, medical data, enterprise data, or business data based on the user-defined syndication web site rating. The syndication web content filter may be adapted to block web sites containing at least one of internet based online news, newspapers, web magazines, academic papers, government court opinions, administrative rulings, regulation updates, opinions, editorials, product reviews, movie reviews, financial or market analyses, discussions of current events, internet media, and advertisements based on the user defined syndication web site rating. The syndication web content filter may be able to block at least one of web pages, weblogs, websites, and web browser content based on the user defined syndication web site rating.

An instant messaging ("IM") application may incorporate a filter. The syndication-capable instant message application may be adapted to filter syndication data feeds that may be received from another instant message application either within an instant message or within an attachment or file shared through an instant messaging system.

An anti-phishing program may incorporate a filter. Internet phishing generally takes the form of a request for user information for the purposes of identity theft, credit card information, or monetary payments. These requests may be sent to a user by email, instant message, or from the web and may incorporate a syndication data feed. A syndication phishing filter may be able to block syndication phishing requests based on the syndication content and definition by the user.

A search engine may incorporate a filter. An Internet search engine may contain a filter adapted to identify sites that provide syndication data feeds responsive to a user's definition. For example, a user may be able to define a search for medical information on heart valves to get only a listing of syndication data feed sites with this information. The filter may employ any of the parameters or filtering techniques described above.

A security appliance may incorporate a filter. Security appliances operate as reverse proxy devices positioned between any type of client and a server to act as an additional layer of security for communications. A security appliance may perform checks for viruses, spam, phishing, or other undesired files sent to a server. The server may be any kind of server such as an application server, email server, or web server. A syndication-capable security appliance may be adapted to analyze syndication data feeds to determine the syndication data feed content and make decisions to block or pass the syndicated content onto the server. The filter may employ any of the parameters or filtering techniques described above. The syndication-capable security appliance may be adapted to filter at least one of unwanted syndication network packet traffic, syndication IP addresses, and syndication MAC addresses from entering a server. The syndication-capable security appliance may be adapted to filter at least one of unwanted syndication digital signatures, syndication passwords or keys, and syndication identity certificates from entering a server.

Database applications (e.g. Oracle) may incorporate syndication filter capabilities. Syndication data files may have the same structure as XML, using tags to indicate the beginning and end of information sections of the information or data. XML and syndication are becoming increasingly popular for holding data because of their small size and data types they may contain. A syndication-capable database application may be adapted to search and filter data from syndication data sources in addition to the same abilities for tables and databases. The syndication-capable database application may be adapted to filter at least one of personal data, financial data, medical data, enterprise data, or business data from syndication sources based on user or application requirements.

Filters may be integrated into an enterprise application. Enterprise applications may be adapted to search and filter data from across corporate or local area networks, as well as wide area networks including the Internet. Enterprise data may be obtained from other applications and/or databases deployed within the enterprise, and the enterprise application may apply suitable connections and converters to read the data and/or convert the data to a common format. A syndication-capable enterprise application may also be adapted to access data in syndication data files and syndication data feeds at local and/or remote locations. The syndication-capable enterprise application may be adapted to use a search engine to locate syndication data feeds on the internet that may have desired data based on a user's definition. The syndication-capable enterprise application may be adapted to filter syndication data feeds or syndication data files based upon one or more of personal data, financial data, medical data, enterprise data, business data. More generally, the syndication-capable enterprise application may employ any of the filtering parameters and techniques described above.

A filter may provide semantic processing to process data according to semantic content or meaning. The filter may be applied to data in tables, databases, and syndication metadata, and it may permit searching or handling of syndicated content based upon user-provided semantic parameters. The semantic filter may employ any of the filtering parameters or techniques described above.

A filter may provide encryption processing to permit filtering of encrypted data. The filter may employ user-provided keys to decrypt syndicated content for further filtering and other processing. The filter may also, or instead, provide encryption processing to permit filtering of data according to encryption characteristics such as encryption type, availability of public keys, and so forth. The encryption filter may employ any of the filtering parameters or techniques described above.

A filter may provide caller ID filtering. The filter may identify and extract caller information from a cellular phone, wired telephone, wireless telephone, VoIP telephone, or other telephonic device. Information may, for example, be published to a data feed or forwarded for other processing. In another aspect, the filter may identify and extract telephone numbers and other contact information from a data feed. The caller ID filter may employ any of the filtering parameters or techniques described above.

A filter may provide content filtering. A channel blocking system may be provided for a device to manage access to broadcast (e.g., radio or television) or other transmissions. The transmission may be accompanied by content ratings or other semantic data that may be employed by the channel blocking system to restrict availability at a receiving device according to user preferences. In one aspect, the ratings may be provided as a syndicated feed. In another aspect, the transmissions may be processed to derive a feed of characteristic information which may, in turn, be applied by the channel blocking system to dynamically restrict access according to current content and any user-provided constraints. The filter may be applied to one or more of a radio broadcast, a television broadcast, a satellite broadcast, a satellite radio broadcast, a cable television channel, or the like. The filter may employ analysis including content analysis and analysis of digital signatures, passwords, keys, or identity certificates, and the like.

A filter may be associated with an analog-to-digital converter (ADC), a digital-to-analog converter (DAC), or a media coder/decoder (CODEC), referred to generally as digital processors. In one embodiment, characterizations of output such as sampling rate, compression ratios, frequency spectra, and the like may be provided to a feed for transmission and processing along with the digital content. In another aspect, a data feed may be provided to guide downstream processing of the digital (or analog) signal. A filter may be applied to sort, select, block, or otherwise process associated media according to the data feed.

Similarly, any digital filter, including audio filters, digital filters, digital subscriber line filters, line filters, surface acoustic wave filters, and the like, may be adapted to receive syndicated data that provide operating parameters for the filter, or it may be adapted to publish a feed of operational data. In an embodiment, the syndication signal processing platform may be adapted to process at least one of an audio signal, electronic signal, analog signal, digital signal, and video signal using a syndication signal processing platform which uses a provided set of parameters from a syndication data file or syndication data feed.

Healthcare institutions, including but not limited to, hospitals, short-term care facilities, long-term care facilities, outpatient treatment centers, hospices, nursing homes, mental health facilities, government facilities (e.g. Veterans' Affairs hospitals), specialty clinics, and the like, must continually monitor a vast array of information to ensure the ongoing delivery of safe and effective clinical treatment, all while operating in an increasingly restrictive fiscal environment. Central to a healthcare institution's ability to manage and maintain high quality care is information. Medical journals regularly report on numerous quality improvements needed in health care delivery, such as minimizing the under use, over use, and/or misuse of care, minimizing clinical errors, reducing costs, and so forth. Approaches such as conformance to clinical standards, total quality management, outcomes measurement, accreditation and accountability, healthcare provider training and performance monitoring, cost tracking and cost-effectiveness analysis, patient education, infrastructure monitoring, and others are all used to systematically measure, analyze, and optimize the healthcare delivery of institutions.

Healthcare institutions are responsible for continuous improvement in healthcare delivery. In order to assess such broad terms as "quality" and "improvement," standards are necessary, as is the ability to obtain information enabling an institution to conduct periodic assessments of performance, policy and procedure. This is essentially an ongoing audit of performance enabling a systematic appraisal of an institution. Conceptually the components of this audit may be thought of as (i) infrastructure (e.g., physical/equipment needs of an institution), (ii) process (what is done, when, how, by whom, etc.), and (iii) outcomes (what occurred, how do these occurrences compare to standards, other institutions, etc.). Data recording, information retrieval and analysis are requisite for a valid audit of institutional structure, process, and outcomes.

For example, evidence-based medicine has as its goal to assist health care practitioners, patients, and policymakers to make better decisions by basing clinical decisions on the best evidence available, such as clinical studies, panel reports, the reports of accreditation bodies, and the like. At its most basic, the goal of evidence-based medicine is to have healthcare providers base their decisions on the best empirical evidence available. As information is added to the collective medical evidence, for example, through new clinical studies, evidence-based medicine provides a means for getting this data to healthcare providers in order to provide a means for continuous learning and for improving care. However, many healthcare providers may have problems acquiring the skills needed to conduct appropriate searches and review the relevant literature or to consult databases within the context of their daily work. Thus, there is wide variation in the delivery of medical care and the quality of the care delivered. Greater access to clinical information should result in reduced morbidity and mortality within healthcare institutions. Syndication technologies may provide opportunities for providing evidence-based data, and many other types of healthcare data, to healthcare providers in order to assist continually improving healthcare delivery.

Despite widespread interest in collecting and disseminating healthcare information and the billions of dollars spent on the infrastructure and training necessary to collect, analyze, disseminate, and use that information, much of institutional healthcare and associated data collection/delivery lags far behind in technical sophistication, efficiency and usefulness. Many institutions do not pursue systems for collecting information that may be used to improving healthcare delivery because the endeavor is simply too costly. Many institutions that do invest in such informational infrastructure often do so to meet only their own unique internal needs and circumstances. Thus, the costly data collected and analyzed at great cost by one institution may be of little or no relevance to another institution due to the lack of congruence in the data needs of the two intuitions. The result may be very costly vertical information systems with minimal horizontal links.

For example, following a series of clinical errors, Hospital A may decide to implement a new information collection and analysis system for monitoring the treatment of cardiovascular patients within the institution. Data such as medication usage, frequency of patient follow-up, referrals, interventions, etc. may all be collected as part of this program, and, most likely, stored in a relational database from which reports may be derived and analyses made. Hospital B may also have a keen interest in these clinical data and collect similar fields in its own proprietary database. For purposes of comparison, benchmarking, patient mix analysis, outcomes, etc. it would be very useful (and cost efficient) for Hospitals A and B to be able to share their data in some anonymous manner. However, suppose, as is often the case, that Hospitals A and B differ in many respects institutionally, and have different uses to which they seek to put the data. Hospital A may have a different pharmaceutical formulary that Hospital B. Hospital A may record medication side effects as "None, Mild, Moderate, Extensive," while Hospital B records side effects as "Nausea, Rash, Increased Blood Pressure, etc." Hospital A may not have a surgical program, thus its patients must be referred to another institution for bypass surgery and so data regarding this treatment and its outcomes is not included in Hospital A's dataset. Conversely, Hospital B may have extensive surgical programs, all of which generate data that is of great interest and included in Hospital B's dataset. These inconsistencies do not entirely rule out the sharing of data between the institutions. For example, it is possible that they could share information about medications that are prescribed at both institutions, and so forth. Unfortunately, minimal overlap, coding differences, and the like make such information sharing require extensive retrospective re-formatting that further increases the cost of the data. Not surprisingly, inter-institutional comparisons other than those formalized in clinical trials are therefore uncommon. If, instead, institutions recorded and had access to syndicated healthcare information, from which unique feeds could be tailored to individual institutional needs, certain problems, such as those of institutional intercommunication described above, may be minimized, with improvement of the usefulness and efficiency of health care information for institutions.

Effective institutional healthcare delivery may require several steps. First, goals and quality standards must be defined, and to the extent possible, must be measurable. Second, specific, measurable indicators relating to those definitions must then be selected. Definitions may come from accrediting bodies, third-party insurers, physician groups (e.g. the AMA), patient advocacy groups, or set to standards and goals that are internal to a particular institution. Third, data are collected. Data quality increases insofar as it is more accessible, has greater validity and completeness, and is relevant to the institutional goal(s) for which it is intended to serve. Fourth, summary and/or analyses of the data are provided. Finally, data delivery must occur, preferably in a manner consistent with the needs, aptitudes, and preferences of the data's end-users.

Layered over this sequential data infrastructure are the domains of a healthcare institution, each with a potentially unique set of circumstances impacting each step of the data infrastructure. For example, conformance to clinical standards, total quality management, outcomes measurement, accreditation and accountability, healthcare provider training and performance monitoring, cost tracking and cost-effectiveness analysis, patient education, infrastructure monitoring, and others may each share a core set of data needs, but have additional data requirements not shared by the other domains. Syndicated data technologies may be useful for implementing the data processing steps described herein in a decentralized manner and enabling different institutional domains to interact with the information collected by the decentralized data infrastructure to systematically measure, analyze, and optimize the healthcare delivery of an institution's domain in the manner best suited to the unique goals of a particular domain of a healthcare institution.

Healthcare institutions must conform to standards of care in order to obtain accreditation, maintain relationships with third-party insurers, and the like. A number of organizations publish and report on standards of care, such as the Joint Commission on the Accreditation of Healthcare Organizations (JCAHO), the National Committee for Quality Assurance (NCQA), and others. Some standards may refer to the management of a healthcare institutions (e.g. maintaining records on the credentials of all staff physicians), while others may be quite specific to a disease state and how to best treat it. NCQA's HEDIS 3.0 database includes measures to assess the effectiveness of care. JCAHO mandates that healthcare institutions collect data on performance, and medical specialty organizations, such as the American College of Cardiology, may derive and publish best practices for a specific condition (e.g. how to evaluate and treat new-onset angina.

In particular, clinical practice guidelines may provide a healthcare institution, its physicians and other healthcare providers with information regarding the appropriate treatment of a wide variety of conditions. Practice guidelines incorporate the best scientific evidence with expert opinion and represent recommendations based on rigorous clinical research and soundly generated professional consensus. Guidelines may also be useful sources of comparative data if the guidelines are explicit and there is good scientific evidence to support the recommendations. For example, there is good evidence to suggest that certain therapies should be administered within the first six hours following a myocardial infarction. This is a rigorously studied guideline and is widely accepted. Syndicated data may be used to disseminate this information to, and within, a healthcare institution, as well as used to collect and disseminate information pertain to the institution's performance and conformance with the guideline. Accrediting institutions, researchers, and other interested parties may, in turn, aggregate this syndicated data across a clinical specialty, geographic region, and so forth to derive norms of care, comparative studies, and the like.

As in other industries, healthcare institutions have found value in quality improvement techniques such as Total Quality Management (TQM), Continuous Quality Improvement (CQI), and other similar methods. TQM and CQI derive from management research on methods for measuring performance and using this information to continuously monitor systemic outcomes and improve the quality of services, goods, and the like. Systematic monitoring of clinical performance within a healthcare institution, permits parties within the institution to receive information on their performance and make improvements where necessary, and permits administrators to evaluate the institution's systems and processes at a macro level, aggregating information on individuals' performances within the institution.

For example, healthcare administrators within an institution may be interested in improving the wait times in the Emergency Room. As part of a TQM/CQI project, data could be collected on each patient who visits the ER within a defined period of time, this data could be combined with other useful information, such as, day of the week, time of day of the visit, injury causing the ER visit, and so on. Once these data are aggregated and analyzed it may be possible to spot trends or problem areas that may be improved. Perhaps Friday nights are associated with particularly long wait times. This information might prompt administrators to increase staffing on these nights, and so on. An effective TQM/CQI project must have valid and reliable information that is readily available to the appropriate parties who may use this information to improve institutional healthcare delivery. Syndicated data may be used to interact with information associated with a TQM/CQI project within a healthcare institution, used to aggregate TQM/CQI data for purposes of comparison, summary, and the like. Similar projects could record clinical errors, events (e.g. intubation required, CPR administered), morbidity, mortality, and so forth, as part of a TQM/CQI process to reduce error rates and improve patient safety. This syndicated data, in turn, could be aggregated at a city, state, or national level for the purposes of administrative decision making, resource allocation, accreditation, and so forth.

Training healthcare providers and the monitoring the performance of providers at all levels are fundamental to a successful healthcare institution. However, measurement in this domain is notoriously difficult. For example, in many instances it is not meaningful to hold a single provider individually responsible for a patient's outcomes, because a given patient's treatment is likely to be shared by several providers, perhaps with different clinical specialties and different levels of training, and even shared across healthcare institutions (e.g. physician group office, hospital, home care, etc.). As another example, it is difficult to establish standards of competence for different training levels, because trainees assimilate information and acquire skills at different rates throughout the prolonged (often multiyear) period of training.

Further complicating measurement in this domain is the case mix of patients in different hospitals. A provider working in a public hospital may see patients in a more advanced disease state than her cross-town colleague working at a private hospital in an affluent neighborhood. The lower socioeconomic status of the public hospital's patients may be associated with a variety of comorbid disorders derived from socioeconomic deficiencies. For example, in the public hospital there may be a high level of uninsured patients who do not as often visit physicians' offices, and delay seeking care when it is needed. Thus, to compare the performance of the public and private hospital providers on a variable such as "Lower Systolic Blood Pressure Ten Points within Three Months of First Consultation" is not a valid comparison, as it is confounded by the different case mix of the two institutions.

In spite of these difficulties, measuring performance, monitoring provider training, and the like are necessary in order to identify areas that need improvement, signal the accomplishment of goals, and respond to the need for accountability. The steering committee of a healthcare institution must ensure that staff members receive proper training, that this training is in evidence within individuals' clinical practice, and that it serves to maintain and/or improve upon desired performance levels. In response to t information pertaining to training and performance, institutional task forces may be formed to focus on specific staff competencies that appear weak. Systematic monitoring of healthcare providers' training and performance within a healthcare institution permits parties within the institution to receive information on their performance and make improvements where necessary, and permits administrators to evaluate the institution's systems and processes at a macro level, aggregating information on individuals' performances within the institution. Cross-institutional data may also be collected, permitting specialty organizations to monitor the training and credentialing process for their residents and fellows.

Syndicated data may be used to monitor providers' training and performance within a healthcare institution in a more passive, decentralize manner. For example, whereas a traditional performance measurement project would very likely specify in advance variables to collect, where and when to collect the data, create a new database or dataset within a database, and so on, a syndicated data infrastructure could systematically tag institutional records for later interaction as part of performance monitoring, but without having to, a priori, decide the specifics of all intended analyses. Training and performance parameters may also be provided to cross-institutional organizations such as medical schools comprising a number of teaching hospitals, or medical specialty organizations.

In addition to clinical effectiveness, healthcare institutions must also continually demonstrate optimal fiscal management. Cost-effectiveness studies, cost benefit analysis, and simple cost tracking are all tools used to measure the economic value of services provided by healthcare institutions. Cost-effectiveness analyses have as their goal to describe the cost of obtaining health outcomes as a means for determining the appropriateness of various treatment options. For example, a cost-effectiveness study may seek to quantify the cost of three treatment options for a narrowed coronary artery (medication, angioplasty, bypass surgery) to obtain the same outcome, such as, "Free of Myocardial Infarction." The study would then quantify the cost for each year that a patient, on average, is free from having a heart attack. More invasive procedures, like bypass surgery, may increase the number of years that a patient is free from heart attack, as compared to pharmaceutical treatment alone, but at a significantly higher cost. This information may then be aggregated with other data (e.g. patient factors, provider factors, institutional factors) that affect outcomes. Data like these are often used to determine the appropriate timetable for health screenings. For example, it is likely that testing males every year from birth for prostate cancer would result in lessening the mortality from this disease to some slight degree. However, so few men under age 35 have prostate cancer that testing all men under this age is not cost effective. Thus, standards must be derived based, in part, on the balance between obtaining a desired outcome (detect cancer) and economic necessities (keep the cost of each cancer detected below $X). The result enables healthcare providers and administrators to balance the desire to meet treatment objectives with prudent fiscal management. Cost benefit analysis is another method for measuring the net benefit of an intervention, but with costs and benefits both expressed in financial units. The data necessary for cost-related analyses may be stored by a healthcare institution in a syndicated format for later interaction.

As with the cost effectiveness of clinical outcomes, healthcare institutions must also gather information regarding the value of patient education programs. Patient education is intended, among other things, to improve compliance with treatment regimens and help patients to better understand and self-manage their health. For example, a healthcare institution may create a patient education program for cardiology patients that includes teaching patients how to recognize symptoms associated with an impending heart attack, so that should such symptoms occur, they are better able to contact healthcare personnel for help. As another example, educational programs may improve patients' compliance in taking their medications and adhering to a follow-up care plan. As a further example, patient education may improve clinical outcomes by improving communication between doctor and patient, as patients learn how to discuss their symptoms with their physician, ask important questions, and clear up any misunderstanding they might have about their health condition. A healthcare institution may collect data relating to patient education programs and measurable clinical outcomes and store these data in a syndicated format for later use in evaluating the usefulness and cost-benefit of the programs.

Contemporary medicine is heavily reliant upon the devices and physical plant of healthcare institutions to administer appropriate care. Complex medical devices and equipment require monitoring and maintenance in order to prevent device-related clinical errors. Device-related mistakes may be due to (i) device failures (e.g. component failure), (ii) external factors (e.g. electrical surges or outages, (iii) system errors (e.g. improper training, poor maintenance), or (iv) operator error (e.g. human misuse of a device). Device-related data, for example pertaining to device-related error, may be stored in a syndicated format. From these syndicated data, for example, it may be possible to create feeds that alert institutions to possible device-related problems. Moreover, For example, institutions may record their device-related data in a syndicated format that is shared with an overseeing body. The overseeing body may aggregate this information from a multitude of institutions and glean useful information on devices that seem to be associated with device failures, that appear to be more difficult to use and, thus, have high operator error, and so forth. This summary information could, in turn, be stored in a syndicated format and feed to institutions so that they may be better aware of current or potential device problems.

In embodiments, healthcare institutions may interact with evidence-based information, such as medical research, clinical trial findings, case studies, peer-reviewed articles, academic presentations, and the like in a syndicated format to enable an institution to continually update its repository of evidence-based medical knowledge via syndicated data obtained through an RSS feed 202, web feed, RSS stream, or RSS channel. The syndicated information may include full academic journal articles, article abstracts, customized article summaries, clinic trial data, clinical trial analyses, published standards of care, published clinical indicators for medications, published indicators for interventions, appropriateness scores for certain classes of clinical profiles and corresponding treatment options, and the like. For example, an institution engaged in a high volume cardiology practice may be able to subscribe to syndicated data feeds for particular research journals, organizations, and the like, and receive regular updates on new clinical findings, recommendations, changes in standards of care, and so forth.

In embodiments, syndicated evidence-based information, such as medical research, clinical trial findings, case studies, peer-reviewed articles, academic presentations, and the like, may be plotted, displayed, analyzed, or the like and distributed to an RSS-enabled client.

In embodiments, syndicated evidence-based information, such as medical research, clinical trial findings, case studies, peer-reviewed articles, academic presentations, and the like, may be associated with an application 406 consisting of a client-side program. As used in this application, the client-side program may be healthcare software and/or an application. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated evidence-based information, such as medical research, clinical trial findings, case studies, peer-reviewed articles, academic presentations, and the like, may be associated with an aggregator 210 to track updates.

In embodiments, the RSS feed 202, web feed, RSS stream, or RSS channel used to present syndicated evidence-based information, such as medical research, clinical trial findings, case studies, peer-reviewed articles, academic presentations, and the like, may be associated with a content management system that may provide summaries of the syndicated data available, dates associated with the syndicated data, links to access the full, non-summarized data, and the like.

In embodiments, healthcare institutions may interact with syndicated evidence-based information, such as medical research, clinical trial findings, case studies, peer-reviewed articles, academic presentations, and the like, through the use of an application 406 providing social networking. As used in this application, social networking may enable two or more individuals to view, receive, send and/or interact with one or more pieces of information. The two or more individuals may be members of a network, such as a network of healthcare providers. The one or more pieces of information may be syndicated information or data, such as syndicated evidence-based information, syndicated data regarding adverse events, standards, clinical practice guidelines and recommendations, clinical processes, training and credentials, performance, errors and outcomes, expenditures on patient care, such as discussed herein.

For example, through social networking an institution may be able to communicate and share syndicated data with other healthcare institutions with whom the institution shares patient populations, clinical specialties, clinical population types, and the like. The clinical factors of relevance to institutions that seek to share syndicated data may be published with detailed tags to provide narrowly tailored or easily filtered RSS feeds 202, web feeds, RSS streams, or RSS channels for ongoing data sharing. Such a process may allow institutions who care for similar patient populations to aggregate data for more robust analysis.

In embodiments, healthcare institutions may interact with syndicated evidence-based information, such as medical research, clinical trial findings, case studies, peer-reviewed articles, academic presentations, and the like, through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated evidence-based information, such as medical research, clinical trial findings, case studies, peer-reviewed articles, academic presentations, and the like, through the use of an application 406 associated with a media viewer or directly through a media viewer. For example, an RSS item may refer to an image source, such as an MRI image in a medical record from a hospital, and may specify a viewer for the source image that is available through a registry such as a registry for services in a services oriented architecture. In operation, a client (e.g. a physician) with appropriate permissions to view the image (also as managed, e.g., through the metadata for the enhanced syndication system), may retrieve the appropriate viewer service from the registry, and apply the viewer to view the source image. In another aspect, viewers or links to viewer software may be syndicated for global access across the healthcare institution so that new media formats or improvements to rendering or other functionality for existing media formats may be published for use throughout the institution. The suitability of a viewer may depend on the hardware capabilities of a client, the operating system of a client, and the like, and the syndicated message containing the image may specify a number of different possible viewers, such as viewers for different client device types.

In embodiments, healthcare institutions may interact with syndicated evidence-based information, such as medical research, clinical trial findings, case studies, peer-reviewed articles, academic presentations, and the like, through the use of an application 406 providing vertical market integration. For example, as hospital physicians update the medications and dosages of their patient population following clinical visits, this data may be aggregated and republished by clinical specialty (e.g. cardiology patients) and this syndicated data may then be provided to the administrators of the respective clinical areas via an RSS feed 202 and may permit the administrators to more efficiently allocate resources, plan personnel, and the like. As used in this application, the application 406 providing for vertical market integration may provide conditional access that allows a participant in a healthcare hierarchy to view, receive, send and/or interact with information according to the participant's position in the hierarchy.

Figure 13:
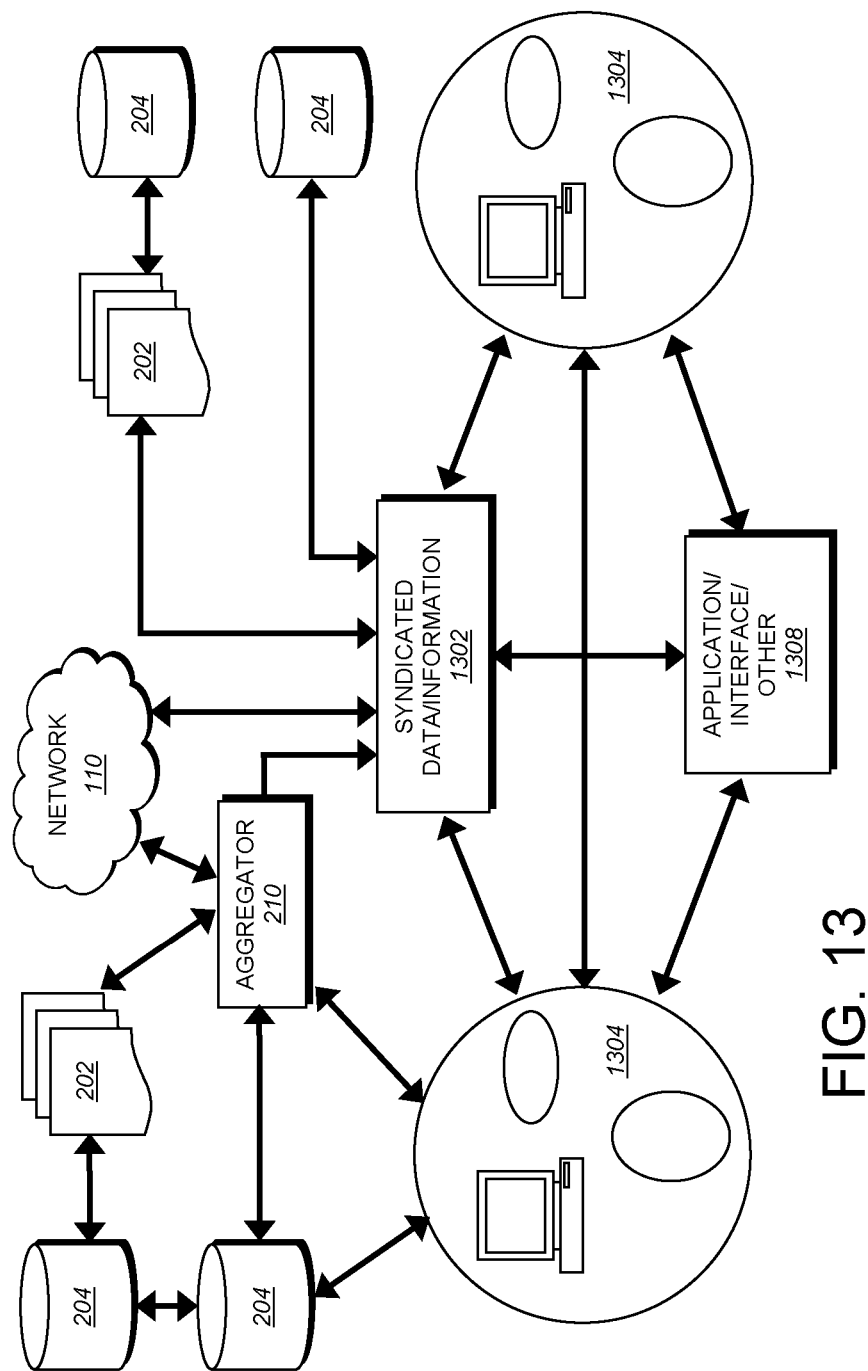
FIG. 13 shows a syndication environment including an application and/or interface.

Referring to FIG. 13, the syndicated data/information 1302 may be syndicated evidence-based information as described herein. The syndicated data/information 1302 may originate on a network 110 or may originate from a content source 204 through a data feed 202 or directly. An aggregator 210 may select and filter one or more sources of evidence-based information for republication. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may also employ or expose services, such as those described in reference to FIG. 4. In certain embodiments the arrows of FIG. 13 may be data feeds, such as data feed 202.

In embodiments, healthcare institutions may interact with syndicated evidence-based information, such as medical research, clinical trial findings, case studies, peer-reviewed articles, academic presentations, and the like, using database functions that may permit the data quality to be verified, provide for transformation of the data, enable searching, filtering, or clustering the patient data, or categorizing the data into hierarchies, interrelationships, interrelated groups, and the like.

Figure 14:
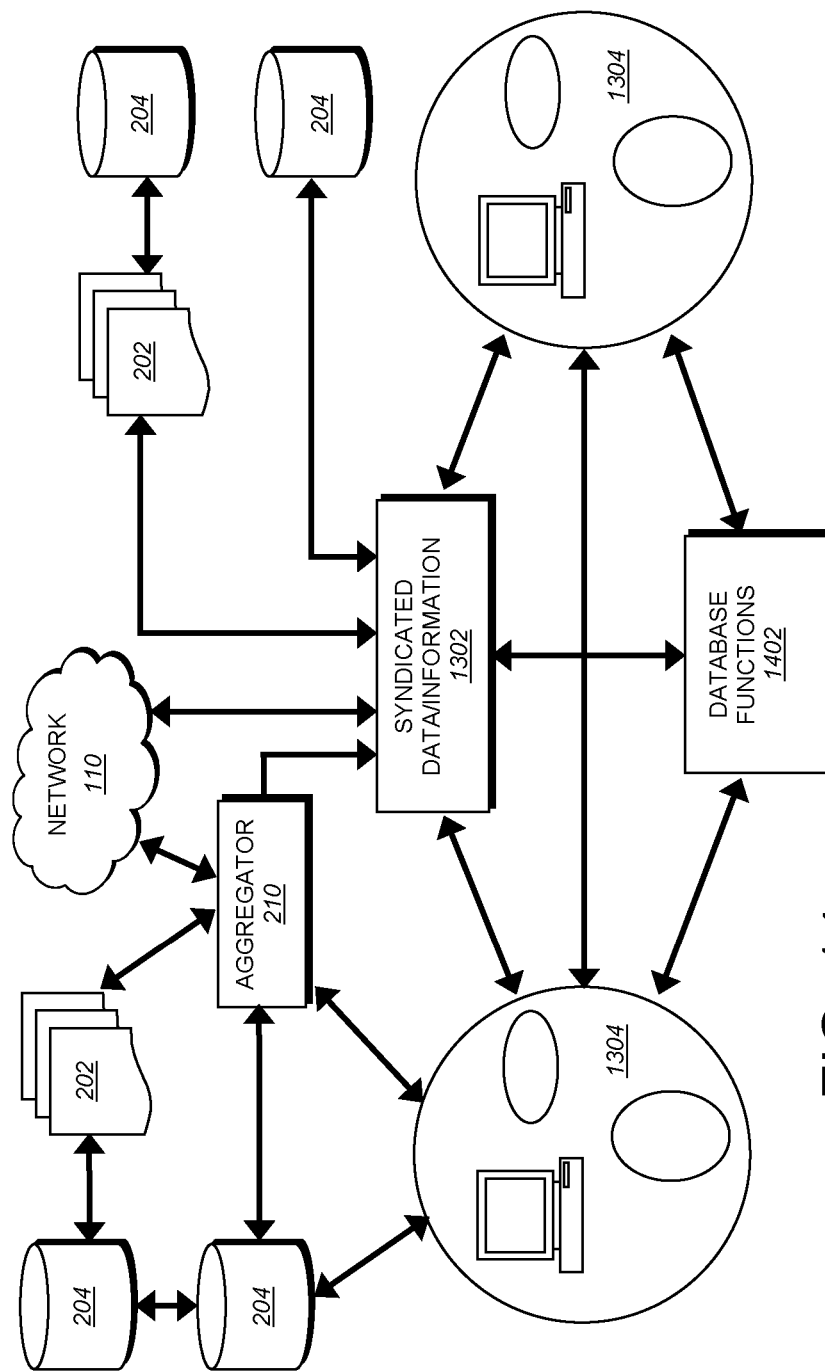
FIG. 14 shows a syndication environment including database functions.

Referring to FIG. 14, the syndicated data/information 1302 may be syndicated evidence-based information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a registry of a services oriented architecture. In certain embodiments the arrows of FIG. 14 may be data feeds, such as data feed 202.

In embodiments, healthcare institutions may interact with syndicated evidence-based information, such as medical research, clinical trial findings, case studies, peer-reviewed articles, academic presentations, and the like, using semantic rules 412 that enable, for example, the creation or processing of metadata. Semantic rules 412 may also provide for metadata enrichment of syndicated or aggregated data, interpretation or translation of aggregated data, as well as permit the creation of knowledge structures expressed, for example, using OPML, and the use of a dictionary or thesaurus.

Figure 15:
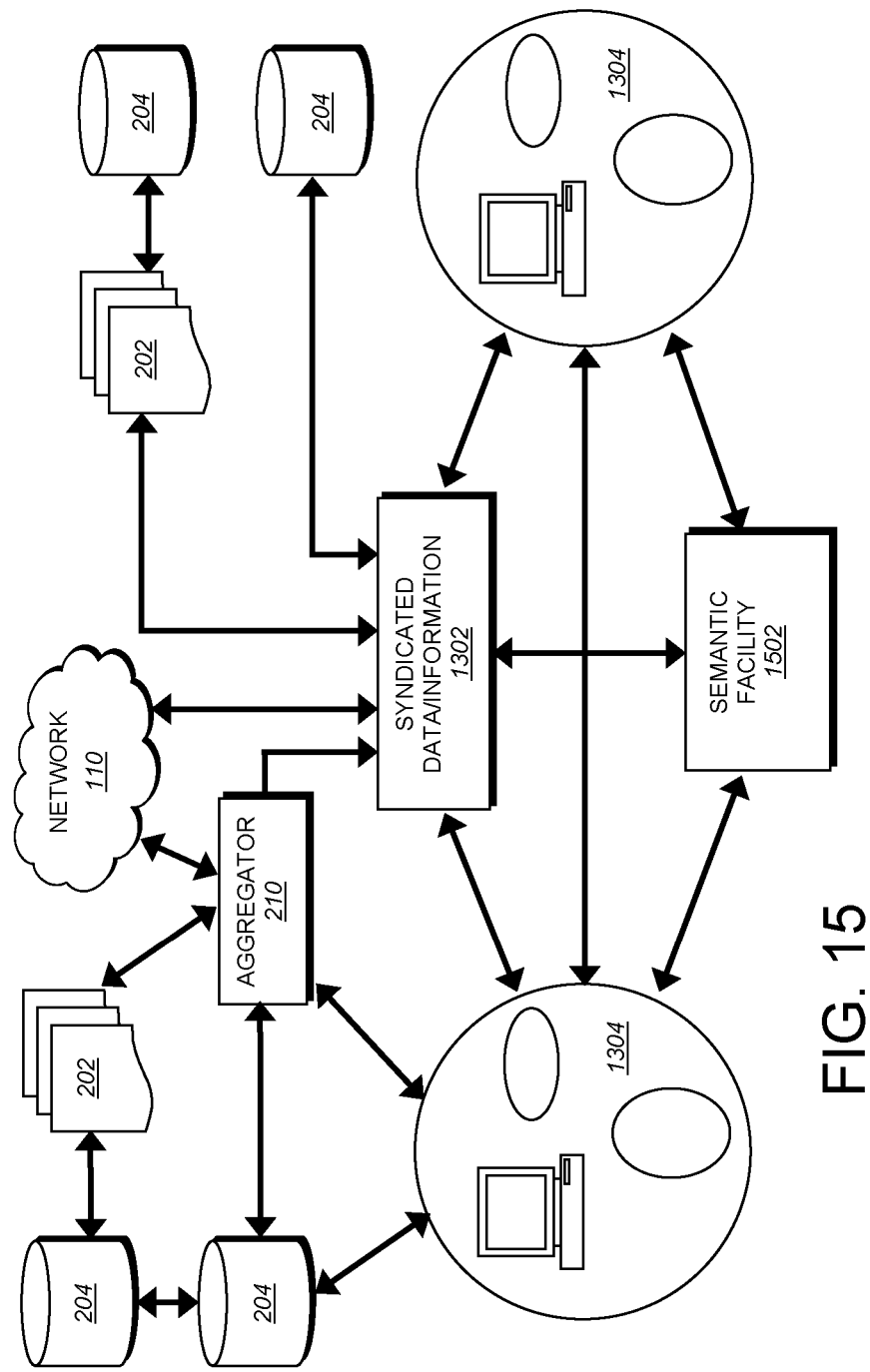
FIG. 15 shows a syndication environment including a semantic facility.

Referring to FIG. 15, the syndicated data/information 1302 may be syndicated evidence-based information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may, for example, provide context for or interpretation of syndicated data to improve end user experience, or may filter syndicated data using semantically oriented rules. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may be deployed as described above with reference to, for example, FIGS. 4 and 5. In certain embodiments the arrows of FIG. 15 may be data feeds, such as data feed 202.

In embodiments, healthcare institutions may publish and/or subscribe to and/or interact with syndicated evidence-based information, such as medical research, clinical trial findings, case studies, peer-reviewed articles, academic presentations, and the like, to which others may subscribe and/or publish and/or with which others may interact. Community physicians, for example, may subscribe to syndicated evidence-based information generated by an academic medical center (e.g., the Mayo Clinic), or by a medical specialty organization (e.g., the American College of Surgeons). Community physicians may also publish their own results as part of a decentralized data collection project sponsored by such an institution, so that the experience of individual physicians is captured as part of the institution's data set.

In embodiments, the syndicated evidence-based information, such as medical research, clinical trial findings, case studies, peer-reviewed articles, academic presentations, and the like, may be further associated with information that may provide for the management of the data. For example, the aggregated data may list the author of the aggregated data, the date on which it was authored, etc. Thus, the data may provide for further aggregation, republication, and the like. In the example above, where community physicians are contributing data to an academic dataset, such community-sourced data may be designated as such, allowing subsequent statistical analysis and substantive analysis to recognize the different parameters accompanying community-based observations as contrasted with academic-based observations. In this example, community-based surgeons may have a different rate of post-operative infection with different microorganisms than the academic-based surgical staff, reflecting the differences in the type of microorganisms found in the two environments, the differences in patient mix and illness severity, and the like.

Figure 16:
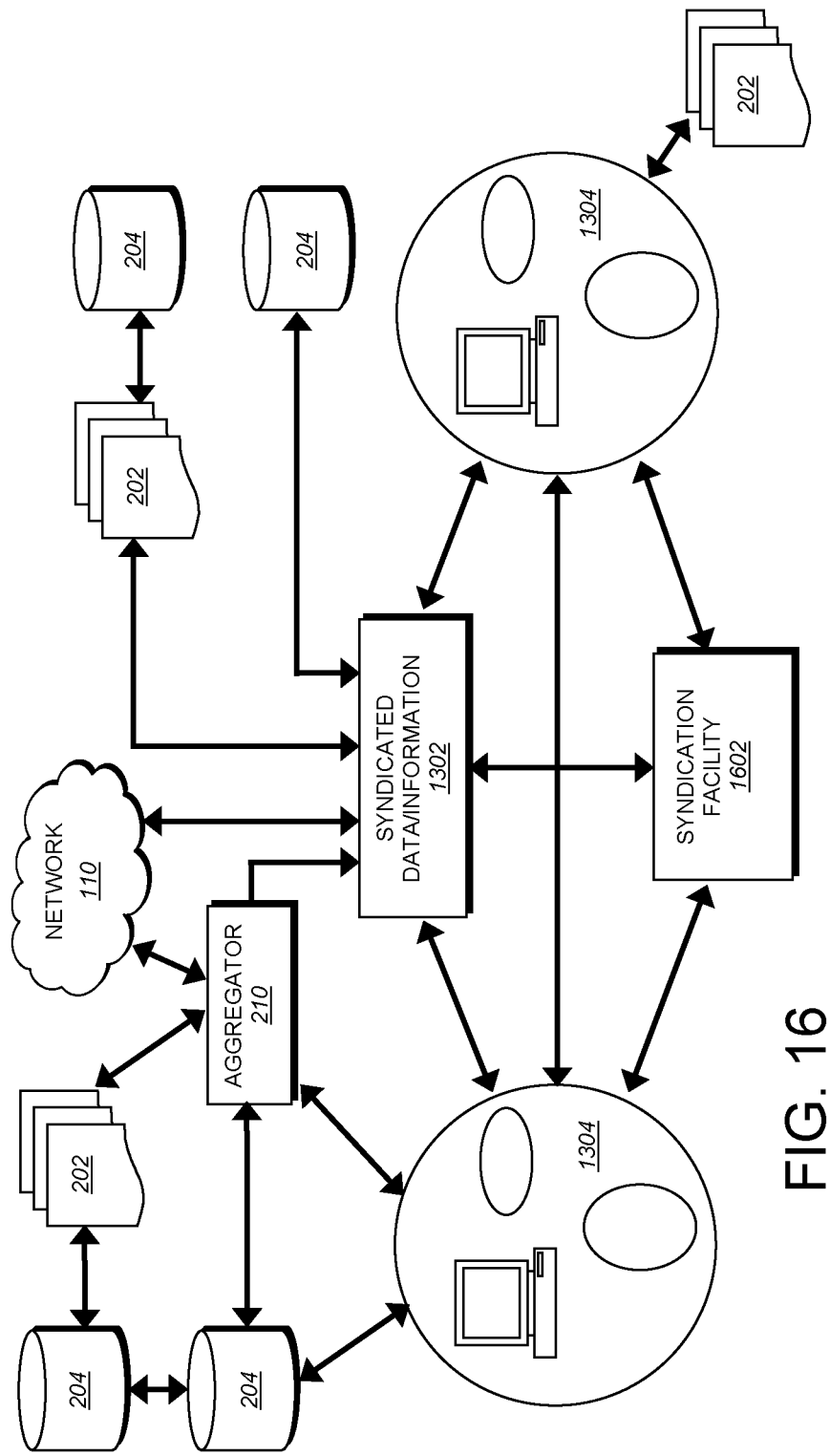
FIG. 16 shows a syndication environment including a syndication facility.

Referring to FIG. 16, the syndicated data/information 1302 may be syndicated evidence-based information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated evidence-based information, such as medical research, clinical trial findings, case studies, peer-reviewed articles, academic presentations, and the like, within an infrastructure 416 that provides for data security, authentication, management of the traffic created by the RSS feeds 202, web feeds, RSS streams, or RSS channels, logging and pinging technology, and/or other communications. A subscriber to an academic medical center's syndicated evidence-based information may need to provide credentials demonstrating her academic affiliation before she can access certain types of data such as complication rates for particular procedures. A researcher investigating, for example, complication rates for a particular procedure as part of a scientific, cross-institutional study may be granted deidentified access to complication data for the academic medical center, but again only after providing certain credentials acceptable to the institution.

Figure 17:
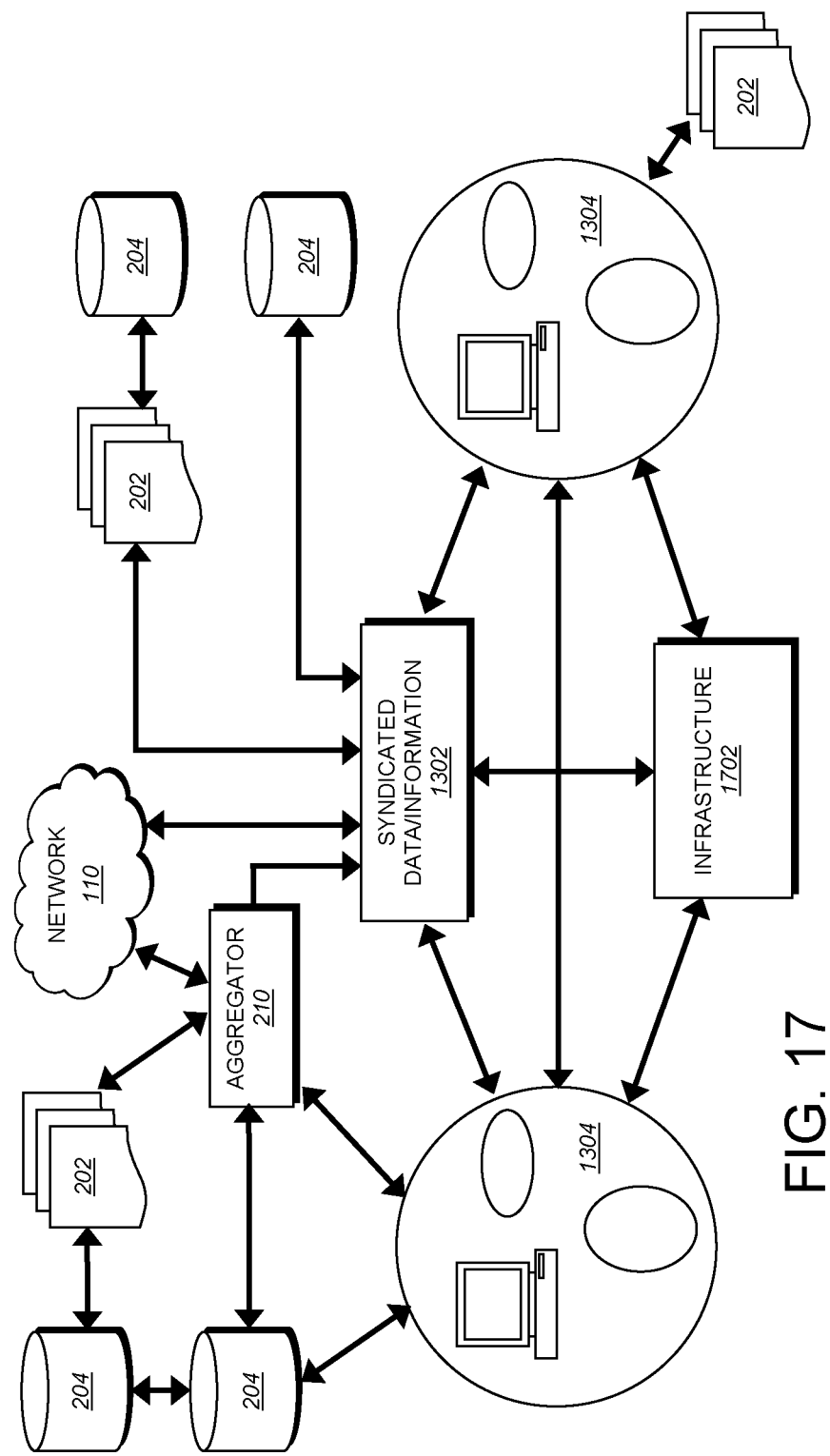
FIG. 17 shows a syndication environment including an infrastructure.

Referring to FIG. 17, the syndicated data/information 1302 may be syndicated evidence-based information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may, for example, provide services for an enhanced syndication environment such as security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated evidence-based information, such as medical research, clinical trial findings, case studies, peer-reviewed articles, academic presentations, and the like, that is associated with special formatting and/or display properties. A case study or series of cases from a medical center may be made available to subscribers, for example, in a format suitable for continuing medical education ("CME") purposes. The CME-oriented case report may be followed by a series of questions to permit CME credits, or the case report may be accompanied by links to related peer-reviewed journal articles or abstracts. Non-CME subscribers to the same case study may not have access to the CME formatting and display.

In embodiments, healthcare institutions may interact with syndicated evidence-based information, such as medical research, clinical trial findings, case studies, peer-reviewed articles, academic presentations, and the like, that is associated with special identification and/or de-identification properties. For example, a syndicated case study from a hospital may be available to subscribers for CME purposes with patient deidentification. The same case study may be accompanied by demographic data if the subscriber is a clinical researcher.

In embodiments, healthcare institutions may interact with syndicated evidence-based information, such as medical research, clinical trial findings, case studies, peer-reviewed articles, academic presentations, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated evidence-based information, such as medical research, clinical trial findings, case studies, peer-reviewed articles, academic presentations, and the like, that is associated with restricted or conditional access properties. Clinical researchers at decentralized institutions participating in a clinical trial, for example, may have access to data accumulated at multiple centers in real time, while other subscribers may not be permitted access until all data have been accumulated for the entire trial.

Figure 18:
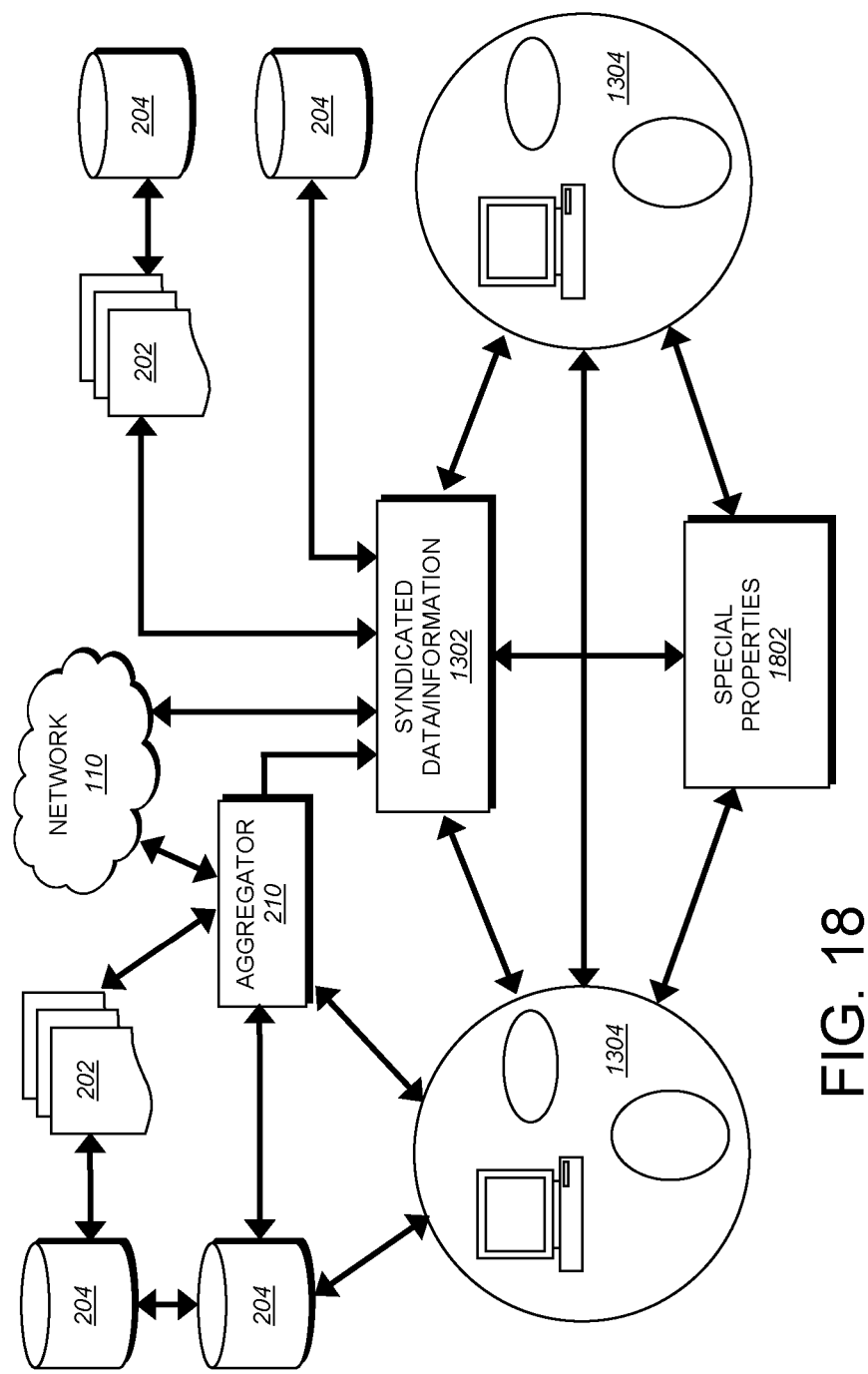
FIG. 18 shows a syndication environment including special properties.

Referring to FIG. 18, the syndicated data/information 1302 may be syndicated evidence-based information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with infrastructure 1702 the syndicated data/information 1302. The users 1304 may also interact with each other. The syndicated data/information 1302 may be associated with special properties 1802. The special properties 1802 may, for example, relate to formatting, display, identification, de-identification, transactions, restricted access and/or conditional access, or other properties or characteristics of syndicated content as described herein. In certain embodiments the arrows of FIG. 18 may be data feeds, such as data feed 202.

In embodiments, healthcare institutions may interact with syndicated data regarding the occurrence and details of adverse events within an institution to enable an institution to continually update its morbidity and mortality data via syndicated data obtained through an RSS feed 202, web feed, RSS stream, or RSS channel. In embodiments, syndicated data regarding the occurrence and details of adverse events within an institution may be plotted, displayed, analyzed, or the like and distributed to an RSS-enabled client. In one aspect, the data may be published in its analyzed form. In another aspect, the data may be published in raw form for analysis and display with a client-side application.

In embodiments, syndicated data regarding the occurrence and details of adverse events within an institution may be plotted, displayed, analyzed, or the like. The processed data may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like. In one aspect, the data may be published in its analyzed form. In another aspect, the data may be published in an unprocessed form for analysis and display with a client-side application.

In embodiments, the RSS feed 202, web feed, RSS stream, or RSS channel used to present syndicated data regarding the occurrence and details of adverse events within an institution may be associated with an aggregator 210 to track updates.

In embodiments, the RSS feed 202, web feed, RSS stream, or RSS channel used to present syndicated data regarding the occurrence and details of adverse events within an institution may be associated with a content management system that may provide summaries of the syndicated data available, dates associated with the syndicated data, links to access the full, non-summarized data, and the like. The content management system may be deployed within an enhanced syndication system using, for example, the security, semantic processing, infrastructure, and other components of the architecture described above with reference to FIG. 4.

In embodiments, healthcare institutions may interact with syndicated data regarding the occurrence and details of adverse events within an institution through the use of an application 406 that provides social networking. For example, through social networking an institution may be able to communicate and share syndicated data with other healthcare institutions with whom the institution shares patient populations, clinical specialties, clinical population types, and the like. The clinical factors of relevance to institutions who seek to share syndicated data may be identified with detailed tags or other metadata that provides narrowly tailored RSS feeds 202, web feeds, RSS streams, or RSS channels for ongoing data sharing. It will be understood that an institution may optionally publish a relatively large number of feeds, each with a narrow semantic domain, or a relatively small number of feeds with suitable metadata or tagging for a subscribing institution to filter the feeds effectively. Such a process may allow institutions who care for similar patient populations to aggregate data for more robust analysis.

In embodiments, healthcare institutions may interact with syndicated data regarding the occurrence and details of adverse events within an institution through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding the occurrence and details of adverse events within an institution through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image. Data regarding adverse events may be captured in graphical form, for example as a digital photograph of a wound resulting from a malfunctioning grounding pad, or a wound resulting from a surgical infection. A media viewer may include a comparator program, so that differences in digital images may be identified. For example, the changes in a wound across time may be monitored so that its healing progress may be monitored and correlated with its severity. A malfunctioning grounding pad that causes a slowly-healing deep second degree burn, for example, poses a greater hazard than a similar device that causes a less severe second degree burn that heals rapidly. Relating sequential digital images to each other with a comparator program may permit the tracking of adverse events.

In embodiments, healthcare institutions may interact with syndicated data regarding the occurrence and details of adverse events within an institution through the use of an application 406 providing vertical market integration.

Referring again to FIG. 13, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding the occurrence and details of adverse events within an institution using one or more database functions that may permit the data quality to be verified, provide for transformation of the data, enable searching, filtering, or clustering the patient data, or categorizing the data into hierarchies, interrelationships, interrelated groups, and the like. Data collected for medical recordkeeping, for example, may be filtered and/or searched to identify adverse events that were not originally catalogued as such. Such database functions may allow for the identification of previously-unrecognized adverse events. For example, the medical records of a series of patients receiving a particular drug may show a transient but significant low white blood cell count that had not been previously associated with administering the drug.

Referring again to FIG. 14, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding the occurrence and details of adverse events within an institution that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like. Abnormalities in blood tests or urine tests may be tagged as designating a particular organ function, for example, so that all tests pertaining to renal function, liver function, cardiac function, and the like, may be identified and aggregated to facilitate identification of adverse events.

Referring again to FIG. 15, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding the occurrence and details of adverse events within an institution to which others may subscribe and/or publish and/or with which others may interact. For example, within an institution all physicians may be able to subscribe to an RSS feed 202, web feed, RSS stream, or RSS channel, "CPR" that regularly updates and retrieves information from across the entire institution on instances of the use of CPR on patients, and which is aggregated with other syndicated data on CPR rates from outside the institution's patient population.

In embodiments, the syndicated data regarding the occurrence and details of adverse events within an institution may be further associated with information that may provide for the management of the data. For example, the aggregated data may list the author of the aggregated data, the date on which it was authored, etc. Thus, the data may provide for further aggregation, republication, and the like. A variety of authors, for example, may contribute syndicated data about a particular adverse event, for example a surgical complication. A surgeon, a nurse and an anesthesiologist may all contribute data to an adverse event file pertaining to post-operative nerve compression syndromes. A physical therapist may contribute additional information pertaining to the recovery of patients who have suffered such injuries. Authorship information may allow management of these contributions as the collection and analysis of data progress.

Referring again to FIG. 16, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding the occurrence and details of adverse events within an institution within an infrastructure 416 that provides for data security, authentication, management of the traffic created by the RSS feeds 202, web feeds, RSS streams, or RSS channels, logging and pinging technology, and/or other communications. The Operating Room supervisor, for example, may desirably be alerted by pinging technology for each adverse event connected to an operating room device. This supervisor, likely a member of the nursing staff, may not have access to data pertaining to surgeon error until after such data have been reviewed in a quality control peer-review setting. Appropriate infrastructure channels and protects such data according to hospital staff "need-to-know" provisions.

Referring again to FIG. 17, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding the occurrence and details of adverse events within an institution that is associated with or contains (such as within metadata) special formatting and/or display properties. In embodiments, healthcare institutions may interact with syndicated data regarding the occurrence and details of adverse events within an institution that is associated with or contains special identification and/or de-identification properties. Such deidentification may permit intra-institutional or inter-institutional researchers to collect data pertaining to adverse events without compromising patient confidentiality and without interfering with institution-based error review procedures. In embodiments, healthcare institutions may interact with syndicated data regarding the occurrence and details of adverse events within an institution that is associated with or contains metadata describing properties allowing for transactional processing. The transactions may be financial transactions, such as related to medical reimbursement and/or subscription fees or other charges for access to the syndicated evidence-based information.

In embodiments, healthcare institutions may interact with syndicated data regarding the occurrence and details of adverse events within an institution that is associated with restricted or conditional access properties. Conditional access may allow researchers access to adverse event data, as described above, while preventing undesirable outsiders similar access. Conditional access may be granted based on certain credentials. Information available via syndication may be restricted to certain classes of data, for example event description without other clinical disclosure, to prevent the information from being used for purposes inconsistent with institutional needs.

Referring again to FIG. 18, the syndicated data/information 1302 may be syndicated information related to adverse events as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service or function, such as the services described above with FIG. 4, that interpret the properties to render or process syndicated content. In certain embodiments the arrows of FIG. 18 may be data feeds, such as data feed 202.

In embodiments, healthcare institutions may interact with syndicated data regarding current standards of clinical care, accreditation standards, and the like obtained through an RSS feed 202, web feed, RSS stream, or RSS channel. In embodiments syndicated data regarding current standards of clinical care, accreditation standards, and the like may be plotted, displayed, analyzed, or the like and distributed to an RSS-enabled client. The data may also, or instead be published in an unprocessed form for subsequent analysis and display using a client-side application.

In embodiments, syndicated data regarding current standards of clinical care, accreditation standards, and the like may be associated with an application 406 consisting of a client-side program. The client-side program may be adapted to operate on client devices such as, a desktop computer, laptop computer, "pocket" personal computer, a cellular phone, Blackberry, personal digital assistant, or other SMS text-enabled device, or the like, and may provide device-specific rendering of syndicated content.

In embodiments, the RSS feed 202, web feed, RSS stream, or RSS channel used to present syndicated data regarding current standards of clinical care, accreditation standards, and the like may be associated with an aggregator 210 to track updates, or otherwise combine, filter, or cluster feeds in any suitable manner for republication. For example, a medical specialty organization may wish to provide updates to its members of clinical best practices or clinical care guidelines.

In embodiments, the RSS feed 202, web feed, RSS stream, or RSS channel used to present syndicated data regarding current standards of clinical care, accreditation standards, and the like may be associated with a content management system that may provide summaries of the syndicated data available, dates associated with the syndicated data, links to access the full, non-summarized data, and the like. The content management system may be deployed within an enhanced syndication system as described above. Standards of clinical care, for example, may be informed by state court case law decisions in medical malpractice cases where the standard of care for a particular medical service was at issue. A state or national medical practice organization (e.g., the Massachusetts Medical Society) may provide syndicated data pertaining to standards of clinical care with links to access the court cases or summaries thereof that are relevant to particular standards.

In embodiments, healthcare institutions may interact with syndicated data regarding current standards of clinical care, accreditation standards, and the like through the use of an application 406 providing social networking. In embodiments, healthcare institutions may interact with syndicated data regarding current standards of clinical care, accreditation standards, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208. A social networking infrastructure may be used for example, to track preferences with respect to alternative treatment methods, to provide user communities according to treatment preferences, or evaluate and communicate trends towards and away from alternative protocols.

In embodiments, healthcare institutions may interact with syndicated data regarding current standards of clinical care, accreditation standards, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding current standards of clinical care, accreditation standards, and the like through the use of an application 406 providing vertical market integration. Clinical best practices, as circulated by a medical specialty organization, for example. may inform the practice of individual physicians, and may also be reviewed and integrated into institutional best practices. A best clinical practice in anesthesiology requiring continuous monitoring of blood oxygen levels may also guide hospital purchasing decisions about acquiring a sufficient number of pulse oximeters for all pre-operative, intraoperative and postoperative patients.

Referring again to FIG. 13, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding current standards of clinical care, accreditation standards, and the like that is associated with database functions that may permit the data quality to be verified, provide for transformation of the data, enable searching, filtering, or clustering the patient data, or categorizing the data into hierarchies, interrelationships, interrelated groups, and the like. A physician within a healthcare institution may use such database functions to search for a standard of care or clinical best practice for an unfamiliar disease, for example. As another example, she may search for a cluster standard of care pertaining to a multifaceted disease process like diabetes.

Referring again to FIG. 14, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding current standards of clinical care, accreditation standards, and the like using semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding current standards of clinical care, accreditation standards, and the like to which others may subscribe and/or publish and/or with which others may interact. Data regarding accreditation standards or standards of clinical care are advantageously made available to a number of decentralized subscribers, for example. As another example, a number of institutions or individuals may publish disclosures of specific illustrations of clinical best practices to fill out a specialty organization's set of guidelines.

In embodiments, the syndicated data regarding current standards of clinical care, accreditation standards, and the like may be further associated with information that may provide for the management of the data. For example, the aggregated data may list the author of the aggregated data, the date on which it was authored, etc. Thus, the data may provide for further aggregation, republication, and the like. In the examples above, authorship information may identify the source of clinical best practice illustrations so that the specialty organization responsible for the overall guidelines may determine the weight to be accorded to any individual contribution.

Referring again to FIG. 16, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding current standards of clinical care, accreditation standards, and the like within an infrastructure 416 that provides for data security, authentication, management of the traffic created by the RSS feeds 202, web feeds, RSS streams, or RSS channels, logging and pinging technology, and/or other communications. Thus, for example, certain data within feeds may be encrypted to restrict access. As another example, access to a feed may be logged to obtain usage data including the popularity of feeds and user data (e.g., by identity, role, affiliation, and so forth).

Referring again to FIG. 17, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding current standards of clinical care, accreditation standards, and the like that is associated with special formatting and/or display properties. In embodiments, healthcare institutions may interact with syndicated data regarding current standards of clinical care, accreditation standards, and the like that is associated with special identification and/or de-identification properties. In one aspect, this may provide anonymity to patients with respect to patient data, or anonymity to users who are accessing syndicated data. In another aspect, this may ensure the identification of a source or user of syndicated data when required, such as for audit purposes, or to inform a patient of a new diagnosis or possible diagnosis suggested by a recently updated standard of clinical care.

In embodiments, healthcare institutions may interact with syndicated data regarding current standards of clinical care, accreditation standards, and the like, that is associated with properties allowing for transactional processing. The transactions may be financial transactions, such as related to medical reimbursement and/or subscription fees or other charges for access to the syndicated evidence-based information. In embodiments, healthcare institutions may interact with syndicated data regarding current standards of clinical care, accreditation standards, and the like that is associated with restricted or conditional access properties. A medical specialty organization may provide syndicated standard of care information only to its members, for example, or only to that subset of members who have paid a subscription fee.

Referring again to FIG. 18, the syndicated data/information 1302 may be syndicated information related to healthcare standards as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be provided by an architecture such as that described above with reference to FIG. 4. In certain embodiments the arrows of FIG. 18 may be data feeds, such as data feed 202.

In embodiments, healthcare institutions may interact with syndicated data regarding clinical practice guidelines, clinical recommendations, clinical discussions, clinical analyses, and the like obtained through an RSS feed 202, web feed, RSS stream, or RSS channel. In embodiments syndicated data regarding clinical practice guidelines, clinical recommendations, clinical discussions, clinical analyses, and the like may be plotted, displayed, analyzed, or the like and distributed to an RSS-enabled client.

In embodiments, syndicated data regarding clinical practice guidelines, clinical recommendations, clinical discussions, clinical analyses, and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like. Such a client-side program and device may permit, for example, the dissemination of clinical information to practitioners in an easy-to-access format. Such a client-side device and program may further permit practitioners to interact with their colleagues about clinical issues, in a format resembling "live chat."

In embodiments, the RSS feed 202, web feed, RSS stream, or RSS channel used to present syndicated data regarding clinical practice guidelines, clinical recommendations, clinical discussions, clinical analyses, and the like may be associated with an aggregator 210 to track updates. Such a system may permit practitioners to access updated information about a particular condition when such information becomes available. A practitioner may subscribe to syndicated data relating, for example, to a clinical condition (e.g., breast cancer), a treatment regimen (e.g., estrogen receptor blockers), or an area of scientific investigation (e.g., genetics of cancer), or an aspect of health care policy (e.g., reimbursement for experimental procedures). Such updates may enhance clinical practice by ensuring that a physician has access to the most current information.

In embodiments, the RSS feed 202, web feed, RSS stream, or RSS channel used to present syndicated data regarding clinical practice guidelines, clinical recommendations, clinical discussions, clinical analyses, and the like may be associated with a content management system that may provide summaries of the syndicated data available, dates associated with the syndicated data, links to access the full, non-summarized data, and the like. A practitioner subscribing to syndicated data about "What's New in Breast Cancer," for example, may receive summaries of the relevant information, accompanied by links to abstracts, full reports or news articles so that he can obtain further information about those items that interest him.

In embodiments, healthcare institutions may interact with syndicated data regarding clinical practice guidelines, clinical recommendations, clinical discussions, clinical analyses, and the like through the use of an application 406 providing social networking. For example, through social networking an institution may be able to communicate and share syndicated data with other healthcare institutions with whom the institution shares patient populations, clinical specialties, clinical population types, and the like. Metadata within syndicated messages may, for example, identify groups, practice areas, or the like to which the message relates. The clinical factors of relevance to institutions that seek to share syndicated data may be expressed in detailed tags that provide narrowly tailored or easily filterable RSS feeds 202, web feeds, RSS streams, or RSS channels for ongoing data sharing. Such a process may allow institutions who care for similar patient populations to aggregate data for more robust analysis.

In embodiments, healthcare institutions may interact with syndicated data regarding clinical practice guidelines, clinical recommendations, clinical discussions, clinical analyses, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding clinical practice guidelines, clinical recommendations, clinical discussions, clinical analyses, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding clinical practice guidelines, clinical recommendations, clinical discussions, clinical analyses, and the like through the use of an application 406 providing vertical market integration. A clinical recommendation that all women over 40 receive annual mammograms impacts individual physicians and their offices, for example, and also becomes relevant to radiologists and their offices, the facilities that house the mammography equipment, and the purchasers who make decisions about obtaining additional mammogram machines.

Referring again to FIG. 13, the syndicated data/information 1302 may be syndicated clinical information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/ other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/ interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding clinical practice guidelines, clinical recommendations, clinical discussions, clinical analyses, and the like that is associated with database functions that may permit the data quality to be verified, provide for transformation of the data, enable searching, filtering, or clustering the patient data, or categorizing the data into hierarchies, interrelationships, interrelated groups, and the like. A physician may use such database functions, for example, in obtaining syndicated data regarding an unfamiliar disease or a multifaceted one like diabetes or hypertension. Database functions in these exemplary situations may allow for obtaining data about aspects of an unfamiliar disease through search functions, or may allow for obtaining information about the many clinical issues that treating a complex disease like diabetes may involve.

Referring again to FIG. 14, the syndicated data/information 1302 may be syndicated clinical information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding clinical practice guidelines, clinical recommendations, clinical discussions, clinical analyses, and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like. Semantic rules may permit a practitioner, for example, to access results from all published clinical trials for a particular product.

Referring again to FIG. 15, the syndicated data/information 1302 may be syndicated clinical information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding clinical practice guidelines, clinical recommendations, clinical discussions, clinical analyses, and the like to which others may subscribe and/or publish and/or with which others may interact. Such syndicated data may be particularly attractive to practitioners, for example, who wish to keep abreast of new developments in a practice area.

In embodiments, the syndicated data regarding clinical practice guidelines, clinical recommendations, clinical discussions, clinical analyses, and the like may be further associated with information that may provide for the management of the data. For example, the aggregated data may list the author of the aggregated data, the date on which it was authored, etc. Thus, the data may provide for further aggregation, republication, and the like. A health care institution, for example a teaching hospital, may publish all of its grand rounds in all its medical specialties and make this information available as syndicated data, for example, "Hospital Grand Rounds This Week." These data may be reaggregated and republished by a CME organization on a specialty-by-specialty basis, along with similar data from other institutions. Such a republication may provide, for example, "Weekly Grand Rounds in Urology," that contains syndicated data derived from the urology grand rounds presented at a number of health care institutions. A practicing urologist may wish to subscribe only to "Weekly Grand Rounds in Urology," as has been reaggregated and republished, while a family practitioner in the community may wish to subscribe to the original syndicated data<"Hospital Grand Rounds This Week," representing the teaching hospital's entire repertoire of grand rounds in every specialty for the week.

Referring again to FIG. 16, the syndicated data/information 1302 may be syndicated clinical information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding clinical practice guidelines, clinical recommendations, clinical discussions, clinical analyses, and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated clinical information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding clinical practice guidelines, clinical recommendations, clinical discussions, clinical analyses, and the like that is associated with special formatting and/or display properties. In embodiments, healthcare institutions may interact with syndicated data regarding clinical practice guidelines, clinical recommendations, clinical discussions, clinical analyses, and the like that is associated with special identification and/or de-identification properties. Individuals participating in clinical discussions, for example, may wish to remain anonymous.

In embodiments, healthcare institutions may interact with syndicated data regarding clinical practice guidelines, clinical recommendations, clinical discussions, clinical analyses, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding clinical practice guidelines, clinical recommendations, clinical discussions, clinical analyses, and the like that is associated with restricted or conditional access properties. Individuals participating in clinical discussions, for example, may need to offer credentials indicating that they are licensed physicians.

Referring again to FIG. 18, the syndicated data/information 1302 may be syndicated clinical information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. In certain embodiments the arrows of FIG. 18 may be data feeds, such as data feed 202.

In embodiments, healthcare institutions may interact with syndicated data regarding clinical processes, clinical interventions, clinical outcomes, clinical personnel, etc. that are part of a quality improvement program, such as total quality management, continuous quality improvement, or the like obtained through an RSS feed 202, web feed, RSS stream, or RSS channel.

In embodiments syndicated data regarding clinical processes, clinical interventions, clinical outcomes, clinical personnel, etc. that are part of a quality improvement program, such as total quality management, continuous quality improvement, or the like may be plotted, displayed, analyzed, or the like and distributed to an RSS-enabled client. The syndicated data may also, or instead contain tags and/or metadata to assist client-side analysis and display.

In embodiments, syndicated data regarding clinical processes, clinical interventions, clinical outcomes, clinical personnel, etc. that are part of a quality improvement program, such as total quality management, continuous quality improvement, or the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding clinical processes, clinical interventions, clinical outcomes, clinical personnel, etc. that are part of a quality improvement program, such as total quality management, continuous quality improvement, or the like may be associated with an aggregator 210 to track updates.

In embodiments, the RSS feed 202, web feed, RSS stream, or RSS channel used to present syndicated data regarding clinical processes, clinical interventions, clinical outcomes, clinical personnel, etc. that are part of a quality improvement program, such as total quality management, continuous quality improvement, or the like may be associated with a content management system that may provide summaries of the syndicated data available, dates associated with the syndicated data, links to access the full, non-summarized data, and the like.

In embodiments, healthcare institutions may interact with syndicated data regarding clinical processes, clinical interventions, clinical outcomes, clinical personnel, etc. that are part of a quality improvement program, such as total quality management, continuous quality improvement, or the like through the use of an application 406 providing social networking. For example, through social networking an institution may be able to communicate and share syndicated data with other healthcare institutions with whom the institution shares patient populations, clinical specialties, clinical population types, and the like. Syndicated content may be filtered or aggregated with other syndicated content according to characteristics of various user communities and groups. The clinical factors of relevance to institutions who seek to share syndicated data may be enhanced with detailed tags to provide narrowly tailored RSS feeds 202, web feeds, RSS streams, or RSS channels for ongoing data sharing, or to enable client-side customization of the presentation of syndicated feeds. Such a process may allow institutions who care for similar patient populations to aggregate and/or filter data for more robust analysis.

In embodiments, healthcare institutions may interact with syndicated data regarding clinical processes, clinical interventions, clinical outcomes, clinical personnel, etc. that are part of a quality improvement program, such as total quality management, continuous quality improvement, or the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208. In one aspect, a feed may contain metadata with recommendations or requirements for display in the user interface 700.

In embodiments, healthcare institutions may interact with syndicated data regarding clinical processes, clinical interventions, clinical outcomes, clinical personnel, etc. that are part of a quality improvement program, such as total quality management, continuous quality improvement, or the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding clinical processes, clinical interventions, clinical outcomes, clinical personnel, etc. that are part of a quality improvement program, such as total quality management, continuous quality improvement, or the like through the use of an application 406 providing vertical market integration.

Referring again to FIG. 13, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding clinical processes, clinical interventions, clinical outcomes, clinical personnel, etc. that are part of a quality improvement program, such as total quality management, continuous quality improvement, or the like is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding clinical processes, clinical interventions, clinical outcomes, clinical personnel, etc. that are part of a quality improvement program, such as total quality management, continuous quality improvement, or the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding clinical processes, clinical interventions, clinical outcomes, clinical personnel, etc. that are part of a quality improvement program, such as total quality management, continuous quality improvement, or the like to which others may subscribe and/or publish and/or with which others may interact.

In embodiments, the syndicated data regarding clinical processes, clinical interventions, clinical outcomes, clinical personnel, etc. that are part of a quality improvement program, such as total quality management, continuous quality improvement, or the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding clinical processes, clinical interventions, clinical outcomes, clinical personnel, etc. that are part of a quality improvement program, such as total quality management, continuous quality improvement, or the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding clinical processes, clinical interventions, clinical outcomes, clinical personnel, etc. that are part of a quality improvement program, such as total quality management, continuous quality improvement, or the like that is associated with special formatting and/or display properties.

In embodiments, healthcare institutions may interact with syndicated data regarding clinical processes, clinical interventions, clinical outcomes, clinical personnel, etc. that are part of a quality improvement program, such as total quality management, continuous quality improvement, or the like that is associated with special identification and/or de-identification properties.

In embodiments, healthcare institutions may interact with syndicated data regarding clinical processes, clinical interventions, clinical outcomes, clinical personnel, etc. that are part of a quality improvement program, such as total quality management, continuous quality improvement, or the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding clinical processes, clinical interventions, clinical outcomes, clinical personnel, etc. that are part of a quality improvement program, such as total quality management, continuous quality improvement, or the like that is associated with restricted or conditional access properties.

Referring again to FIG. 18, the syndicated data/information 1302 may be syndicated quality improvement information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, healthcare institutions may interact with syndicated data regarding its healthcare providers' training history, current credentials, continuing medical education credits, training needs, planned training and the like obtained through an RSS feed 202, web feed, RSS stream, or RSS channel. Present systems may depend on providers submitting documentation of their training history, credentials and CME. Making this information available in a syndicated format may streamline the quality review process that an institution undertakes for any particular provider.

In embodiments, healthcare institutions may interact with syndicated data regarding its healthcare providers' training history, current credentials, continuing medical education credits, training needs, planned training and the like may be plotted, displayed, analyzed, or the like and distributed to an RSS-enabled client.

In embodiments, syndicated data regarding its healthcare providers' training history, current credentials, continuing medical education credits, training needs, planned training and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding its healthcare providers' training history, current credentials, continuing medical education credits, training needs, planned training and the like may be associated with an aggregator 210 to track updates. In this way, for example, an institution may monitor the progress an individual physician is making towards satisfying the CME requirements that pertain to medical relicensure.

In embodiments, the RSS feed 202, web feed, RSS stream, or RSS channel used to present syndicated data regarding its healthcare providers' training history, current credentials, continuing medical education credits, training needs, planned training and the like may be associated with a content management system that may provide summaries of the syndicated data available, dates associated with the syndicated data, links to access the full, non-summarized data, and the like. For example, an institution may access further information about a CME program that a practitioner has completed to keep track of special competencies that individual practitioners are maintaining. A hospital granting an individual operating room privileges for craniofacial surgery may check that individual's training program and CME submissions to be sure that the training program and CME updates are consistent with the scope of surgical privileges granted.

In embodiments, healthcare institutions may interact with syndicated data regarding its healthcare providers' training history, current credentials, continuing medical education credits, training needs, planned training and the like through the use of an application 406 providing social networking. Within an academic department at a medical center, for example, individual physicians may share materials or information from their continuing medical education. As another example, review of such materials may allow medical departments to plan future CME exercises.

In embodiments, healthcare institutions may interact with syndicated data regarding its healthcare providers' training history, current credentials, continuing medical education credits, training needs, planned training and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding its healthcare providers' training history, current credentials, continuing medical education credits, training needs, planned training and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding its healthcare providers' training history, current credentials, continuing medical education credits, training needs, planned training and the like through the use of an application 406 providing vertical market integration. The individual physician and her practice may keep track of credentials and CME, for example, and the hospital may keep track of the same information. Such syndicated data may also be used by the hospital marketing department to identify individuals with particular skills that should be publicized.

Referring again to FIG. 13, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding its healthcare providers' training history, current credentials, continuing medical education credits, training needs, planned training and the like that is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding its healthcare providers' training history, current credentials, continuing medical education credits, training needs, planned training and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding its healthcare providers' training history, current credentials, continuing medical education credits, training needs, planned training and the like to which others may subscribe and/or publish and/or with which others may interact.

In embodiments, the syndicated data regarding its healthcare providers' training history, current credentials, continuing medical education credits, training needs, planned training and the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding its healthcare providers' training history, current credentials, continuing medical education credits, training needs, planned training and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding its healthcare providers' training history, current credentials, continuing medical education credits, training needs, planned training and the like that is associated with special formatting and/or display properties.

In embodiments, healthcare institutions may interact with syndicated data regarding its healthcare providers' training history, current credentials, continuing medical education credits, training needs, planned training and the like that is associated with special identification and/or de-identification properties.

In embodiments, healthcare institutions may interact with syndicated data regarding its healthcare providers' training history, current credentials, continuing medical education credits, training needs, planned training and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding its healthcare providers' training history, current credentials, continuing medical education credits, training needs, planned training and the like that is associated with restricted or conditional access properties.

Referring again to FIG. 18, the syndicated data/information 1302 may be syndicated training and qualification information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, healthcare institutions may interact with syndicated data regarding its healthcare providers' performance, errors, clinical outcomes, resource use, referral patterns, billing history, malpractice history, and the like obtained through an RSS feed 202, web feed, RSS stream, or RSS channel.

In embodiments, healthcare institutions may interact with syndicated data regarding its healthcare providers' performance, errors, clinical outcomes, resource use, referral patterns, billing history, malpractice history, and the like may be plotted, displayed, analyzed, or the like and distributed to an RSS-enabled client.

In embodiments, syndicated data regarding its healthcare providers' performance, errors, clinical outcomes, resource use, referral patterns, billing history, malpractice history, and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding its healthcare providers' performance, errors, clinical outcomes, resource use, referral patterns, billing history, malpractice history, and the like may be associated with an aggregator 210 to track updates.

In embodiments, the RSS feed 202, web feed, RSS stream, or RSS channel used to present syndicated data regarding its healthcare providers' performance, errors, clinical outcomes, resource use, referral patterns, billing history, malpractice history, and the like may be associated with a content management system that may provide summaries of the syndicated data available, dates associated with the syndicated data, links to access the full, non-summarized data, and the like.

In embodiments, healthcare institutions may interact with syndicated data regarding its healthcare providers' performance, errors, clinical outcomes, resource use, referral patterns, billing history, malpractice history, and the like through the use of an application 406 providing social networking. For example, through social networking an institution may be able to communicate and share syndicated data with other healthcare institutions with whom the institution shares patient populations, clinical specialties, clinical population types, and the like. The clinical factors of relevance to institutions that seek to share syndicated data may be published with detailed tags to provide narrowly tailored or easily filtered RSS feeds 202, web feeds, RSS streams, or RSS channels for ongoing data sharing. Such a process may allow institutions who care for similar patient populations to aggregate data for more robust analysis.

In embodiments, healthcare institutions may interact with syndicated data regarding its healthcare providers' performance, errors, clinical outcomes, resource use, referral patterns, billing history, malpractice history, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding its healthcare providers' performance, errors, clinical outcomes, resource use, referral patterns, billing history, malpractice history, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding its healthcare providers' performance, errors, clinical outcomes, resource use, referral patterns, billing history, malpractice history, and the like through the use of an application 406 providing vertical market integration.

Referring again to FIG. 13, the syndicated data/information 1302 may be syndicated performance information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding its healthcare providers' performance, errors, clinical outcomes, resource use, referral patterns, billing history, malpractice history, and the like that is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated performance information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding its healthcare providers' performance, errors, clinical outcomes, resource use, referral patterns, billing history, malpractice history, and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated performance information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding its healthcare providers' performance, errors, clinical outcomes, resource use, referral patterns, billing history, malpractice history, and the like to which others may subscribe and/or publish and/or with which others may interact.

In embodiments, the syndicated data regarding its healthcare providers' performance, errors, clinical outcomes, resource use, referral patterns, billing history, malpractice history, and the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated performance information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding its healthcare providers' performance, errors, clinical outcomes, resource use, referral patterns, billing history, malpractice history, and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated performance information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding its healthcare providers' performance, errors, clinical outcomes, resource use, referral patterns, billing history, malpractice history, and the like that is associated with special formatting and/or display properties.

In embodiments, healthcare institutions may interact with syndicated data regarding its healthcare providers' performance, errors, clinical outcomes, resource use, referral patterns, billing history, malpractice history, and the like that is associated with special identification and/or de-identification properties. Within the health care setting, it may not be possible to collect meaningful data regarding its healthcare providers' performance, errors, clinical outcomes, resource use, referral patterns, billing history, malpractice history, and the like, for example, unless provisions are made for deidentifying it.

In embodiments, healthcare institutions may interact with syndicated data regarding its healthcare providers' performance, errors, clinical outcomes, resource use, referral patterns, billing history, malpractice history, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding its healthcare providers' performance, errors, clinical outcomes, resource use, referral patterns, billing history, malpractice history, and the like that is associated with restricted or conditional access properties. Within the health care setting, for example, collection and distribution of meaningful syndicated data regarding its healthcare providers' performance, errors, clinical outcomes, resource use, referral patterns, billing history, malpractice history, and the like, may require that access to such data be restricted.

Referring again to FIG. 18, the syndicated data/information 1302 may be syndicated performance information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like obtained through an RSS feed 202, web feed, RSS stream, or RSS channel.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like may be plotted, displayed, analyzed, or the like and distributed to an RSS-enabled client.

In embodiments, syndicated data regarding its expenditures for patient care, such as office visits, admissions, outpatient care, medications, surgical interventions, resource utilization, etc. as part of cost-effectiveness research, cost-benefit analyses, and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding its expenditures for patient care, such as office visits, admissions, outpatient care, medications, surgical interventions, resource utilization, etc. as part of cost-effectiveness research, cost-benefit analyses, and the like may be associated with an aggregator 210 to track updates.

In embodiments, the RSS feed 202, web feed, RSS stream, or RSS channel used to present syndicated data regarding its expenditures for patient care, such as office visits, admissions, outpatient care, medications, surgical interventions, resource utilization, etc. as part of cost-effectiveness research, cost-benefit analyses, and the like may be associated with a content management system that may provide summaries of the syndicated data available, dates associated with the syndicated data, links to access the full, non-summarized data, and the like.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like through the use of an application 406 providing social networking. For example, through social networking an institution may be able to communicate and share syndicated data with other healthcare institutions with whom the institution shares patient populations, clinical specialties, clinical population types, and the like. The clinical factors of relevance to institutions that seek to share syndicated data may be published with detailed tags to provide narrowly tailored or easily filtered RSS feeds 202, web feeds, RSS streams, or RSS channels for ongoing data sharing. Such a process may allow institutions who care for similar patient populations to aggregate data for more robust analysis.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like through the use of an application 406 providing vertical market integration.

Referring again to FIG. 13, the syndicated data/information 1302 may be syndicated expenditure information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like that is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated expenditure information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated expenditure information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding its expenditures for patient care, such as office visits, admissions, outpatient care, medications, surgical interventions, resource utilization, etc. as part of cost-effectiveness research, cost-benefit analyses, and the like to which others may subscribe and/or publish and/or with which others may interact.

In embodiments, the syndicated data regarding its expenditures for patient care, such as office visits, admissions, outpatient care, medications, surgical interventions, resource utilization, etc. as part of cost-effectiveness research, cost-benefit analyses, and the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated expenditure information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated expenditure information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like that is associated with special formatting and/or display properties.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like that is associated with special identification properties. Within the health care setting, attention to patient confidentiality, for example, may require deidentifying such data.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding its expenditures for patient care, such as office visits, admissions, outpatient care, medications, surgical interventions, resource utilization, etc. as part of cost-effectiveness research, cost-benefit analyses, and the like that is associated with restricted or conditional access properties. Within the health care setting, for example, collection and distribution of such sensitive data may require that access to such data be restricted.

Referring again to FIG. 18, the syndicated data/information 1302 may be syndicated expenditure information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, healthcare institutions may interact with syndicated data regarding its patient education programs, levels of understanding within its patient population, historical information appropriate to ascertaining a patient's education level and medical understanding, and the like obtained through an RSS feed 202, web feed, RSS stream, or RSS channel.

In embodiments, healthcare institutions may interact with syndicated data regarding its patient education programs, levels of understanding within its patient population, historical information appropriate to ascertaining a patient's education level and medical understanding, and the like may be plotted, displayed, analyzed, or the like and distributed to an RSS-enabled client.

In embodiments, syndicated data regarding its patient education programs, levels of understanding within its patient population, historical information appropriate to ascertaining a patient's education level and medical understanding, and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding its patient education programs, levels of understanding within its patient population, historical information appropriate to ascertaining a patient's education level and medical understanding, and the like may be associated with an aggregator 210 to track updates.

In embodiments, the RSS feed 202, web feed, RSS stream, or RSS channel used to present syndicated data regarding its patient education programs, levels of understanding within its patient population, historical information appropriate to ascertaining a patient's education level and medical understanding, and the like may be associated with a content management system that may provide summaries of the syndicated data available, dates associated with the syndicated data, links to access the full, non-summarized data, and the like.

In embodiments, healthcare institutions may interact with syndicated data regarding its patient education programs, levels of understanding within its patient population, historical information appropriate to ascertaining a patient's education level and medical understanding, and the like through the use of an application 406 providing social networking.

In embodiments, healthcare institutions may interact with syndicated data regarding its patient education programs, levels of understanding within its patient population, historical information appropriate to ascertaining a patient's education level and medical understanding, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding its patient education programs, levels of understanding within its patient population, historical information appropriate to ascertaining a patient's education level and medical understanding, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding its patient education programs, levels of understanding within its patient population, historical information appropriate to ascertaining a patient's education level and medical understanding, and the like through the use of an application 406 providing vertical market integration.

Referring again to FIG. 13, the syndicated data/information 1302 may be syndicated patient education information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding its patient education programs, levels of understanding within its patient population, historical information appropriate to ascertaining a patient's education level and medical understanding, and the like that is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated patient education information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding its patient education programs, levels of understanding within its patient population, historical information appropriate to ascertaining a patient's education level and medical understanding, and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated patient education information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding its patient education programs, levels of understanding within its patient population, historical information appropriate to ascertaining a patient's education level and medical understanding, and the like to which others may subscribe and/or publish and/or with which others may interact.

In embodiments, the syndicated data regarding its patient education programs, levels of understanding within its patient population, historical information appropriate to ascertaining a patient's education level and medical understanding, and the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated patient education information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding its patient education programs, levels of understanding within its patient population, historical information appropriate to ascertaining a patient's education level and medical understanding, and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated patient education information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding its patient education programs, levels of understanding within its patient population, historical information appropriate to ascertaining a patient's education level and medical understanding, and the like that is associated with special formatting and/or display properties.

In embodiments, healthcare institutions may interact syndicated data regarding its patient education programs, levels of understanding within its patient population, historical information appropriate to ascertaining a patient's education level and medical understanding, and the like that is associated with special identification and/or de-identification properties.

In embodiments, healthcare institutions may interact syndicated data regarding its patient education programs, levels of understanding within its patient population, historical information appropriate to ascertaining a patient's education level and medical understanding, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding its patient education programs, levels of understanding within its patient population, historical information appropriate to ascertaining a patient's education level and medical understanding, and the like that is associated with restricted or conditional access properties.

Referring again to FIG. 18, the syndicated data/information 1302 may be syndicated patient education information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, healthcare institutions may interact with syndicated data regarding device failures, external factors involved in errors, system errors, operator errors, and the like obtained through an RSS feed 202, web feed, RSS stream, or RSS channel.

In embodiments, healthcare institutions may interact with syndicated data regarding device failures, external factors involved in errors, system errors, operator errors, and the like and distributed to an RSS-enabled client.

In embodiments, syndicated data regarding device failures, external factors involved in errors, system errors, operator errors, and the like may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to present syndicated data regarding device failures, external factors involved in errors, system errors, operator errors, and the like may be associated with an aggregator 210 to track updates.

In embodiments, the RSS feed 202, web feed, RSS stream, or RSS channel used to present syndicated data regarding device failures, external factors involved in errors, system errors, operator errors, and the like may be associated with a content management system that may provide summaries of the syndicated data available, dates associated with the syndicated data, links to access the full, non-summarized data, and the like.

In embodiments, healthcare institutions may interact with syndicated data regarding device failures, external factors involved in errors, system errors, operator errors, and the like through the use of an application 406 providing social networking.

In embodiments, healthcare institutions may interact with syndicated data regarding device failures, external factors involved in errors, system errors, operator errors, and the like through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, healthcare institutions may interact with syndicated data regarding device failures, external factors involved in errors, system errors, operator errors, and the like through the use of an application 406 associated with a media viewer or directly through a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, healthcare institutions may interact with syndicated data regarding device failures, external factors involved in errors, system errors, operator errors, and the like through the use of an application 406 providing vertical market integration.

Referring again to FIG. 13, the syndicated data/information 1302 may be syndicated failure and error information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, healthcare institutions may interact with syndicated data regarding device failures, external factors involved in errors, system errors, operator errors, and the like that is associated with database functions that may permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be syndicated failure and error information events as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare institutions may interact with syndicated data regarding device failures, external factors involved in errors, system errors, operator errors, and the like that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be syndicated failure and error information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, healthcare institutions may publish and/or subscribe to and/or interact with syndicated data regarding device failures, external factors involved in errors, system errors, operator errors, and the like to which others may and/or publish and/or with which others may interact.

In embodiments, the syndicated data regarding device failures, external factors involved in errors, system errors, operator errors, and the like may be further associated with information that may provide for the management of the data. For example, the aggregated data may list the author of the aggregated data, the date on which it was authored, etc. Thus, the data may provide for further aggregation, republication, and the like.

Referring again to FIG. 16, the syndicated data/information 1302 may be syndicated failure and error information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, healthcare institutions may interact with syndicated data regarding device failures, external factors involved in errors, system errors, operator errors, and the like within an infrastructure 416 that provides for data security, authentication, management of the traffic created by the RSS feeds 202, web feeds, RSS streams, or RSS channels, logging and pinging technology, and/or other communications.

Referring again to FIG. 17, the syndicated data/information 1302 may be syndicated failure and error information as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare institutions may interact with syndicated data regarding device failures, external factors involved in errors, system errors, operator errors, and the like that is associated with special formatting and/or display properties.

In embodiments, healthcare institutions may interact syndicated data regarding device failures, external factors involved in errors, system errors, operator errors, and the like that is associated with special identification and/or de-identification properties.

In embodiments, healthcare institutions may interact syndicated data regarding device failures, external factors involved in errors, system errors, operator errors, and the like, that is associated with properties allowing for transactional processing. The transactions may be financial transactions, such as related to medical reimbursement and/or subscription fees or other charges for access to the syndicated evidence-based information.

In embodiments, healthcare institutions may interact with syndicated data regarding device failures, external factors involved in errors, system errors, operator errors, and the like that is associated with restricted or conditional access properties.

Referring again to FIG. 18, the syndicated data/information 1302 may be syndicated failure and error information as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

An important component of improving a patient's health care experience is providing a medical practice setting that is efficiently and effectively managed. Inefficiencies may frustrate the patient in his or her encounter with the provider, and may increase the costs in time and money to patient and provider alike. For example, inefficient management of a patient's office visits, diagnostic tests and therapeutic procedures may result in wasting the patient's time, delaying appropriate treatments and carrying out interventions without adequate information. Similarly, ineffective management may deprive a patient of needed services or may impose additional costs on patient or provider. For example, ineffective management of relationships with third-party payers may result in delay or denial of approval for medical services, unnecessary out-of-pocket costs to patients, and less-than-appropriate reimbursement to the health care provider.

Efficient and effective medical office management advantageously integrates systems governing the use of time, the flow of information and the organization of business functions. Scheduling a procedure, for example, involves features of time management such as identifying appointment times that fit with the diagnostic plan (e.g., mammogram scheduled before MRI, and both tests completed before biopsy) and that fit with the doctor's, the patient's and the facility's availability. A time management protocol may be advantageously integrated with information management, so that both doctor and patient can access the data derived from a sequence of tests in order to inform subsequent decisions. A time management protocol may also be advantageously integrated with business functions within the office. For example, procedures should be scheduled only when proper approval has been obtained for third-party reimbursement coverage. As another example, patients should have access to information about the economic consequences of scheduling a particular medical procedure (e.g., partial coverage for certain procedures or deductible levels that must be met) before the scheduling takes place.

In the medical practice setting, a number of users from different constituencies participate in time management systems, information management systems and business management systems, increasing the complexity of integrating these systems. For example, doctors, support staff, patients and schedulers may all participate in decisions surrounding time use, along with related institutions such as diagnostic centers and hospitals. As another example, doctors, patients, clinical staff and back office staff may all help direct the flow of health care or practice management information, along with external communities such as medical specialty organizations, patient interest groups and service providers like accountants and lawyers. As a further example, patients, office staff, physicians and third parties are all involved in decisions pertaining to certain business functions, such as obtaining reimbursement for a particular procedure.

In more detail, where reimbursement issues are involved for example, the patient is concerned about whether the procedure will be covered by her health care insurance, and about the amount of her co-pay, while the office staff is concerned about proper diagnosis and procedure coding, and about the claim filing processes that a particular payer requires. The physician, also concerned about accurate coding for diagnosis and treatment, is further concerned about conforming to certain third-party procedures for arranging appropriate coverage for a patient. Before surgery, for example, physicians may need to draft letters to the prospective payer requesting coverage or justifying their treatment decisions, or physicians may need to document their diagnostic findings in a particular way. As will be understood by those of ordinary skill in the art, diagnoses may be identified by numeric codes, for example those provided by the International Classification of Diseases ("ICD") coding systems, most recently revised as ICD-10, by Diagnostic Related Groups ("DRG") codes, and the like, and procedures may be identified by numeric codes, for example those provided by the AMA Current Procedure Terminology ("CPT") coding system and the like. External institutions such as the federal Department of Health and Human Services Centers for Medicare and Medicaid Services ("CMS"), state-based Medicaid organizations, managed care organizations ("MCOs"), health maintenance organizations ("HMOs"), health care insurance indemnity plans and the like may further affect the reimbursement process by enacting changes in coding, in preapproval procedures or in reimbursement schedules. Changes enacted by third parties may materially alter the behavior of patient, physician or office staff with respect to reimbursement-related business functions.

There is a constant interplay among systems and among constituencies in an office-based medical practice. Reimbursement restrictions for a patient may impact, for example, what treatment she elects or which provider she sees. A patient thus may select a provider based on that provider's participation in the patient's health plan. But information management systems within a practice may sway the patient's original, economically-motivated decision. Thus, systems that a practice provides for informing patients about their medical conditions and their treatment options may support a particular patient's decision to seek treatment within that practice, even if those providers are outside her preferred provider network. As another example, information systems may allow a patient to opt for a more cost-effective treatment plan, or a treatment plan that coincides with her health plan's reimbursement restrictions. A physician, similarly, may utilize information systems to learn about the reimbursement impacts of various treatment plans so that she adds an appropriate economic dimension to her discussion of the risks, benefits and alternatives of a particular course of treatment. Reimbursement affects time management, too. A patient may wish to schedule all the stages of a procedure within a calendar year so that she will only have to pay one year's deductible.

Furthermore, communities of users may form loosely around a certain management issue, and dissolve when the issue has resolved. Scheduling an operation commonly involves arranging a number of tests and office visits before surgery, booking time in the operating room, and determining the nature of post-operative inpatient and/or outpatient follow-up. The scheduler bases these arrangements on patient availability, physician availability and resource availability (operating room, intensive care facility, hospital room, personnel, equipment, and the like). The scheduler in the medical office, the patient and the surgeon all form a loose community around the issue of arranging the procedure and its concomitants. After the surgery and related health care appointments and resources are all scheduled, the community may dissolve. If problems in the original schedule arise, the same community may reassemble, or new/different participants may join.

As the examples herein illustrate, a medical practice is an open environment, interacting with various external systems and institutions. Management of these interactions forms an important aspect of running an efficient and effective medical practice. Reimbursement specialists within medical practices, for example, must keep informed about changes in third-party reimbursement regulations or procedures, which may differ among payers and across time. Policy changes in CMS, for example, may likewise impact the reimbursement process within an office. A reimbursement specialist may increase efficiencies in claim processing by having ready and organized access to each payer's policies and procedures. As another example, medical offices and physicians have constant interaction with the external systems comprising the legal system. A multitude of legal rules and regulations affect medical behavior. Reimbursement, governed by diagnosis and procedure codes as mentioned herein, takes place under an overarching legal scheme that strictly penalizes willful inaccuracies and claim fraud. Doctors, office managers and legal advisors all share an interest in conforming the practice's reimbursement-related behavior to this regulatory framework. As yet another example, on-call schedules for physicians belonging to a medical practice must intersect with hospital staff requirements for emergency service coverage. These schedules in turn are designed to be consistent with legal guidelines for medical malpractice risk management.

In certain embodiments, physicians, schedulers, patients, diagnostic facilities, hospitals, treatment centers and the like may interact with medical practice time management systems in a syndicated format via syndicated data obtained through an RSS feed 202, web feed, RSS stream, or RSS channel, to enable more efficient and effective use of time for all constituents within a medical practice setting. The syndicated time management systems may include patient schedules, facility schedules, physician availability, office appointment schedules and the like. Using an enhanced syndication system, each user may periodically publish updated availability as a syndicated feed. Access to each user's feed may be controlled using a conditional access service. An aggregator may gather availability streams from the users and publish an event scheduling feed. This feed may, for example, include periods of common availability, or may include requests for revisions to published availability. In another aspect, each user may derive a daily, weekly, or monthly schedule using the scheduling information within that user's feed, along with any appropriate filters. The schedule may be converted into a useful format for the user, such as a word document, HTML document, or Microsoft Outlook calendar entries. In another aspect, a user may process a scheduling feed to generate and publish a new feed of reminders based upon, for example, user preferences.

In embodiments, the saving, storing, merging, retrieval and publication of syndicated time management information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one, such as an integrated office practice scheduler, and may use proprietary software or commercially available software such as Microsoft Outlook. As an example, a physician may retrieve her schedule for any particular day on her Palm Pilot or Blackberry, with real-time updating.

In embodiments, the RSS feed 202, web feed, RSS stream, or RSS channel used to interact with the syndicated time management systems may be associated with an aggregator 210 to track updates. A scheduler in a medical office, for example, can keep track of changing availability of appointment times in a consultant's office so that she can coordinate a patient's consultation appointment with arranging the tests that the patient needs before he sees the consultant.

In embodiments, the RSS feed 202, web feed, RSS stream, or RSS channel used to interact with syndicated time management systems may be associated with a content management system that may provide summaries of the syndicated data available, dates associated with the syndicated data, links to access the full, non-summarized data, parameters associated with particular scheduling decisions, and the like. For example, an office scheduler who accesses a data summary indicating that a certain consultant is unavailable may retrieve full, non-summarized data that contains information about who will be covering for the consultant in his absence, so that she can select one of the covering physicians to see the patient instead. Alternatively, for example, a patient may access the same data summary and full, non-summarized data about available consultants, and he may perform further research on the consultants before informing the office manager which one(s) would be acceptable. The full, non-summarized data available from the RSS feed 202, web feed, RSS stream, or RSS channel may include, for example, information about each consultant's education and training, areas of specialization, academic affiliations, and publications.

In embodiments, patients, providers, office staff, consultants, hospitals, diagnostic centers, treatment facilities such as operating rooms and interventional radiology suites, and specialized equipment vendors may interact with syndicated time management systems through the use of a RSS-enabled application 406 providing social networking. As an example, an interventional cardiologist who has been consulted for a coronary diagnostic/therapeutic angiography/angioplasty that may involve stent placement may track the temporal progress of a patient's preliminary diagnostic tests to determine when the patient will be ready for the procedure. The office equipment manager may also track the patient's progress through the preliminary tests to be sure that the proper stent will be on hand for the procedure, or that the proper stent is available just-in-time for the anticipated intervention. In like manner, the equipment vendor providing stents may keep track of the cardiologist's inventory and map against upcoming scheduled procedures to be sure that the proper stent is available for each procedure. The cardiologist's office staff may track an as-yet-unscheduled angiography patient's overall temporal progress through his pre-procedure appointments so that the staff allocates time in the angiography suite and arrange physician and nursing availability only after certain preliminary tests have been scheduled and their results obtained. Arranging the angiographic procedure, for example, may be delayed until a radionuclide scan for cardiac function has been performed. The cardiologist's office staff may wish to ensure operating suite availability for emergencies before scheduling an interventional angiography (i.e., one with angioplasty and stent placement). To continue this example, the primary care office staff, in collaboration with the cardiologist's practice management system, may interrogate other syndicated practice time management systems to arrange multidisciplinary follow-up for the angiography patient's cardiovascular disease, including setting up dietician consultations, cardiac rehabilitation exercise programs, concurrent disease management (e.g., diabetes or hypertension education and treatment programs), and the like.

In embodiments, patients, providers, office staff, consultants, hospitals, diagnostic centers, treatment facilities, and specialized equipment vendors may interact with syndicated time management systems through the use of a RSS-enabled application 406 providing a user interface 700 for viewing data, records and the like. For example, a client 102 may, in response to user input such as clicking on a date in a calendar format in the user interface, retrieve the underlying item from the content source 204 as indicated by an arrow 208. The underlying item may include data about a test result for a scheduled diagnostic procedure that has been completed, or tracking information that shows how the data pertaining to a diagnostic test is being "processed." For example, a tissue sample may be provided with a bar code or other identifier that allows it to be tracked through the laboratory. Syndicated information about its path through the laboratory may be available as the sample progresses through the laboratory. A client 102 who clicks on a calendar date in the user interface 700 may learn that the tissue sample obtained on that calendar date was received in the pathology lab on the same date and was examined by the pathologist on the same date by frozen section, but has not yet been examined by permanent section. The user interface 700 may allow the client 102 to follow the sample's progress through the diagnostic process, so that he is notified when the pathologist dictates the final report on the sample, or so that a copy of the pathologist's report is transmitted to the client 102 when available.

In embodiments, patients, providers, office staff, consultants, hospitals, diagnostic centers, treatment facilities and specialized equipment vendors may interact with syndicated time utilization management systems through the use of a RSS-enabled application 406 providing a media viewer. For example, a client 102 who clicks on a calendar date corresponding to the date of a patient's XRay, CT scan, MRI, echocardiogram, angiogram, ultrasound and the like may obtain the corresponding images as still images or as video images. In certain embodiments, the media viewer may include an image management program permitting, for example, three-dimensional reconstruction of images, template planning for prosthetic reconstruction or for hardware construction. An orthopedic technician, for example, may use a template program superimposed upon the media viewer that allows him to order appropriate implants based on diagnostic images of a patient's fracture. As another example, the radiologist using the media viewer to view a mammogram performed on a certain date may access an image database to retrieve the patient's previous mammograms for comparison, and may thereafter compare them electronically through use of a comparator program or algorithm.

As yet another example, a physician who has read the pathology report on a particular tissue sample may click on links to images of the specimen obtained during its microscopic examination. The media viewer for the microscopic images of the specimen may include links to tissue sample reference images so that the physician may compare the specimen image with the image of a normal specimen. An additional program may be available within the media viewer to compare features of the sample with normal histological features to highlight pathological diagnoses, permitting, for example, comparison with the dictated pathology report. In such an example, a diagnostic image-recognition program may point out on the tissue specimen image areas where tumor cells have invaded the tissue itself, or have spread into lymphatics or blood vessels, along with areas where the tumor cells remain within the ducts, all features on the image that are consistent with a dictated pathology report that recites "invasive breast cancer with lymphatic and vascular invasion, accompanied by an extensive intraductal component." A media viewer for a tissue specimen may be adapted for social networking, for example, for patient viewing during consultations where the physician wishes to show the patient the results of her biopsy, or for reviewing a case with colleagues.

In embodiments, patients, providers, office staff, consultants, hospitals, diagnostic centers, treatment facilities, and specialized equipment vendors may interact with syndicated time utilization management systems associated with special formatting and/or display properties. In response to a patient query, for example, data may be formatted to provide a pre-operative and post-operative schedule of appointments pertaining to a surgical procedure that has been arranged. In response to a physician query, data may be formatted to set forth the particular patient's schedule as part of the physician's overall calendar that includes on-call responsibilities, time in the office and time out of the office.

In embodiments, patients, providers, office staff, consultants, hospitals, diagnostic centers, treatment facilities, and specialized equipment vendors may interact with syndicated time utilization management systems having special identification properties, or having restricted or conditional access properties. Controlling access to data within a time utilization management system has particular importance in the medical office management context because of the overarching regulatory requirements of the Health Insurance Portability and Accountability Act of 1996 ("HIPAA"), which sets forth, inter alia, Privacy Rules and Security Rules governing interactions between patients and health care providers. As will be understood by those of skill in the art, the HIPAA Security Rules, while technology-neutral, require an evaluation of the security measures in place for a particular provider or health care facility, an accurate and thorough risk analysis, and a series of documented solutions derived from a number of complex factors unique to that institution. In deciding which security measures to use, a provider or health care facility (both termed "covered entities" in the HIPAA regulations) takes into account its size, the costs of appropriate security measures and their operational impact. For example, covered entities are expected to balance risks of inappropriate disclosure or use of electronically protected health information ("EPHI") against the impact of various security-protective measures, so that smaller, less sophisticated practices will not have to implement as extensive a security system as larger, more complex entities. Security standards under HIPAA are divided into three categories: administrative, physical and technical safeguards. Technical safeguards, in particular, are suitable for integration with an enhanced syndication system that includes a formatting service to format content for display in accordance with security parameters. Technical safeguards may include authentication controls to verify that the person requesting access to EPHI is authorized for such access, and encryption for data being transmitted or stored. An authentication and encryption service may provide selective access to certain data, such as identification on patient health information, or such a service may provide password-protected access to certain data modules.

In embodiments, patients, providers, office staff, consultants, hospitals, diagnostic centers, treatment facilities, and specialized equipment vendors may interact with syndicated time utilization management systems associated with database functions that permit the data quality to be verified, provide for transformation of data, enable searching, filtering or clustering of data, or categorizing the data into hierarchies, interrelationships, interrelated groups and the like. For example, database functions applied to syndicated time utilization management systems may allow for identification of a practice's most commonly performed procedures by collecting data from physician schedules, or for determination of a practice's demographics by collecting data from office visits or de-identified patient records. Such information, in turn, may be used to justify practice resource allocation or marketing strategies. Similarly, database functions applied to syndicated time utilization management systems may provide statistics about procedure outcomes, including length of hospital stay for a particular diagnosis, number of post-operative visits, resources utilized, complications and the like, statistics that are useful within the managed care context for negotiating with carriers.

As another example, syndicated time utilization management systems associated with database functions may facilitate physician credentialing and monitoring of continuing medical education ("CME"). Formal educational sessions like conferences, for example, may be entitled to a particular level of CME credit, and less formal activities (self-study, journal club and the like) may be entitled to a different level of CME credit. Medical license renewal may require a designated number of credit hours at each level. Hospital or operating facility credentialing may require a designated number of credit hours pertaining to particular topics, or may require documentation of a particular number of procedures performed. A syndicated time utilization management system may permit the physician to log all CME-related activities in a database so that the activities may be sorted by type of CME activity (course, workshop, grand rounds, journal review, article-writing, teaching, etc.), by medical topic (infectious diseases, primary care, general surgery, risk management, medical economics), or by any other desirable parameter. The syndicated time utilization management system may then allow sorted information to be retrieved, for example, by physicians cataloguing their own experience for credentialing, license renewal or malpractice insurance purposes. The system may further allow information to be retrieved, for example, by interested third parties such as malpractice carriers, hospital credentialing committees, medical specialty organizations, state boards of registration in medicine, and the like.

In embodiments, patients, providers, office staff, consultants, hospitals, diagnostic centers, treatment facilities, and specialized equipment vendors may interact with syndicated time utilization management systems associated with semantic rules that may enable the creation of metadata. Semantic rules 412 may also provide for metadata enrichment, interpretation or translation of syndicated time utilization management systems, as well as permit the creation of knowledge structures (e.g., using OPML) and the use of a dictionary, thesaurus or the like. Use of metadata for syndicated time utilization management systems may permit the retrieval, for example, of all physician encounters with a particular disease entity within a certain time frame. In this way, the collective practice experience with the disease entity can be collected and reported, including patient visits, continuing medical education conferences, journal club articles and the like. Such information may be useful as an adjunct to risk management, for physician self-education, or as a basis for practice marketing.

In embodiments, patients, providers, office staff, consultants, hospitals, diagnostic centers, treatment facilities, and specialized equipment vendors may interact with syndicated time utilization management systems to which others may subscribe. For example, within a medical practice all physicians may be able to subscribe to an RSS feed 202, web feed, RSS stream or RSS channel that sets forth the office schedule, on-call schedule and prospective out-of-office plans for each physician so that this information can guide them in making plans for attending conferences, setting up complicated operations that require multi-physician coverage, or arranging family vacations. As another example, all physicians within a practice may be able to subscribe to an RSS feed 202, web feed, RSS stream or RSS channel that displays parameters of physician workload and/or performance.

In embodiments, the time management systems may be associated with information that may provide for further processing and management of the data. For example, the data may list the time management system source, the date on which it was last updated, etc. Thus, the data may provide for further aggregation, republication and the like.

In embodiments, patients, providers, office staff, consultants, hospitals, diagnostic centers, treatment facilities, and specialized equipment vendors may interact with syndicated time utilization management systems within an infrastructure 416 that provides for data security, authentication, management of the traffic created by the RSS feeds 202, web feeds, RSS streams, or RSS channels, logging and pinging technology, and/or other communications. Such an infrastructure may permit patient notification when test results are available, for example, by a pinging system. Similarly, a patient who is awaiting an opening in a busy practice schedule may be pinged to alert her to access the time utilization management system and reserve the open slot. If she does not respond in time, and the slot becomes filled, another message or ping may be sent to alert her that the opening is no longer available. As another example, the infrastructure may correlate physician CME activities with various regulatory requirements, to track the physician's progress in accumulating CME credits and map it against the timeframe within which such credits should be accumulated. The physician may then receive a message indicating that his CME progress has fallen off-track, so that he can take steps to acquire the necessary credits.

In embodiments, patients, physicians and/or support staff personnel or supporting healthcare institutions may interact with syndicated information management systems via syndicated data obtained through an RSS feed 202, web feed, RSS stream, or RSS channel, to enable more efficient and effective use of information for all constituents within a medical practice setting. The syndicated information management systems may include medical record data, virtual patient management data, patient input or output data, tracking data and the like. The syndicated information management systems may employ any of the functions and features of the enhanced syndication system described above, including security, conditional access, traffic management, logging, semantic analysis, database services, and so forth. In one aspect, a syndicated information management system as disclosed herein may provide the functionality of an enterprise content management system using syndicated content and outlines delivered through the enhanced syndication system.

In embodiments, the saving, storing, merging, retrieval and publication of syndicated information management information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one for the input and management of medical information. As an example, a client-side program and device may permit input of medical information obtained during off-site patient encounters, such as examinations performed or treatment plans formulated during hospital rounds. This information may be made available in the office-based official medical record, and it may be retrieved by practitioners in the medical practice, or by other practitioners (within the hospital setting, for example) who subscribe to the medical practice's syndicated information management system.

In embodiments, the RSS feed 202, web feed, RSS stream, or RSS channel used to interact with the syndicated information management systems may be associated with an aggregator 210 to track updates. In this way, medical information may be collected chronologically, as patient-related data (test results, reports and the like) and management decisions evolve over time. In this way, for example, changes in a patient's treatment plan may be tracked and updated over time, so that a patient, a physician or a third party such as an emergency room or a commercial pharmacy may retrieve the patient's current medication schedule.

In embodiments, the RSS feed 202, web feed, RSS stream, or RSS channel used to interact with syndicated information management systems may be associated with a content management system that may provide summaries of the syndicated data available, dates associated with the syndicated data, links to access the full, non-summarized data, parameters associated with medical information, and the like. In certain embodiments, the content management system may include a proprietary program for developing and maintaining electronic medical records. A content management system as applied to prescribing medications, for example, may include with each prescription the physician package insert, a patient-friendly summary of the package insert, a list of other medications that the patient is taking, a database and algorithm for identifying conflicts among prescribed medications, a patient-customized schedule for when to take medications (before meals, with food, at bedtime, etc.), and the like. It will be understood by practitioners of ordinary skill that a variety of content management systems may be advantageous, for example in caring for patients with complex disorders with multiple medications (e.g., HIV, diabetes, cancers, etc.).

In embodiments, patients, physicians and/or support staff personnel or supporting healthcare institutions may interact with syndicated information management systems through the use of a RSS-enabled application 406 providing social networking. As an example, a consultant may retrieve and share syndicated data with other healthcare providers with whom she shares care for a patient, a clinical specialty, clinical population type, and the like. Clinical factors of relevance to physicians who seek to share medical information may use detailed tags to provide narrowly tailored RSS feeds 202, web feeds, RSS streams, or RSS channels for ongoing data sharing with colleagues. Such a process may allow physicians who care for a common patient or patient population to share data more efficiently and to improve cross-specialty collaboration in patient care. With a syndicated information management system, a visit by a particular patient to a consultant and any associated data becomes available to the primary care physician for retrieval via RSS feed 202, web feed, RSS stream, or RSS channel without the delay associated with paper records or specifically-delivered electronic communications (faxes, emails and the like). Such systems may permit virtual case management for a particular patient.

With a syndicated information management system, a patient's interactions with providers outside the medical practice may be seamlessly integrated into an overall patient management protocol. An orthopedist's operative notes and office visit records, for example, may be available to the physical therapist or visiting nurse who is providing post-operative care; similarly, the orthopedist may retrieve via RSS feed 202, web feed, RSS stream, or RSS channel those notes produced by the therapist or visiting nurse pertaining to the post-operative care of the patient. Tags attached to the notes may alert the physician to situations where the outside provider observes a deviation from the physician's treatment plan or a deviation from normal progress milestones, so that the physician may take appropriate measures.

A syndicated information management system may, for example, permit a medical practice to establish a comprehensive home monitoring program. The physician may provide a treatment plan with specific elements available to particular providers in the community. Such providers may also retrieve patient data that is relevant to their role in patient care. A physical therapist, for example, would need different patient information than a dietician or a social worker. Different patient care roles may correspond to different security levels or access routes within the syndicated information management system.

A syndicated information management system may further provide for communications from a patient via email or other electronic submissions. Email correspondence from a patient may be tagged with identifiers that indicate its subject matter, level of urgency, and the like. The email correspondence may be triaged to the appropriate respondent, whether physician, nurse, office manager, physical therapist, etc. A syndicated information management system may include other input from the patient, such as a logbook of symptoms (e.g., angina experienced at 6 AM, 10 AM and 3 PM on Dec. 10, 2005), a record of data (e.g., Dec. 10, 2005 weight, blood pressure and dietary intake), a record of health-maintenance activities (e.g., Dec. 10, 2005 cardiac exercise class 1.0 hours, brisk walking 0.5 hours, resistance exercises 0.5 hours, yoga 1.0 hours), and the like, allowing providers to review the patient's participation in or compliance with treatment plans.

In embodiments, patients, physicians and/or support staff personnel or supporting healthcare institutions may interact with syndicated information management systems through the use of an application providing a media viewer. For example, a RSS item may refer to an image source, such as an MRI image in the medical record from a hospital, and may specify a viewer for the source image that is available through the registry. In operation, a client with appropriate permissions may view the image (also as managed, e.g., through the metadata for the enhanced syndication system), may retrieve the appropriate viewer service from the registry and may apply the viewer to view the source image. For example, a physical therapist may retrieve a patient's XRays or MRIs before instituting a therapy protocol. As another example, a visiting nurse may capture images of a healing wound that the physician can retrieve to track a patient's progress. When images are captured using a stable or calibrated image scale, they may be compared over time to determine whether a wound is getting better or worse. A visiting nurse or a patient may also capture digital video images, digital audio, diagnostic instrument output and the like as real-time or archived data. A patient experiencing a worrisome symptom, for example, may transmit real-time data via webcam to a physician who may then use the data as a basis for diagnosis or treatment. Those of ordinary skill in the art are familiar with a variety of instruments for professional or home care (digital otoscopes, ophthalmoscopes, blood pressure monitors etc.) that are suitable for these purposes. Such tools for image capture and for digital data capture in the community setting may permit patient monitoring and patient care to be carried out remotely.

A syndicated information management system may further provide for communications to a patient via email or other electronic means. For example, a surgeon's office may provide descriptive information or instructions regarding an operation or post-operative care for retrieval via RSS feed 202, web feed, RSS stream, or RSS channel. Such information or instructions may involve documents, audible instructions, graphics, still images, emails, live chat or video clips. For example, a patient with questions about how to apply a surgical dressing or how to carry out a particular physical therapy exercise may download a video that illustrates performing the technique. As another alternative, the patient may interact with a health care provider (e.g., nurse or therapist) via live chat or via email to have specific questions answered. Advantageously, interactions with the syndicated information management system may be logged, recorded and permanently archived for medicolegal purposes, or may be incorporated in the patient's medical record.

As another example, a syndicated information management system may permit patients to interact with other patients or healthcare providers via RSS feed 202, web feed, RSS stream or RSS channel to obtain or exchange information about a particular procedure or medical condition. As described herein, HIPAA and other regulatory frameworks may require special identification properties, or restricted or conditional access properties for information to be exchanged in this way. Interactions with the syndicated medical information management system and the properties restricting this access may be logged, recorded and permanently archived for legal purposes or to demonstrate compliance with applicable regulations.

In embodiments, patients, physicians and/or support staff personnel or supporting healthcare institutions may interact with syndicated information management systems through the use of an application providing a user interface 700 for viewing information related to a particular health-care issue. For example, a customized user interface may be available to a patient about to undergo a particular procedure, so that she can readily access her medical records and test results, can review post-operative instructions and discuss them with office personnel via live chat, can obtain further procedure-specific information from the practice patient education library, and can interact with other patients who have consented to participate in procedure-related discussions. A client 102 may, in response to user input such as clicking on a title of an item in the user interface 700, retrieve the underlying item from the content source 204 as indicated by the arrow 208.

For example, a user interface 700 captioned with the particular procedure ("My Angioplasty") may be designed with icons or other graphic designators that facilitate patient access to relevant information. Within the interface site, a patient may click, for example, on a "My Diagnosis" icon to view all test results, with a query button ("What does this mean?") to provide a patient-friendly explanation. The interface may offer a search function or a general query function, so that a patient may easily find answers to questions about when a particular pre-op procedure is scheduled, for example, or what articles he will need to bring with him to the hospital. A patient may also follow a logical path through angioplasty-related information that could be represented graphically on the interface. A clickable image may display a timeline pertaining to the patient's illness, for example, allowing retrieval of information pertaining to steps in symptom development, diagnosis, treatment or recovery. A timeline showing all the salient dates so far in a patient's illness may begin, for example, with Sunday, Jan. 1, 2006 and include dates through Friday, Jan. 20, 2006. Clicking on the "Sunday, Jan. 1, 2006" segment of the timeline may display information pertaining to the patient's onset of cardiac symptoms, his presentation in the emergency room, and the initial diagnostic evaluation and therapeutic intervention performed on that day. Clicking on the "Friday, Jan. 20, 2006" segment of the timeline may display information pertaining to the patient's definitive procedure, for example, the angioplasty scheduled for that day. As another approach to the same information, the patient may click on an icon called "My Diagnosis" or "My Treatment" to access a page providing, for example, chronological listing of diagnostic procedures and their results, or a listing of treatment interventions, their reasons, their outcomes and their follow-up. Clickable links on any given page may permit ready navigation throughout the interface In embodiments, patients, physicians and/or support staff personnel or supporting healthcare institutions may interact with syndicated information management systems through the use of an application providing vertical market integration. Vertical market integration may proceed in a top-down or bottom-up way. For example, as managed care organizations or prescription drug benefits plans alter their formularies, this information may be provided top-down to physicians caring for the affected patient populations (covered lives of a managed care organization, or Medicare recipients, for example). Physicians then may use formulary information in their prescribing decisions. Along the same lines, if physicians in a practice consistently prescribe a drug that is not included in the formulary, compiling information about the drug's indications and clinical efficacy may be submitted bottom-up to managed care organizations and the like to support including that drug in future formulary listings.

In embodiments, patients, physicians and/or support staff personnel or supporting healthcare institutions may interact with syndicated information management systems that support special formatting and/or display properties of syndicated content. Formatting and display properties may, for example, be embedded in metadata associated with a syndicated feed.

In embodiments, patients, physicians and/or support staff personnel or supporting healthcare institutions may interact with syndicated information management systems that support use of special identification properties, which may be used, for example, to provide personalization, depersonalization, access control, privacy, security, HIPAA compliance, and so forth.

In embodiments, patients, physicians and/or support staff personnel or supporting healthcare institutions may interact with syndicated information management systems that are associated with restricted or conditional access properties. A medical practice may accumulate information about outcomes from a particular procedure on a patient-by-patient basis, for example, including length of hospital stay, complications and other sequelae. Such information may be available with patient identifiers to physicians within the practice, but may not be accessible to other health care institutions except on a de-identified basis. The practice may decide not to allow the general population of patients access to such information at all, or may only grant patients or prospective patients access to certain aspects of the information, for example statistics about length of hospital stay or statistics about incidence of complications.

In embodiments, patients, physicians and/or support staff personnel or supporting healthcare institutions may interact with syndicated information management systems associated with database functions that permit the data quality to be verified, provide for transformation of data, enable searching, filtering or clustering of data, or categorizing the data into hierarchies, interrelationships, interrelated groups and the like. For example, database functions applied to syndicated information management systems may allow an individual to search for information that a practice has accumulated regarding a particular surgical procedure. Such information may include the practice's pre- and post-operative protocols, the number of procedures each physician has performed within the practice, statistics regarding procedure outcomes, contact information for other patients who have agreed (following proper informed consent) to act as resources for others undergoing the procedure, patient satisfaction data, and the medical and scientific publications and references that the practice has accumulated pertaining to the procedure. Access to such information may be regulated by restricted or conditional access properties, limiting such access to certain patient populations (for example, those who have scheduled the procedure already), or to certain categories of healthcare personnel.

In embodiments, patients, physicians and/or support staff personnel or supporting healthcare institutions may interact with syndicated information management systems associated with semantic rules that enable, for example, the creation of metadata. Semantic rules 412 may also provide for metadata enrichment, interpretation or translation of syndicated information management systems, as well as permit the creation of knowledge structures (e.g., using OPML) and the use of a dictionary, thesaurus or the like. Use of metadata for syndicated information management systems may permit, for example, the accumulation, organization and compilation of procedure-related information such as procedure outcome, adverse events, duration of hospitalization, number of post-operative visits and other parameters of physician performance and practice resource utilization. Such compilations may provide support for economic decisions within the practice, for physician credentialing or for negotiations with malpractice carriers or third-party payers.

In embodiments, patients, physicians and/or support staff personnel or supporting healthcare institutions may interact with syndicated information management systems to which others may subscribe. For example, all patients within a medical practice may be able to subscribe to an RSS feed 202, web feed, RSS stream or RSS channel that regularly retrieves and updates information the practice provides pertaining to a particular diagnosis or procedure, and that collects for the patient publicly available information on the same topic. Physicians in a particular practice setting may subscribe to an RSS feed 202, web feed, RSS stream or RSS channel that regularly retrieves and updates information pertaining to particular scientific, medical or socioeconomic topics (e.g., a neurologist may wish to retrieve scientific information pertaining to stem cells, medical information pertaining to treatment of Parkinson's disease (including using stem cells in such treatment), and socioeconomic information about the ethics of using stem cells and the legislative debate regarding their availability for research and therapy).

In embodiments, the information management systems may be further associated with information that may provide for the management of the data. For example, the data may list the information management system source, the date on which it was last updated, etc. Thus, the data may provide for further aggregation, republication and the like. A surgeon who has performed a series of successful operations, for example, may publish the series through the syndicated information management system so that other subscribing surgeons in the specialty may learn from her experience. While such publication does not provide the quality control of a peer-reviewed medical journal, it may offer practitioners more immediate access to developments in an area of specialization.

In embodiments, patients, physicians and/or support staff personnel or supporting healthcare institutions may interact with syndicated information management systems within an infrastructure 416 that provides for data security, authentication, management of the traffic created by the RSS feeds 202, web feeds, RSS streams, or RSS channels, logging and pinging technology, and/or other communications. Such an infrastructure may, for example, provide for patient alerts when new information becomes available or when deadlines are nearing. As an example, a practice may alert all its Medicare patients when an update on Medicare Part D coverage becomes available, either through the practice itself or through a reliable outside source. Further, the infrastructure may include reminders or countdowns as deadlines approach. Medicare patients who have not selected a prescription drug program may be reminded periodically as the deadline approaches, until they make their selection. Or, as another example, a patient who needs to avoid eating and drinking ("NPO") for a period before a procedure can be offered a "countdown" notification during the hours before the NPO restriction begins.

In embodiments, patients, physicians and/or support staff personnel or supporting healthcare institutions, and third-parties such as payers, billing services, medical specialty organizations, service providers and the like, may interact with syndicated business management systems via syndicated data obtained through an RSS feed 202, web feed, RSS stream, or RSS channel, to enable more efficient and effective use of business functions for all constituents within a medical practice setting. As used herein, an individual or entity having a business relationship with the health care practice, such as those individuals and entities listed herein, may be considered a business associate of the health care practice. The syndicated business management systems may include managed care coverage schedules, third-party reimbursement schedules, accounting and financial management systems, billing and collection systems, cost projection systems, economic analysis systems and the like. Business management systems may rely upon proprietary or commercially available software, and may utilize all types of syndicated data.

In embodiments, the saving, storing, merging, retrieval and publication of syndicated information management information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one for the input and management of business, financial or economic data. The client-side program may also be provided by a third party, for example, a proprietary accounting program that has been prepared for the medical office by an accountant or consultant. As another example, medical specialty societies may provide practice management programs that are particularly useful to practitioners in a certain field. Cosmetic surgery, dermatology, etc. practices with a high volume of cash-paying patients may find certain software advantageous, while Medicare or Medicaid-dominated specialties may find other types of software advantageous.

In embodiments, the RSS feed 202, web feed, RSS stream, or RSS channel used to interact with the syndicated business management systems may be associated with an aggregator 210 to track updates. In this way, business-related information may be collected chronologically, as reimbursement schedules change over time, for example, or as components (e.g., rent, utilities, equipment costs, insurance charges etc.) of a practice's cost structure change. In this way, for example, a practice's income and expense projections can be updated to take changing assumptions into consideration.

In embodiments, the RSS feed 202, web feed, RSS stream, or RSS channel used to interact with syndicated business management systems may be associated with a content management system that may provide summaries of the syndicated data available, dates associated with the syndicated data, links to access the full, non-summarized data, parameters associated with business information, and the like. Business management systems may draw from other sources of syndicated data, so that they may provide customized information for a query. For example, a patient with a new diagnosis of breast cancer may wish to compare the costs, time expenditures and medical outcomes associated with two available treatment modalities (e.g., mastectomy vs. wide excision with radiation). Business management systems together with time utilization management systems and information management systems may provide the customized answers to the patient queries.

In embodiments, patients, physicians and/or support staff personnel or supporting healthcare institutions, and third-parties such as payers, billing services, medical specialty organizations, service providers and the like, may interact with syndicated business management systems through the use of a RSS-enabled application 406 providing social networking. The business manager may prepare a monthly budget, for example, in collaboration with the practice accountant. The budget may be integrated with an inventory management system that keeps track of supplies and instruments that are on hand. Other members of the office staff may then view the budget, the inventory tracker and an ongoing tabulation of practice expenses to make decisions about purchasing supplies or capital equipment.

In embodiments, patients, physicians and/or support staff personnel or supporting healthcare institutions, and third-parties such as payers, billing services, medical specialty organizations, service providers and the like, may interact with syndicated business management systems through the use of an RSS-enabled application 406 providing a user interface for viewing data, records, and the like. For example, a client 102 may, in response to user input such as clicking on a title of an item in the user interface 700, retrieve the underlying item from the content source 204 as indicated by an arrow 208. For example, a user interface 700 may be tailored to the needs of a back-office accounts manager to look up the status of insurance claims processing for a set of patients, or a user interface 700 may be set up to allow the patient to track the status of coverage approval for an upcoming procedure.

In embodiments, patients, physicians and/or support staff personnel or supporting healthcare institutions, and third-parties such as payers, billing services, medical specialty organizations, service providers and the like, may interact with syndicated business management systems through the use of an application providing a media viewer.

In embodiments, patients, physicians and/or support staff personnel or supporting healthcare institutions, and third-parties such as payers, billing services, medical specialty organizations, service providers and the like, may interact with syndicated business management systems associated with special formatting and/or display properties. Certain accounting information, for example, may be converted into graphic representations that the user could retrieve.

In embodiments, patients, physicians and/or support staff personnel or supporting healthcare institutions, and third-parties such as payers, billing services, medical specialty organizations, service providers and the like, may interact with syndicated business management systems associated with special identification properties. In embodiments, patients, physicians and/or support staff personnel or supporting healthcare institutions, and third-parties such as payers, billing services, medical specialty organizations, service providers and the like, may interact with syndicated business management systems associated with restricted or conditional access properties. Certain members of the office staff, such as the business manager, may have access to all business management information, while other members of the office staff have only limited access. Similarly, individual physicians may be able to track the progress of insurance coverage decisions for their own patients, but may not be able to view information about other patients in the practice. The practice accountant, for example, may be able to retrieve all financial and resource utilization data, without access to identifiable patient data.

In embodiments, patients, physicians and/or support staff personnel or supporting healthcare institutions, and third-parties such as payers, billing services, medical specialty organizations, service providers and the like, may interact with syndicated business management systems associated with database functions that permit the data quality to be verified, provide for transformation of data, enable searching, filtering or clustering of data, or categorizing the data into hierarchies, interrelationships, interrelated groups and the like. For example, database functions applied to syndicated business management systems may allow a practice manager to compile information about the resources expended in treating a particular condition, or about the resource utilization of a particular physician. A certain condition, for example, diabetes, may be more expensive to treat, while other conditions, such as an acute infectious disease, may be less expensive to the practice. Decisions about how to grow the practice may be based in part on data about the costliness or the profitability of a particular practice area. Such information could also guide hiring decisions, such as whether to hire a diabetes specialist or an infectious diseases doctor, or whether to hire additional nursing personnel for a certain area of the practice. Similarly, data about outcome and resource utilization may be collected to determine the efficiency and profitability of a particular physician. Such information could guide decisions about compensation, promotion and overall practice development.

In embodiments, patients, physicians and/or support staff personnel or supporting healthcare institutions, and third-parties such as payers, billing services, medical specialty organizations, service providers and the like, may interact with syndicated business management systems associated with semantic rules that may enable the creation of metadata. Semantic rules 412 may also provide for metadata enrichment, interpretation or translation of syndicated information management systems, as well as permit the creation of knowledge structures (e.g., using OPML) and the use of a dictionary, thesaurus or the like. Use of metadata for syndicated business management systems may permit, for example, the accumulation, organization and compilation of diagnosis-related information such as reimbursement amount for each third-party payer, length of time before reimbursement, practice resources consumed, number of patients with the diagnosis within the practice, demographic information about the incidence of the diagnosis, and other diagnoses associated with the primary diagnosis. Such compilations may allow for economic projections pertaining to the primary diagnosis, including income projections, expense projections and practice development projections.

In embodiments, patients, physicians and/or support staff personnel or supporting healthcare institutions, and third-parties such as payers, billing services, medical specialty organizations, service providers and the like, may interact with syndicated business management systems to which others may subscribe. A billing service may, for example, access the procedure and reimbursement information for a medical practice and send bills such as balance bills to patients as appropriate.

In embodiments, the information management systems may be further associated with information that may provide for the management of the data. For example, the data may list the information management system source, the date on which it was last updated, etc. Thus, the data may provide for further aggregation, republication and the like. An accountant or consultant specializing in medical practices, for example, may aggregate information from a number of practice clients to identify trends among the client population, and to allow the individual practice clients to compare themselves to the larger population of medical practice clients. The accountant or consultant may further compare the group of practice clients with larger trends in the profession, and share these comparisons with the individual clients.

In embodiments, patients, physicians and/or support staff personnel or supporting healthcare institutions, and third-parties such as payers, billing services, medical specialty organizations, service providers and the like, may interact with syndicated business management systems within an infrastructure 416 that provides for data security, authentication, management of the traffic created by the RSS feeds 202, web feeds, RSS streams, or RSS channels, logging and pinging technology, and/or other communications. For example, a business management system may permit automated inventory control, with an automatic restocking order to be generated when a certain number of medical supplies have been used, and with tracking of supply usage. Excess supply utilization may produce an alert for the office manager so that he can investigate the utilization further. An appropriately-credentialed vendor may also monitor usage patterns in the office to facilitate just-in-time provisioning, or to offer volume-related discounts.

While the illustrative embodiments herein have described syndicated time utilization, information and management systems as applied to medical practices and related support personnel and institutions, it will be understood by those of ordinary skill that syndicated time utilization, information and management systems (as well as other disclosure included herein) may also be applied to other health care practices, including but not limited to dental practices, psychotherapeutic practices, cosmeceutical practices, chiropractic practices, osteopathic practices, physical therapy and rehabilitation practices, podiatrist practices and the like. In addition, those of ordinary skill will further appreciate that syndicated time utilization, information and management systems may be applied to alternative, allopathic or nontraditional health care services.

As medical, scientific and other academic research becomes more complex, it is desirable to have many investigators across diverse geographic settings participate in a project. It is also desirable that all participants have access to a complex mix of data sources that may include scientific background information, experimental data, clinical data about disease states or targets, laboratory notes, regulatory requirements and the like. Researchers may collaborate to produce a publication or other report concerning a study and its results. Researchers working together on a project may also interact with third parties (collectively termed "reviewers") who review, evaluate and/or comment upon the research, its data or its conclusions. Seamless communication among collaborating researchers advances scientific progress by making it more efficient. Transparent interaction between the research team and reviewers expedites publication of research results and facilitates decision-making about grants and regulatory approval.

It is desirable, therefore, to provide researchers with access to the internal research data, the external scientific literature, and the real-time discoveries of their collaborators. It is further desirable to allow researchers to collaborate on authoring reports of their research for publication or for submission to reviewing agencies. It is also desirable to permit researchers to interact with interested third parties. Interested third parties may be reviewers, whose interaction with researchers may include feedback or other comments pertaining to the experimental or reporting aspects of the scientific research. Interested third parties may also include other stakeholders such as patients, sponsors or advocacy groups, whose interaction with researchers may keep the stakeholders informed about relevant scientific investigations and may keep the researchers informed about community and industry needs.

In certain embodiments researchers may interact with collaboration management systems in a syndicated format via syndicated data obtained through an RSS feed 202, web feed, RSS stream, or RSS channel, to enable more efficient and effective communication about research endeavors. The syndicated collaboration management systems may include systems for reporting experimental methods and materials, systems for documenting experimental results, systems for analyzing experimental data, systems for designing clinical trials, and the like.

In embodiments, the saving, storing, merging, retrieval and publication of collaboration management system information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one, and may use proprietary software or commercially available software such as Microsoft Outlook. As an example, a researcher at one location may retrieve the experimental data of a collaborating colleague on her Palm Pilot or Blackberry, with real-time updating.

In embodiments, the RSS feed 202, web feed, RSS stream, or RSS channel used to interact with the syndicated collaboration management systems may be associated with an aggregator 210 to track updates. A researcher who is part of a multisite research endeavor, for example, can keep track of the results being obtained by collaborating colleagues at other sites.

In embodiments, the RSS feed 202, web feed, RSS stream, or RSS channel used to interact with collaboration management systems may be associated with a content management system that may provide summaries of the syndicated data available, statistical analysis of the syndicated data, parameters associated with the data collection, or a graphical representation of the syndicated data for example on an experiment-by-experiment basis, on a site-by-site basis, or on an aggregate basis. The content management system may further provide links that direct the user from a data summary to the full, non-summarized data. The full, non-summarized data available from the RSS feed 202, web feed, RSS stream, or RSS channel may include, for example, information about the experiments conducted and the raw data obtained.

In embodiments, researchers may interact with collaboration management systems through the use of a RSS-enabled application 406 providing social networking. As an example, a medicinal chemist involved in drug discovery may wish to review the preclinical research being carried out in his company that pertains to a certain drug or class of drugs. By monitoring the bench or animal research conducted on a particular drug or class of drugs, the chemist may gain insights that would guide his selection of other drug candidates. Collaboration management systems, by facilitating communication among researchers in diverse geographic locations, may inherently involve social networking. Social networking may involve, for example, sharing of a patient or subject population, sharing of a clinical specialty or sharing of a research interest, optionally from different perspectives. As an example, the public health services of a host country may wish to monitor the findings of a research team conducting studying a particular disease or condition that seriously affects that country's population. Availability of a social networking application may, for example, make a clinical trial protocol particularly attractive to a host country where the results could translate directly into improved health for the local citizenry. Social networking may involve, for example, collaboration among researchers, patients, subjects, sponsors, reviewers, overseers, monitors or regulators.

In embodiments, researchers may interact with collaboration management systems through the use of a RSS-enabled application 406 providing a user interface 700 for viewing data, records and the like. For example, a client 102 may keep track of the progress of various research projects by clicking an icon in the user interface to retrieve the underlying item from the content source 204 as indicated by an arrow 208. The underlying item may include clinical or laboratory data obtained by a group of researchers, data pertaining to subjects enrolled in a clinical trial, data about the management of the clinical trial, or scientific and/or business information obtained from academic journals, web postings and the like. For example, a clinical trial subject may be tracked through the clinical trial so that individual experimental results about that subject may be seen. Administrative information pertaining to an individual subject may also be tracked so that the trial organizer can be sure that the appropriate steps have been taken for enrolling and pre-evaluating each trial subject. As an example, a client 102 researcher who clicks on an icon representing a clinical protocol may be able to determine how many patients have been enrolled at which sites, whether the appropriate informed consent has been obtained, whether patient follow-up is proceeding on track, whether certain patients need more individualized follow-up, and the like.

Similarly, a client 102 subject who clicks on an icon representing the protocol in which she is participating may access information governing her participation, including tests or other requirements that she must fulfill, materials generated by the researchers pertaining to the trial or to the condition being studied, communications with other participants and the like. The information associated with the icon may be sourced as a syndicated data stream that may be periodically updated to provide current information.

In embodiments, researchers may interact with collaboration management systems through the use of a RSS-enabled application 406 providing a media viewer. For example, a client 102 who clicks on an icon representing his company's preclinical research on a drug may be able to view images corresponding to pathology results for a set of experimental animals who received the drug. Other images may be viewed in like manner, including photographs, MRI images, CT scans, XRay images, ultrasound, echocardiogram, angiography, and the like, with images captured as still images or as video images. In certain embodiments, the media viewer may include an image management program permitting, for example, three-dimensional reconstruction of images, or other image manipulation. For example, 3-dimensional reconstruction of images may be performed on CT scans from an experimental animal treated with experimental placement of bone fixation plates, allowing researchers to determine how the animal's bone structure responds to the plates. As another example, a pathologist evaluating the histological slides from a series of experimental animals may be able to compare them with each other using an algorithm-based image comparator program. In similar manner, a group of pathologists located at different research centers may be able to access and compare images of the histology of all specimens collected during the research program. The media viewer for the microscopic images of the specimen may include links to tissue sample reference images so that the physician may compare the specimen image with the image of a normal specimen. An additional program may be available within the media viewer to compare features of the sample with normal histological features to highlight pathological diagnoses.

In embodiments, researchers may interact with collaboration management systems through the use of an RSS-enabled application 406 providing vertical market integration. For example, clinicians using a product in a clinical trial or after its approval may be kept informed of developments during laboratory research on that same product. Long-term animal studies performed in the lab on a product like Vioxx, for example, may inform clinicians who are involved in clinical trials so that they may pay particular attention to findings that may not have previously appeared relevant.

In embodiments, researchers may interact with collaboration management systems associated with special formatting and/or display properties. In response to a researcher's query from one clinical trial site, for example, data for her own patients may be personalized while data for other clinical trial patients may be anonymized. As another example, researchers in blinded or double-blinded studies may not be able to view patient information that discloses the treatment regimen each patient is receiving.

In embodiments, researchers may interact with collaboration management systems having special identification properties, or having restricted or conditional access properties. Such properties may allow for patient data to be blinded, for example, or may allow for patient data to be depersonalized. Researchers who also provide clinical care to a patient population may have access to individual patient identifiers, for example, while other researchers may be restricted from accessing this information. Or experimental results may be viewed anonymously by trial sponsors who click on the subject identification number.

As a further example, in certain embodiments all meaningful patient identifiers may be held in a syndicated pod independent of other clinical data, where a researcher would need an access key consistent with a particular access level. In this way, information that has been blinded to researcher and patient alike may be sequestered in a syndicated pod only to be accessed under certain conditions. The randomization results that contain information about who received the study drug and who received the placebo may be held in a syndicated pod, for example, accessible only to certain monitors if a predetermined pattern of adverse events or of overwhelming drug success becomes evident. The designated monitors who can access the data pod and "crack the code" may be determined in advance and provided with appropriate credentials. Similarly, the circumstances under which the randomization code should be broken may be determined in advance and incorporated into the conditions allowing access to the sequestered data pod.

In embodiments, researchers may interact with collaboration management systems associated with database functions that permit the data quality to be verified, provide for transformation of data, enable searching, filtering or clustering of data, or categorizing the data into hierarchies, interrelationships, interrelated groups and the like. For example, database functions applied to collaboration management systems may allow for the identification of adverse event patterns from a collection of trial sites or for review of the demographics of clinical trial enrollees. Database functions applied to data collected by a group of researchers may facilitate ordering the data for subsequent statistical analysis. In one example, syndicated data banking may permit non-centralized storing of multi-site data. Database functions applied to the banked data may prepare the experimental results for subsequent analysis and publication.

In embodiments, researchers may interact with collaboration management systems associated with semantic rules that may enable the creation of metadata. Semantic rules 412 may also provide for metadata enrichment, interpretation or translation of syndicated collaboration management systems, as well as permit the creation of knowledge structures (e.g., using OPML) and the use of a dictionary, thesaurus or the like. Use of metadata for syndicated collaboration management systems may permit, for example, the retrieval of all test results of a certain type for patients within a clinical trial. All kidney function tests performed on subjects in a clinical trial, for example, could be retrieved in accordance with semantic rules that permit the identification of tests of all types that relate to renal function (such as blood tests including blood urea nitrogen, serum creatinine, serum potassium, and the like, urine tests including urinalysis and urine sediment analysis and creatinine clearance studies, kidney ultrasounds and radiological studies like intravenous pyelogram). Retrieving a variety of data that pertain to a particular organ may allow the early identification of patterns indicating the organ to be damaged by the study drug. As another example, metadata applied to study results may indicate when abnormal results have been obtained, i.e., a test result that is outside the parameters of what is considered normal. A surveillance monitor may then retrieve via RSS feed 202, web feed, RSS stream or RSS channel an update on abnormal results from all test sites as a clinical trial progresses, allowing her to identify problematic trends.

In embodiments, researchers may interact with collaboration management systems to which others may subscribe, and researchers may publish their results within the collaboration management systems. For example, a sponsor of a clinical trial may be able to subscribe to an RSS feed 202, web feed, RSS stream or RSS channel that sets forth the progress of the trial from multiple sites, including enrollment statistics, images of signed informed consent documents, and data from individual anonymized subjects. As another example, clinicians at trial sites may be able to subscribe to an RSS feed 202, web feed, RSS stream or RSS channel that provides updated data from bench studies or animal studies that are relevant to the product being tested clinically. As a further example, an individual researcher may subscribe to a RSS feed 202, web feed, RSS stream or RSS channel that sets forth data obtained by other researchers at different locations. Such subscription may make collaboration possible among individuals under the same institutional umbrella. With proper access restrictions limiting users and limiting access to data sets, such subscription may also permit collaboration among individuals from different institutions or from different corporations.

In embodiments, the collaboration management systems may be associated with information that may provide for further processing and management of the data. For example, the data from a clinical trial may further provide information about the site from which it was obtained, the demographics of the anonymized patient, the date when the test was performed, etc. Thus, the data may provide for further aggregation, republication and the like.

In embodiments, researchers may interact with collaboration management systems within an infrastructure 416 that provides for data security, authentication, management of the traffic created by the RSS feeds 202, web feeds, RSS streams, or RSS channels, logging and pinging technology, and/or other communications. Such an infrastructure may protect vital proprietary data during multisite clinical trials or within a large organization. Such an infrastructure may also protect patient confidentiality during clinical trials. Moreover, such an infrastructure may permit notifications to be delivered to appropriate individuals, for example, notification of sponsors when an adverse event occurs, or notification of other researchers.

In embodiments, researchers, research assistants, research analysts, report drafters, sponsors and data collectors (collectively termed "authors") may interact with syndicated authorship management systems via syndicated authorship information obtained through an RSS feed 202, web feed, RSS stream, or RSS channel, to collaboration in the collection, exchange and reporting of data or other information obtained during research. The syndicated authorship information may involve research-related information and all varieties of experimental and observational data such as basic scientific data, social scientific data, epidemiological or statistical data, preclinical data, clinical data and the like, alone or in combination with narratives including discussions, descriptions, analyses or other reports pertaining to the information and/or data. Relevant authorship systems may include systems for reporting experimental methods and materials, systems for preparing manuscripts, systems for preparing presentations, systems for preparing regulatory submissions and systems for preparing proposals.

In embodiments, the saving, storing, merging, retrieval and publication of syndicated authorship management information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one for the input and management of research-related information, data and narrative. As an example, a client-side program and device may permit input, analysis and discussion of data obtained by a group of researchers conducting independent experiments, thereby permitting multicenter collaborative reporting. As another example, a client-side program and device may permit data input by one researcher and statistical analysis by another researcher. As a further example, a client-side program and device may permit collaboration among researchers on a manuscript draft undergoing revisions in real-time.

In embodiments, the RSS feed 202, web feed, RSS stream, or RSS channel used to interact with the syndicated authorship management systems may be associated with an aggregator 210 to track updates. In this way, research information may be continuously updated, so that new information becomes available to all collaborators. As an example, comments on a manuscript may be readily collected so that the primary author can integrate the input from her collaborators.

In embodiments, the RSS feed 202, web feed, RSS stream, or RSS channel used to interact with syndicated authorship management systems may be associated with a content management system that may provide summaries of the syndicated data available, dates associated with the syndicated data, links to access the full, non-summarized data, parameters associated with research information, and the like. In certain embodiments, the content management system may include a proprietary program for maintaining the records of a research program. Such a program may be responsive to the requirements by regulatory agencies so that the research data is maintained in a format that is readily accessible for regulatory review.

In embodiments, researchers, research assistants, research analysts, report drafters, sponsors and data collectors may interact with syndicated authorship management systems through the use of a RSS-enabled application 406 providing social networking. As an example, an epidemiological researcher may collect data from a number of geographically dispersed investigators and provide them comments on the design of their data collection methods. Through this interplay, the collection methods may be improved so that the research results are more meaningful. As another example, collaborators on a report for publication may each work on a particular segment of the report and elicit comments from the other collaborators in real time. Versions and revisions may be available to the entire collaboration team as each author works on his or her segment.

In embodiments, researchers, research assistants, research analysts, report drafters, sponsors and data collectors may interact with syndicated authorship management systems through the use of an application providing a media viewer. For example, a RSS item may refer to an image source, such as a digital photomicrograph or a digital photograph, and may specify a viewer for the source image that is available through the registry. In operation, a client with appropriate permissions may view the image (also as managed, e.g., through the metadata for the enhanced syndication system), may retrieve the appropriate viewer service from the registry and may apply the viewer to view the source image.

In embodiments, researchers, research assistants, research analysts, report drafters, sponsors and data collectors may interact with syndicated authorship management systems through the use of an application providing a user interface 700 for viewing information related to a particular research project. For example, a customized user interface may be available to all members of a collaborative team so that each researcher may have access to materials like data from different clinical trial sites, relevant journal articles or other references that are identified during the course of the research, and administrative documents pertaining to the research project. A client 102 may, in response to user input such as clicking on a title of an item in the user interface 700, retrieve the underlying item from the content source 204 as indicated by the arrow 208.

In embodiments, researchers, research assistants, research analysts, report drafters, sponsors and data collectors may interact with syndicated authorship management systems through the use of an application providing vertical market integration.

In embodiments, researchers, research assistants, research analysts, report drafters, sponsors and data collectors may interact with syndicated authorship management systems that are associated with special formatting and/or display properties.

In embodiments, researchers, research assistants, research analysts, report drafters, sponsors and data collectors may interact with syndicated authorship management systems that are associated with special identification properties.

In embodiments, researchers, research assistants, research analysts, report drafters, sponsors and data collectors may interact with syndicated authorship management systems that are associated with restricted or conditional access properties. A sponsor may have access to all information produced during a series of clinical trials, for example, while the individual researchers are restricted to accessing the data obtained from their individual trials. The sponsor may decide when the primary investigator or the group of investigators may review all data, in anticipation of producing a published report of the study.

In embodiments, researchers, research assistants, research analysts, report drafters, sponsors and data collectors may interact with syndicated authorship management systems associated with database functions that permit the data quality to be verified, provide for transformation of data, enable searching, filtering or clustering of data, or categorizing the data into hierarchies, interrelationships, interrelated groups and the like. Applying database functions to research data from a number of research sites may permit easier analysis of the data and easier access to the analyzed data by collaborating authors.

In embodiments, researchers, research assistants, research analysts, report drafters, sponsors and data collectors may interact with syndicated authorship management systems associated with semantic rules that may enable the creation of metadata. Semantic rules 412 may also provide for metadata enrichment, interpretation or translation of syndicated authorship management systems, as well as permit the creation of knowledge structures (e.g., using OPML) and the use of a dictionary, thesaurus or the like. Use of metadata for syndicated authorship management systems may permit the ready identification of data trends by a collaborating group of authors.

In embodiments, researchers, research assistants, research analysts, report drafters, sponsors and data collectors may interact with syndicated authorship management systems to which others may subscribe. For example, registrants for a conference may be able to subscribe to an RSS feed 202, web feed, RSS stream or RSS channel that regularly retrieves and updates accepted submissions to the conference, including slides, video, audio, and data to be included in conference presentations. As another example, a collaborating group of authors may circulate their preliminary report to a network of peers coincident with or in advance of formal submission for publication.

In embodiments, the authorship management systems may be further associated with information that may provide for the management of the data. For example, the information may list the source of the data in a work of authorship, the date on which it was last updated, etc. Thus, the data may provide for further aggregation, republication and the like. A group of researchers, for example, who has identified noteworthy trends in their investigations may publish the series through the syndicated authorship management system so that other subscribing scientists in the field may learn from their experience. While such publication does not provide the quality control of a peer-reviewed scientific journal, it may offer more immediate access to the earliest research findings.

*[Collaborative Research—Q29-34] In embodiments, researchers, research assistants, research analysts, report drafters, sponsors and data collectors may interact with syndicated authorship management systems within an infrastructure 416 that provides for data security, authentication, management of the traffic created by the RSS feeds 202, web feeds, RSS streams, or RSS channels, logging and pinging technology, and/or other communications. Such an infrastructure may, for example, provide for alerts when statistically significant findings have been recorded, or when a segment of a research report is available for other authors to review.

In embodiments, researchers and interested third parties such as reviewers, regulators, patients, advocacy groups, sponsors, research-supporting institutions and the like, may interact with syndicated research reporting systems via syndicated research report data obtained through an RSS feed 202, web feed, RSS stream, or RSS channel, to facilitate communications between the researchers and the interested third parties. Enhanced communication between researchers and reviewers may advantageously streamline publication of research results. Enhanced communication between researchers and regulators may advantageously expedite regulatory approval of drugs and devices. Enhanced communication between researchers and patients and advocacy groups advantageously may increase scientists' awareness of community needs and may educate members of the community about research trends. Enhanced communication between researchers and sponsors and research-supporting institutions may advantageously increase the funding available for a particular research endeavor. The syndicated research reporting data may include submissions for peer review, submissions for regulatory approval, disclosures to patient or community groups, reports to business sponsors, applications for grants, requests for research proposals, requests for grant applications and the like.

In embodiments, the saving, storing, merging, retrieval and publication of syndicated research reporting information through RSS feed 202, web feed, RSS stream or RSS channel may be associated with an application 406 consisting of a client-side program. The client-side program may be formatted to operate on client devices such as a desktop computer, a laptop computer, a pocket personal computer, a cellular phone, Blackberry, personal digital assistant, or other SMS text-enabled device, or the like. The client-side program may be an individual one, such as a Palm Pilot scheduler, or an enterprise one for the input and management of data, documents, or comments.

In embodiments, the RSS feed 202, web feed, RSS stream, or RSS channel used to interact with the syndicated research reporting systems may be associated with an aggregator 210 to track updates. In this way, a researcher may track his grant application through the review process and see what comments, suggestions or criticisms have been entered by different reviewers. This real-time feedback may allow him to revise experimental protocols or change his application strategy so that his proposals are more likely to be favorably received.

In embodiments, the RSS feed 202, web feed, RSS stream, or RSS channel used to interact with syndicated research reporting systems may be associated with a content management system that may provide summaries of the syndicated data available, dates associated with the syndicated data, links to access the full, non-summarized data, parameters associated with research information, and the like. Research reporting systems may draw from other sources of syndicated data, so that they include references to the scientific literature or cross-references to other studies or data submissions by the same researchers. For example, a submission to a regulatory agency may include links to full, non-summarized sets of preclinical toxicology and pharmacology data in an easy-to-access format. A syndicated research reporting system may make data more accessible to reviewers and allow them to comment on the data more rapidly. Furthermore, syndicated research reporting systems may provide customized information for a query.

In embodiments, researchers and interested third parties such as reviewers, regulators, patients, advocacy groups, sponsors, research-supporting institutions and the like, may interact with syndicated research reporting systems through the use of a RSS-enabled application 406 providing social networking. The regulator, for example, may review some early data and may comment to the sponsor. The sponsor, in turn, may provide this feedback to the researchers, who will themselves provide response to the regulator's comments. Syndicated research reporting systems may establish easily-navigated channels of communication among the parties involved in designing the trial, submitting the data and evaluating the data for regulatory approval.

In embodiments, researchers and interested third parties such as reviewers, regulators, patients, advocacy groups, sponsors, research-supporting institutions and the like, may interact with syndicated research reporting systems through the use of an RSS-enabled application 406 providing a user interface for viewing data, records, and the like. For example, a client 102 may be able to click on an icon representing a grant application in the user interface 700 to retrieve the application and all supporting data from the content source 204 as indicated by an arrow 208. A user interface 700 may be designed, for example, to allow collaborating authors to collect documents, data and analytic reports for an article. As another example, a user interface 700 may permit the authors of a submitted publication to track its review progress and to access reviews and comments as they are entered.

In embodiments, researchers and interested third parties such as reviewers, regulators, patients, advocacy groups, sponsors, research-supporting institutions and the like, may interact with syndicated research reporting systems through the use of an application providing a media viewer.

In embodiments, researchers and interested third parties such as reviewers, regulators, patients, advocacy groups, sponsors, research-supporting institutions and the like, may interact with syndicated research reporting systems associated with special formatting and/or display properties.

In embodiments, researchers and interested third parties such as reviewers, regulators, patients, advocacy groups, sponsors, research-supporting institutions and the like, may interact with syndicated research reporting systems associated with special identification properties. Reviewers, for example, may rely on special identification properties that allow them to remain anonymous while interacting with the researcher. In embodiments, researchers and interested third parties such as reviewers, regulators, patients, advocacy groups, sponsors, research-supporting institutions and the like, may interact with syndicated research reporting systems associated with restricted or conditional access properties. Certain reviewers of a grant proposal may have access only to certain portions of it, for example, so as to preserve confidentiality of submitted materials. Certain portions of a regulatory submission may be viewed by regulators, for example, but may not be generally available to the public.

In embodiments, researchers and interested third parties such as reviewers, regulators, patients, advocacy groups, sponsors, research-supporting institutions and the like, may interact with syndicated research reporting systems associated with database functions that permit the data quality to be verified, provide for transformation of data, enable searching, filtering or clustering of data, or categorizing the data into hierarchies, interrelationships, interrelated groups and the like. For example, database functions applied to syndicated research reporting systems may allow a reviewer for a regulatory agency to reorganize the data that has been submitted to see what other patterns emerge.

In embodiments, researchers and interested third parties such as reviewers, regulators, patients, advocacy groups, sponsors, research-supporting institutions and the like, may interact with syndicated research reporting systems associated with semantic rules that may enable the creation of metadata. Semantic rules 412 may also provide for metadata enrichment, interpretation or translation of syndicated information management systems, as well as permit the creation of knowledge structures (e.g., using OPML) and the use of a dictionary, thesaurus or the like.

In embodiments, researchers and interested third parties such as reviewers, regulators, patients, advocacy groups, sponsors, research-supporting institutions and the like, may interact with syndicated research reporting systems to which others may subscribe. Patients who have participated in a clinical trial, for example, may wish to track the regulatory submission pertaining to the trial product. In embodiments, the research reporting systems may be further associated with information that may provide for the management of the reporting, or that provide for further aggregation, republication and the like.

While the research reporting systems discussed so far have been inaugurated by a researcher seeking to interact with a reviewer or other third party, research reporting systems may also be set in motion by the third party who wishes to interact with subscribing researchers. A research-supporting institution such as the NIH, for example, may push requests for proposals to relevant clinicians or academics in a syndicated feed. Similarly, a research-supporting institution may publish to subscribing researchers descriptions of funded proposals or descriptions of earmarked fund allocations. A research reporting system may permit response by the researcher to communications initiated by a third party such as a research-supporting institution.

In embodiments, researchers and interested third parties such as reviewers, regulators, patients, advocacy groups, sponsors, research-supporting institutions and the like, may interact with syndicated research reporting systems within an infrastructure 416 that provides for data security, authentication, management of the traffic created by the RSS feeds 202, web feeds, RSS streams, or RSS channels, logging and pinging technology, and/or other communications. For example, a research reporting system may permit notifying the researchers when a regulatory submission passes through initial review, or when a regulatory submission has an identified deficiency.

While the illustrative embodiments herein have described syndicated collaboration management, authorship management and research reporting systems as applied to scientific and clinical research, it will be understood by those of ordinary skill that syndicated collaboration management, authorship management and research reporting systems (and the other disclosures provided herein) may be applied to research in all scientific disciplines, including but not limited to psychology, sociology, anthropology, ethnography, oceanography, ecology and other social, physical or biological investigations. In addition, those of ordinary skill will further appreciate that syndicated collaboration management, authorship management and research reporting systems may be applied to collaborative non-scientific research, for example in the liberal arts.

Figure 19:
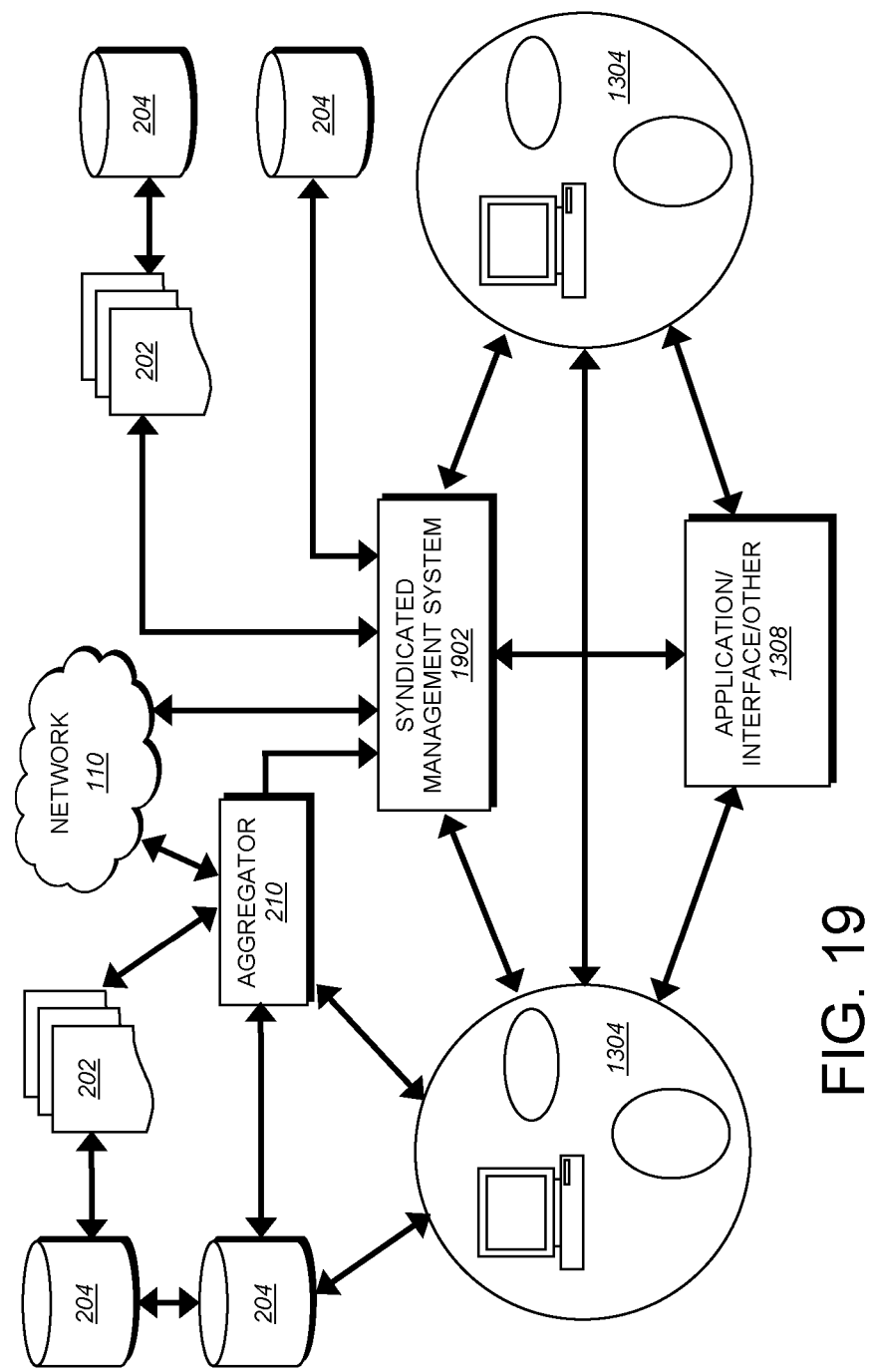
FIG. 19 shows a syndicated management system including an application and/or interface.

Referring to FIG. 19, the syndicated management system 1902 may be a time management system, a time utilization management system, a medical information management system, a business systems management system, a collaboration systems management system, an authorship management system and/or a research reporting management system, such as described herein. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. Users 1304, such as users 404 and clients 102, may view and/or receive information from and/or send information to and/or interact with the syndicated management system 1902 directly or through an application/interface/other 1308. The users 1304 may also interact with each other. The application/interface/other 1308 may be a client-side program, such as the healthcare program discussed herein, a content management system, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 19 may be data feeds, such as data feed 202.

Figure 20:
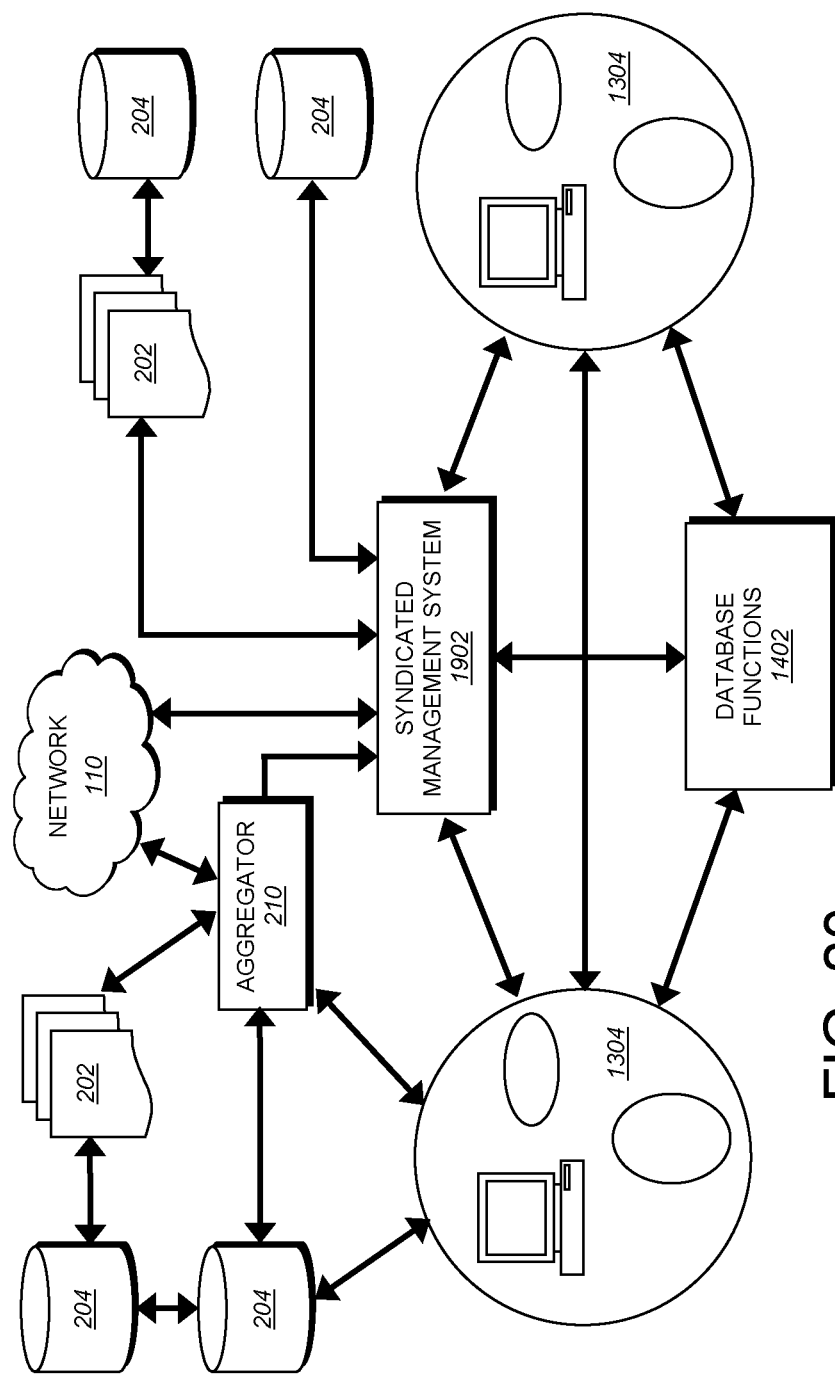
FIG. 20 shows a syndicated management system including database functions.

Referring to FIG. 20, the syndicated management system 1902 may be a time management system, a time utilization management system, a medical information management system, a business systems management system, a collaboration systems management system, an authorship management system and/or a research reporting management system, such as described herein. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. Users 1304, such as users 404 and clients 102, may view and/or receive information from and/or send information to and/or interact with the syndicated management system 1902 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 20 may be data feeds, such as data feed 202.

Figure 21:
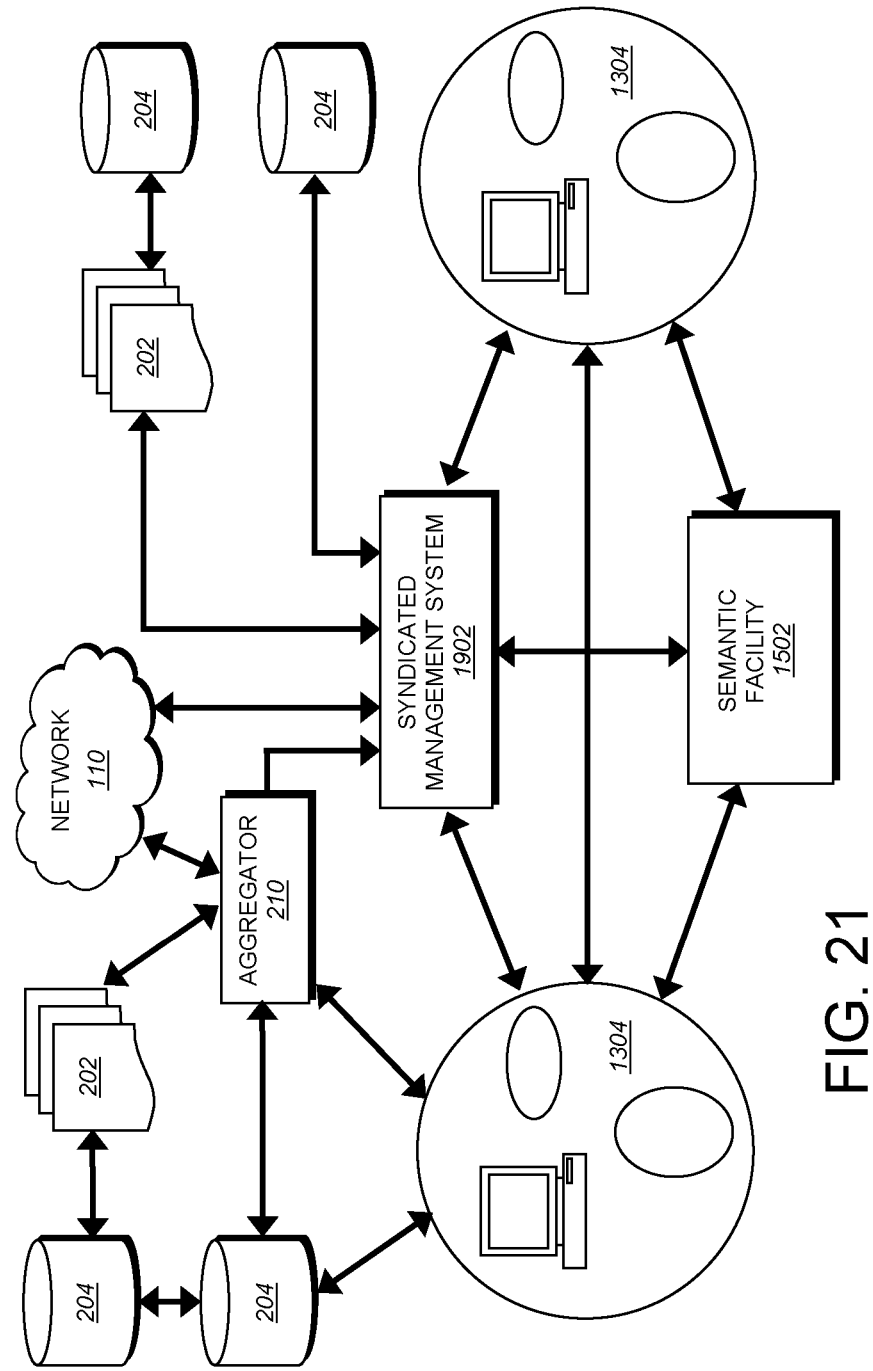
FIG. 21 shows a syndicated management system including a semantic facility.

Referring to FIG. 21, the syndicated management system 1902 may be a time management system, a time utilization management system, a medical information management system, a business systems management system, a collaboration systems management system, an authorship management system and/or a research reporting management system, as described herein. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. Users 1304, such as users 404 and clients 102, may view and/or receive information from and/or send information to and/or interact with the syndicated management system 1902 directly or through a semantic facility 1502. The semantic facility 1502 may also interact directly with the syndicated management system 1902. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 21 may be data feeds, such as data feed 202.

Figure 22:
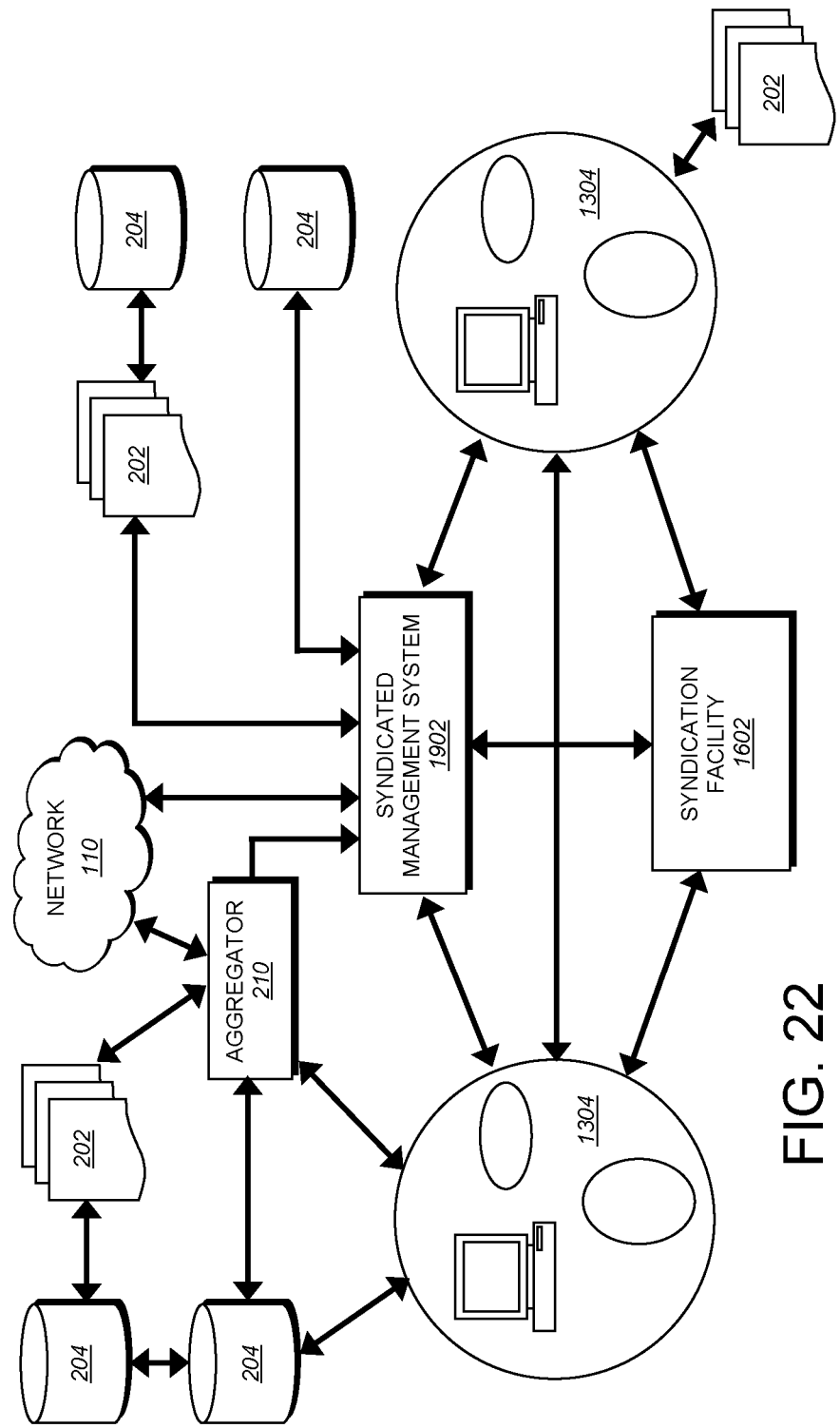
FIG. 22 shows a syndicated management system including a syndication facility.

Referring to FIG. 22, the syndicated management system 1902 may be a time management system, a time utilization management system, a medical information management system, a business systems management system, a collaboration systems management system, an authorship management system and/or a research reporting management system, as described herein. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. Users 1304, such as users 404 and clients 102, may view and/or receive information from and/or send information to and/or interact with the syndicated management system 1902 directly or through a syndication facility 1602. The syndication facility 1602 may also interact directly with the syndicated management system 1902. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 22 may be data feeds, such as data feed 202. A user 1304 may also publish, republish and/or subscribe to a content source 204, data feed 202, aggregator 210 and/or syndication facility 1602.

Figure 23:
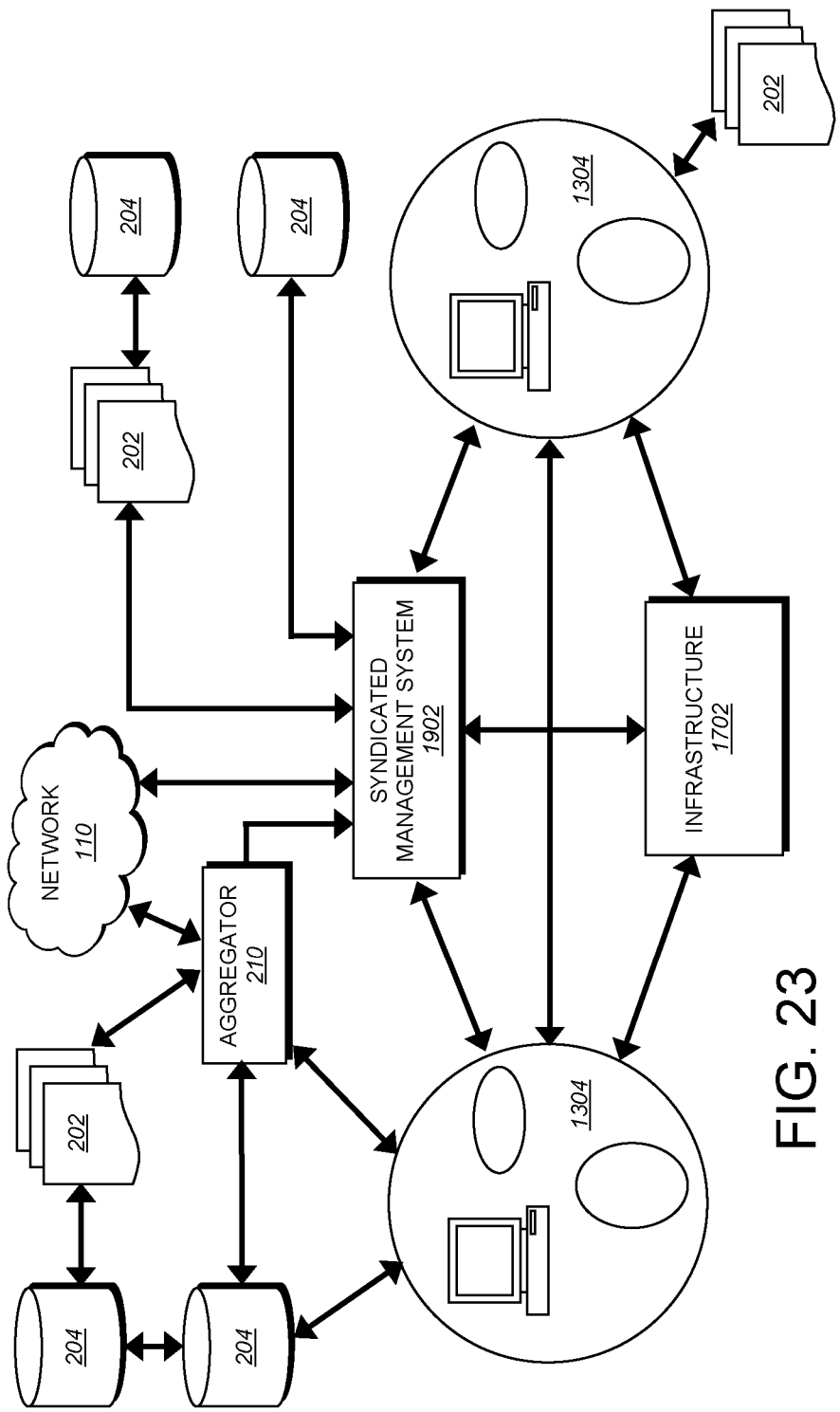
FIG. 23 shows a syndicated management system including an infrastructure.

Referring to FIG. 23, the syndicated management system 1902 may be a time management system, a time utilization management system, a medical information management system, a business systems management system, a collaboration systems management system, an authorship management system and/or a research reporting management system. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. Users 1304, such as users 404 and clients 102, may view and/or receive information from and/or send information to and/or interact with the syndicated management system 1902 directly or through an infrastructure 1702. The infrastructure 1702 may also interact directly with the syndicated management system 1902. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 23 may be data feeds, such as data feed 202.

Figure 24:
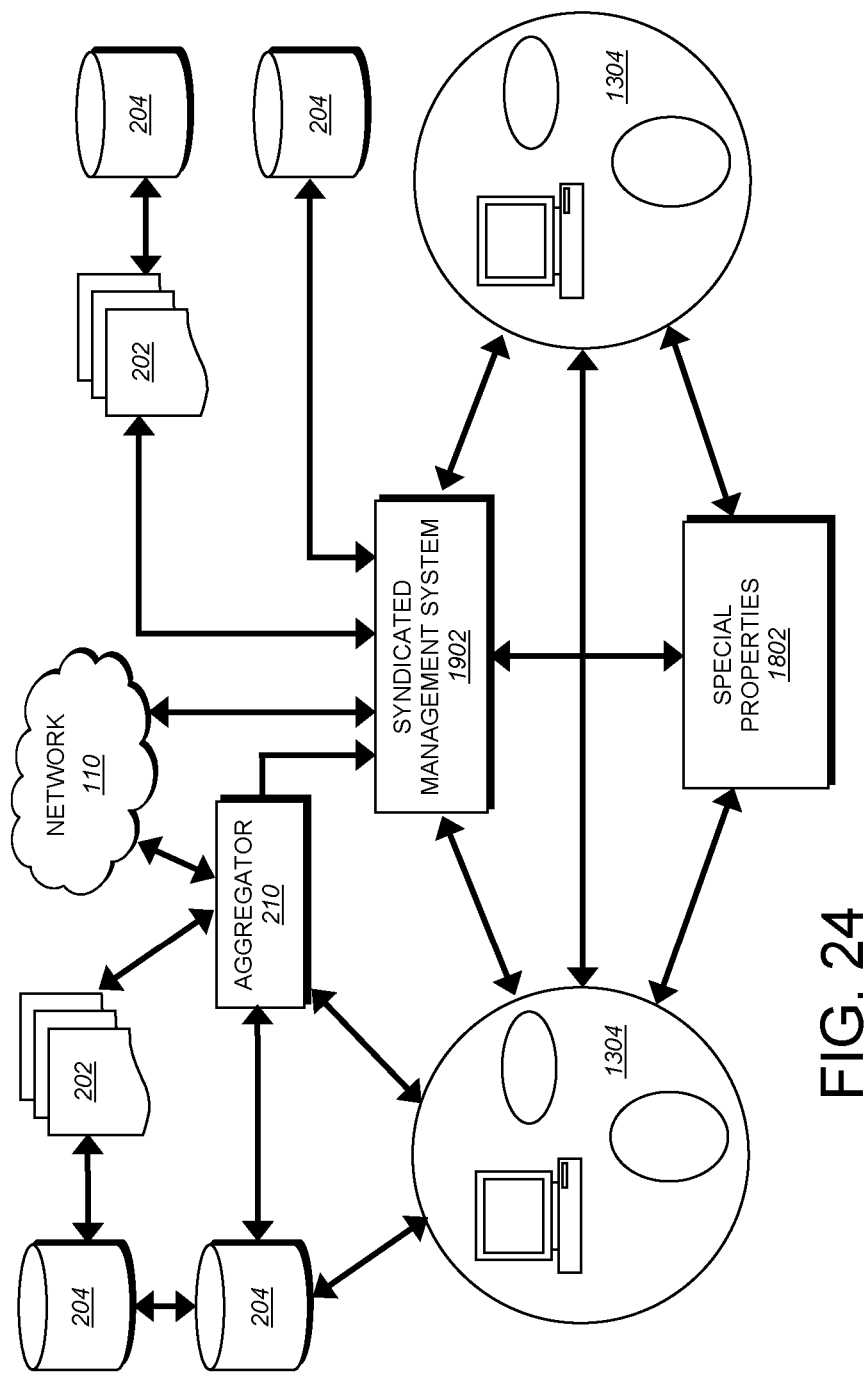
FIG. 24 shows a syndicated management system including special properties.

Referring to FIG. 24, the syndicated management system 1902 may be a time management system, a time utilization management system, a medical information management system, a business systems management system, a collaboration systems management system, an authorship management system and/or a research reporting management system, as described herein. The syndicated management system 1902 function may be associated with a healthcare environment, healthcare practice environment, research environment, medical environment and/or another environment. The data and/or information, including syndicated data and/or information, may originate on a network 110 or may originate from a content source 204 through a data feed 202 or directly. An aggregator 210 may be employed as described above. The infrastructure 1702 may also interact directly with the syndicated management system 1902. The users 1304 may also interact with each other. The syndicated management system 1902 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 24 may be data feeds, such as data feed 202.

An important component of improving health care quality is translating research evidence to standard medical practice, and integrating other useful information into clinical care to assist decision making. Many well-documented, effective therapies remain underutilized in spite of clinical trial results published in respected medical journals and extensive media attention. For example, despite the documented clinical efficacy of ACE inhibitors within multiple disease classes, the drugs remain under-prescribed in the clinical populations for which they are indicated. Documented evidence of an effective therapy does not immediately lead to its adoption into clinical practice. Adoption of effective therapies may be slowed by physician-, institution-, and patient-based barriers.

One of the many challenges of a physician's practice concerns medical decision making. At its most basic, medical decision making refers to making the decision about which medical treatment is most appropriate (or inappropriate) for a patient at a point in time, given the current medical evidence and the patient's unique demographic and clinical circumstances. The difficulties of medical decision making stem, in part, from the multitude of patient factors influencing treatment choice, the continually evolving nature of medical treatments, their understanding, and therapeutic advances, and the time stresses of physicians that make it increasingly difficult for them to analyze new medical studies and integrate new medical findings into their patient practices. For example, in the course of a standard twenty minute check-up with a patient, a cardiologist must evaluate a patient's vital signs, inquire about "how the patient has been feeling," inquire about other health ailments (e.g. disease comorbidities), ensure that new medications don't need to be prescribed, that current medication dosages don't need to be altered, that other physicians have not prescribed medications that may have negative interactions with the patient's heart medications, have a working knowledge of recent developments in medical research that may have a bearing on a patient with the demographic and clinical profile of the current patient, and so on. The information load is substantial. Often physicians must, knowingly or unknowingly, take informational shortcuts in the course of care. For example, a cardiologist may be confident that Medication A is indicated for the patient, but may not recall a study from the New England Journal of Medicine demonstrating that the effects of Medication A are significantly improved when it is taken in conjunction with Medication B. The patient is conscientiously prescribed only Medication A by the cardiologist and, as a result of not receiving Medication B as well, achieves sub-optimal healthcare outcomes due to the physician's informational limitation. Compounding the problem is that the physician may not have an opportunity to realize the error and, thus, will replicate it with other patients.

Physicians and their support institutions, such as hospitals and academic centers, have tried to narrow the information gap in a number of ways. Many institutions are moving to the electronic medical chart and similar electronic medical storage systems. The electronic medical chart is designed to move an institution from a paper-based records management system to a digital model in which records are more easily searched, stored, merged, and retrieved. If a physician can key a query for an informational element she seeks and pull it up on a screen, then she doesn't have to sort through stacks of paper records looking for a patient's current list of medications or the hundreds of other data elements she may need.

In spite of the improvement of the electronic medical record over the paper-based system, it still has many limitations. For one, it is generally a relational database-type product that is an isolated storage unit, most often within a single health care system. Thus the electronic medical record does not retrieve information from outside a given institution. If a patient is on vacation, becomes ill, and is forced to visit a hospital away from home, the hospital he visits with an electronic data retrieval ability will very likely not have access to the patient's medical record at the institution(s) in the patient's hometown. Likewise, other data sources must be referenced for other of a physician's information needs. Medication lists may be stored in an institution's formulary database. New research findings may have to be accessed via the Internet and a database, such as Medline, and so forth. In sum, the sources of medical data are often grouped according to the internal consistencies and similarities of the data alone, rather than grouped by the unique needs of physicians and institutions in order to make optimal medical decisions that promote beneficial health outcomes. The syndication technologies described in detail herein provide methods and systems for interacting with healthcare information on the basis of the needs of physicians and institutions to make informed medical decisions.

As with physicians and institutions, patients need information to make medical decisions and many currently lack the resources for making educated decisions regarding treatment options, trade-offs between medications, and the like. A well-informed patient is able to participate in the decisions affecting his medical well-being and participate in shared decision-making with his physician, rather than simply passively entrusting his care entirely to a doctor's judgment. Shared decision making inserts patients' preferences and values into the decision making process and is preferred by patients. Shared-decision making may enhance a patient's understanding of his medical condition, provide him with realistic expectations of healthcare outcomes following treatment, and improve patient satisfaction. Patient compliance with therapy may also improve when a patient and physician participate in a process of shared decision-making.

Some of the circumstances in which shared decision-making is most important include (i) when trade-offs exist between near-term and long-term outcomes, (ii) when there is a small risk of an extremely negative outcome, (iii) when treatment options appear to have minimal differences, (iv) when there are dramatic differences in the kinds of outcomes offered by treatment options, (v) when there are major differences in the probabilities of complications, (vi) when a patient is risk-averse, (vii) when a patient is risk insensitive, and (viii) when a patient places extreme value on certain outcomes.

Physicians often present patients information in qualitative terms (e.g., "There is a very good chance that, with a lumpectomy, the cancer will not return and you will return to a healthy life.") despite evidence that patients are better able to more accurately remember facts presented in numeric, probabilistic terms (e.g., "A woman of your age can expect an X % chance that cancer will return within 10 years, and an X % 10-year survival rate following surgery."). Thus, the use of information to assist patient decision-making should, at minimum, include numeric outcome estimates. Estimates may inform patients of procedural risks, possible side effects, probable outcomes, and potential trade-offs between treatment options. One likely reason that physicians don't always present such information to patients is that to remember such a vast quantity of numeric information as it applies to the many patients that a physician cares for, each with their own unique clinical circumstances, is not mentally possible. To stop in the middle of a time-limited office visit to do the necessary research online to compute such numeric estimates may be equally unrealistic.

Apart from the direct health benefits that may result from informed patients participating in shared decision making with their physicians, better informed patients are also able to make medical decisions that are more congruent with the outcome(s) they most desire. This level of congruence is likely to improve patients' satisfaction with their healthcare that, in turn, has many economic and regulatory benefits for physicians, healthcare institutions, and insurers. For example, some surgical procedures may improve patients' survival, but at a cost of the patient enduring a painful intervention and lengthy, difficult recovery period. A patient presented with this information may be able to choose the option that is most in line with her wishes and better accept the clinical consequences that flow from this decision.

The syndication technologies described in detail herein provide methods and systems for interacting with healthcare information on the basis of the needs of patients to make informed medical decisions.

Healthcare data that may improve the quality of medical decision making come from many sources, including, patients' medical records, records of physician performance, standards of care that are published by regulatory and other groups, billing information, epidemiologic information on the complications, events, side effects and the like that are associated with medical procedures, devices, medications, and the like. In spite of the usefulness of this information for improving medical decision making, it often exists in formats that are not conducive to easy retrieval by interested parties in the course of patient care. For example, the American Heart Association may publish guidelines for optimal treatment of hypertension in paper and electronic format. However, it would be unwieldy for a physician to carry paper copies of all relevant guidelines and standards pertaining to her patient population, and the electronic versions are likely to be website postings, as opposed to more readily searchable electronic formats. With syndicated data, a physician, institution, patient or other interested party may create unique sets (i.e. feeds) of metadata comprised of data elements from multiple sources that are associated principally by a user-defined element (e.g. a patient's name, a disease state, a clinical specialty). This specificity of data retrieval, coupled with the non-centralized storage/retrieval processes of syndicated data, may make it well-suited for providing informational support for medical decision making.

In embodiments, a physician's, or other health care provider's, RSS feed 202, web feed, RSS stream, or RSS channel may be configured by the physician, institution for whom the physician is employed, a third-party enterprise managing physician's accounts, or the like. This configuration may be based at least in part on the physician's clinical area of specialization (e.g. cardiology, endocrinologist, general practitioner), the institution within which the physician practices (e.g. solo practice, physician group practice, hospital, academic center), the clinical mix of the physician's patients (e.g. elderly cardiology patients with atherosclerosis, minors with autism), the ICD-10 codes of the patients currently under the physician's care (e.g. "1.8.6 (H40-H42)"=Glaucoma), patients' diagnostic related groups (DRG's), the geographic location of the physician's practice (e.g. US zipcode, "Southern, rural America," Mexico), the medication-prescribing history of the physician (e.g. Beta-blocker, Prozac, Zocor), the interventions performed by the physician (e.g. angioplasty, colonoscopy), organizations to which the physician holds a current membership (e.g. the American Medical Association), medical journals to which the physician subscribes (e.g. The Lancet), medical boards from which the physician has certification, continuing medical education events that physician has attended, and so forth.

In embodiments, a physician and/or her support staff personnel, or supporting healthcare institution, may save, store, merge, retrieve, and publish the records of a physician's patients in a syndicated format to enable interested persons to retrieve the clinical patient data through an RSS feed 202, web feed, RSS stream, or RSS channel. The records may include patients' demographic information, such as, age, sex, race, religion, area code, home address, work address, billing address, family information (e.g., mother's maiden name), emergency contacts, birthplace, driver's license number, employer, position, and the like. The records may include patients' historical clinical information, such as, medication histories and dosages, allergies, family medical history, past interventions received, major illnesses, congenital abnormalities, previous healthcare providers and their contact information, past insurance information, and the like. The records may include patients' current clinical information, such as, disease status, comorbidities, vital signs, relevant clinical test summaries, allergies, current medications and associated dosages, functional status, other healthcare providers caring for a patient and the associated contact information, and the like.

In embodiments, the saving, storing, merging, retrieval, and publication of patients' data through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to save, store, merge, retrieve, and publish patients' records may be associated with an aggregator 210 to track updates.

In embodiments, the RSS feed 202, web feed, RSS stream, or RSS channel used to save, store, merge, retrieve, and publish patients' records may be associated with a content management system that may provide summaries of the syndicated data available, dates associated with the syndicated data, links to access the full, non-summarized data, and the like.

In embodiments, a physician and/or her support staff personnel, or supporting healthcare institution, may save, store, merge, retrieve, and publish syndicated patient data through the use of an application 406 providing social networking. For example, through social networking a physician may be able to communicate and share syndicated data with other healthcare providers with whom the physician shares care for a patient, a clinical specialty, clinical population type, and the like. The clinical factors of relevance to physicians who seek to share clinical data may be published with detailed tags to provide narrowly tailored or easily filtered RSS feeds 202, web feeds, RSS streams, or RSS channels for ongoing data sharing with colleagues. Such a process may allow physicians who care for a common patient to more efficiently share the patient's data and improve cross-specialty collaboration in patient care. For example, a cardiologist may be unaware of very recent visits that one of her patients has made to other healthcare providers. With a syndicated data store associated with this patient, a visit by the patient the prior day to his endocrinologist and any associated data entering his medical record could be made available to the cardiologist for retrieval via RSS feed 202, web feed, RSS stream, or RSS channel without the delay associated with paper records or current relational-type database. Such a process may provide for physicians to conduct virtual case studies with colleagues around the world and learn clinical details, treatment strategies and the like in a more efficient and less costly manner than the traditional face-to-face physician case study meetings.

In embodiments, a physician and/or her support staff personnel, or supporting healthcare institution, may interact with syndicated patient data through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, a physician and/or her support staff personnel, or supporting healthcare institution, may interact with syndicated patient data through the use of an application 406 providing a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, a physician and/or her support staff personnel, or supporting healthcare institution, may interact with syndicated patient data through the use of an application 406 providing vertical market integration. For example, as hospital-physicians update the medications and dosages of their patient population following clinical visits, this syndicated data may be provided to the hospital's pharmacy via an RSS feed 202 and may permit the pharmacy to more efficiency conduct ordering, inventory management, and the like.

In embodiments, a physician and/or her support staff personnel, or supporting healthcare institution, may interact with syndicated patient data that is associated with database functions that may permit the data quality to be verified, provide for transformation of the patients' data, enable searching, filtering, or clustering the patient data, or categorizing the data into hierarchies, interrelationships, interrelated groups, and the like.

In embodiments, a physician and/or her support staff personnel, or supporting healthcare institution, may interact with syndicated patient data that is associated with semantic rules 412 that enable the creation of intra-, or inter-patient, -clinical state, -institution, etc. metadata. Semantic rules 412 may also provide for metadata enrichment, interpretation or translation of patient data, as well as permit the creation of knowledge structures (e.g., using OPML) and the use of a dictionary, thesaurus or the like.

In embodiments, a physician and/or her support staff personnel, or supporting healthcare institution, may interact with syndicated patient data to which others may publish and/or subscribe. For example, within a pediatric physician group all physicians may be able to publish and/or subscribe to an RSS feed 202, web feed, RSS stream, or RSS channel, "influenza" that regularly updates and retrieves information from across the entire practice on rates of childhood influenza that are being seen and treated by the physicians within the practice.

In embodiments, the syndicated patient data may be further associated with information that may provide for the management of the data. For example, the data may list the author of the data, the date on which it was authored, etc. Thus, the data may provide for further aggregation, republication, and the like.

In embodiments, a physician and/or her support staff personnel, or supporting healthcare institution, may interact with syndicated patient data within an infrastructure 416 that provides for data security, authentication, management of the traffic created by the RSS feeds 202, web feeds, RSS streams, or RSS channels, logging and pinging technology, and/or other communications.

In embodiments, a physician and/or her support staff personnel, or supporting healthcare institution, may interact with syndicated patient data that is associated with special formatting and/or display properties.

In embodiments, a physician and/or her support staff personnel, or supporting healthcare institution, may interact with syndicated patient data that is associated with special identification properties or transaction related properties.

In embodiments, a physician and/or her support staff personnel, or supporting healthcare institution, may interact with syndicated patient data that is associated with restricted or conditional access properties.

In embodiments, a physician and/or her support staff personnel, or supporting healthcare institution, may aggregate the records of a physician's patients in a syndicated format to enable interested persons to retrieve the all pertinent patient data through an RSS feed 202, web feed, RSS stream, or RSS channel. For example, a patient may have laboratory tests taken at one facility, meet with a primary care physician at another facility, receive a surgical intervention at a third facility, and so on. By aggregating the RSS feeds 202, web feeds, RSS streams, or RSS channels associated with each location of contact with the patient, all interested healthcare providers and institutions may have access to the full complement of a patient's data. The records may include laboratory test values. The records may include records from prior healthcare providers and institutions. The records may include patients' demographic information, such as, age, sex, race, religion, area code, home address, work address, billing address, family information (e.g., mother's maiden name), emergency contacts, birthplace, driver's license number, employer, position, and the like. The records may include patients' historical clinical information, such as, medication histories and dosages, allergies, family medical history, past interventions received, major illnesses, congenital abnormalities, previous healthcare providers and their contact information, past insurance information, and the like. The records may include patients' current clinical information, such as, disease status, comorbidities, vital signs, relevant clinical test summaries, allergies, current medications and associated dosages, functional status, other healthcare providers caring for a patient and the associated contact information, and the like.

In embodiments, the aggregation of patients' syndicated records may include longitudinal information that may be plotted, displayed, analyzed, or the like and distributed to an RSS-enabled client in order to permit longitudinal tracking of a patient or patient population. For example, aggregated, longitudinal data within a clinical indicator (e.g. blood pressure over time) for a single patient may be used to generate physician alerts based upon statistically significant deviations from norms, a patient's historical average, etc. This aggregated data may also be used to provide physician's with intra-patient temporal comparisons of clinical indicators (e.g. blood pressure on first visit with blood pressure one year after first visit), or for healthcare administrators to monitor healthcare provider performance (e.g. is Physician A better managing patients' hypertension than Physician B).

In embodiments, the aggregation of patients' data through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to aggregate patients' records may be associated with an aggregator 210 to track updates. In embodiments, the RSS feed 202, web feed, RSS stream, or RSS channel used aggregate patients' records may be associated with a content management system that may provide summaries of the syndicated data available, dates associated with the syndicated data, links to access the full, non-summarized data, and the like.

In embodiments, a physician and/or her support staff personnel, or supporting healthcare institution, may aggregate syndicated patient data through the use of an application 406 providing social networking. For example, through social networking a physician may be able to communicate and share syndicated data with other healthcare providers with whom the physician shares care for a patient, a clinical specialty, clinical population type, and the like. The clinical factors of relevance to physicians who seek to share clinical data may be published with detailed tags to provide narrowly tailored or easily filtered RSS feeds 202, web feeds, RSS streams, or RSS channels for ongoing data sharing with colleagues. Such a process may allow physicians who care for a common patient to aggregate all of that patient's data and more efficiently share the patient's data and improve cross-specialty collaboration in patient care. For example, a cardiologist may be unaware of very recent visits that one of her patients has made to other healthcare providers. With a syndicated data store associated with this patient, a visit by the patient the prior day to his endocrinologist and any associated data entering his medical record could be made available to the cardiologist for retrieval via RSS feed 202, web feed, RSS stream, or RSS channel without the delay associated with paper records or current relational-type database. Such a process may provide for physicians to conduct virtual case studies with colleagues around the world and learn clinical details, treatment strategies and the like in a more efficient and less costly manner than the traditional face-to-face physician case study meetings. Also, aggregating the syndicated data of patients who share certain clinical indications may facilitate intra-clinical-group tracking and inter-clinical-group comparisons.

In embodiments, a physician and/or her support staff personnel, or supporting healthcare institution, may aggregate syndicated patient data through the use of an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, a physician and/or her support staff personnel, or supporting healthcare institution, may aggregate syndicated patient data through the use of an application 406 associated with a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, a physician and/or her support staff personnel, or supporting healthcare institution, may aggregate syndicated patient data through the use of an application 406 providing vertical market integration. For example, as hospital-physicians update the medications and dosages of their patient population following clinical visits, this data may be aggregated by clinical specialty (e.g. cardiology patients) and this syndicated data may then be provided to the administrators the respective clinical areas via an RSS feed 202 and may permit the administrators to more efficiency allocate resources, plan personnel, and the like.

In embodiments, a physician and/or her support staff personnel, or supporting healthcare institution, may aggregate syndicated patient data that is associated with database functions that may permit the data quality to be verified, provide for transformation of the data, enable searching, filtering, or clustering the patient data, or categorizing the data into hierarchies, interrelationships, interrelated groups, and the like.

In embodiments, a physician and/or her support staff personnel, or supporting healthcare institution, may aggregate syndicated patient data that is associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

In embodiments, a physician and/or her support staff personnel, or supporting healthcare institution, may aggregate syndicated patient data to which others may subscribe and/or publish. For example, within a pediatric physician group all physicians may be able to subscribe and/or publish to an a 202, web feed, RSS stream, or RSS channel, "influenza" that regularly updates and retrieves information from across the entire practice on rates of childhood influenza that are being seen and treated by the physicians within the practice, and which is aggregated with other syndicated data on influenza rates from outside the physician's specific practice group.

In embodiments, the aggregated syndicated patient data may be further associated with information that may provide for the management of the data. For example, the aggregated data may list the author of the aggregated data, the date on which it was authored, etc. Thus, the data may provide for further aggregation, republication, and the like.

In embodiments, a physician and/or her support staff personnel, or supporting healthcare institution, may aggregate syndicated patient data within an infrastructure 416 that provides for data security, authentication, management of the traffic created by the RSS feeds 202, web feeds, RSS streams, or RSS channels, logging and pinging technology, and/or other communications.

In embodiments, a physician and/or her support staff personnel, or supporting healthcare institution, may aggregate syndicated patient data that is associated with special formatting and/or display properties.

In embodiments, a physician and/or her support staff personnel, or supporting healthcare institution, aggregate syndicated patient data that is associated with special identification and transaction related properties.

In embodiments, a physician and/or her support staff personnel, or supporting healthcare institution, aggregate syndicated patient data that is associated with restricted or conditional access properties.

In embodiments, researchers, physicians, healthcare providers, institutions, think tanks, regulatory bodies, accreditation groups, and the like may interact with syndicated medical research, clinical trial findings, case studies, peer-reviewed articles, academic presentations, and the like in a syndicated format to enable interested persons to share and continually update their medical knowledge via syndicated data obtained through an RSS feed 202, web feed, RSS stream, or RSS channel. The syndicated information may include full academic journal articles, article abstracts, customized article summaries, clinic trial data, clinical trial analyses, published standards of care, published clinical indicators for medications, published indicators for interventions, appropriateness scores for certain classes of clinical profiles and corresponding treatment options, and the like.

In embodiments, the interaction with syndicated medical research, clinical trial findings, case studies, peer-reviewed articles, academic presentations, and the like through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated medical research, clinical trial findings, case studies, peer-reviewed articles, academic presentations, and the like may be associated with an aggregator 210 to track updates.

In embodiments, the RSS feed 202, web feed, RSS stream, or RSS channel used to interact with syndicated medical research, clinical trial findings, case studies, peer-reviewed articles, academic presentations, and the like may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like through the use of an RSS-enabled application 406 providing social networking.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like through the use of an RSS-enabled application 406 providing a media viewer. For example, an RSS item consisting of a multimedia academic conference presentation may refer to graphic images, such as PowerPoint slides, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like through the use of an application 406 providing vertical market integration. For example, if cardiologists within a hospital practice are frequently viewing American College of Cardiology conference presentations via an RSS-enabled application 406, this information may be used by the hospital CFO to justify budgeting for the hospital's cardiologists to attend the annual event.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like that is associated with semantic rules 412 that enable the creation of metadata. Semantic rules 412 may also provide for metadata enrichment, interpretation or translation of medical research, clinical trial findings, case studies, peer-reviewed articles, academic presentations, and the like, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like to which others may subscribe and/or publish. For example, within a pediatric physician group all physicians may be able to subscribe and/or publish to an RSS feed 202, web feed, RSS stream, or RSS channel, "New England Journal of Medicine" that regularly updates and retrieves information from the academic medical journal relevant to pediatric medicine and distributes the information to the physicians within the practice.

In embodiments, the syndicated medical research, clinical trial findings, case studies, peer-reviewed articles, academic presentations, and the like may be further associated with information that may provide for the management of the data. For example, the data may list the author of the data, the date on which it was authored, etc. Thus, the data may provide for further aggregation, republication, and the like.

In embodiments, researchers, physicians, healthcare providers, institutions, think tanks, regulatory bodies, accreditation groups, and the like may interact with syndicated medical research, clinical trial findings, case studies, peer-reviewed articles, academic presentations, and the like within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like associated with special formatting and/or display properties.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like associated with special identification and/or transactional properties.

In embodiments, researchers, physicians, healthcare providers, institutions, think tanks, regulatory bodies, accreditation groups, may interact with syndicated medical research, clinical trial findings, case studies, peer-reviewed articles, academic presentations, and the like associated with restricted or conditional access properties.

In embodiments, researchers, physicians, healthcare providers, institutions, think tanks, regulatory bodies, accreditation groups, and the like may interact with medical decision making "trees" in a syndicated format to enable healthcare providers to better evaluate treatment options via syndicated data obtained through an RSS feed 202, web feed, RSS stream, or RSS channel. The syndicated information may include empiric data summaries describing the probabilities of certain outcomes that are associated with various treatment options, and the like.

In embodiments, the saving, storing, merging, retrieval, and publication of syndicated medical decision making trees through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated medical decision making trees may be associated with an aggregator 210 to track updates.

In embodiments, the RSS feed 202, web feed, RSS stream, or RSS channel used to interact with syndicated medical decision making trees may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated medical decision making trees through the use of an RSS-enabled application 406 providing social networking.

In embodiments, researchers, physicians, healthcare providers, institutions, think tanks, regulatory bodies, accreditation groups, may interact with syndicated medical decision making trees through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated medical decision making trees through the use of an RSS-enabled application 406 providing a media viewer or for vertical market integration.

In embodiments, researchers, physicians, healthcare providers, institutions, think tanks, regulatory bodies, accreditation groups, may interact with syndicated medical decision making trees associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated medical decision making trees associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated medical decision making trees to which others may subscribe and/or publish. For example, within a cardiology physician group all physicians may be able to subscribe and/or publish to an RSS feed 202, web feed, RSS stream, or RSS channel, "Angioplasty" that regularly updates and retrieves medical decision making trees that summarize the clinical outcome probabilities for patients either undergoing, or not undergoing angioplasty for a variety of clinical groups, classes, and indicators, and distributes the information to the physicians within the practice.

In embodiments, the syndicated medical decision making trees may be further associated with information that may provide for the management of the data. For example, the data may list the source of the decision making tree, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated medical decision making trees within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated medical decision making trees associated with special formatting and/or display properties.

In embodiments, researchers, physicians, healthcare providers, institutions, think tanks, regulatory bodies, accreditation groups, may interact with syndicated medical decision making trees associated with special identification and transactional properties.

In embodiments, researchers, physicians, healthcare providers, institutions, think tanks, regulatory bodies, accreditation groups, may interact with syndicated medical decision making trees associated with restricted or conditional access properties.

In embodiments, researchers, physicians, healthcare providers, institutions, think tanks, regulatory bodies, accreditation groups, and the like may interact with clinical standards of care for clinical indicators in a syndicated format to enable healthcare providers to verify the appropriate standard at the point of decision making via syndicated data obtained through an RSS feed 202, web feed, RSS stream, or RSS channel. The syndicated information may include information on recommended medication dosages, use of interventions, surgeries, and other information relating to the care of patients.

In embodiments, the saving, storing, merging, retrieval, and publication of syndicated clinical standards of care for clinical indicators through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated clinical standards of care for clinical indicators may be associated with an aggregator 210 to track updates.

In embodiments, the RSS feed 202, web feed, RSS stream, or RSS channel used to interact with syndicated clinical standards of care for clinical indicators may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with clinical standards of care for clinical indicators through the use of an RSS-enabled application 406 providing for social networking and vertical market integration.

In embodiments, researchers, physicians, healthcare providers, institutions, think tanks, regulatory bodies, accreditation groups, may interact with syndicated clinical standards of care for clinical indicators through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated clinical standards of care for clinical indicators through the use of an RSS-enabled application 406 providing a media viewer.

*[0042—W10-15] In embodiments, researchers, physicians, healthcare providers, institutions, think tanks, regulatory bodies, accreditation groups, may interact with syndicated clinical standards of care for clinical indicators associated with database functions that may permit the data quality to be verified, provide for transformation of the data, enable searching, filtering, or clustering the patient data, or categorizing the data into hierarchies, interrelationships, interrelated groups, and the like.

*[0042—W17-21] In embodiments, researchers, physicians, healthcare providers, institutions, think tanks, regulatory bodies, accreditation groups, may interact with syndicated clinical standards of care for clinical indicators associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated clinical standards of care for clinical indicators to which others may subscribe and/or publish. For example, within a cardiology physician group all physicians may be able to subscribe and/or publish to an RSS feed 202, web feed, RSS stream, or RSS channel, "Standard of Care: Hypertension" that regularly updates and retrieves clinical standards of care for clinical indicators that summarize the standards of care for the treatment of hypertension and distributes the information to the physicians within the practice.

In embodiments, the syndicated clinical standards of care for clinical indicators may be further associated with information that may provide for the management of the data. For example, the data may list the source of the clinical standard of care, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated clinical standards of care for clinical indicators within an infrastructure 416 that provides for data security, authentication, management of the traffic created by the RSS feed 202s, web feeds, RSS streams, or RSS channels, logging and pinging technology, and/or other communications.

In embodiments, researchers, physicians, healthcare providers, institutions, think tanks, regulatory bodies, accreditation groups, may interact with syndicated clinical standards of care for clinical indicators associated with special formatting and/or display properties.

In embodiments, researchers, physicians, healthcare providers, institutions, think tanks, regulatory bodies, accreditation groups, may interact with syndicated clinical standards of care for clinical indicators associated with special identification and transactional properties.

In embodiments, researchers, physicians, healthcare providers, institutions, think tanks, regulatory bodies, accreditation groups, may interact with syndicated clinical standards of care for clinical indicators associated with restricted or conditional access properties.

In embodiments, researchers, physicians, healthcare providers, institutions, think tanks, regulatory bodies, accreditation groups, and the like may interact with analyses of the congruence between a patient's treatment and clinical standards of care for clinical indicators matching that patient in a syndicated format to enable verification of appropriate treatment decisions via syndicated data obtained through an RSS feed 202, web feed, RSS stream, or RSS channel. The syndicated information may be associated with an analytic backend that can perform analyses on syndicated data stream and summarize the results in a syndicated format for distribution/retrieval. For example, an RSS-enabled client may present frequency distributions, contingency tables, descriptive statistics, predictive statistics, and the like of salient features of a physician's practice, trends, in comparison with standards of care. This analysis may be applied to qualitative or quantitative data.

In embodiments, the saving, storing, merging, retrieval, and publication of syndicated analyses of the congruence between a patient's treatment and clinical standards of care through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated analyses of the congruence between a patient's treatment and clinical standards of care may be associated with an aggregator 210 to track updates.

In embodiments, the RSS feed 202, web feed, RSS stream, or RSS channel used to interact with syndicated analyses of the congruence between a patient's treatment and clinical standards of care may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with analyses of the congruence between a patient's treatment and clinical standards of care through the use of an RSS-enabled application 406 providing for social networking and vertical market integration.

In embodiments, researchers, physicians, healthcare providers, institutions, think tanks, regulatory bodies, accreditation groups, may interact with syndicated analyses of the congruence between a patient's treatment and clinical standards of care through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated analyses of the congruence between a patient's treatment and clinical standards of care through the use of an RSS-enabled application 406 providing a media viewer.

In embodiments, researchers, physicians, healthcare providers, institutions, think tanks, regulatory bodies, accreditation groups, may interact with syndicated analyses of the congruence between a patient's treatment and clinical standards of care associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated analyses of the congruence between a patient's treatment and clinical standards of care associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated analyses of the congruence between a patient's treatment and clinical standards of care to which others may subscribe and/or publish.

In embodiments, the syndicated analyses of the congruence between a patient's treatment and clinical standards of care may be further associated with information that may provide for the management of the data. For example, the data may list the source of the clinical standard of care, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated analyses of the congruence between a patient's treatment and clinical standards of care within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated analyses of the congruence between a patient's treatment and clinical standards of care associated with special formatting and/or display properties.

In embodiments, researchers, physicians, healthcare providers, institutions, think tanks, regulatory bodies, accreditation groups, may interact with syndicated analyses of the congruence between a patient's treatment and clinical standards of care associated with special identification and transactional properties.

In embodiments, researchers, physicians, healthcare providers, institutions, think tanks, regulatory bodies, accreditation groups, may interact with syndicated analyses of the congruence between a patient's treatment and clinical standards of care associated with restricted or conditional access properties.

In embodiments, researchers, physicians, healthcare providers, institutions, think tanks, regulatory bodies, accreditation groups, and the like may interact with summaries of intervention complication rates, medication side effects (e.g. incidence and prevalence), survival rates associated with interventions and medications, surgical success rates, remission rates, and the like for retrieval through an RSS feed 202, web feed, RSS stream, or RSS channel.

In embodiments, interaction with syndicated summaries of intervention complication rates, medication side effects (e.g. incidence and prevalence), survival rates associated with interventions and medications, surgical success rates, remission rates, and the like through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated summaries of intervention complication rates, medication side effects (e.g. incidence and prevalence), survival rates associated with interventions and medications, surgical success rates, remission rates, and the like may be associated with an aggregator 210 to track updates.

In embodiments, the RSS feed 202, web feed, RSS stream, or RSS channel used to interact with syndicated summaries of intervention complication rates, medication side effects (e.g. incidence and prevalence), survival rates associated with interventions and medications, surgical success rates, remission rates, and the like may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with summaries of intervention complication rates, medication side effects (e.g. incidence and prevalence), survival rates associated with interventions and medications, surgical success rates, remission rates, and the like through the use of an RSS-enabled application 406 providing for social networking and vertical market integration.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like through the use of an RSS-enabled application 406 providing a media viewer.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like indicators to which others may subscribe and/or publish. For example, within a cardiology physician group all physicians may be able to subscribe and/or publish to an RSS feed 202, web feed, RSS stream, or RSS channel, "Side Effects: Zocor" that regularly updates and retrieves data on side effects associated with the medication Zocor, perhaps stratified by certain patient characteristics (e.g. age) and distributes the information to the physicians within the practice.

In embodiments, the syndicated summaries of intervention complication rates, medication side effects (e.g. incidence and prevalence), survival rates associated with interventions and medications, surgical success rates, remission rates, and the like may be further associated with information that may provide for the management of the data. For example, the data may list the source of the records, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated summaries of intervention complication rates, medication side effects (e.g. incidence and prevalence), survival rates associated with interventions and medications, surgical success rates, remission rates, and the like within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like associated with special formatting and/or display properties.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like associated with special identification properties.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like associated with restricted or conditional access properties.

In embodiments, researchers, physicians, healthcare providers, institutions, think tanks, regulatory bodies, accreditation groups, and the like may interact with data regarding the occurrence and details of adverse events within a patient population for retrieval through an RSS feed 202, web feed, RSS stream, or RSS channel.

In embodiments, the saving, storing, merging, retrieval, and publication of syndicated data regarding the occurrence and details of adverse events within a patient population through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated data regarding the occurrence and details of adverse events within a patient population may be associated with an aggregator 210 to track updates.

In embodiments, the RSS feed 202, web feed, RSS stream, or RSS channel used to interact with syndicated data regarding the occurrence and details of adverse events within a patient population may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated data regarding the occurrence and details of adverse events within a patient population through the use of an RSS-enabled application 406 providing for social networking and vertical market integration.

In embodiments, researchers, physicians, healthcare providers, institutions, think tanks, regulatory bodies, accreditation groups, may interact with syndicated data regarding the occurrence and details of adverse events within a patient population through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated data regarding the occurrence and details of adverse events within a patient population through the use of an RSS-enabled application 406 providing a media viewer.

In embodiments, researchers, physicians, healthcare providers, institutions, think tanks, regulatory bodies, accreditation groups, may interact with syndicated data regarding the occurrence and details of adverse events within a patient population associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated data regarding the occurrence and details of adverse events within a patient population associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated data regarding the occurrence and details of adverse events within a patient population indicators to which others may subscribe and/or publish. For example, within a cardiology physician group physicians may be able to subscribe and/or publish to an RSS feed 202, web feed, RSS stream, or RSS channel, "Sudden Cardiac Death" that regularly updates and retrieves data on patients experiencing sudden cardiac death within their group practice, hospital, etc, perhaps stratified by certain patient characteristics (e.g. age) and distributes the information to the physicians within the practice.

In embodiments, the syndicated data regarding the occurrence and details of adverse events within a patient population may be further associated with information that may provide for the management of the data. For example, the data may list the source of the records, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated data regarding the occurrence and details of adverse events within a patient population within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated data regarding the occurrence and details of adverse events within a patient population associated with special formatting and/or display properties.

In embodiments, researchers, physicians, healthcare providers, institutions, think tanks, regulatory bodies, accreditation groups, may interact with syndicated data regarding the occurrence and details of adverse events within a patient population associated with special identification and transactional properties.

In embodiments, researchers, physicians, healthcare providers, institutions, think tanks, regulatory bodies, accreditation groups, may interact with syndicated data regarding the occurrence and details of adverse events within a patient population associated with restricted or conditional access properties.

In embodiments, researchers, physicians, healthcare providers, institutions, and the like may interact with data patient records matched according to user-assigned criteria of clinical relevance to a pending medical decision regarding a current patient's treatment for retrieval through an RSS feed 202, web feed, RSS stream, or RSS channel. For example, a physician may be consulting with Patient A about the course of her cardiology treatment and which of the available medication options available might be best for her. As part of this decision making process the physician may retrieve the syndicated data of a Patient B, or group of patients, matching relevant clinical criteria of Patient A (e.g. age, sex, race, disease status, comorbidities, etc.). This data may serve to inform the patient, using experiential patient data, of, for example, the side effects that other patients have experienced with the various drugs available to her for treatment. Data derived from groups of patients may also serve to provide Patient A with the probabilities associated with certain events arising from taking each of the medications available to her. In this manner, the physician and patient may be better informed and able to way the pros and cons of each choice in a personalized fashion.

In embodiments, the saving, storing, merging, retrieval, and publication of syndicated patient records matched according to user-assigned criteria of clinical relevance to a pending medical decision regarding a current patient's treatment through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated patient records matched according to user-assigned criteria of clinical relevance to a pending medical decision regarding a current patient's treatment may be associated with an aggregator 210 to track updates.

In embodiments, the RSS feed 202, web feed, RSS stream, or RSS channel used to interact with syndicated patient records matched according to user-assigned criteria of clinical relevance to a pending medical decision regarding a current patient's treatment may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated patient records matched according to user-assigned criteria of clinical relevance to a pending medical decision regarding a current patient's treatment through the use of an RSS-enabled application 406 providing for social networking and vertical market integration.

In embodiments, researchers, physicians, healthcare providers, institutions, and the like, may interact with syndicated patient records matched according to user-assigned criteria of clinical relevance to a pending medical decision regarding a current patient's treatment through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, and the like, may interact with patient records matched according to user-assigned criteria of clinical relevance to a pending medical decision regarding a current patient's treatment through the use of an RSS-enabled application 406 providing a media viewer.

In embodiments, researchers, physicians, healthcare providers, institutions, and the like, may interact with syndicated patient records matched according to user-assigned criteria of clinical relevance to a pending medical decision regarding a current patient's treatment associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, and the like, may interact with syndicated patient records matched according to user-assigned criteria of clinical relevance to a pending medical decision regarding a current patient's treatment associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, and the like, may interact with syndicated patient records matched according to user-assigned criteria of clinical relevance to a pending medical decision regarding a current patient's treatment to which others may subscribe and/or publish.

In embodiments, the syndicated patient records matched according to user-assigned criteria of clinical relevance to a pending medical decision regarding a current patient's treatment may be further associated with information that may provide for the management of the data. For example, the data may list the source of the records, the date on which it was last updated, etc. Thus, the data may provide for further aggregation, republication, and the like.

In embodiments, researchers, physicians, healthcare providers, institutions, and the like, and the like may interact with syndicated patient records matched according to user-assigned criteria of clinical relevance to a pending medical decision regarding a current patient's treatment within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, and the like, may interact with syndicated patient records matched according to user-assigned criteria of clinical relevance to a pending medical decision regarding a current patient's treatment associated with special formatting and/or display properties.

In embodiments, researchers, physicians, healthcare providers, institutions, and the like, may interact with syndicated patient records matched according to user-assigned criteria of clinical relevance to a pending medical decision regarding a current patient's treatment associated with special identification and transactional properties.

In embodiments, researchers, physicians, healthcare providers, institutions, and the like, may interact with syndicated patient records matched according to user-assigned criteria of clinical relevance to a pending medical decision regarding a current patient's treatment associated with restricted or conditional access properties.

In embodiments, researchers, physicians, healthcare providers, institutions, think tanks, regulatory bodies, accreditation groups, and the like may interact with syndicated comparisons of patients' outcomes with national norms for retrieval through an RSS feed 202, web feed, RSS stream, or RSS channel.

In embodiments, interaction with syndicated comparisons of patients' outcomes with national norms through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated comparisons of patients' outcomes with national norms within a patient population may be associated with an aggregator 210 to track updates.

In embodiments, the RSS feed 202, web feed, RSS stream, or RSS channel used to interact with syndicated comparisons of patients' outcomes with national norms within a patient population may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated comparisons of patients' outcomes with national norms within a patient population through the use of an RSS-enabled application 406 providing for social networking and vertical market integration.

In embodiments, researchers, physicians, healthcare providers, institutions, think tanks, regulatory bodies, accreditation groups, may interact with syndicated comparisons of patients' outcomes with national norms through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, researchers, physicians, healthcare providers, institutions, think tanks, regulatory bodies, accreditation groups, may interact with syndicated comparisons of patients' outcomes with national norms within a patient population through the use of an RSS-enabled application 406 providing a media viewer.

In embodiments, researchers, physicians, healthcare providers, institutions, think tanks, regulatory bodies, accreditation groups, may interact with syndicated comparisons of patients' outcomes with national norms within a patient population associated with database functions that may permit the data quality to be verified, provide for transformation of the data, enable searching, filtering, or clustering the patient data, or categorizing the data into hierarchies, interrelationships, interrelated groups, and the like.

In embodiments, researchers, physicians, healthcare providers, institutions, think tanks, regulatory bodies, accreditation groups, may interact with syndicated comparisons of patients' outcomes with national norms within a patient population associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, researchers, physicians, healthcare providers, institutions, think tanks, regulatory bodies, accreditation groups, may interact with syndicated comparisons of patients' outcomes with national norms to which others may subscribe and/or publish. For example, within a cardiology physician group physicians may wish to compare how their patients fare following a certain intervention type as compared to other patients within a practice group, with local norms, national norms, etc. Similarly, an institution, regulatory body or accreditation group may seek to compare the outcomes of different institutions, providers, and the like.

In embodiments, the syndicated comparisons of patients' outcomes with national norms may be further associated with information that may provide for the management of the data. For example, the data may list the source of the national norms, the date on which it was last updated, etc. Thus, the data may provide for further aggregation, republication, and the like.

In embodiments, researchers, physicians, healthcare providers, institutions, think tanks, regulatory bodies, accreditation groups, and the like may interact with syndicated comparisons of patients' outcomes with national norms within a patient population within an infrastructure 416 that provides for data security, authentication, management of the traffic created by the RSS feeds 202, web feeds, RSS streams, or RSS channels, logging and pinging technology, and/or other communications.

In embodiments, researchers, physicians, healthcare providers, institutions, think tanks, regulatory bodies, accreditation groups, may interact with syndicated comparisons of patients' outcomes with national norms within a patient population associated with special formatting and/or display properties.

In embodiments, researchers, physicians, healthcare providers, institutions, think tanks, regulatory bodies, accreditation groups, may interact with syndicated comparisons of patients' outcomes with national norms within a patient population associated with special identification and transactional properties.

In embodiments, researchers, physicians, healthcare providers, institutions, think tanks, regulatory bodies, accreditation groups, may interact with syndicated comparisons of patients' outcomes with national norms within a patient population associated with restricted or conditional access properties.

In embodiments, a patient's RSS feed 202, web feed, RSS stream, or RSS channel may be configured by a patient, attending physician, nurse, other healthcare provider, hospital, physician practice, insurer, patient advocacy group, or third-party enterprise, or the like. This configuration may be based at least in part on a patient's demographic profile (e.g. age, sex, race), clinical indications (e.g. cardiovascular disease, lung cancer), the institution(s) visited by the patient to receive healthcare (e.g. solo practitioner, physician group, hospital, academic center), the ICD-10 codes of the patient's current clinical indications (e.g. "1.8.6 (H40-H42)"=Glaucoma), the ICD-10 codes of the patient's past clinical indications, the geographic locations of the patient's current and former addresses, current list of medications the patient is taking (e.g. Beta-blocker, Prozac, Zocor), the patient's medication history, the interventions the patient has received (e.g. angioplasty, colonoscopy), allergies, insurers, and so forth.

In embodiments, a patient's RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, or personal digital assistant, other SMS text-enabled device, or the like.

In embodiments, a patient's RSS feed 202, web feed, RSS stream, or RSS channel may be associated with an aggregator 210 to track updates.

In embodiments, a patient's RSS feed 202, web feed, RSS stream, or RSS channel may be associated with a content management system that may provide summaries of the syndicated data available, dates associated with the syndicated data, links to access the full, non-summarized data, and the like.

In embodiments, a patient's RSS feed 202, web feed, RSS stream, or RSS channel may be associated with an application 406 providing social networking. For example, through social networking a patient may be able to share syndicated data with other patients, physician's and the like, with whom the patient shares a clinical issue, disease, medication prescription, clinical course of care, intervention history, pending intervention, and the like. The clinical factors of relevance to patients who seek to share syndicated data may be published with detailed tags to provide narrowly tailored or easily filtered RSS feeds 202, web feeds, RSS streams, or RSS channels for ongoing data sharing with others. Such a process may allow patients to form support groups, information-sharing collaborations, to link with others who have undergone treatments that a patient is contemplating undergoing herself, and the like.

In embodiments, a patient's RSS feed 202, web feed, RSS stream, or RSS channel may be associated with an application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, a patient's RSS feed 202, web feed, RSS stream, or RSS channel may be associated with an application 406 providing a media viewer. For example, an RSS item may refer to an image source, such as an MRI image in a medical record from a hospital, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments, a patient's RSS feed 202, web feed, RSS stream, or RSS channel may be associated with an application 406 providing vertical market integration. For example, a retail pharmacy may obtain syndicated data on a patient's medications and dosages through an RSS feed 202, web feed, RSS stream, or RSS channel, permitting the pharmacy to receive updates and changes to a customer's pharmaceutical needs.

In embodiments, a patient's RSS feed 202, web feed, RSS stream, or RSS channel may be associated with database functions that may permit the data quality to be verified, provide for transformation of the patients' data, enable searching, filtering, or clustering the patient data, or categorizing the data into hierarchies, interrelationships, interrelated groups, and the like.

In embodiments, a patient's RSS feed 202, web feed, RSS stream, or RSS channel may be associated with semantic rules 412 that enable the creation of intra-, or inter-patient, -clinical state, -institution, etc. metadata. Semantic rules 412 may also provide for metadata enrichment, interpretation or translation of patient data, as well as permit the creation of knowledge structures (e.g., using OPML) and the use of a dictionary, thesaurus or the like.

In embodiments, a patient's RSS feed 202, web feed, RSS stream, or RSS channel may interact with syndicated data to which others may subscribe and/or publish. For example, a patient undergoing chemotherapy may receive syndicated data from her healthcare providers regarding the progress of ridding his lungs of cancer. The patient may, in turn, record this information and his thoughts, feelings, symptoms, and the like in a weekly written log that is stored as syndicated data, and create a feed called "My Experiences with Chemotherapy." Others who have an interest in learning about a very personal summary of the effects of chemotherapy, perhaps because they are about to undergo similar treatment, have a loved one who is, may subscribe and/or publish to this feed.

In embodiments, a patient's RSS feed 202, web feed, RSS stream, or RSS channel may be associated with information that may provide for the management of the data. For example, the data may list the author of the data, the date on which it was authored, etc. Thus, the data may provide for further aggregation, republication, and the like.

In embodiments, a patient's RSS feed 202, web feed, RSS stream, or RSS channel may be associated with an infrastructure 416 that provides for data security, authentication, management of the traffic created by the RSS feeds 202, web feeds, RSS streams, or RSS channels, logging and pinging technology, and/or other communications.

In embodiments, a patient's RSS feed 202, web feed, RSS stream, or RSS channel may be associated with special formatting and/or display properties.

In embodiments, a patient's RSS feed 202, web feed, RSS stream, or RSS channel may be associated with special identification and transactional properties.

In embodiments, a patient's RSS feed 202, web feed, RSS stream, or RSS channel may be associated with restricted or conditional access properties.

In embodiments, patients may interact with syndicated comparisons of physicians' performance, treatment outcomes, event rates, and the like with national norms for retrieval through an RSS feed 202, web feed, RSS stream, or RSS channel.

In embodiments, interaction with syndicated comparisons of physicians' performance, treatment outcomes, event rates, and the like with national norms through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated comparisons of physicians' performance, treatment outcomes, event rates, and the like with national norms may be associated with an aggregator 210 to track updates.

In embodiments, the RSS feed 202, web feed, RSS stream, or RSS channel used to interact with syndicated comparisons of physicians' performance, treatment outcomes, event rates, and the like with national norms may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated comparisons of physicians' performance, treatment outcomes, event rates, and the like with national norms through the use of an RSS-enabled application 406 providing for social networking and vertical market integration.

In embodiments, patients may interact with syndicated comparisons of physicians' performance, treatment outcomes, event rates, and the like with national norms through the use of an RSS-enabled application 406 providing a user interface 700 for viewing data, records, and the like. In another embodiment, a patient may configure a comparison using syndicated data or data pools containing raw data for events, treatment outcomes, and the like. For example, a client 102 may, in response to user input such as clicking on a title of an item in the user interface 700, retrieve the underlying item from the content source 204 as indicated by an arrow 208.

In embodiments, patients may interact with syndicated comparisons of physicians' performance, treatment outcomes, event rates, and the like with national norms through the use of an RSS-enabled application 406 providing a media viewer.

In embodiments, patients may interact with syndicated comparisons of physicians' performance, treatment outcomes, event rates, and the like with national norms associated with database functions that may permit the data quality to be verified, provide for transformation of the data, enable searching, filtering, or clustering the patient data, or categorizing the data into hierarchies, interrelationships, interrelated groups, and the like.

In embodiments, patients may interact with syndicated comparisons of physicians' performance, treatment outcomes, event rates, and the like with national norms associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, patients may interact with syndicated comparisons of physicians' performance, treatment outcomes, event rates, and the like with national norms to which others may subscribe and/or publish. For example, a state regulatory agency may publish syndicated data on the event rates following coronary artery bypass grafting for all healthcare institutions within the state performing the intervention. This syndicated data may, in turn, comprise an RSS feed 202, "CABG Event Rates by Institution in State X," to which other interested parties may subscribe.

In embodiments, the syndicated comparisons of physicians' performance, treatment outcomes, event rates, and the like with national norms may be further associated with information that may provide for the management of the data. For example, the data may list the date on which it was last updated, etc. Thus, the data may provide for further aggregation, republication, and the like.

In embodiments, patients may interact with syndicated comparisons of physicians' performance, treatment outcomes, event rates, and the like with national norms within an infrastructure 416 that provides for data security, authentication, management of the traffic created by the RSS feeds 202, web feeds, RSS streams, or RSS channels, logging and pinging technology, and/or other communications.

In embodiments, patients may interact with syndicated comparisons of physicians' performance, treatment outcomes, event rates, and the like with national norms associated with special formatting and/or display properties.

In embodiments, patients may interact with syndicated comparisons of physicians' performance, treatment outcomes, event rates, and the like with national norms associated with special identification and transactional properties.

In embodiments, patients may interact with syndicated comparisons of physicians' performance, treatment outcomes, event rates, and the like with national norms associated with restricted or conditional access properties.

In embodiments, patients may interact with, and share with healthcare providers, syndicated summaries of their current health status, functional status, quality of life, clinical values, and the like for retrieval through an RSS feed 202, web feed, RSS stream, or RSS channel. For example, a patient returning home following knee-replacement surgery may complete self-report health status questionnaires regarding items such as his overall health status (e.g., as measure by a standardized questionnaire like the SF-36), the range of motion in his operative leg, his pain level, overall functional status and mobility, and the like. This information may be retrieved by his surgeon, primary care physician, physical therapist, insurer and so on in order to continually monitor his recovery and more easily note significant aberrations from the expected course of recovery that may necessitate an immediate consultation. Similarly, a diabetic patient may record his daily glucose levels in a syndicated format for retrieval by healthcare personnel.

In embodiments, interaction with syndicated summaries of patients' current health status, functional status, quality of life, clinical values, and the like through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated summaries of patients' current health status, functional status, quality of life, clinical values, and the like may be associated with an aggregator 210 to track updates.

In embodiments, the RSS feed 202, web feed, RSS stream, or RSS channel used to interact with syndicated summaries of patients' current health status, functional status, quality of life, clinical values, and the like may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated summaries of patients' current health status, functional status, quality of life, clinical values, and the like through the use of an RSS-enabled application 406 providing for social networking and vertical market integration.

In embodiments, patients may interact with syndicated summaries of patients' current health status, functional status, quality of life, clinical values, and the like through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, patients may interact with syndicated summaries of patients' current health status, functional status, quality of life, clinical values, and the like with national norms through the use of an RSS-enabled application 406 providing a media viewer.

In embodiments, patients may interact with syndicated summaries of patients' current health status, functional status, quality of life, clinical values, and the like associated with database functions that may permit the data quality to be verified, provide for transformation of the data, enable searching, filtering, or clustering the patient data, or categorizing the data into hierarchies, interrelationships, interrelated groups, and the like.

In embodiments, patients may interact with syndicated summaries of patients' current health status, functional status, quality of life, clinical values, and the like associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, patients may interact with syndicated summaries of patients' current health status, functional status, quality of life, clinical values, and the like to which others may subscribe and/or publish.

In embodiments, the syndicated summaries of patients' current health status, functional status, quality of life, clinical values, and the like may be further associated with information that may provide for the management of the data. For example, the data may list the date on which it was last updated, etc. Thus, the data may provide for further aggregation, republication, and the like.

In embodiments, patients may interact with syndicated summaries of patients' current health status, functional status, quality of life, clinical values, and the like within an infrastructure 416 that provides for data security, authentication, management of the traffic created by the RSS feeds 202, web feeds, RSS streams, or RSS channels, logging and pinging technology, and/or other communications.

In embodiments, patients may interact with syndicated summaries of patients' current health status, functional status, quality of life, clinical values, and the like associated with special formatting and/or display properties.

In embodiments, patients may interact with syndicated summaries of patients' current health status, functional status, quality of life, clinical values, clinical values, and the like associated with special identification and/or transactional properties.

In embodiments, patients may interact with syndicated summaries of patients' current health status, functional status, quality of life, clinical values, and the like associated with restricted or conditional access properties.

In embodiments, patients may interact with syndicated medical research, clinical trial findings, case studies, peer-reviewed articles, academic presentations, and the like in a syndicated format to enable interested persons to share and continually update their medical knowledge via syndicated data obtained through an RSS feed 202, web feed, RSS stream, or RSS channel. The syndicated information may include full academic journal articles, article abstracts, customized article summaries, clinic trial data, clinical trial analyses, published standards of care, published clinical indicators for medications, published indicators for interventions, appropriateness scores for certain classes of clinical profiles and corresponding treatment options, and the like.

In embodiments, the interaction with syndicated medical research, clinical trial findings, case studies, peer-reviewed articles, academic presentations, and the like through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated medical research, clinical trial findings, case studies, peer-reviewed articles, academic presentations, and the like may be associated with an aggregator 210 to track updates.

In embodiments, the RSS feed 202, web feed, RSS stream, or RSS channel used to interact with syndicated medical research, clinical trial findings, case studies, peer-reviewed articles, academic presentations, and the like may be associated with a content management system that may provide summaries of the syndicated data available, dates associated with the syndicated data, links to access the full, non-summarized data, and the like.

In embodiments, patients may interact with syndicated medical research, clinical trial findings, case studies, peer-reviewed articles, academic presentations, and the like through the use of an RSS-enabled application 406 providing social networking and/or vertical market integration.

In embodiments, patients may interact with syndicated medical research, clinical trial findings, case studies, peer-reviewed articles, academic presentations, and the like through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, patients may interact with syndicated medical research, clinical trial findings, case studies, peer-reviewed articles, academic presentations, and the like through the use of an RSS-enabled application 406 providing a media viewer. For example, an RSS item consisting of a multimedia academic conference presentation may refer to graphic images, such as PowerPoint slides, and may specify a viewer for the source image that is available through the registry. In operation, a client (e.g. a physician) with appropriate permissions to view the image (also as managed, e.g., through the metadata for the enhanced syndication system), may retrieve the appropriate viewer service from the registry, and apply the viewer to view the source image.

In embodiments patients may interact with syndicated medical research, clinical trial findings, case studies, peer-reviewed articles, academic presentations, and the like associated with database functions that may permit the data quality to be verified, provide for transformation of the data, enable searching, filtering, or clustering the patient data, or categorizing the data into hierarchies, interrelationships, interrelated groups, and the like.

In embodiments, patients may interact with syndicated medical research, clinical trial findings, case studies, peer-reviewed articles, academic presentations, and the like that is associated with semantic rules 412 that enable the creation of metadata. Semantic rules 412 may also provide for metadata enrichment, interpretation or translation of medical research, clinical trial findings, case studies, peer-reviewed articles, academic presentations, and the like, as well as permit the creation of knowledge structures (e.g., using OPML) and the use of a dictionary, thesaurus or the like.

In embodiments, patients may interact with syndicated medical research, clinical trial findings, case studies, peer-reviewed articles, academic presentations, and the like to which others may subscribe and/or publish. For example, a cardiology patient, her family, or other interested persons may be able to subscribe and/or publish to an RSS feed 202, web feed, RSS stream, or RSS channel, "Developments in Cardiology" that regularly updates and retrieves information from the academic medical journal relevant to cardiology and distributes the information to patients and other interested persons.

In embodiments, the syndicated medical research, clinical trial findings, case studies, peer-reviewed articles, academic presentations, and the like may be further associated with information that may provide for the management of the data. For example, the data may list the author of the data, the date on which it was authored, etc. Thus, the data may provide for further aggregation, republication, and the like.

In embodiments, patients may interact with syndicated medical research, clinical trial findings, case studies, peer-reviewed articles, academic presentations, and the like within an infrastructure 416 that provides for data security, authentication, management of the traffic created by the RSS feeds 202, web feeds, RSS streams, or RSS channels, logging and pinging technology, and/or other communications.

In embodiments, patients may interact with syndicated medical research, clinical trial findings, case studies, peer-reviewed articles, academic presentations, and the like associated with special formatting and/or display properties.

In embodiments, patients may interact with syndicated medical research, clinical trial findings, case studies, peer-reviewed articles, academic presentations, and the like associated with special identification and/or transactional properties.

In embodiments, patients may interact with syndicated medical research, clinical trial findings, case studies, peer-reviewed articles, academic presentations, and the like associated with restricted or conditional access properties.

In embodiments, patients may interact with medical decision making trees in a syndicated format to enable healthcare providers to better evaluate treatment options via syndicated data obtained through an RSS feed 202, web feed, RSS stream, or RSS channel. The syndicated information may include empiric data summaries describing the probabilities of certain outcomes that are associated with various treatment options, and the like.

In embodiments, the saving, storing, merging, retrieval, and publication of syndicated medical decision making trees through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated medical decision making trees may be associated with an aggregator 210 to track updates.

In embodiments, the RSS feed 202, web feed, RSS stream, or RSS channel used to interact with syndicated medical decision making trees may be associated with a content management system that may provide summaries of the syndicated data available, dates associated with the syndicated data, links to access the full, non-summarized data, and the like.

In embodiments, patients may interact with syndicated medical decision making trees through the use of an RSS-enabled application 406 providing social networking and/or vertical market integration.

In embodiments, patients may interact with syndicated medical decision making trees through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

In embodiments, patients may interact with syndicated medical decision making trees through the use of an RSS-enabled application 406 providing a media viewer.

In embodiments, patients may interact with syndicated medical decision making trees associated with special formatting and/or display properties.

In embodiments, patients may interact with syndicated medical decision making trees associated with special identification and/or transactional properties.

In embodiments, patients may interact with syndicated medical decision making trees associated with restricted or conditional access properties.

In embodiments, patients may interact with syndicated medical decision making trees associated with database functions that may permit the data quality to be verified, provide for transformation of the data, enable searching, filtering, or clustering the patient data, or categorizing the data into hierarchies, interrelationships, interrelated groups, and the like.

In embodiments, patients may interact with syndicated medical decision making trees associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, patients may interact with syndicated medical decision making trees to which others may subscribe and/or publish. For example, a cardiology patient may be able to subscribe and/or publish to an RSS feed 202, web feed, RSS stream, or RSS channel, "Angioplasty" that regularly updates and retrieves medical decision making trees that summarize the clinical outcome probabilities for patients either undergoing, or not undergoing angioplasty for a variety of clinical groups, classes, and indicators, and distributes the information to the patient.

In embodiments, the syndicated medical decision making trees may be further associated with information that may provide for the management of the data. For example, the data may list the source of the decision making tree, the date on which it was last updated, etc. Thus, the data may provide for further aggregation, republication, and the like.

In embodiments, patients may interact with syndicated medical decision making trees within an infrastructure 416 that provides for data security, authentication, management of the traffic created by the RSS feeds 202, web feeds, RSS streams, or RSS channels, logging and pinging technology, and/or other communications.

In embodiments, patients may interact with summaries of intervention complication rates, medication side effects (e.g. incidence and prevalence), survival rates associated with interventions and medications, surgical success rates, remission rates, and the like for retrieval through an RSS feed 202, web feed, RSS stream, or RSS channel.

In embodiments, interaction with syndicated summaries of intervention complication rates, medication side effects (e.g. incidence and prevalence), survival rates associated with interventions and medications, surgical success rates, remission rates, and the like through an RSS feed 202, web feed, RSS stream, or RSS channel may be associated with an application 406 consisting of a client-side program. The client-side program may be formatted to operate on client devices such as, a desktop computer, laptop computer, "pocket" personal computer, a cellular phone, Blackberry, personal digital assistant, or other SMS text-enabled device, or the like.

In embodiments, the RSS feed 202, web feed, RSS stream, or RSS channel used to interact with syndicated summaries of intervention complication rates, medication side effects (e.g. incidence and prevalence), survival rates associated with interventions and medications, surgical success rates, remission rates, and the like may be associated with an aggregator 210 to track updates.

In embodiments, the RSS feed 202, web feed, RSS stream, or RSS channel used to interact with syndicated summaries of intervention complication rates, medication side effects (e.g. incidence and prevalence), survival rates associated with interventions and medications, surgical success rates, remission rates, and the like may be associated with a content management system that may provide summaries of the syndicated data available, dates associated with the syndicated data, links to access the full, non-summarized data, and the like.

In embodiments, researchers, physicians, healthcare providers, institutions, think tanks, regulatory bodies, accreditation groups, may interact with syndicated summaries of intervention complication rates, medication side effects (e.g. incidence and prevalence), survival rates associated with interventions and medications, surgical success rates, remission rates, and the like through the use of an RSS-enabled application 406 providing for social networking and vertical market integration.

*[0042—AG'6 In embodiments, patients may interact with syndicated summaries of intervention complication rates, medication side effects (e.g. incidence and prevalence), survival rates associated with interventions and medications, surgical success rates, remission rates, and the like through the use of an RSS-enabled application 406 providing a user interface 700 for viewing data, records, and the like. For example, a client 102 may, in response to user input such as clicking on a title of an item in the user interface 700, retrieve the underlying item from the content source 204 as indicated by an arrow 208.

*[0042—AG'7 In embodiments, patients may interact with syndicated summaries of intervention complication rates, medication side effects (e.g. incidence and prevalence), survival rates associated with interventions and medications, surgical success rates, remission rates, and the like through the use of an RSS-enabled application 406 providing a media viewer.

In embodiments, patients may interact with syndicated summaries of intervention complication rates, medication side effects (e.g. incidence and prevalence), survival rates associated with interventions and medications, surgical success rates, remission rates, and the like associated with database functions that may permit the data quality to be verified, provide for transformation of the data, enable searching, filtering, or clustering the patient data, or categorizing the data into hierarchies, interrelationships, interrelated groups, and the like.

In embodiments, patients may interact with syndicated summaries of intervention complication rates, medication side effects (e.g. incidence and prevalence), survival rates associated with interventions and medications, surgical success rates, remission rates, and the like associated with semantic rules 412 that enable the creation of metadata. Semantic rules 412 may also provide for metadata enrichment, interpretation or translation of medical decision making trees, as well as permit the creation of knowledge structures (e.g., using OPML) and the use of a dictionary, thesaurus or the like.

In embodiments, patients may interact with syndicated summaries of intervention complication rates, medication side effects (e.g. incidence and prevalence), survival rates associated with interventions and medications, surgical success rates, remission rates, and the like indicators to which others may subscribe and/or publish. For example, a cardiology patient may be able to subscribe and/or publish to an RSS feed 202, web feed, RSS stream, or RSS channel, "Hypertension Medications" that regularly updates and retrieves data on side effects associated with extant and new hypertension medications, perhaps stratified by certain patient characteristics (e.g. age) and distributes the information to the physicians within the practice.

In embodiments, the syndicated summaries of intervention complication rates, medication side effects (e.g. incidence and prevalence), survival rates associated with interventions and medications, surgical success rates, remission rates, and the like may be further associated with information that may provide for the management of the data. For example, the data may list the source of the records, the date on which it was last updated, etc. Thus, the data may provide for further aggregation, republication, and the like.

In embodiments, patients may interact with syndicated summaries of intervention complication rates, medication side effects (e.g. incidence and prevalence), survival rates associated with interventions and medications, surgical success rates, remission rates, and the like within an infrastructure 416 that provides for data security, authentication, management of the traffic created by the RSS feeds 202, web feeds, RSS streams, or RSS channels, logging and pinging technology, and/or other communications.

In embodiments, patients may interact with syndicated summaries of intervention complication rates, medication side effects (e.g. incidence and prevalence), survival rates associated with interventions and medications, surgical success rates, remission rates, and the like associated with special formatting and/or display properties.

In embodiments, patients may interact with syndicated summaries of intervention complication rates, medication side effects (e.g. incidence and prevalence), survival rates associated with interventions and medications, surgical success rates, remission rates, and the like associated with special identification and/or transactional properties.

In embodiments, patients may interact with syndicated summaries of intervention complication rates, medication side effects (e.g. incidence and prevalence), survival rates associated with interventions and medications, surgical success rates, remission rates, and the like associated with restricted or conditional access properties.

Referring again to FIG. 13, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

Referring again to FIG. 14, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

Referring again to FIG. 15, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

Referring again to FIG. 16, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

Referring again to FIG. 17, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

Referring again to FIG. 18, the syndicated data/information 1302 may be patient information, patient record information, journal and research information, decision making tree information, clinical standards of care information, congruence information, rate information, adverse event information, matched patient record information, comparison information, recipient information, comparative performance information, current status information, community medical information, treatment information and treatment rate information, as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

Practitioners of ordinary skill in the art will readily discern that the systems and methods of the present invention are useful in therapeutic, diagnostic and administrative settings in a health care facility. With more specificity, these systems and methods may be useful for managing a diagnostic system, a therapeutic system, an administrative system or some combination thereof in a health care facility. As used herein, the term health care facility includes hospitals, clinics, outpatient centers, community health centers, nursing homes, hospices and home care settings, school health facilities, doctors' offices, mobile health facilities, morgues, mobile emergency or disaster response units, ambulances, labs, pharmacies, or any place, location, facility where health or medical care and/or information relating to health or medical care is offered and/or provided. The term patient, as used herein, does not require that an abnormal state exists in that individual, and the term includes individuals of all ages and further includes the unborn.

Diagnostic systems in a health care facility may be directed to identifying the presence or absence of diseases or medical conditions, evaluating the severity of abnormalities or diseases, or predicting their prognosis. For example, an electrocardiogram, whether normal or abnormal, may be part of a diagnostic system generally useful in internal medicine, cardiology and the like. Moreover, diagnostic systems may be useful in monitoring the response of a patient to a therapeutic intervention, or in predicting the response of a patient to a therapeutic intervention. Blood glucose tests, performed for example with a home blood glucose meter, may be part of a diagnostic system generally useful in diabetes care as the patient's insulin doses are varied or as the patient's lifestyle changes. As another example, measurement of estrogen receptors on a breast cancer specimen may be part of a diagnostic system generally useful in oncology as an assessment of tumor susceptibility to tamoxifen. Diagnostic systems may specify a normal or abnormal profile in a patient who has not yet exhibited any signs or symptoms of disease. Identifying the presence of a Huntington's chorea gene in a neurologically normal patient may be part of a diagnostic system generally useful in predicting an extremely high likelihood of developing this devastating neurological disorder. Similarly, identifying the presence of abnormally high cholesterol in an otherwise asymptomatic patient may be part of a diagnostic system generally useful in predicting the likelihood of subsequent cardiovascular disease. Data pertaining to, used by, collected by or generated by a diagnostic system may be termed diagnostic data.

In more detail, diagnostic systems may include a variety of diagnostic devices. Diagnostic devices may be used in a number of settings within a health care facility, including a laboratory setting, a diagnostic imaging setting and a clinical setting. Diagnostic devices in a laboratory setting may include devices used in measuring clinical chemistry or toxicology profiles, in examining blood or tissue specimens (hematology, pathology, blood banking, tissue typing, etc.), in identifying infectious agents (microbiology, virology, etc), in evaluating immunological profiles, in profiling gene patterns or protein patterns, and the like. Diagnostic devices in a diagnostic imaging setting may include those devices that permit direct visualization of body parts or structures and capture of images therefrom (microscopes, endoscopes, etc.), those devices that utilize sound waves, Xrays, magnetic resonance or other forms or electromagnetic radiation, and those devices that further involve administering a contrast medium or an imaging agent (angiography, barium contrast studies, nuclear medicine studies, etc.), and the like. Diagnostic devices in a clinical setting may include devices useful for anesthesiology and critical care, cardiovascular medicine, dental practice, otorhinolaryngology (ear/nose/throat), gastroenterology, urology, general hospital and personal use, general and plastic surgery, obstetrics and gynecology, ophthalmology, physical medicine, and other clinical fields. Illustrative examples of diagnostic devices are set forth herein. It is understood that a diagnostic device may also be a combination devices where one component satisfies a diagnostic function. A pulmonary function device, for example, may provide a measurement of pulmonary function parameters (a diagnostic function) and may also administer an inhaler treatment (a therapeutic function), optionally followed by a second measurement of pulmonary function parameters. Combination devices may also include those diagnostic devices that combine a plurality of diagnostic functions.

Therapeutic systems in a health care facility may be directed to altering or improving the course of a disease or of a physiological or pathological process. Interventions carried out to alter or improve the course of a disease or of a physiological or pathological process may be also termed "treatments" or "therapies." The therapeutic intervention supplied by a therapeutic system need not be successful for the system to be considered therapeutic, and the intervention need not yield an overall health benefit. A therapeutic intervention may include a conventional medical intervention or a nontraditional intervention including chiropracty, naturopathy, herbalism, acupuncture, and the like. Therapeutic systems may be invasive or noninvasive. Examples of invasive systems are those that entail a penetration of or an entry into a body part. Injecting a substance into a patient, inserting an endoscope into a patient, removing a mole or an organ from a person, or setting a patient's fracture are all invasive. By contrast, noninvasive interventions generally do not involve penetrating the body or entering a natural or unnatural bodily orifice. Massage, ultrasonic physical therapy, and dental hygiene, for example, are noninvasive. Data pertaining to, used by, collected by or generated by a therapeutic system may be termed therapeutic data.

In more detail, therapeutic devices may include devices useful for anesthesiology and critical care, cardiovascular medicine, dental practice, otorhinolaryngology (ear/nose/throat), gastroenterology, urology, general hospital and personal use, general and plastic surgery, obstetrics and gynecology, ophthalmology, physical medicine, and other clinical fields. Illustrative examples of therapeutic devices are set forth herein. It is understood that a therapeutic device may also be a combination devices where one component satisfies a therapeutic function. An endoscope, for example, may permit visualization of a lesion (a diagnostic function) and placement of a dilating stent (a therapeutic function).

In embodiments, anesthesiology and critical carediagnostic and therapeutic devices may be able to interact with syndicated data, or publish one or more syndicated feeds. For example, anesthesiology diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an ultrasonic air embolism monitor may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other anesthesiology and critical care diagnostic and therapeutic devices that may interact with syndicated data in the above manner include, but are not limited to a Powered algesimeter, Argon gas analyzer, Indwelling blood oxyhemoglobin concentration analyzer, Indwelling blood carbon dioxide partial pressure (PCO2) analyzer, Indwelling blood hydrogen ion concentration (pH) analyzer, Indwelling blood oxygen partial pressure (PO2) analyzer, Carbon dioxide gas analyzer, Carbon monoxide gas analyzer, Enflurane gas analyzer, Halothane gas analyzer, Helium gas analyzer, Neon gas analyzer, Nitrogen gas analyzer, Nitrous oxide gas analyzer, Oxygen gas analyzer, Oxygen uptake computer, Pressure plethysmograph, Volume plethysmograph, Inspiratory airway pressure meter, Rhinoanemometer, Diagnostic spirometer, Monitoring spirometer, Peak-flow meter for spirometry, Gas volume calibrator, Pulmonary-function data calculator, Predictive pulmonary-function value calculator, Diagnostic pulmonary-function interpretation calculator, Esophageal stethoscope with electrical conductors, Water vapor analyzer, Gas calibration flowmeter, Breathing frequency monitor, Apnea monitor, Nitric oxide analyzer, Nitrogen dioxide analyzer, Lung water monitor, Cutaneous carbon dioxide (PcCO2) monitor, Cutaneous oxygen (PcO2) monitor, Pneumotachometer, Airway pressure monitor, Gas pressure gauge, Gas pressure calibrator, Pressure regulator, Electrical peripheral nerve stimulator, Differential pressure transducer, Gas flow transducer, Gas pressure transducer, Gas machine for anesthesia or analgesia, Nitric oxide administration apparatus, Breathing system heater, Breathing gas mixer, Heat and moisture condenser (artificial nose), Electroanesthesia apparatus, Gas-scavenging apparatus, Portable oxygen generator, Hyperbaric chamber, Anesthetic gas mask, Nonrebreathing mask, Oxygen mask, Scavenging mask, Venturi mask, Membrane lung for long-term pulmonary support, Nebulizer, Portable liquid oxygen unit, Powered percussor, Nonpowered oxygen tent, Electrically powered oxygen tent, Autotransfusion apparatus, Anesthetic vaporizer, Continuous ventilator, Noncontinuous ventilator (IPPB), Powered emergency ventilator, External negative pressure ventilator, i.e., iron lung, Intermittent mandatory ventilation attachment, or a Positive end expiratory pressure breathing attachment.

In embodiments, cardiovascular diagnostic and therapeutic devices may be able to interact with syndicated data, or publish one or more syndicated feeds. For example, cardiovascular diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an echocardiograph may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other cardiovascular diagnostic and therapeutic devices that may interact with syndicated data in the above manner include, but are not limited to a Arrhythmia detector and alarm (including ST-segment measurement and alarm), Blood pressure alarm, Blood pressure computer, Blood pressure cuff, Noninvasive blood pressure measurement system, Venous blood pressure manometer, Diagnostic intravascular catheter, Continuous flush catheter, Electrode recording catheter or electrode recording probe, Fiberoptic oximeter catheter, Intracavitary phonocatheter system, Steerable catheter, Steerable catheter control system, Programmable diagnostic computer, Single-function, preprogrammed diagnostic computer, Densitometer, Angiographic injector and syringe, Indicator injector, External programmable pacemaker pulse generator, Withdrawal-infusion pump, Thermodilution probe, Biopotential amplifier and signal conditioner, Transducer signal amplifier and conditioner, Cardiovascular blood flowmeter, Extravascular blood flow probe, Cardiac monitor (including cardiotachometer and rate alarm), Apex cardiograph (vibrocardiograph), Ballistocardiograph, Electrocardiograph, Electrocardiograph lead switching adaptor, Electrocardiograph electrode, Electrocardiograph surface electrode tester, Phonocardiograph, Vectorcardiograph, Medical cathode-ray tube display, Signal isolation system, Line isolation monitor, Portable leakage current alarm, Oscillometer, Oximeter, Ear oximeter, Impedance phlebograph, Impedance plethysmograph, Hydraulic, pneumatic, or photoelectric plethysmographs, Medical magnetic tape recorder, Paper chart recorder, Apex cardiographic transducer, Extravascular blood pressure transducer, Heart sound transducer, Catheter tip pressure transducer, Ultrasonic transducer, Vessel occlusion transducer, Patient transducer and electrode cable (including connector), Radiofrequency physiological signal transmitter and receiver, Telephone electrocardiograph transmitter and receiver, Intra-aortic balloon and control system Ventricular bypass (assist) device, External pacemaker pulse generator, Implantable pacemaker pulse generator, Pacemaker lead adaptor, Pacemaker generator function analyzer, Indirect pacemaker generator function analyzer, Pacemaker charger, Cardiovascular permanent or temporary pacemaker electrode, Pacemaker test magnet, Pacemaker programmers, Pacemaker electrode function tester, Pacemaker service tools, Carotid sinus nerve stimulator, Cardiopulmonary bypass accessory equipment, Cardiopulmonary bypass bubble detector, Cardiopulmonary bypass heart-lung machine console, Cardiopulmonary bypass defoamer, Cardiopulmonary bypass heat exchanger, Cardiopulmonary bypass temperature controller, Cardiopulmonary bypass gas control unit, Cardiopulmonary bypass coronary pressure gauge, Cardiopulmonary bypass pulsatile flow generator, Cardiopulmonary bypass on-line blood gas monitor, Cardiopulmonary bypass level sensing monitor and/or control, Cardiopulmonary bypass oxygenator, Nonroller-type cardiopulmonary bypass blood pump, Roller-type cardiopulmonary bypass blood pump, Cardiopulmonary bypass pump speed control, Cardiopulmonary bypass in-line blood gas sensor, Cardiopulmonary bypass cardiotomy return sucker, Cardiopulmonary bypass intracardiac suction control, Patient care suction apparatus, Embolectomy catheter, Septostomy catheter, External cardiac compressor, External counter-pulsating device, DC-defibrillator (including paddles), Defibrillator tester, External transcutaneous cardiac pacemaker (non-invasive), Thermal regulating system, or a Automatic rotating tourniquet.

In embodiments, clinical chemistry and clinical toxicology diagnostic and therapeutic devices may be able to interact with syndicated data, or publish one or more syndicated feeds. For example, clinical chemistry and clinical toxicology diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an automated urinalysis system may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other clinical chemistry and clinical toxicology devices that may interact with syndicated data in the above manner include, but are not limited to a Calibrator, Quality control material (assayed and unassayed), General purpose laboratory equipment, Calculator/data processing module, Centrifugal chemistry analyzer, Continuous flow sequential multiple chemistry analyzer, Discrete photometric chemistry analyzer, Micro chemistry analyzer, Gas liquid chromatography system, High pressure liquid chromatography system, Thin-layer chromatography system, Colorimeter, photometer, or spectrophotometer, Clinical sample concentrator, Beta or gamma counter, Densitometer/scanner (integrating, reflectance, TLC, or radiochromatogram), Electrophoresis apparatus, Enzyme analyzer, Flame emission photometer, Fluorometer, Microtitrator, Nephelometer, Plasma oncometer, Osmometer, Pipetting and diluting system, Refractometer, Atomic absorption spectrophotometer, Mass spectrometer, Plasma viscometer, or a Clinical toxicology calibrator.

In embodiments, clinical chemistry and clinical toxicology testing devices may be able to interact with syndicated data, or publish one or more syndicated feeds. For example, clinical chemistry and clinical toxicology testing devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an acid phosphatase (total or prostatic) test system may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other clinical chemistry and clinical toxicology testing devices that may interact with syndicated data in the above manner include, but are not limited to a Adrenocorticotropic hormone (ACTH) test system, Alanine amino transferase, (ALT/SGPT) test system, Albumin test system, Aldolase test system, Aldosterone test system, Alkaline phosphatase or isoenzymes test system, Delta-aminolevulinic acid test system, Ammonia test system, Amylase test system, Androstenedione test system, Androsterone test system, Angiotensin I and renin test system, Angiotensin converting enzyme (A,C, E,) test system, Ascorbic acid test system, Aspartate amino transferase (AST/SGOT) test system, Bilirubin (total or direct) test system, Bilirubin (total and unbound) in the neonate test system, Urinary bilirubin and its conjugates (nonquantitative) test system, B-type natriuretic peptide test system, Biotinidase test system, Blood gases (PO2) and blood pH test system, Blood volume test system, C-peptides of proinsulin test system, Calcitonin test system, Calcium test system, Human chorionic gonadotropin (HCG) test system, Bicarbonate/carbon dioxide test system, Catecholamines (total) test system, Chloride test system, Cholesterol (total) test system, Cholylglycine test system, Chymotrypsin test system, Compound S (11-deoxycortisol) test system, Conjugated sulfolithocholic acid (SLCG) test system, Copper test system, Corticoids test system, Corticosterone test system, Cortisol (hydrocortisone and hydroxycorticosterone) test system, Creatine test system, Creatine phosphokinase/creatine kinase or isoenzymes test system, Creatinine test system, Cyclic AMP test system, Cyclosporine test system, Cystine test system, Dehydroepiandrosterone (free and sulfate) test system, Desoxycorticosterone test system, 2,3-Diphosphoglyceric acid test system, Estradiol test system, Estriol test system, Estrogens (total, in pregnancy) test system, Estrogens (total, nonpregnancy) test system, Estrone test system, Etiocholanolone test system, Fatty acids test system, Folic acid test system, Follicle-stimulating hormone test system, Formiminoglutamic acid (FIGLU) test system, Galactose test system, Galactose-1-phosphate uridyl transferase test system, Gastric acidity test system, Gastrin test system, Globulin test system, Glucagon test system, Urinary glucose (nonquantitative) test system, Glucose test system, Gammaglutamyl transpeptidase and isoenzymes test system, Glutathione test system, Human growth hormone test system, Histidine test system, Urinary homocystine (nonquantitative) test system, Hydroxybutyric dehydrogenase test system, 17-Hydroxycorticosteroids (17-ketogenic steroids) test system, 5-Hydroxyindole acetic acid/serotonin test system, 17-Hydroxyprogesterone test system, Hydroxyproline test system, Immunoreactive insulin test system, Iron (non-heme) test system, Iron-binding capacity test system, Isocitric dehydrogenase test system, 17-Ketosteroids test system, Ketones (nonquantitative) test system, Lactate dehydrogenase test system, Lactate dehydrogenase isoenzymes test system, Lactic acid test system, Lecithin/sphingomyelin ratio in amniotic fluid test system, Leucine aminopeptidase test system, Lipase test system, Lipid (total) test system, Lipoprotein test system, Luteinizing hormone test system, Lysozyme (muramidase) test system, Magnesium test system, Malic dehydrogenase test system, Mucopolysaccharides (nonquantitative) test system, Methylmalonic acid (nonquantitative) test system, Nitrite (nonquantitative) test system, Nitrogen (amino-nitrogen) test system, 5'-Nucleotidase test system, Plasma oncometry test system, Omithine carbamyl transferase test system, Osmolality test system, Oxalate test system, Parathyroid hormone test system, Urinary pH (nonquantitative) test system, Phenylalanine test system, Urinary phenylketones (nonquantitative) test system, 6-Phosphogluconate dehydrogenase test system, Phosphohexose isomerase test system, Phospholipid test system, Phosphorus (inorganic) test system, Human placental lactogen test system, Porphobilinogen test system, Porphyrins test system, Potassium test system, Pregnanediol test system, Pregnanetriol test system, Pregnenolone test system, Progesterone test system, Prolactin (lactogen) test system, Protein (fractionation) test system, Total protein test system, Protein-bound iodine test system, Urinary protein or albumin (nonquantitative) test system, Pyruvate kinase test system, Pyruvic acid test system, Sodium test system, Sorbitol dehydrogenase test system, Tacrolimus test system, Testosterone test system, Thyroxine-binding globulin test system, Thyroid stimulating hormone test system, Free thyroxine test system, Total thyroxine test system, Triglyceride test system, Total triiodothyronine test system, Triiodothyronine uptake test system, Triose phosphate isomerase test system, Trypsin test system, Free tyrosine test system, Urea nitrogen test system, Uric acid test system, Urinary calculi (stones) test system, Urinary urobilinogen (nonquantitative) test system, Uroporphyrin test system, Vanilmandelic acid test system, Vitamin A test system, Vitamin B[bdi1][bdi2] test system, Vitamin E test system, Xylose test system, Vitamin D test system, Acetaminophen test system, Amikacin test system, Alcohol test system, Breath-alcohol test system, Amphetamine test system, Antimony test system, Arsenic test system, Barbiturate test system, Benzodiazepine test system, Clinical toxicology calibrator, Carbon monoxide test system, Cholinesterase test system, Cocaine and cocaine metabolite test system, Codeine test system, Digitoxin test system, Digoxin test system, Diphenylhydantoin test system, Ethosuximide test system, Gentamicin test system, Kanamycin test system, Lead test system, Lidocaine test system, Lithium test system, Lysergic acid diethylamide (LSD) test system, Mercury test system, Methamphetamine test system, Methadone test system, Methaqualone test system, Morphine test system, Neuroleptic drugs radioreceptor assay test system, Opiate test system, Phenobarbital test system, Phenothiazine test system, Primidone test system, Propoxyphene test system, Quinine test system, Salicylate test system, Sulfonamide test system, Cannabinoid test system, Theophylline test system, Tobramycin test system, Tricyclic antidepressant drugs test system, or a Vancomycin test system.

In embodiments, dental diagnostic and therapeutic devices may be able to interact with syndicated data, or publish one or more syndicated feeds may be able to interact with syndicated data, or publish one or more syndicated feeds, or publish one or more syndicated feeds. For example, dental diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a caries detection device may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other dental diagnostic and therapeutic devices that may interact with syndicated data in the above manner include, but are not limited to a Pulp tester, Laser fluorescence caries detection device, Extraoral source x-ray system, Intraoral source x-ray system, Dental x-ray exposure alignment device, Cephalometer, Sulfide detection device, Pantograph, Intraoral dental drill, Dental handpiece and accessories, Rotary scaler, Ultrasonic scaler, Dental electrosurgical unit and accessories, Airbrush, Anesthetic warmer, Dental chair and accessories, Heat source for bleaching teeth, Dental operative unit and accessories, Boiling water sterilizer, or a Endodontic dry heat sterilizer.

In embodiments, ear, nose and throat diagnostic and therapeutic devices may be able to interact with syndicated data, or publish one or more syndicated feeds may be able to interact with syndicated data, or publish one or more syndicated feeds, or publish one or more syndicated feeds. For example, ear, nose and throat diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an audiometer may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other ear, nose and throat diagnostic and therapeutic devices that may interact with syndicated data in the above manner include, but are not limited to a Acoustic chamber for audiometric testing, Short increment sensitivity index (SISI) adapter, Audiometer calibration set, Auditory impedance tester, Electronic noise generator for audiometric testing, Electroglottograph, Gustometer, Air or water caloric stimulator, Surgical nerve stimulator/locator, Toynbee diagnostic tube, Hearing Aid, Hearing aid calibrator and analysis system, Master hearing aid, Tinnitus masker, Ear, nose, and throat electric or pneumatic surgical drill, Ear, nose, and throat fiberoptic light source and carrier, Argon laser for otology, rhinology, and laryngology, Ear, nose, and throat microsurgical carbon dioxide laser, Bronchoscope (flexible or rigid) and accessories, Esophagoscope (flexible or rigid) and accessories, Mediastinoscope and accessories, Laryngostroboscope, Nasopharyngoscope (flexible or rigid) and accessories, Otoscope, Ear, nose, and throat drug administration device, Ear, nose, and throat examination and treatment unit, Suction antichoke device, Tongs antichoke device, or a Antistammering device.

In embodiments, gastroenterology and urology diagnostic and therapeutic devices may be able to interact with syndicated data, or publish one or more syndicated feeds may be able to interact with syndicated data, or publish one or more syndicated feeds, or publish one or more syndicated feeds. For example, gastroenterology and urology diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an endoscope may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other gastroenterology and urology diagnostic and therapeutic devices that may interact with syndicated data in the above manner include, but are not limited to a Ingestible telemetric gastrointestinal capsule imaging system, Stomach pH electrode, Urodynamics measurement system, Gastrointestinal motility monitoring system, Electrogastrography system, Urine flow or volume measuring system, Enuresis alarm, Penile inflatable implant, Endoscopic electrosurgical unit and accessories, Gastroenterology-urology evacuator, Electrohydraulic lithotriptor, Ureteral stone dislodger, Urological table and accessories, Colonic irrigation system, Implanted electrical urinary continence device, Nonimplanted, peripheral electrical continence device, Nonimplanted electrical continence device, Sorbent regenerated dialysate delivery system for hemodialysis, Peritoneal dialysis system and accessories, Water purification system for hemodialysis, Hemodialysis system and accessories, Hemodialyzer with disposable insert (Kiil type), High permeability hemodialysis system, Sorbent hemoperfusion system, Isolated kidney perfusion and transport system and accessories, or a Extracorporeal shock wave lithotripter.

In embodiments, general and plastic surgery diagnostic and therapeutic devices may be able to interact with syndicated data, or publish one or more syndicated feeds may be able to interact with syndicated data, or publish one or more syndicated feeds, or publish one or more syndicated feeds. For example, general and plastic surgery diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a suction lipoplasty system may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other general and plastic surgery diagnostic and therapeutic devices that may interact with syndicated data in the above manner include, but are not limited to a Surgical camera and accessories, Cryosurgical unit and accessories, Electrosurgical cutting and coagulation device and accessories, Ultraviolet lamp for dermatologic disorders, Surgical microscope and accessories, Powered suction pump, Laser surgical instrument for use in general and plastic surgery and in dermatology, Surgical instrument motors and accessories/attachments, Operating tables and accessories and operating chairs and accessories, Air-handling apparatus for a surgical operating room, Topical oxygen chamber for extremities, or a Pneumatic tourniquet.

In embodiments, general hospital and personal use diagnostic and therapeutic devices may be able to interact with syndicated data, or publish one or more syndicated feeds may be able to interact with syndicated data, or publish one or more syndicated feeds, or publish one or more syndicated feeds. For example, general hospital and personal use diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a spinal fluid pressure monitor may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other general hospital and personal use diagnostic and therapeutic devices that may interact with syndicated data in the above manner include, but are not limited to a Liquid crystal forehead temperature strip, Bed-patient monitor, Electronic monitor for gravity flow infusion systems, Clinical color change thermometer, Clinical electronic thermometer, Clinical mercury thermometer, Apgar timer, AC-powered adjustable hospital bed, Hydraulic adjustable hospital bed, Infant radiant warmer, Pediatric hospital bed, Neonatal incubator, Neonatal transport incubator, Patient care reverse isolation chamber, Alternating pressure air flotation mattress, Temperature regulated water mattress, Pediatric position holder, Neonatal phototherapy unit, Infusion pump, Medical chair and table, Ultrasonic cleaner for medical instruments, AC-powered medical examination light, Liquid medication dispenser, Medical ultraviolet air purifier, Medical ultraviolet water purifier, Vacuum-powered body fluid suction apparatus, Ethylene oxide gas sterilizer, Dry-heat sterilizer, Steam sterilizer, or a Liquid crystal vein locator.

In embodiments, hematology and pathology diagnostic and therapeutic devices may be able to interact with syndicated data, or publish one or more syndicated feeds may be able to interact with syndicated data, or publish one or more syndicated feeds, or publish one or more syndicated feeds. For example, hematology and pathology devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a cytocentrifuge may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other hematology and pathology devices that may interact with syndicated data in the above manner include, but are not limited to a Cell and tissue culture supplies and equipment, Mycoplasma detection media and components, Tissue processing equipment, Device for sealing microsections, Microscopes and accessories, Automated slide stainer, Automated tissue processor, Automated cell counter, Automated differential cell counter, Automated blood cell diluting apparatus, Automated cell-locating device, Red cell indices device, Microsedimentation centrifuge, Coagulation instrument, Multipurpose system for in vitro coagulation studies, Automated hematocrit instrument, Automated hemoglobin system, Automated heparin analyzer, Automated platelet aggregation system, Automated sedimentation rate device, Automated slide spinner, Blood volume measuring device, Bleeding time device, Electrophoretic hemoglobin analysis system, Calibrator for cell indices, Calibrator for hemoglobin or hematocrit measurement, Calibrator for platelet counting, Calibrator for red cell and white cell counting, Automated blood grouping and antibody test system, Blood grouping view box, Blood mixing devices and blood weighing devices, Blood and plasma warming device, Cell-freezing apparatus and reagents for in vitro diagnostic use, Automated blood cell separator, Blood bank centrifuge for in vitro diagnostic use, Automated cell-washing centrifuge for immuno-hematology, Automated Coombs test systems, Environmental chamber for storage of platelet concentrate, Blood storage refrigerator and blood storage freezer, Heat-sealing device, Hematocrit measuring device, Occult blood test, Osmotic fragility test, Platelet adhesion test, Platelet aggregometer, Erythrocyte sedimentation rate test, Adenosine triphosphate release assay, Antithrombin III assay, Red blood cell enzyme assay, Activated whole blood clotting time tests, Erythropoietin assay, Euglobulin lysis time tests, Factor deficiency test, Fibrin monomer paracoagulation test, Fibrinogen/fibrin degradation products assay, Fibrinogen determination system, Erythrocytic glucose-6-phosphate dehydrogenase assay, Glutathione reductase assay, Hemoglobin A[bdi2] assay, Abnormal hemoglobin assay, Carboxyhemoglobin assay, Fetal hemoglobin assay, Glycosylated hemoglobin assay, Sulfhemoglobin assay, Whole blood hemoglobin assays, Heparin assay, Leukocyte alkaline phosphatase test, Leukocyte peroxidase test, Platelet factor 4 radioimmunoassay, Prothrombin consumption test, Prothrombin-proconvertin test and thrombotest, Prothrombin time test, Sickle cell test, Thrombin time test, Thromboplastin generation test, or a Partial thromboplastin time test.

In embodiments, immunology and microbiology diagnostic and therapeutic devices may be able to interact with syndicated data, or publish one or more syndicated feeds may be able to interact with syndicated data, or publish one or more syndicated feeds, or publish one or more syndicated feeds. For example, immunology and microbiology devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an anaerobic chamber may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other immunology and microbiology devices that may interact with syndicated data in the above manner include, but are not limited to a Fully automated short-term incubation cycle antimicrobial susceptibility system, Automated colony counter, Automated medium dispensing and stacking device, Microtiter diluting and dispensing device, Microbiological incubator, Microbial growth monitor, Automated zone reader, Immunoelectrophoresis equipment, Immunofluorometer equipment, Immunonephelometer equipment, or Rocket immunoelectrophoresis equipment.

In embodiments, immunology and microbiology testing devices may be able to interact with syndicated data, or publish one or more syndicated feeds may be able to interact with syndicated data, or publish one or more syndicated feeds, or publish one or more syndicated feeds. For example, immunology and microbiology testing devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a C-reactive protein immunological test system may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other immunology and microbiology testing devices that may interact with syndicated data in the above manner include, but are not limited to a Albumin immunological test system, Prealbumin immunological test system, Human allotypic marker immunological test system, Alpha-1-antichymotrypsin immunological test system, Antimitochondrial antibody immunological test system, Antinuclear antibody immunological test system, Antiparietal antibody immunological test system, Antismooth muscle antibody immunological test system, Alpha-1-antitrypsin immunological test system, Bence-Jones proteins immunological test system, Beta-globulin immunological test system, Breast milk immunological test system, Carbonic anhydrase B and C immunological test system, Ceruloplasmin immunological test system, Cohn fraction II immunological test system, Colostrum immunological test system, Complement components immunological test system, Complement C[bdi2] inhibitor (inactivator) immunological test system, Complement C3b inactivator immunological test system, Properdin factor B immunological test system, Factor XIII, A, S, immunological test system, Ferritin immunological test system, Fibrinopeptide A immunological test system, Cohn fraction IV immunological test system, Cohn fraction V immunological test system, Free secretory component immunological test system, Alpha-globulin immunological test system, Alpha-1-glycoproteins immunological test system, Alpha-2-glycoproteins immunological test system, Beta-2-glycoprotein I immunological test system, Beta-2-glycoprotein III immunological test system, Haptoglobin immunological test system, Hemoglobin immunological test system, Hemopexin immunological test system, Hypersensitivity pneumonitis immunological test system, Immunoglobulins A, G, M, D, and E immunological test system, Immunoglobulin G (Fab fragment specific) immunological test system, Immunoglobulin G (Fc fragment specific) immunological test system, Immunoglobulin G (Fd fragment specific) immunological test system, Immunoglobulin (light chain specific) immunological test system, Lactic dehydrogenase immunological test system, Lactoferrin immunological test system, Alpha-1-lipoprotein immunological test system, Lipoprotein X immunological test system, Low-density lipoprotein immunological test system, Alpha-2-macroglobulin immunological test system, Beta-2 microglobulin immunological test system, Infectious mononucleosis immunological test system, Multiple autoantibodies immunological test system, Myoglobin immunological test system, Whole human plasma or serum immunological test system, Plasminogen immunological test system, Prothrombin immunological test system, Radioallergosorbent (RAST) immunological test system, Retinol-binding protein immunological test system, Rheumatoid factor immunological test system, Anti-Saccharomyces cerevisiae (S, cerevisiae) antibody (ASCA) test systems, Seminal fluid (sperm) immunological test system, Systemic lupus erythematosus immunological test system, Total spinal fluid immunological test system, Thyroid autoantibody immunological test system, Transferrin immunological test system, Inter-alpha trypsin inhibitor immunological test system, or a Tumor-associated antigen immunological test system.

In embodiments, mammography devices may be able to interact with syndicated data, or publish one or more syndicated feeds may be able to interact with syndicated data, or publish one or more syndicated feeds, or publish one or more syndicated feeds. For example, mammography devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a screen-film mammography device may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other mammography devices that may interact with syndicated data in the above manner include, but are not limited to, xeromammography, mammography unit or image processor, X-ray generator, an X-ray control, a tube housing assembly, a beam limiting device, and/or the supporting structures for these components.

In embodiments, neurological diagnostic and therapeutic devices may be able to interact with syndicated data, or publish one or more syndicated feeds may be able to interact with syndicated data, or publish one or more syndicated feeds, or publish one or more syndicated feeds. For example, neurological diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an ataxiagraph may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other neurological diagnostic and therapeutic devices that may interact with syndicated data in the above manner include, but are not limited to a Rigidity analyzer, Two-point discriminator, Echoencephalograph, Cortical electrode, Cutaneous electrode, Depth electrode, Nasopharyngeal electrode, Needle electrode, Electroencephalograph, Electroencephalograph electrode/lead tester, Electroencephalogram (EEG) signal spectrum analyzer, Electroencephalograph test signal generator, Nystagmograph, Neurological endoscope, Galvanic skin response measurement device, Nerve conduction velocity measurement device, Skin potential measurement device, Powered direct-contact temperature measurement device, Alpha monitor, Intracranial pressure monitoring device, Ocular plethysmograph, Rheoencephalograph, Physiological signal amplifier, Physiological signal conditioner, Evoked response electrical stimulator, Evoked response mechanical stimulator, Evoked response photic stimulator, Evoked response auditory stimulator, Ultrasonic scanner calibration test block, Tremor transducer, Neurosurgical chair, Cryogenic surgical device, Powered compound cranial drills, burrs, trephines, and their accessories, Powered simple cranial drills, burrs, trephines, and their accessories, Electric cranial drill motor, Pneumatic cranial drill motor, Radiofrequency lesion generator, Neurosurgical headrests, Neurosurgical head holder (skull clamp), Microsurgical instrument, Stereotaxic instrument, Leukotome, Radiofrequency lesion probe, Skull punch, Powered rongeur, Skull-plate screwdriver, Biofeedback device, Aversive conditioning device, Lesion temperature monitor, Cranial electrotheraphy stimulator, External functional neuromuscular stimulator, Implanted cerebellar stimulator, Implanted diaphragmatic/phrenic nerve stimulator, Implanted intracerebral/subcortical stimulator for pain relief, Implanted spinal cord stimulator for bladder evacuation, Implanted neuromuscular stimulator, Implanted peripheral nerve stimulator for pain relief, Implanted spinal cord stimulator for pain relief, Transcutaneous electrical nerve stimulator for pain relief, Electroconvulsive therapy device, or a Cranial orthosis, In embodiments, obstetrical and gynecological diagnostic and therapeutic devices may be able to interact with syndicated data, or publish one or more syndicated feeds may be able to interact with syndicated data, or publish one or more syndicated feeds, or publish one or more syndicated feeds. For example, obstetrical and gynecological diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an uterotubal carbon dioxide insufflator may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other obstetrical and gynecological diagnostic and therapeutic devices that may interact with syndicated data in the above manner include, but are not limited to a Viscometer for cervical mucus, Transabdominal amnioscope (fetoscope) and accessories, Colposcope, Culdoscope and accessories, Transcervical endoscope (amnioscope) and accessories, Hysteroscope and accessories, Hysteroscopic insufflator, Gynecologic laparoscope and accessories, Laparoscopic insufflator, Obstetric data analyzer, Obstetric-gynecologic ultrasonic imager, Fetal cardiac monitor, Fetal electroencephalographic monitor, Fetal phonocardiographic monitor and accessories, Fetal ultrasonic monitor and accessories, Fetal scalp circular (spiral) electrode and applicator, Fetal scalp clip electrode and applicator, Intrauterine pressure monitor and accessories, External uterine contraction monitor and accessories, Home uterine activity monitor, Perinatal monitoring system and accessories, Fetal stethoscope, Obstetric ultrasonic transducer and accessories, Telethermographic system, Liquid crystal thermographic system, Endoscopic electrocautery and accessories, Gynecologic electrocautery and accessories, Bipolar endoscopic coagulator-cutter and accessories, Unipolar endoscopic coagulator-cutter and accessories, Fetal vacuum extractor, Gynecologic surgical laser, Obstetric table and accessories, Metreurynter-balloon abortion system, Vacuum abortion system, Abdominal decompression chamber, Powered vaginal muscle stimulator for therapeutic use, or Assisted reproduction water and water purification systems, In embodiments, ophthalmic diagnostic and therapeutic devices may be able to interact with syndicated data, or publish one or more syndicated feeds may be able to interact with syndicated data, or publish one or more syndicated feeds, or publish one or more syndicated feeds. For example, ophthalmic diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as an adaptometer (biophotometer) may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other ophthalmic diagnostic and therapeutic devices that may interact with syndicated data in the above manner include, but are not limited to a Anomaloscope, Haidlinger brush, Opthalmic camera, Ophthalmic chair, Color vision plate illuminator, Distometer, Optokinetic drum, Corneal electrode, Euthyscope, Exophthalmometer, Fixation device, Afterimage flasher, Haploscope, Keratoscope, Visual field laser instrument, Lens measuring instrument, Ophthalmic contact lens radius measuring device, Maxwell spot, Corneal radius measuring device, Stereopsis measuring instrument, Eye movement monitor, Ophthalmoscope, Perimeter, AC-powered photostimulator, Ophthalmic preamplifier, Ophthalmic bar prism, Ophthalmic rotary prism, Ophthalmic isotope uptake probe, Ophthalmic projector, Pupillograph, Pupillometer, Ophthalmic refractometer, Retinoscope, Tangent screen (campimeter), Stereoscope, Tonometer and accessories, Powered corneal burr, Radiofrequency electrosurgical cautery apparatus, Thermal cautery unit, Vitreous aspiration and cutting instrument, Cryophthalmic unit, Ophthalmic electrolysis unit, Intraocular pressure measuring device, Ocular surgery irrigation device, (adaptable—electronic control) Keratome, Ophthalmic laser, Nd:YAG laser for posterior capsulotomy and peripheral iridotomy, Electronic metal locator, AC-powered magnet, Phacofragmentation system, Ophthalmic photocoagulator, Ophthalmic instrument table, Ophthalmic beta radiation source, Closed-circuit television reading system, or an Electronic vision aid.

In embodiments, physical medicine diagnostic and therapeutic devices may be able to interact with syndicated data, or publish one or more syndicated feeds may be able to interact with syndicated data, or publish one or more syndicated feeds, or publish one or more syndicated feeds. For example, physical medicine diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a chronaximeter may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other physical medicine diagnostic and therapeutic devices that may interact with syndicated data in the above manner include, but are not limited to a Electrode cable, Diagnostic electromyograph, Diagnostic electromyograph needle electrode, Powered reflex hammer, Force-measuring platform, Intermittent pressure measurement system, Miniature pressure transducer, Diagnostic muscle stimulator, Isokinetic testing and evaluation system, Electric positioning chair, Rigid pneumatic structure orthosis, Powered wheeled stretcher, Powered communication system, Powered environmental control system, Powered table, Air-fluidized bed, Powered flotation therapy bed, Powered patient rotation bed, Moist steam cabinet, Microwave diathermy, Shortwave diathermy, Ultrasonic diathermy, Measuring exercise equipment, Powered exercise equipment, Powered finger exerciser, Infrared lamp, Iontophoresis device, Powered external limb overload warning device, Powered inflatable tube massager, Therapeutic massager, Powered heating pad, Pressure-applying device, Powered muscle stimulator, Ultrasound and muscle stimulator, Power traction equipment, Powered heating unit, or a Therapeutic vibrator.

In embodiments, radiology diagnostic and therapeutic devices may be able to interact with syndicated data, or publish one or more syndicated feeds may be able to interact with syndicated data, or publish one or more syndicated feeds, or publish one or more syndicated feeds. For example, radiology diagnostic and therapeutic devices may be able to publish syndicated data, subscribe to and receive syndicated data feeds, and store syndicated data. This data may be published, shared, used, received and/or stored locally with the device, and/or in association with a remote architecture (e.g., server, database, etc.) accessible to the device (e.g., through the internet, WAN, LAN, wireless connection, etc.). For example, a device such as a scintillation (gamma) camera may subscribe to a syndicated data feed that is published, shared, used by the device's manufacturer to inform of device updates, recalls, and the like. This information may be stored locally with the machine, and/or stored on an associated architecture, such as a hospital's central network, where the syndicated information may be reviewed by staff. The device may also publish a syndicated data feed. This data may include, but is not limited to, the performance of the device (e.g., consistency with established safety parameters), the amount of device usage, personnel using the device, patients with whom the device was operated, and so forth.

Other radiology diagnostic and therapeutic devices that may interact with syndicated data in the above manner include, but are not limited to a Magnetic resonance diagnostic device, Positron camera, Nuclear whole body counter, Bone densitometer, Emission computed tomography system, Fluorescent scanner, Nuclear rectilinear scanner, Nuclear tomography system, Nuclear uptake probe, Nuclear whole body scanner, Nuclear scanning bed, Radionuclide dose calibrator, Radionuclide rebreathing system, Nuclear sealed calibration source, Nuclear electrocardiograph synchronizer, Nonfetal ultrasonic monitor, Ultrasonic pulsed doppler imaging system, Ultrasonic pulsed echo imaging system, Diagnostic ultrasonic transducer, Angiographic x-ray system, Diagnostic x-ray beam-limiting device, Cine or spot fluorographic x-ray camera, Electrostatic x-ray imaging system, Radiographic film marking system, Image-intensified fluoroscopic x-ray system, Non-image-intensified fluoroscopic x-ray system, Spot-film device, Stationary x-ray system, Diagnostic x-ray high voltage generator, Mammographic x-ray system, Mobile x-ray system, Photofluorographic x-ray system, Tomographic x-ray system, Computed tomography x-ray system, Diagnostic x-ray tube housing assembly, Diagnostic x-ray tube mount, Pneumoencephalographic chair, Radiologic patient cradle, Radiographic film/cassette changer, Radiographic film/cassette changer programmer, Automatic radiographic film processor, Radiographic head holder, Radiologic quality assurance instrument, Radiographic ECG/respirator synchronizer, Radiologic table, Transilluminator for breast evaluation, Medical image storage device, Medical image communications device, Medical image digitizer, Medical image hardcopy device, Picture archiving and communications system, Medical charged-particle radiation therapy system, Medical neutron radiation therapy system, Manual radionuclide applicator system, Remote controlled radionuclide applicator system, Radiation therapy beam-shaping block, Radionuclide radiation therapy system, Powered radiation therapy patient support assembly, Light beam patient position indicator, Radiation therapy simulation system, and X-ray radiation therapy system.

Administrative systems in a health care facility may be directed to those functions within a health care setting that do not directly involve patient care. Administrative systems may include systems such as a facility system, an environment system, a staffing system, a compliance system, a resource allocation system, an inventory system, a scheduling system, a financial system, and the like. In more detail, administrative systems may pertain to functions such as billing and accounts payable, human resources, physical plant maintenance, supply ordering, nonclinical service provision (meals, housekeeping, etc.), transportation, scheduling, regulatory compliance, document management and the like. For example, administrative systems may be used to collect, share, use and/or store data for purposes such as, but not limited to, compliance with facility rules, procedures, processes and regulations; providing a historical record for refuting malpractice claims; substantiating billing charges, and/or Medicaid/Medicare and/or insurance claims; participating in or coordinating medical and/or health care related studies; ordering and filling prescriptions and/or laboratory tests and/or procedures; and/or monitoring patient compliance with medical and/or health related regimens and/or instructions. Data pertaining to, used by, collected by or generated by an administrative system may be termed administrative data.

In embodiments, hospital, facility, medical and healthcare related data, programs, applications, and systems may be able to interact with syndicated data, or publish one or more syndicated feeds. For example, hospital, facility, medical and healthcare related programs, applications, processes, devices and/or systems may be able to publish syndicated data, subscribe to and receive syndicated data feeds, and store syndicated data. This data may be published, shared, used, received and/or stored locally with the hospital, facility, medical and healthcare related programs, applications, processes, devices and/or systems, and/or in association with a remote architecture (e.g., server, database, etc.) accessible to the hospital, facility, medical and healthcare related programs, applications, processes, devices and/or systems (e.g., through the internet, WAN, LAN, wireless connection, etc.). For example, a hospital, facility, medical and healthcare related program, application, process, device and/or system such as an emergency room triage evaluation program may subscribe to a syndicated data feed that is published, shared, used by program's supplier, service provider, and/or administrator, to inform of program updates, recalls and the like. This information may be stored locally with the program, and/or stored on an associated architecture, such as a hospital's, laboratory's, clinic's, medical office's, research facility's, and/or pharmacy's central network, where the syndicated information may be reviewed by staff. The program may also publish a syndicated data feed. This data may include, but is not limited to, the performance of the program (e.g., compliance with established medical procedures); coordination of the program with other systems such as administrative programs relating to staff schedules (e.g., schedules of doctors of varying specialties can be converted to a syndicated format and published, shared, used as a data feed as staff becomes available or unavailable) and/or sign-in procedures for staff employed to monitor presence and/or availability; identification of personnel authorized to use the program; and/or tracking of patient data.

Other hospital, facility, medical and healthcare related data, programs, applications, and systems that may interact with syndicated data in the above manner include, but are not limited to, allocation of clinical programs; allocation of facilities and staffing resources for operating theatres, hyperbaric chambers, birthing rooms, clean rooms and/or other environmentally controlled resources; collection, evaluation and/or selection of research study subjects; compliance programs relating, but not limited, to insurance, Medicaid/Medicare, infectious disease control procedures, HIPPA compliance.

In embodiments, administrative programs, procedures, processes and applications may be able to interact with syndicated data, or publish one or more syndicated feeds. For example, administrative programs, procedures, processes and applications may be able to publish syndicated data, subscribe to and receive syndicated data feeds, and store syndicated data. This data may be published, shared, used, received and/or stored locally with the program, procedure, process and/or application, and/or in association with a remote architecture (e.g., server, database, etc.) accessible to the administrative programs, procedures, processes and applications (e.g., through the internet, WAN, LAN, wireless connection, etc.). For example, an administrative program, procedure, process and application such as a patient billing program may subscribe to a syndicated data feed that is published, shared, used by the program's manufacturer, service provider, and/or administrator, to inform of program updates, recalls and the like. This information may be stored locally with the program, and/or stored on an associated architecture, such as a hospital's, laboratory's, clinic's, medical office's, research facility's, and/or pharmacy's central network, where the syndicated information may be reviewed by staff. The program may also publish a syndicated data feed. This data may include, but is not limited to, the data collected during the operation of the program, data verifying the appropriate collection of data (i.e., performance) of the program (e.g., compliance with HIPPA regulations), the amount of program usage, personnel using the program, patients for whom the program is collecting data and so forth.

Other administrative applications, programs, processes, devices, applications, databases and transaction processing systems that may interact with syndicated data in the above manner include, but are not limited to, administrative programs relating to medical records; diagnoses; insurance authorization, capture of charges and/or reimbursement applications; Medicare/Medicaid compliance applications; research programs; systems, applications, programs and/or devices for monitoring patient compliance with medical or healthcare instructions; systems for monitoring dispensing of controlled substances, prescription history, new prescription writing; systems for monitoring usage of supplies and/or equipment for inventory control; and systems, applications, programs relating to on-call and personnel schedules, and staffing.

In embodiments, systems, programs, applications, devices and processes relating to physical plant, facilities and/or environmental conditions may be able to interact with syndicated data, or publish one or more syndicated feeds. For example, systems, programs, applications, devices and/or processes relating to physical plant, facilities and/or environmental conditions may be able to publish syndicated data, subscribe to and receive syndicated data feeds, and store syndicated data. This data may be published, shared, used, received and/or stored locally with the system, program, application, device and/or process relating to physical plant, facilities and/or environmental conditions, and/or in association with a remote architecture (e.g., server, database, etc.) accessible to the systems, programs, applications, devices and processes relating to physical plant, facilities and/or environmental conditions (e.g., through the internet, WAN, LAN, wireless connection, etc.). For example, a system and/or device relating to temperature controls such as a thermostat may subscribe to a syndicated data feed that is published, shared, used by system's and/or device's manufacturer, service provider, and/or administrator, to inform of system or device updates, recalls and the like. This information may be stored locally with the system and/or device, and/or stored on an associated architecture, such as a hospital's, laboratory's, clinic's, medical office's, research facility's, and/or pharmacy's central network, where the syndicated information may be reviewed by staff. The system and/or device may also publish a syndicated data feed. This data may include, but is not limited to, the performance of the system and/or device (e.g., consistency with established safety parameters), the amount of system and/or device usage, personnel using the system and/or device, special conditions relating to the patients for whom the system and/or device was operated and so forth.

Other systems, programs, applications, devices and processes relating to physical plant, facilities and/or environmental conditions that may interact with syndicated data in the above manner include, but are not limited to, clean rooms, electric light sensors, automatic door openers, camera security systems, public address systems, nursing or assistance call buttons, phone systems, alarm systems, temperature sensors, humidistats, autoclaves, and/or air quality or ambient environment sensors.

In embodiments, location devices and/or systems may be able to interact with syndicated data, or publish one or more syndicated feeds. For example, location devices and/or systems may be able to publish syndicated data, subscribe to and receive syndicated data feeds, and store syndicated data. This data may be published, shared, used, received and/or stored locally with the location device and/or system, and/or in association with a remote architecture (e.g., server, database, etc.) accessible to the location device and/or system (e.g., through the internet, WAN, LAN, wireless connection, etc.). For example, a location device and/or system such as a patient location monitoring device may subscribe to a syndicated data feed that is published, shared, used by device's manufacturer, service provider, and/or administrator, to inform of device updates, recalls and the like. This information may be stored locally with the device, and/or stored on an associated architecture, such as a hospital's, nursing home's, clinic's, medical office's, and/or research facility's central network, where the syndicated information may be reviewed by staff. The device may also publish a syndicated data feed. This data may include, but is not limited to, the performance of the device (e.g., consistency with established safety parameters), the amount of device usage, personnel responsible for monitoring the device, and/or patients with whom the device is operating and so forth.

Other location devices and/or systems that may interact with syndicated data in the above manner include, but are not limited to, beeper systems, GPS enabled location devices and systems, equipment location tracking devices, and/or anti-theft devices and/or systems.

In embodiments, measuring devices and/or apparatuses may be able to interact with syndicated data, or publish one or more syndicated feeds. For example, measuring devices and/or apparatuses may be able to publish syndicated data, subscribe to and receive syndicated data feeds, and store syndicated data. This data may be published, shared, used, received and/or stored locally with the measuring device and/or apparatus, and/or in association with a remote architecture (e.g., server, database, etc.) accessible to the measuring device and/or apparatus (e.g., through the internet, WAN, LAN, wireless connection, etc.). For example, a measuring device and/or apparatus such as a scale may subscribe to a syndicated data feed that is published, shared, used by the device's manufacturer to inform of device updates, recalls and the like. This information may be stored locally with the device, and/or stored on an associated architecture, such as a hospital's, laboratory's, clinic's, medical office's, research facility's, and/or pharmacy's central network, where the syndicated information may be reviewed by staff. The device may also publish a syndicated data feed. This data may include, but is not limited to, the measurement taken (e.g., weight), a time stamp, the performance of the device or apparatus (e.g., consistency with established safety parameters), the amount of device or apparatus usage, personnel using the device or apparatus, patients with whom the device or apparatus was operated and so forth. The data may be employed by an aggregator that maintains a patient history or by a treating physician who filters weight data to identify records for patients of interest.

Other measuring devices and/or apparatuses that may interact with syndicated data in the above manner include, but are not limited to, blood pressure cuffs; and/or thermometers.

In one embodiment, the treating physician may obtain a compilation including, but not limited to, a time stamped record of all quantitative data, diagnoses, treatments, and so forth for a patient during a hospital visit through appropriate subscription and filtering of content provided by devices within the hospital. Other situations in which such data compilations might be used include, but not limited to, epidemiology surveys, and/or research programs.

In embodiments, pharmacy and/or laboratory systems, programs, applications, devices and/or processes may be able to interact with syndicated data, or publish one or more syndicated feeds. For example, pharmacy and/or laboratory systems, programs, applications, apparatuses, devices and/or processes may be able to publish syndicated data, subscribe to and/or receive syndicated data feeds, and/or store syndicated data. This data may be published, shared, used, received and/or stored locally with the pharmacy and/or laboratory systems, programs, applications, apparatuses, devices and processes, and/or in association with a remote architecture (e.g., server, database, etc.) accessible to the pharmacy and/or laboratory systems, programs, applications, devices and processes (e.g., through the internet, WAN, LAN, wireless connection, etc.). For example, a pharmacy and/or laboratory system, program, application, apparatus, device and/or process such as a medication dispensing apparatus may subscribe to a syndicated data feed that is published, shared, used by the apparatus's manufacturer and/or service provider to inform of apparatus updates, recalls and the like. This information may be stored locally with the apparatus, and/or stored on an associated architecture, such as a hospital's, laboratory's, clinic's, medical office's, research facility's, and/or pharmacy's central network, where the syndicated information may be reviewed by staff. The apparatus may also publish a syndicated data feed. This data may include, but is not limited to, the performance of the apparatus (e.g., verification of calibrations), the amount of apparatus usage, personnel using the apparatus, patients for whose medications the apparatus was operated and so forth.

In another embodiment, prescription data may be published, shared, used as new prescriptions are issued from doctors within a facility or to a remote facility. In a further embodiment, a patient-designated pharmacy may subscribe to prescription feeds and filter new prescriptions to identify and prepare relevant prescriptions for customers.

Other pharmacy, medication dispensaries, and/or laboratory processes, programs, applications, apparatuses, and/or devices that may interact with syndicated data in the above manner include, but are not limited to, ordering lab tests or follow-up tests based on preliminary results; calibrating equipment; monitoring equipment status; record keeping; and/or providing information on medication recalls, alerts, and/or updates on usage, side effects, and/or other information.

In embodiments, mobile devices and/or apparatuses may be able to interact with syndicated data, or publish one or more syndicated feeds. For example, mobile devices and/or apparatuses may be able to publish syndicated data, subscribe to and receive syndicated data feeds, and store syndicated data. This data may be published, shared, used, received and/or stored locally with the mobile devices and/or apparatuses, and/or in association with a remote architecture (e.g., server, database, etc.) accessible to the mobile devices and/or apparatuses (e.g., through the internet, WAN, LAN, wireless connection, etc.). For example, a mobile device and/or apparatus such as a blood gas monitor may subscribe to a syndicated data feed that is published, shared, used by the monitor's manufacturer, service provider, and/or technician, to inform of monitor updates, recalls and the like. This information may be stored locally with the monitor, and/or stored on an associated architecture, such as a hospital's, laboratory's, clinic's, medical office's, research facility's, and/or pharmacy's central network, where the syndicated information may be reviewed by staff. The monitor may also publish a syndicated data feed. This data may include, but is not limited to, the performance of the monitor (e.g., consistency with established safety parameters), the amount of monitor usage, personnel using the monitor, patients with whom the monitor was operated and so forth.

Other mobile devices and/or apparatuses that may interact with syndicated data in the above manner include, but are not limited to, X-ray machines, scooping devices, EEG devices, EKG devices, medication dose delivery devices, blood flow monitors, oxygen meters and/or pulsometers.

In one aspect, a health care environment dashboard may be provided, including a user interface for locating, subscribing to, filtering, and otherwise processing feeds from any of the devices described above. Other devices, such as databases, billing systems, calendars, and the like may also publish feeds that may be monitored using the health care environment dashboard. The dashboard may be user configurable, and may provide user tools for selecting, displaying, and manipulating various feeds within a hospital or other health care context.

Figure 25:
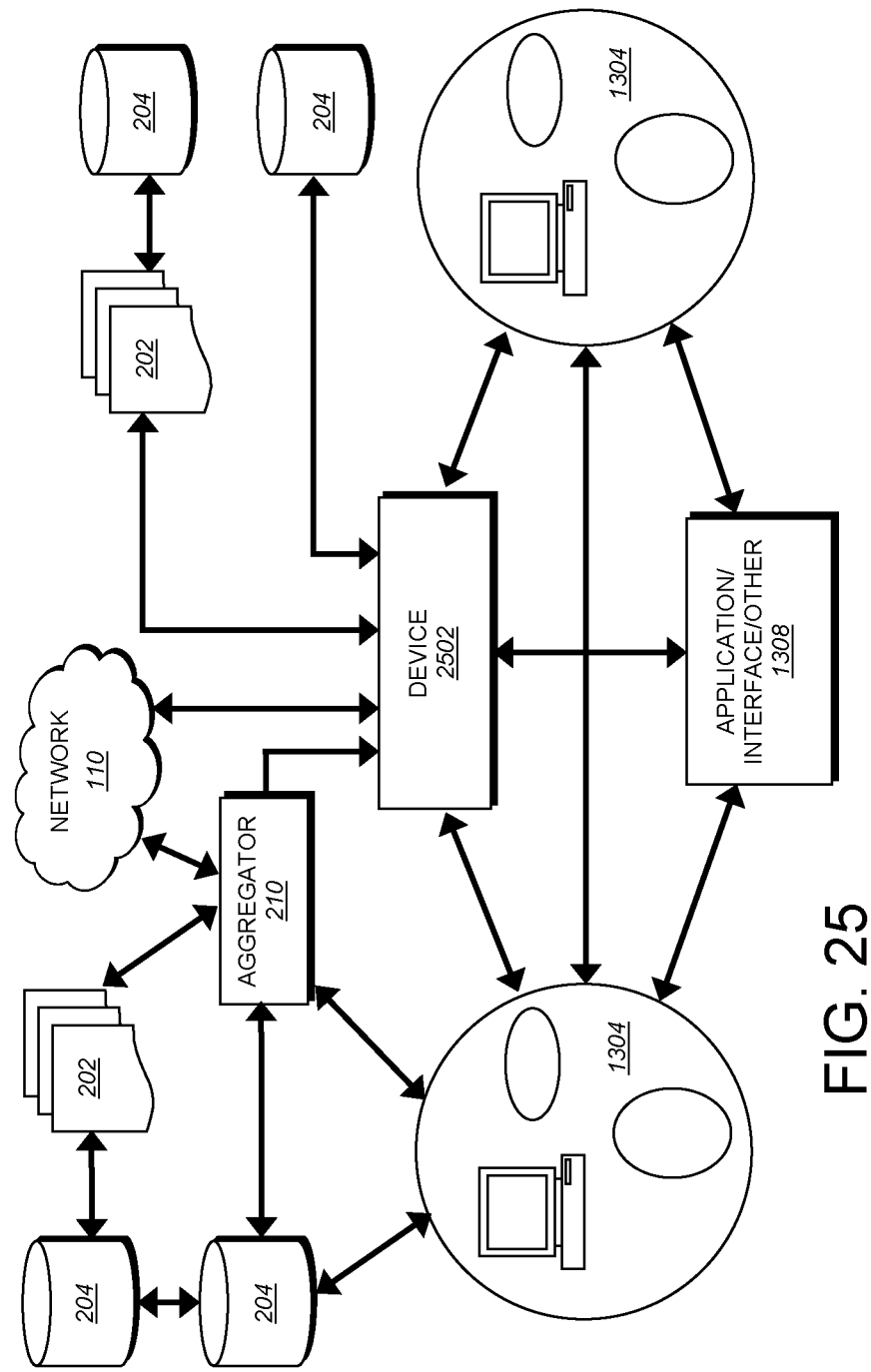
FIG. 25 shows a syndication environment including a medical device and an application and/or interface.

Referring to FIG. 25, the device 2502 may be a diagnostic device, therapeutic device and/or administrative device, such as described herein. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. Users 1304, such as users 404 and clients 102, may view and/or receive information from and/or send information to and/or interact with the device 2502 directly or through an application/interface/other 1308. The users 1304 may also interact with each other. The application/interface/other 1308 may be a client-side program, such as the healthcare program discussed herein, a content management system, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 25 may be data feeds, such as data feed 202.

Figure 26:
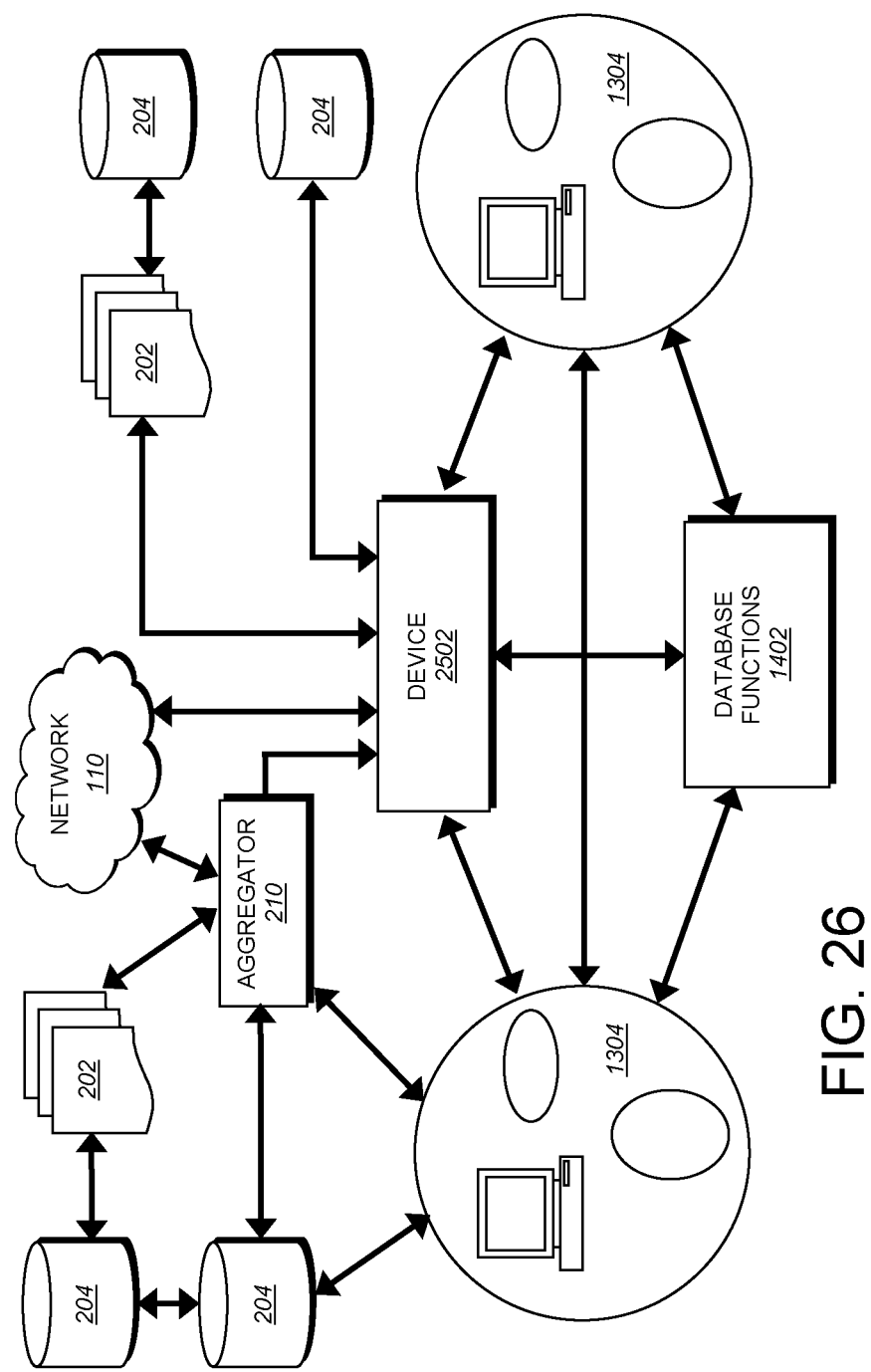
FIG. 26 shows a syndication environment including a medical device and database functions.

Referring to FIG. 26, the device 2502 may be a diagnostic device, therapeutic device and/or administrative device, such as described herein. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. Users 1304, such as users 404 and clients 102, may view and/or receive information from and/or send information to and/or interact with the device 2502 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 26 may be data feeds, such as data feed 202.

Figure 27:
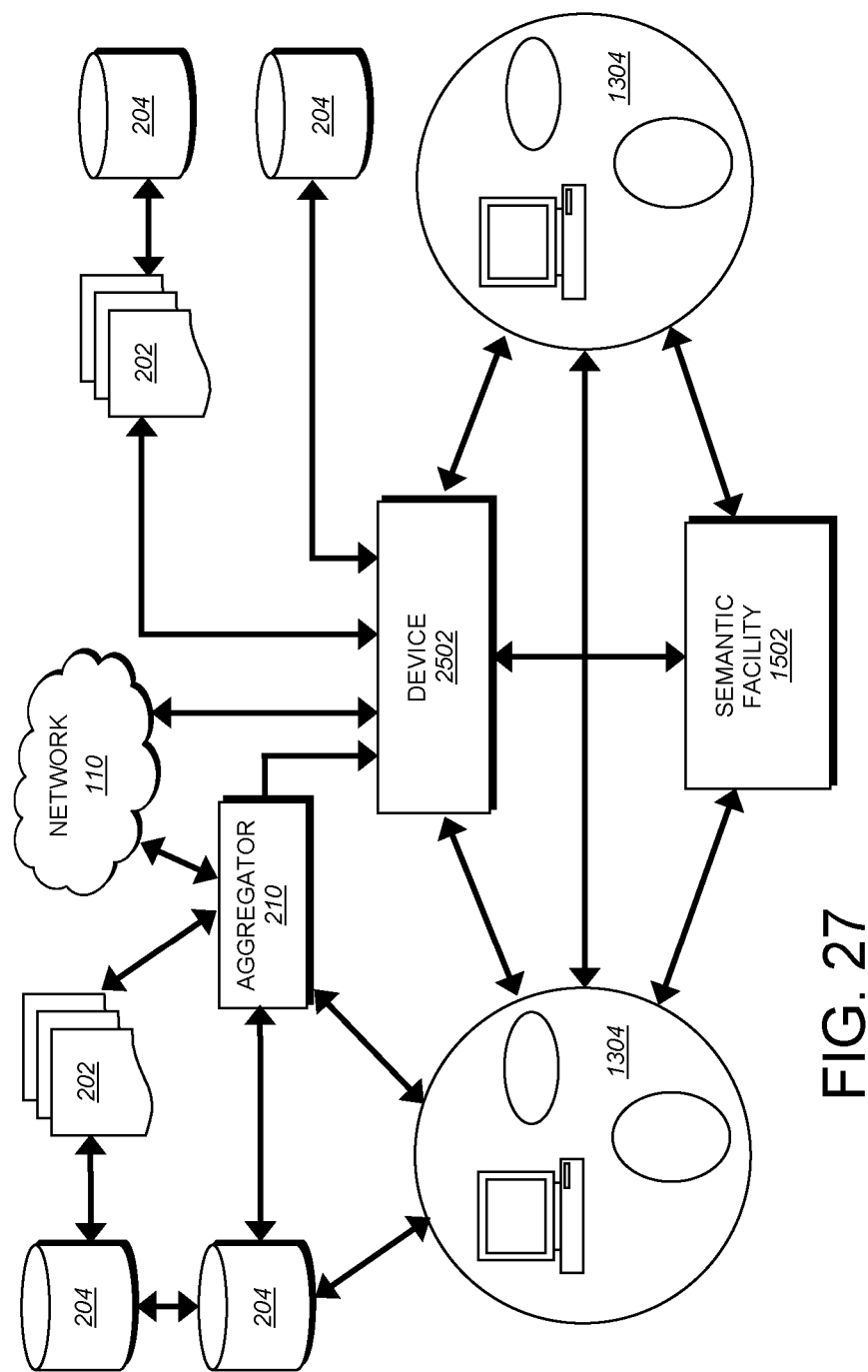
FIG. 27 shows a syndication environment including a medical device and a semantic facility.

Referring to FIG. 27, the device 2502 may be a diagnostic device, therapeutic device and/or administrative device, as described herein. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. Users 1304, such as users 404 and clients 102, may view and/or receive information from and/or send information to and/or interact with the device 2502 directly or through a semantic facility 1502. The semantic facility 1502 may also interact directly with the device 2502. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 27 may be data feeds, such as data feed 202.

Figure 28:
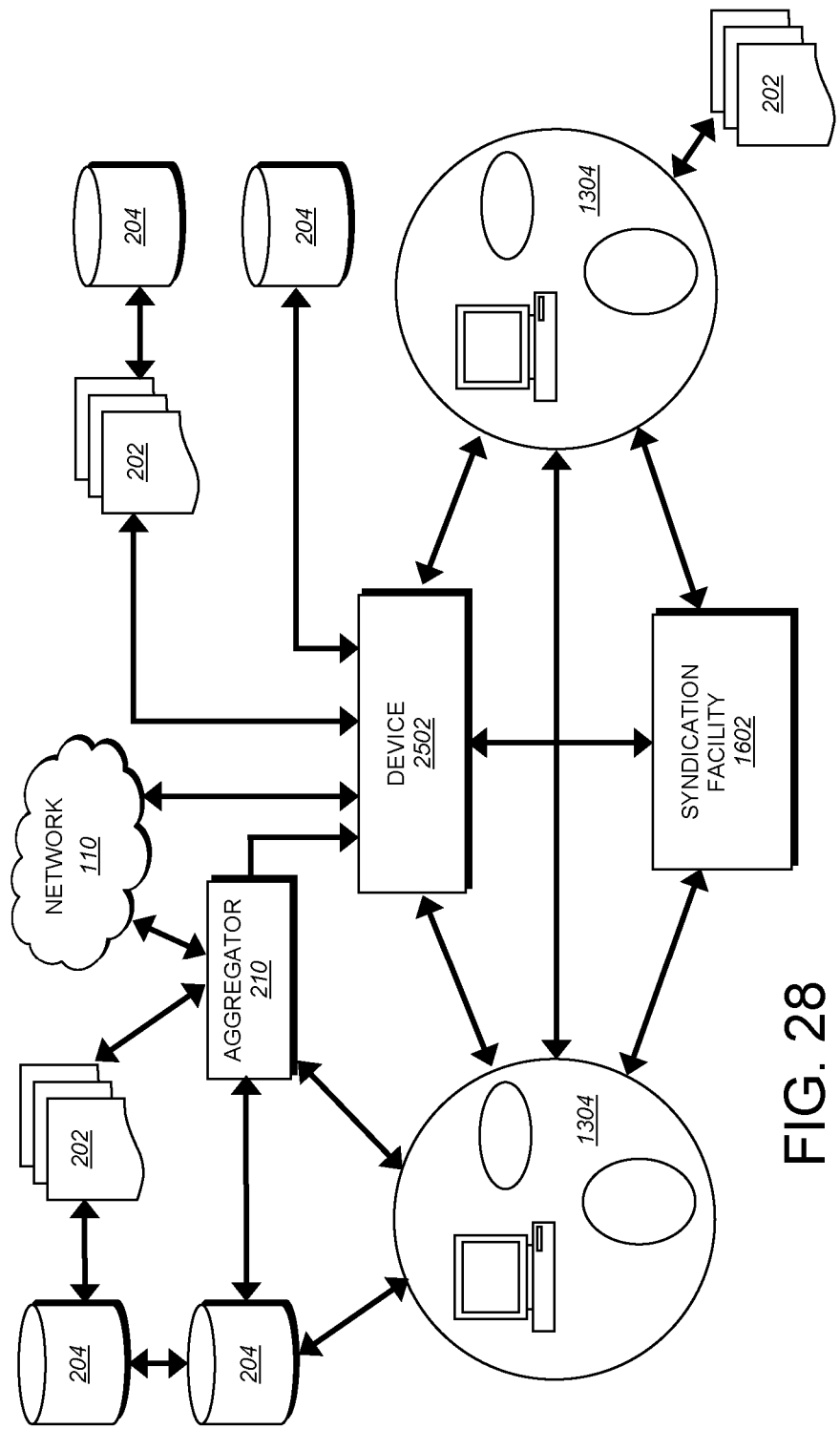
FIG. 28 shows a syndication environment including a medical device and a syndication facility.

Referring to FIG. 28, the device 2502 may be a diagnostic device, therapeutic device and/or administrative device, as described herein. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. Users 1304, such as users 404 and clients 102, may view and/or receive information from and/or send information to and/or interact with the device 2502 directly or through a syndication facility 1602. The syndication facility 1602 may also interact directly with the device 2502. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 28 may be data feeds, such as data feed 202. A user 1304 may also publish, republish and/or subscribe to a content source 204, data feed 202, aggregator 210 and/or syndication facility 1602.

Figure 29:
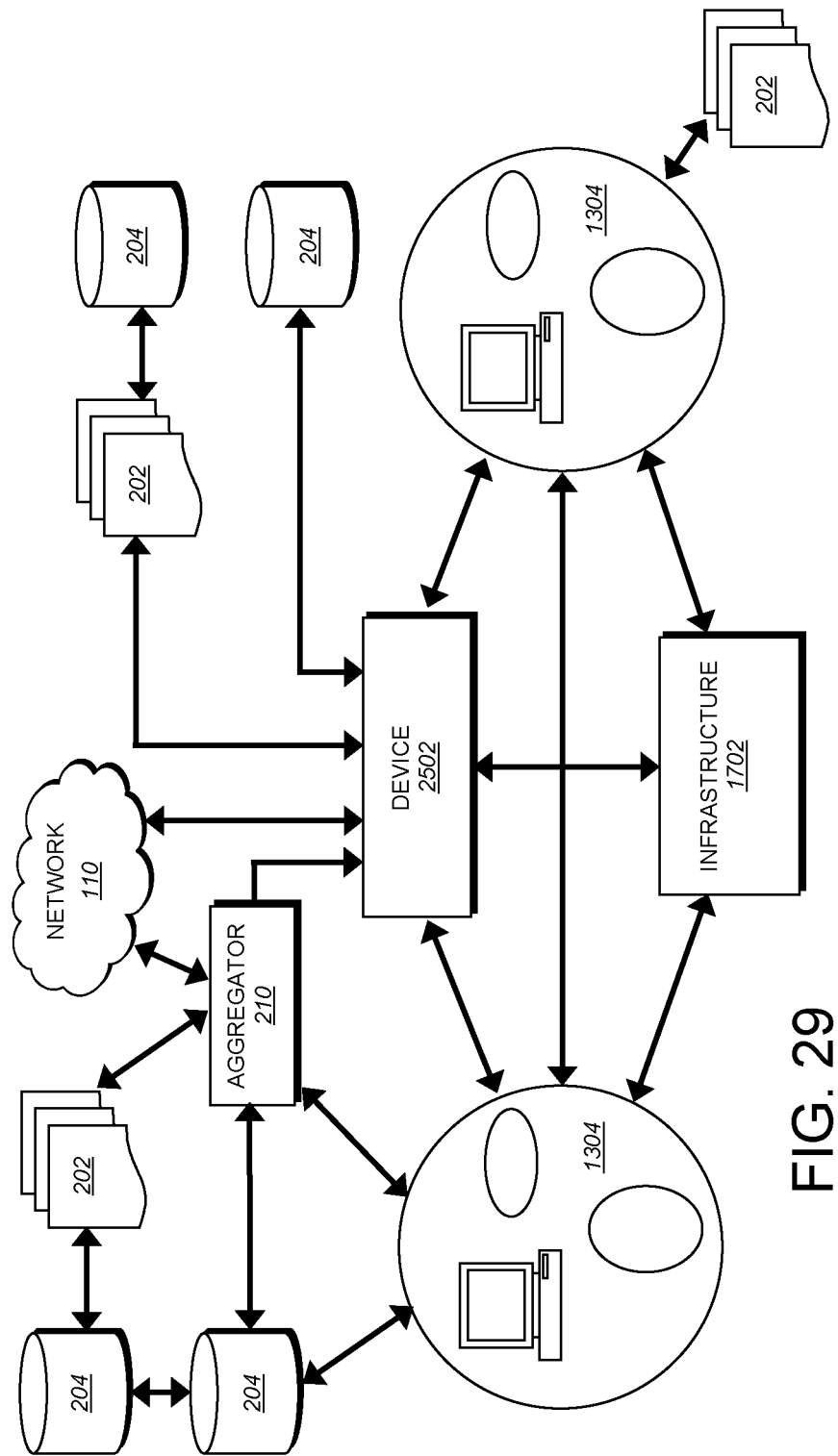
FIG. 29 shows a syndication environment including a medical device and an infrastructure.

Referring to FIG. 29, the device 2502 may be a diagnostic device, therapeutic device and/or administrative device. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. Users 1304, such as users 404 and clients 102, may view and/or receive information from and/or send information to and/or interact with the device 2502 directly or through an infrastructure 1702. The infrastructure 1702 may also interact directly with the device 2502. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 29 may be data feeds, such as data feed 202.

Figure 30:
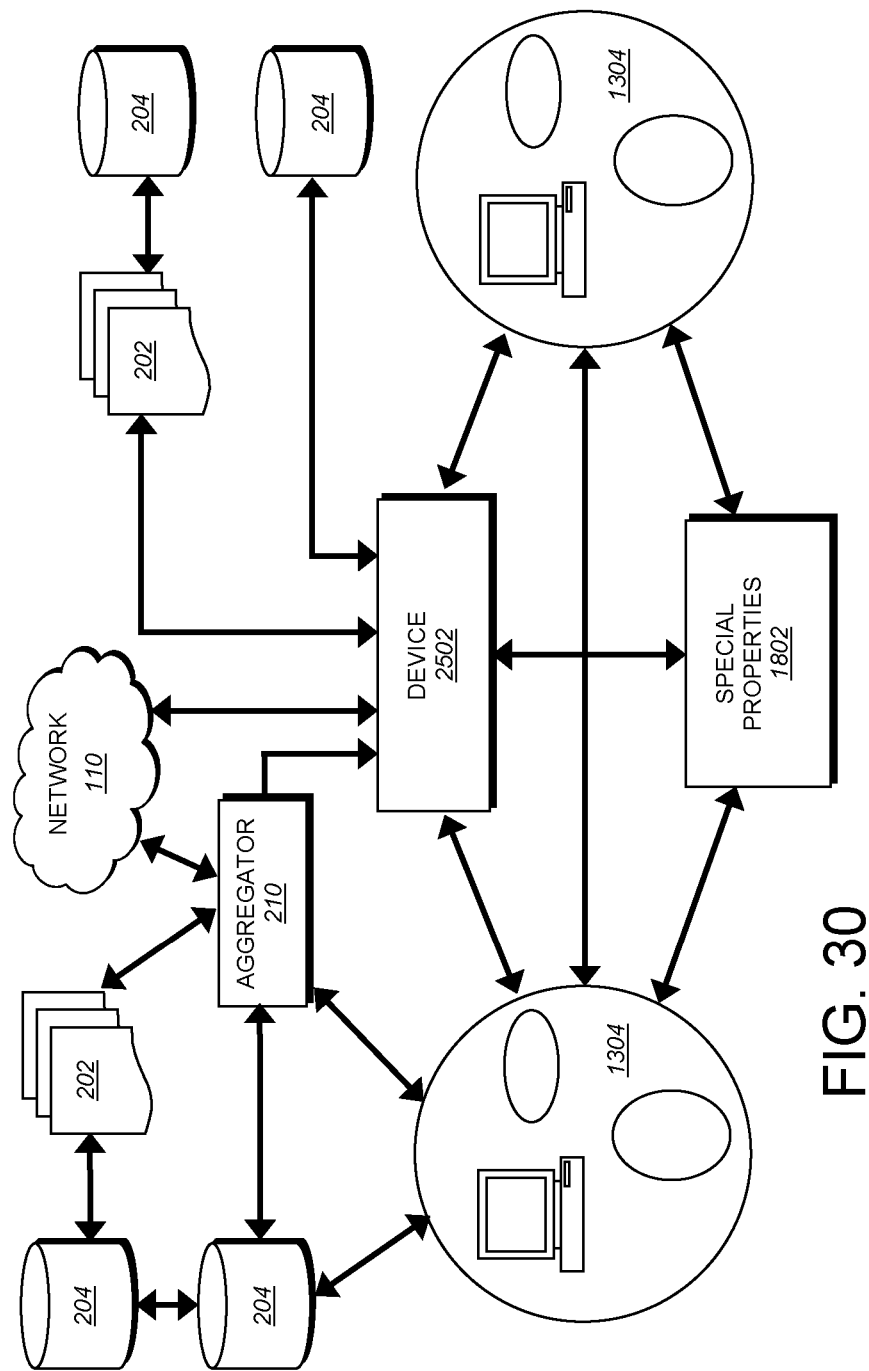
FIG. 30 shows a syndication environment including a medical device and special properties.

Referring to FIG. 30, the device 2502 may be a diagnostic device, therapeutic device and/or administrative device, as described herein. The device 2502 may be associated with a healthcare environment, healthcare practice environment, research environment, medical environment and/or another environment. The data and/or information, including syndicated data and/or information, may originate on a network 110 or may originate from a content source 204 through a data feed 202 or directly. The device 2502 may publish or subscribe to a syndicated data feed or stream, such as an RSS feed, web feed, RSS stream and/or RSS channel. An aggregator 210 may be employed as described above. The infrastructure 1702 may also interact directly with the device 2502. The users 1304 may also interact with each other. The device 2502 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 30 may be data feeds, such as data feed 202.

Figure 10:
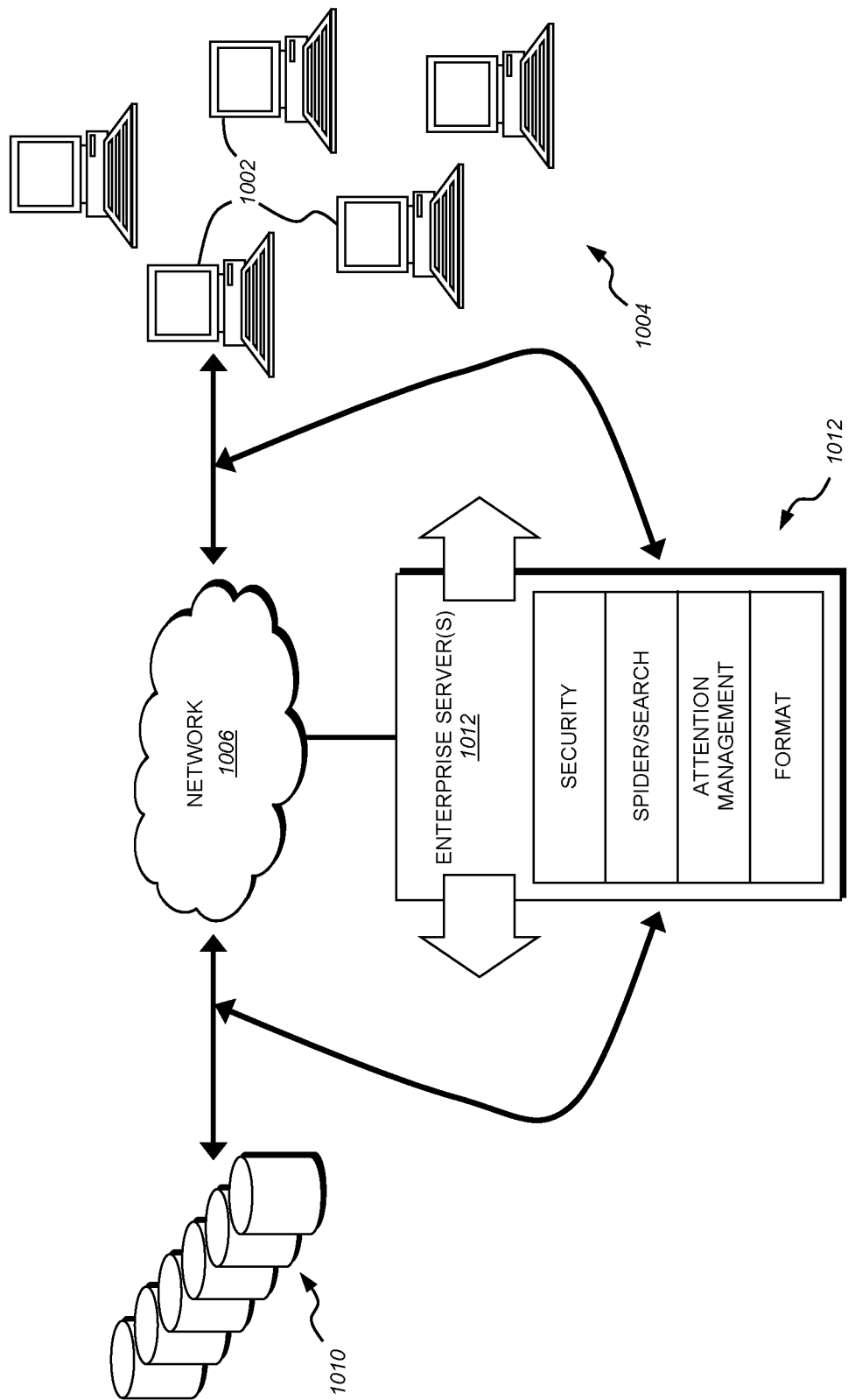
FIG. 10 shows a data pool environment.

A syndication platform including, e.g., RSS and/or OPML, along with suitable enhancements for security and other enterprise class system features, may be used to manage health care information. Health care data may be maintained in pools 1010, such as the pools described above with reference to FIG. 10, by entities in a health care system such as hospitals, individuals, health insurance providers, and/or academic or research facilities, and data from these pools 1010 may be selectively interrelated using an outlining grammar such as OPML for specific views of the otherwise unstructured data. Conditional access may also be supported, and may provide for anonymous or personalized data depending on the information requester. Any of the syndicated information and data described herein may be an element in or source for one or more pools 1010 and/or comprise a pool 1010.

In embodiments, the RSS feed 202, web feed, RSS stream, or RSS channel associated with a healthcare pool 1010 may be associated with an aggregator 210 to track updates.

In embodiments, the RSS feed 202, web feed, RSS stream, or RSS channel associated with a healthcare pool 1010 may be associated with a content management system that provides summaries of the syndicated data available, dates associated with the syndicated data, links to access the full, non-summarized data, and the like. In one aspect, the content management system may be deployed using an enhanced syndication system as described above.

In embodiments, the healthcare pools 1010 may be associated with an application 406 providing social networking, a user interface, a media viewer and/or vertical market integration.

Referring again to FIG. 13, the syndicated data/information 1302 may be one or more healthcare pools 1010 as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an application/interface/other 1308. The users 1304 may also interact with each other. The application/interface/other 1308 may be a client-side program, such as the healthcare program discussed herein, a social networking application, a user interface, such as user interface 700, 800 and/or 900, an application in connection with a media viewer, a media viewer and/or an application providing for vertical market integration, such as described herein. The application/interface/other 1308 may, for example, be deployed as a service in a services oriented architecture or using the other techniques described above with reference to FIGS. 4 and 5. In certain embodiments the arrows of FIG. 13 may be data feeds, such as data feed 202.

In embodiments, the healthcare pools 1010 may be associated with database functions that permit the data quality to be verified, provide for transformation of the data, enable searching, filtering, or clustering the patient data, or categorizing the data into hierarchies, interrelationships, interrelated groups, and the like.

Referring again to FIG. 14, the syndicated data/information 1302 may be one or more healthcare pools 1010 as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a database function 1402. The database function 1402 may also interact directly with the syndicated data/information 1302. The users 1304 may also interact with each other. The database function 1402 may be a database function as described herein, such as related to data quality, data transformation, searching, filtering, clustering, a search engine, information relationships, hierarchical relationships and categorization, such as described herein. The database function 1402 may, for example, be deployed as a service in a services oriented architecture or using the other techniques described above with reference to FIGS. 4 and 5. In certain embodiments the arrows of FIG. 14 may be data feeds, such as data feed 202.

In embodiments, healthcare pools 1010 may be associated with semantic rules 412 that enable the creation of metadata. Semantic rules 412 may also provide for metadata enrichment of aggregated data, interpretation or translation of aggregated data, as well as permit the creation of knowledge structures (e.g., using OPML) and the use of a dictionary, thesaurus or the like.

Referring again to FIG. 15, the syndicated data/information 1302 may be one or more healthcare pools 1010 as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a semantic facility 1502. The semantic facility 1502 may also interact directly with the syndicated data/information 1302. The users 1304 may also interact with each other. The semantic facility 1502 may provide or be related to semantic rules, metadata creation, metadata enrichment, interpretation of aggregated data, such as syndicated data/information 1302, translation of aggregated data, such as syndicated data/information 1302, creation of knowledge structures, a dictionary and/or a thesaurus, such as described herein. The semantic facility 1502 may, for example, be deployed as a service in a services oriented architecture or using the other techniques described above with reference to FIGS. 4 and 5. In certain embodiments the arrows of FIG. 15 may be data feeds, such as data feed 202.

In embodiments, users may publish and/or subscribe to and/or interact with one or more healthcare pools 1010 to which others may subscribe and/or publish and/or with which others may interact.

In embodiments, healthcare pools 1010 may be further associated with information that may provide for the management of the data. For example, the aggregated data may list the author of the aggregated data, the date on which it was authored, etc. Thus, the data may provide for further aggregation, republication, and the like.

Referring to FIG. 16, the syndicated data/information 1302 may comprise one or more healthcare pools 1010 as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through a syndication facility 1602. The syndication facility 1602 may also interact directly with the syndicated data/information 1302. The users 1304 may also interact with each other. The syndication facility 1602 may publish, subscribe to, aggregate and republish aggregated data, such as syndicated data/information 1302, such as described herein. The syndication facility 1602 may also manage syndication information 1302, such as described herein. The syndication facility 1602 may, for example, be deployed as a service in a services oriented architecture or using the other techniques described above with reference to FIGS. 4 and 5. In certain embodiments the arrows of FIG. 16 may be data feeds, such as data feed 202. A user 1304 may also publish, republish and/or subscribe to a content source 204, data feed 202, aggregator 210 and/or syndication facility 1602.

In embodiments, the healthcare pools 1010 may be provided within an infrastructure 416 that provides for data security, authentication, management of the traffic created by the RSS feeds 202, web feeds, RSS streams, or RSS channels, logging and pinging technology, and/or other communications.

Referring to FIG. 17, the syndicated data/information 1302 may be one or more healthcare pools 1010 as described herein. The syndicated data/information 1302 may originate on a network 110 or may originate from a content source 204 through a data feed 202 or directly. An aggregator 210 may be employed as described above. Users 1304, such as users 404 and clients 102, may view, receive, send and/or interact with the syndicated data/information 1302 directly or through an infrastructure 1702. The infrastructure 1702 may also interact directly with the syndicated data/information 1302. The users 1304 may also interact with each other. The infrastructure 1702 may provide or be related to security, authentication, traffic management, logging, pinging and/or communications, such as described herein. The infrastructure 1702 may, for example, be deployed as a service in a services oriented architecture or using the other techniques described above with reference to FIGS. 4 and 5. In certain embodiments the arrows of FIG. 17 may be data feeds, such as data feed 202.

In embodiments, healthcare pools 1010 may be associated with special formatting and/or display properties.

In embodiments, healthcare pools 1010 may be associated with special identification and/or de-identification properties.

In embodiments, healthcare pools 1010 may be associated with properties allowing for transactional processing. The transactions may be financial transactions, such as related to medical reimbursement and/or subscription fees or other charges for access to the syndicated evidence-based information.

In embodiments, healthcare pools 1010 may be associated with restricted or conditional access properties.

Referring to FIG. 18, the syndicated data/information 1302 may be one or more healthcare pools 1010 as described herein. The syndicated data/information 1302 may originate on a network 110 or may originate from a content source 204 through a data feed 202 or directly. An aggregator 210 may be employed as described above. The infrastructure 1702 may also interact directly with the syndicated data/information 1302. The users 1304 may also interact with each other. The syndicated data/information 1302 may be associated with special properties 1802. The special properties 1802 may be related to formatting, display, identification, de-identification, transactions, restricted access and/or conditional access, such as described herein. The special properties 1802 may also be associated with a service application 406, 408, 410, 412, 414 and/or 416. In certain embodiments the arrows of FIG. 18 may be data feeds, such as data feed 202.

In embodiments, the one or more healthcare pools 1010 may be associated with a pool management infrastructure 1012 as described herein.

The systems and methods disclosed herein include systems and methods for managing medical information. The systems and methods may involve: storing medical information in a syndication format; retrieving the medical information through a syndication collection facility; parsing the information into personal and non-personal information; storing the personal information in a personal information data pool 1010; and storing the non-personal information in a non-personal information pool 1010.

The systems and methods disclosed herein include systems and methods for storing medical information in a syndicated format. The systems and methods may involve storing the medical information in an RSS format, an OPML format or other appropriate syndication format. In embodiments, the medical information is stored in two data pools 1010. Personal information relating to the medical information may be stored in one of the two data pools 1010. Non-personal information relating to the medical information is stored in the other of the two data pools 1010.

The systems and methods disclosed herein include systems and methods for storing medical information in a syndicated format. In embodiments, the medical information comprises at least two parts. The at least two parts may be categorized as personal information and non-personal information. The personal information relating to the medical information may be stored in one data pool 1010. The non-personal information relating to the medical information may be stored in another data pool 1010. The information residing in the two pools 1010 may have been related at one point in time, but were later separated and stored in separate pools 1010 for various reasons. In embodiments, the information residing in either pool 1010 or both pools 1010 may contain references, associations, pointers, tags, links, directors, and the like to the information contained in the other pool 1010. In embodiments, the information residing in the pool 1010 with personal information is the only information of the two pools 1010 of information containing references, associations, pointers, tags, links, directors, and the like to the information in the non-personal pool 1010 of data. In embodiments, the information residing in the pool 1010 with non-personal information is the only information of the two pools 1010 containing references, associations, pointers, tags, links, directors, and the like to the information in the personal pool 1010 of data.

The systems and methods disclosed herein include systems and methods for managing medical information. The methods and systems may involve storing medical information in a syndication format, wherein the medical information has two parts. In embodiments, the two parts are personal and non-personal information. Records that require access to the personal information pool, such as a composite medical record for a patient, may be constructed from an OPML file or similar file that includes embedded access rights to specific data within the personal information pool. Thus, an OPML file or the like may be provided that personalizes certain medical data, and identifies any data within the available pools that relates to, e.g., a specific patient. The OPML file may be controlled by the patient using any suitable computer security and/or physical security techniques, and the owner may grant transient access as need to medical care givers. Thus, there is in one aspect disclosed herein a relational medical record that defines a patient medical history by external reference to a plurality of data pools including at least one secure pool and at least one insecure pool. In such a system, an array of data that would otherwise be confined to private medical records may be shared with the health care community for use in research, evaluation, and so forth.

Embodiments of the present invention are related to the management of pools 1010 and streams of information through syndication. The information may relate to medical, healthcare, business, personal or other information syndicated for collection and/or analysis. In embodiments, a secure pool 1010 of data may be formed and the secure pool 1010 of data may have been produced through the collection of syndicated information. In embodiments, a pool 1010 of data with reduced security relating to the secure pool 1010 of data may be generated. In embodiments, the information residing in the secure pool 1010 and the information residing in the unsecured pool 1010, or reduced security pool 1010, may be recombined through an association. The association may be latent (e.g. residing in metadata) or explicit (e.g., residing in an explicitly expressed relationship spanning, e.g., one or more OPML files). In embodiments, the data in the secure pool 1010 may be have references, associations, pointers, tags, links, directors, and the like to make the association with the data in the reduced security pool 1010 to make the reconstruction. In embodiments, the data in the reduced security pool 1010 may not have references, associations, pointers, tags, links, directors, and the like to make the recombination with the secure data. Removing, or not permitting, an association may be implemented as an additional security measure.

As generally described herein, health care data may be depersonalized and published for general use using a syndication platform or other data publication system. Personalization data may be maintained in a separate, secure facility, and/or tracked through relationships defined using, for example, an outline grammar such as OPML. In an embodiment, personal data (e.g., name, social security number, birth date, and/or any other data that may be used to identify an individual) may be maintained in a conditional access system that provides various degrees and types of access for different users such as government authorities, medical professionals, individuals identified by the personal data, law enforcement authorities, and so forth. Thus various degrees of access to personalized and/or anonymous data may be supported and controlled. In addition, group data may be derived through a personalization engine that provides limited access to personal data for purposes of identifying data for individuals within a demographic or other category. While a health care information system applying these principals is one possible embodiment, and is described in greater detail herein, it will be appreciated that the principles of this disclosure may be used with a wide range of data sets and potential applications such as a financial data, financial services data, consumer data, customer list data, and so forth.

Aspects of the present invention relate to storing healthcare information in separate pools 1010 of data wherein the separate pools 1010 store information relating to personal and non-personal information. In embodiments, the personal and non-personal information is stored with an association between them (e.g. directly or through a relation in a relational database). In embodiments, there is no relation between the personal and non-personal information. In embodiments, the personal and non-personal information may have been related at one point in time and then later separated into unrelated information or related in such a way that either the personal or non-personal information may be accessed separately or in a combined fashion. In embodiments, there is an association between the information in the related pools 1010. In embodiments, there is an association that is only made by using information residing in one of the pools 1010. The relationships (or lack thereof) may be managed independently from the data using, for example, an outlining grammar such as OPML.

Figure 31:
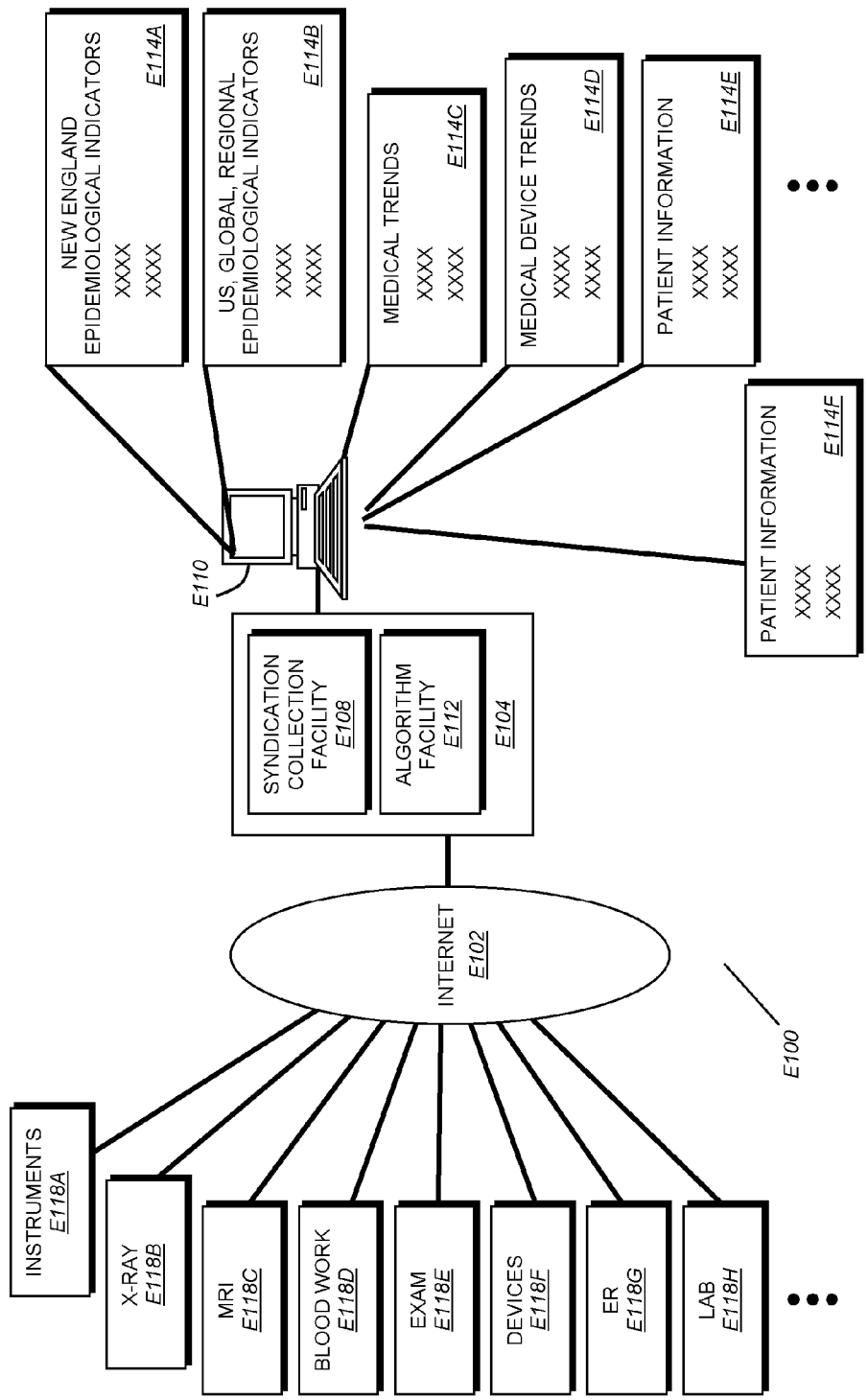
FIG. 31 shows a health care information management system.

FIG. 31 illustrates a healthcare information platform E100. Healthcare platform E100 may be used to facilitate the generation of healthcare reports E114. The reports E114 may be generated as a result of collecting syndicated information from healthcare related sources E118. In this illustration, there are several sources of healthcare or medical information E118. The healthcare information sources E118 may produce data in a syndicated format (e.g. RSS, OPML, XML, etc.). The information sources may be medical instruments E118A, x-ray equipment E118B, MRI equipment E118C, CAT scan equipment, other forms of medical imaging equipment, blood work data E118D, genetic information, medical exam information E118E, physician's notes, pharmaceutical or prescription records, patient diagnosis records, patient treatment records, patient condition records, medical device information E118F, information from emergency rooms E118G, information from medical labs E118H, diet information, exercise information, metabolic information, medical history information, age information, gender information, behavior information, race information, or information from other systems related to the healthcare and/or medical field. The information from the sources of information E118A may be disparate information or the information may be related in some way. For example, the information produced from each of the sources E118 may relate to the same person but the information may be collected through facilities throughout a geographic region. A patient may go to his doctor for a medical exam and the doctor may produce information pertaining to the exam in a syndicated format so it can be collected by a syndication collection facility later. The patient may also go to a hospital located in a town separate from the physician's office where the medical exam was conducted, the patient may have an MRI or other test performed. Again, the information produced by the tests could be produced in a syndicated format to be later collected. The patients primary care physician may, for example, go to a syndication collection facility E108 and collect all of such information produced relating to the patient as a way of collecting all of the information in one place. The syndicated information may be time stamped, or the like, such that only newly produced medical information is collected and stored. The doctor may then run reports (e.g. patient report E114F) on the collected information to assemble a clear history of the patient. Information from the several sources may also be processed through an algorithm facility E112 to further refine the information, correlate the information internally or with external information, produce segmented reporting based on the primary issues at hand (e.g. has the patient had any adverse reactions to medicines).

The information produced by the several medical information sources E118 may be accessible through the Internet E102 or other network. A syndication collection facility 108 such as a spider or syndicated content search engine may operate in association with a computer facility E110. The syndication collection facility E108 may be directed to collect all information relating to a particular subject (e.g. a patient and patient medical records, trend information, disease information within a geographic region, etc.). Syndication collection facilities are described in more detail herein as well as in the reference material incorporated by reference herein. The information collected through the syndication collection facility E108 may be processed through an algorithm facility E112. The algorithm facility E112 may be adapted to run any type of algorithm designed to manipulate and/or interact with data collected by the syndication collection facility E108. The algorithm facility may also be adapted to produce reports E114, and the like, and the reports E114 may be displayed on the computer facility E110. The computer facility may be any computer processing equipment such as a desktop computer, laptop computer, notebook computer, palmtop computer, wireless computer, wired computer, PDA, mobile communication facility, cell phone, phone, or other system adapted to perform such processes.

Reports E114 may pertain to an individual, a population, region, disease, health risk, virus, or other entity or health or medical information. A syndication collection facility E108 may be adapted to collect all of the information pertaining to a particular health related concern for example. For example, the concern may relate to encephalitis within the coastal communities of Massachusetts and the syndication collection facility may be adapted to collect any and all information relating to encephalitis within that geographic area, or outside that geographic area, collected from healthcare information systems E118. Three patients in the area may have been recently physically examined and blood work may have been completed. The exams and blood results may indicate they have contracted the disease. The collection facility E118 may collect this information and the algorithm facility E112 may manipulate the information, along with other related information (e.g. climate conditions in the area, weather expected in the area, mosquito activities, mosquito extermination activities, etc.) to produce reports E114, predictions, estimates, historical trends and the like. Examples of reports produced through the collection of syndicated health and/or medical information are regional epidemiological reports E114A and E114B, medical trends E114C, medical device trends E114D, medical instrument trends E114E, patient reports E114F and the like.

Figure 32:
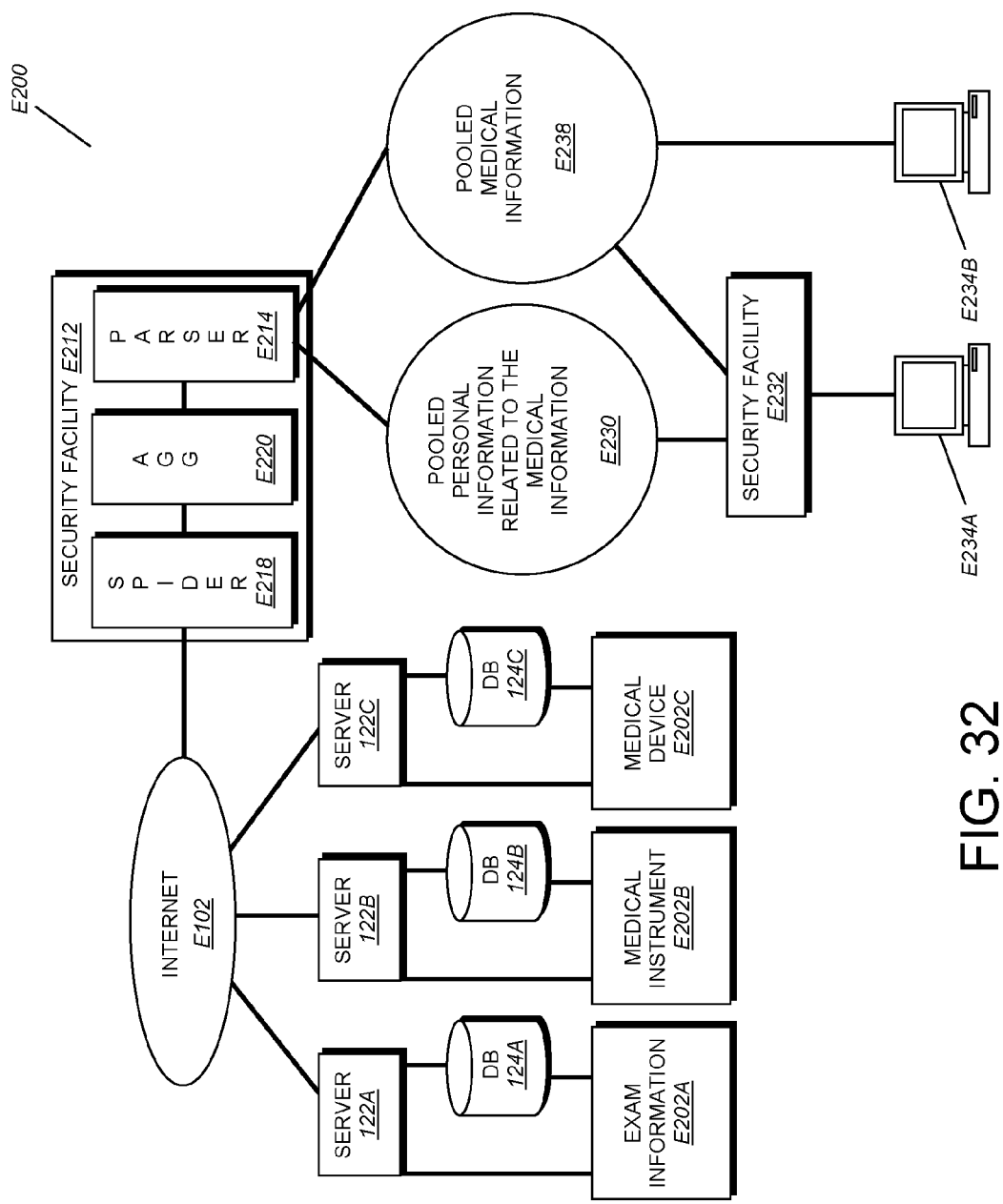
FIG. 32 shows a health care information management system.

An aspect of the present invention relates to the syndication of medical information and the collection of the syndicated information for the generation of reports and the like. Another aspect of the present invention relates to producing information in a way that protects the privacy of individuals while providing broad access to information that may be used to identify trends, histories, predictions, as well as for other uses. Referring to FIG. 32, a medical information platform using pooled information E200 is illustrated. The medical information platform using pooled information may be described as a system designed to produce pooled information wherein a plurality of pools 1010 may be produced, one pool 1010 containing personal information E230 (e.g. patient name, social security number, insurance information) and one pool 1010 containing non-personal information E238 (e.g. medical information such as examination results disassociated with a patient's personal information).

The medical information systems E202 may produce syndicated medical information that is stored in an associated database E124. The producing facility E202 and its associated database E124 may also be associated with a server E122 to aid in the collection of the syndicated information they produce. The server E122 may be associated with the internet or other network E102. A syndication collection facility may be adapted, with a spider E218 for example, for collecting the syndicated information from the plurality of databases E124. An aggregation facility E220 may also be in use to aggregate the information collected by the spider E218 and the aggregated information may be parsed through a parsing facility E214. The processes used in the collection and manipulation of the syndicated medical information may be operating in association with syndication collection security facility E212 to ensure privacy and transactional security.

The information that is parsed by the parsing facility E214 may be collected into two or more pools 1010 of information for example. One pool 1010 may contain parsed personal data E230 relating to the syndicated information collected by the spider E218 and the other pool 1010 may contain non-personal information E238 (e.g. exam results, medical history). The pools 1010 of information may be used for a variety of reasons. For example, the pool 1010 containing medical non-personal information E238 may be used by epidemiologists or other healthcare professionals to gather information related to trends or the like without sacrificing privacy of patients or having to rely on obtaining information releases from the many people to whom the information pertains. The information pool 1010 containing the personal information relating to the medical information E230 may be used, through a security facility E232, by itself or to be re-associated with the medical information residing in the medical information pool 1010 E238 to generate patient specific reports and the like.

In another embodiment, some or all of the health care data may be de-personalized and syndicated using the systems described herein. Information needed to personalize data, i.e., associate the data with a particular patient or group of patients, may be retained at a different location, such as a secure data repository. In one embodiment, personalization information may be maintained in an outline such as an OPML document. Similarly, OPML or the secure data repository may be employed to sort data with partial personalization, such as to obtain demographic data or the like. For example, a personalization facility may be employed to gather all data for individuals having certain objective characteristics, such as a specified age, weight, gender, medical condition, or the like, without identifying any of the specific individuals for whom data is being provided.

The information provided by the medical information sources E202, which may be, for example, any of the medical devices described above, may be formatted in a syndication format, such as RSS or OPML. The spider E218 may look for and gather the syndicated information as a result of a targeted syndication search. The parser may parse the information in a number of ways. For example, if the syndicated information is provided in an OPML format, the parser may extract information relating to the medical condition, diagnosis, testing, prognosis, symptoms, test results, images and the like to be sent to the pooled medical information E238, while personal information may be extracted and sent to the personal information pool 1010. The personal information may still retain tags or outline parameters that may be used to reconnect the personal information to the non-personal medical information in the pooled medical information E238.

Figure 33:
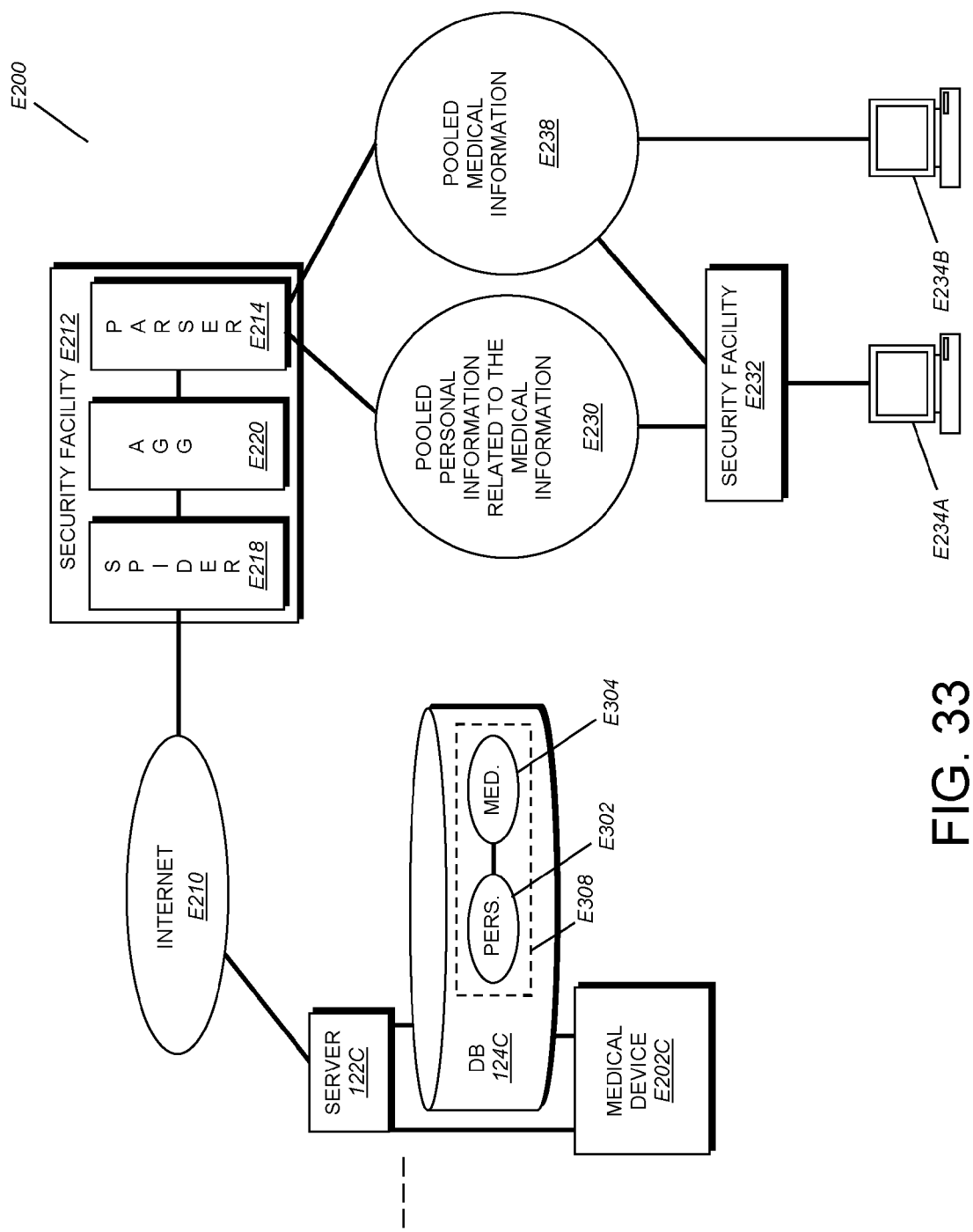
FIG. 33 shows a health care information management system.

FIG. 33 illustrates another method of pooling medical data E200 to retain privacy and security. Method E200 relates in part to storing the information in two separate, but referenced pools 1010 of data. For example, the medical device E202C may store information in a related database E124C in separate but related sections in the database. The information may be stored using a syndicated format such that a spider or other syndication collection facility could be used to collect the medical information. In embodiments, the personal and non-personal information is stored in a relational database with syndication tags and the relational database may be open to certain syndication collection activities. With the information stored in two pools 1010, one relating to personal information and one relating to non-personal information, a spider may be directed to collect the non-personal information E304 through server E122C. Information from several like sources, or several records from the medical device E202C, may be aggregated E220 and parsed E214 if desired. In addition, the personal information E302 may be collected, aggregated, from several like sources, or several records from the medical device E202C, and parsed if desired. A collection of aggregated and/or parsed personal data and aggregated and/or parsed non-personal medical information may be stored in separate pools 1010 E230 and E238. In another embodiment, personalizing data may not be stored within the system, but may be maintained separately by data users. Thus for example, an individual may maintain a list of references to all diagnosis, treatment, and other health care information for the individual within the pools 1010 of data. This list may be preserved within a separate, secure facility with encryption techniques employed for authenticity and non-repudiation of references to actual records pertaining to the individual within the pool 1010($s$).

Continuing to refer to FIG. 33, the information pool 1010 containing the personal information relating to the medical information E230 may be used, through a security facility E232, to be re-associated with the medical information residing in the medical information pool E238 to generate patient specific reports and the like. This approach may be employed to review or analyze medical information relating to one or more people through a computer facility E234A. It may be appropriate in certain circumstances to obtain consent from In embodiments, access to pooled medical information E238 may be the only information provided and it may be accessed through computer facility E234B. Computer E234B may also be associated with a security facility (not shown). In other embodiments, personal information may be correlated to data within the information pools 1010 using, e.g., an outline grammar such as OPML. A patient record OPML file may be separately and securely maintained. In one embodiment, only an authorized medical professional may have access to the patient record OPML file. In another embodiment, an owner of the data (i.e., the person to whom the data relates) may have read-only access to the OPML file.

Aspects of the present invention relate to pooling syndicated information. Pools 1010 may contain information relating to information that was found in data streams. The information may have been found in the data stream at particular times or in particular places. For example, a financial market may produce a stream of data relating to trades made during a trading session and a pool 1010 of data extracted from the stream may be produced to be accessed later. As another example, medical information may be produced by a medical device and the medical device information may be pushed into a data stream. The medical information from the data stream may be extracted from the stream and loaded into a pool 1010.

Pools 1010 of data can be merged with other pools 1010 of data to form larger pools 1010 (e.g. to combine things of like file type, semantic meaning, etc.). In embodiments, pools 1010 may be drained, and in doing so new data streams may be created. For example, streaming a series of offers to sell goods (or services, securities, etc.) at a given price, out of a pool 1010 of such offers. In embodiments, the data stream may be buffered until relevant decision points are achieved.

In embodiments, a filter may be associated with a pool 1010 of data. A pool 1010 of data may be created from unfiltered data (e.g. an unfiltered data stream), then over time the pool 1010 can be run through filters to produce a cleaner/more relevant pool 1010 of data. The filter could be a semantic filter, a collaborative filter, a logical filter, or a human filter (such as a community that validates the presence of content in the pool 1010). E.g., a pool 1010 could contain "good movies" that are monitored by a community.

In embodiments, pools 1010 may be linked to other pools 1010, so that one pool 1010 spills into the other (e.g., a pool 1010 of data that takes input from another pool 1010 upon occurrence of an event, such as availability of a resource for processing (e.g., a resource becomes available to process an incoming message requesting help from a software help desk and is handed into a pool 1010 of similar requests for handling by someone who is responsible for that type of request)). Pools 1010 of data can evaporate (that is, data items can be made to expire from the pool 1010, either based on age, or based on the right conditions (e.g., if a price of a security drops low enough, then limit orders may be triggered; if time passes, an option can expire, etc.). Pools 1010 may be filled by different sources (a main source, as well as secondary sources or streams that augment the main source streams).

An aspect of the present invention relates to using syndicated heath related data and health related syndicated data pools 1010. The following embodiments, illustrate a few of the envisioned uses of such information.

In embodiments, community-based health data may be communicated to healthcare professionals, the public or other persons or entities through syndication feeds associated with the community-based health data. The syndication feeds may consist of syndicated health data collected by community health clinics, emergency personnel, hospitals, hospices, nursing homes, public health screening sites, mobile screening facilities, community health drives, blood drives, school clinics, emergency rooms, physician offices, and/or other sites where health data may be collected. Community-based health data includes, but is not limited to, cases of disease, such as heart disease, cancer, diabetes, stroke, mortality, serious accidents, child immunizations, influenza, and so forth. This information may be linked with other demographic data, such as age, sex, race, social security number, religion, area code, home address, work address, billing address, credit card information, family information, birthplace, driver's license number, employer, position, and income bracket. Community-based health data may be communicated through syndication feeds continuously, at set intervals, at predetermined intervals, upon an event or updated information, or at another appropriate time.

In embodiments, community-based health data may be communicated through a syndicated feed based on syndicated heath data stored in a centralized facility or in several data repositories. The storage and associated data analysis may occur within a community public health clinic, state public health clinic, university research facility, medical school, and/or national public health entity such as the National Institutes of Health or the Centers for Disease Control and Prevention. Such a system of reporting may permit macro and micro temporal tracking of health trends.

In embodiments, syndication feeds relating to community health status data may be randomly sampled to calculate public health indicators. For example, a county public health agency may receive a plurality of syndication feeds containing community health data. The agency may have a need to know about the most prevalent health ailments found among children living in the county. Rather than analyze all the health data available about children, it may be advantageous financially and empirically to randomly sample from the available health data. This may reduce the analytic task by lessening the data required for analysis as well as improve the validity of the analysis by permitting the agency to ensure that the data used for analysis adequately represents the community as a whole (i.e., minimizes bias). Furthermore, the health data may be used by the agency for other public health study formats. For example, community health data communicated through syndicated feeds may be used to compute disease incidence, disease prevalence, identify new outbreaks of disease and/or infection, calculate the distribution of disease across demographic variables, and/or identify populations that are vulnerable to future health concerns.

In embodiments syndicated feeds related to community-based health status data may be linked to location information, such as Global Positioning System (GPS) data or information relating to a home address or clinic address. This coupling of health and geographic data may permit analysis of environmental factors that may be affecting the health of the community. For example, by linking the rates of obesity with the geographic location of the green spaces it may be possible to infer whether there is a relationship between increasing rates of obesity and access to parks and other recreational areas. Similarly, environmental data on particulate matter released by local industries may be linked with the location of recent lung cancer cases to assist in determining the influence of air pollution on cancer incidence.

In embodiments, syndicated data on community health may be presented for use by health care providers through syndication feeds and the like. For example, healthcare facilities, such as hospitals, may be in need of information on the rates of disease and the distribution of health needs within the population residing in the facility's catchment area. For example, when planning its fiscal budget, a county hospital may be in need of information to assist it in allocating resources between kidney dialysis services and diabetes treatment. The community health data, discoverable through a syndicated feed, may indicate declining rates of kidney disease and increasing rates of diabetes, thereby increasing the confidence the hospital administrators may have in choosing to divert resources to increase funding for diabetes treatment.

In embodiments, health education materials may be made available to the public through syndication feeds that are sent in accordance with health data retrieved during community health screenings. For example, during a community health screening patients may have their blood glucose levels checked. For those patients with abnormal glucose levels, a syndication data feed regarding proper blood sugar management may be set up for review and/or printing by the patient. Additional systems could record which patients receive these educational materials to permit future analyses of the effectiveness of the educational materials in helping patients manage their health. For example, when such data is viewed, new syndicated data may be developed and sent back to an available pool 1010 of such data. An association may be made between the data indicating the material was received and past and/or future health care related information.

In embodiments, data regarding the clinical practices of healthcare providers and institutions may be stored in a syndicated format. Just as the medical chart currently follows the patient throughout his treatment within an institution, so too could a data feed adapted to capture such information from a pool 1010 of such syndicated information. A device could syndicate salient information at each step of the treatment process, from intake to discharge, to follow-up consultations. For example, upon intake, a patient's demographic information may be collected, such as age, sex, race, social security number, religion, area code, home address, work address, billing address, credit card information, family information, birthplace, driver's license number, employer, position, and income bracket and the information may be syndicated (e.g. tagged to be later retrieved through a syndication feed). Throughout the patient's interaction with the healthcare provider(s) additional information may be collected and syndicated to be later collected through syndication feeds. This information may include, but is not limited to, admission time, time of first consultation, health status/diagnosis on intake (e.g., ICD-10 code), the patient's currently prescribed medications, timing of treatment(s), treatment dosages, duration of treatment, symptoms, change in symptoms (health status), self-assessed health status/quality of life, time of discharge, and morbidity/mortality outcomes.

In embodiments, data collected about the clinical practices of healthcare providers and institutions communicated through syndication feeds may be stored and analyzed as part of a continuous quality improvement regime to ascertain efficiency. It is necessary for healthcare providers to provide treatment to patients in an efficient manner that optimizes the patient's health while minimizing institutional waste. Information is required to monitor the efficiency of any institution and this is especially important within the field of healthcare due to the many different services and service providers that impact institutional efficiency. Just as the medical chart currently follows the patient throughout his treatment within an institution, so too could a syndication by collecting all relevant information from a pool 1010 of syndicated data. A device could record salient information at each step of the treatment process, from intake to discharge, to follow-up consultations. Once this information was sent to a storage facility, it may be made available for administrators or researchers for analysis of whether services were efficiently provided to patients. Information that may be used in this manner may include, but is not limited to, admission time, time of first consultation, health status/diagnosis on intake (e.g., ICD-10 code), the patient's currently prescribed medications, timing of treatment(s), treatment dosages, duration of treatment, time of discharge, and timing of follow-up consultations.

In embodiments, data collected about the clinical practices of healthcare providers and institutions communicated through syndication feeds may be stored and analyzed as part of a continuous quality improvement regime to ascertain effectiveness.

In embodiments, data collected about the clinical practices of healthcare providers and institutions communicated through syndication feeds may be stored and analyzed as part of a continuous quality improvement regime to ascertain the cost effectiveness of services. The clinical data collected from individual patients may be collected, syndicated, and stored. It may then be monitored in conjunction with a healthcare provider's financial information to determine the cost-effectiveness of the treatment's administered. These results may then be compared to national norms for the purposes of benchmarking individual healthcare providers or institutions.

In embodiments, data collected about the clinical practices of healthcare providers and institutions communicated through syndication feeds may be stored and analyzed as part of a program to ensure conformance with accepted standards of care. For many clinical conditions there are published standards of care to guide physicians and other healthcare personnel in proper medical decision making. For example, blood pressure is considered to be "high" typically if a patient(s) systolic pressure is over 120 and/or diastolic pressure exceeds 80. Thus, a basic standard of care provides that a patient with a blood pressure reading exceeding these levels should be treated for hypertension. However, there are many additional factors that must be considered before the healthcare provider can make the appropriate treatment recommendation. For instance, the age of the patient, the patient's current medications, the patient's concurrent morbidities, and many other factors influence the decision to treat the hypertension through dietary change, exercise, medication, or some combination of these. A healthcare provider's effectiveness, and the effectiveness of the institution within which she serves patients, may be determined in part by the degree to which treatment conforms to these standards of care. By using syndicated data to continuously record information about the patient's treatment, this information may be accessed in real-time, or retrospectively, and analyzed to determine conformance with accepted standards of care.

In embodiments, a syndicated feed relating to data about a patient's course of treatment could trigger alerts to physicians and other healthcare providers when the treatment regimen diverges from the accepted standard of care. For example, such information may be used to record a patient's current medications upon intake to a hospital or the medications may be determined through a related syndicated feed. During the course of treatment at the hospital, additional data may be added to a pool 1010 of syndicated information, including new medications that may be administered. Should there be a new medication that is prescribed that has a known negative interaction with a mediation that the patient was currently taking, but for whatever reason was not recognized by the healthcare provider, an alert could be forwarded by syndicated feed to a physician's device alerting the physician of the potential problem. The algorithms used to determine diversions from accepted clinical standards of care may be stored on a central server, or locally on a client, for example, and act as filters or predictors based on the incoming syndication data relating to the patients' records. Furthermore, the algorithms may be updated to reflect findings from new clinical research and changing standards of care.

In embodiments, syndication feeds may be prospectively used to assist medical decision making. As described herein, throughout a patient's clinical treatment, data may be collected, including admission time, time of first consultation, health status/diagnosis on intake (e.g., ICD-10 code), the patient's currently prescribed medications, timing of treatment(s), treatment dosages, duration of treatment, symptoms, change in symptoms (health status), self-assessed health status/quality of life, time of discharge, and morbidity/mortality outcomes. A healthcare provider may store algorithms on a server reflecting the clinical standards of care for the types of patients treated by that healthcare provider. As data are collected throughout the patient's treatment, the incoming syndication feed may be filtered or otherwise associated with these algorithms and used to derive recommendations that may, in turn, be forward to healthcare providers for consultation during the clinical decision making process. For example, medical researchers employed by a hospital may learn through a recent medical journal article that a particular dosage of statins was found to reduce subsequent heart attacks in patients receiving coronary artery bypass surgery. The researchers may manifest this new knowledge in the form of an algorithm that filters or otherwise manipulates all incoming patient syndication data feeds looking for patients that have received bypass surgery, and then determining the current dosage of statins that each patient is currently taking. Bypass surgery patients that are not taking statins, or that are not taking the correct dosage (i.e., is not conforming to the accepted standard of care), may be identified and an alert forwarded to a healthcare provider by RSS feed to let the provider know that there is a high probability that this patient should have her statin dosage adjusted. Furthermore, the algorithms may be continuously updated to reflect findings from new clinical research and changing standards of care.

In embodiments, syndication data streams may be used to optimize enrollment in clinical trials. One of the challenges and significant costs incurred by clinical trials is identifying patients who are appropriate for study. Often there are extensive lists of inclusion criteria based on demographic, health status, and other indicators that are used to determine which patients are appropriate for enrollment. In addition, may clinical trials have complicated, stratified trial designs and subject pools 1010 that are enrolled across a geographically diverse population requiring extensive coordination to ensure that only appropriate subjects are enrolled and that no class of subjects is over-, or under-enrolled. By using a syndication feed of patients' information, all indicators that are relevant to the inclusion criteria of a given clinical trial may be continuously monitored. This process of review may be centralized or may occur within each healthcare provider point of patient contact, for example. For example, upon intake, a patient's demographic information may be collected, such as age, sex, race, social security number, religion, area code, home address, work address, billing address, credit card information, family information, birthplace, driver's license number, employer, position, and income bracket. Throughout the patient's interaction with the healthcare provider(s) additional information may be collected and sent via syndication feeds. This information may include, but is not limited to, admission time, time of first consultation, health status/diagnosis on intake (e.g., ICD-10 code), the patient's currently prescribed medications, timing of treatment(s), treatment dosages, duration of treatment, symptoms, change in symptoms (health status), self-assessed health status/quality of life, time of discharge, and morbidity/mortality outcomes. A clinical trial's inclusion criteria could manifest as an algorithm on a central server against which the individual patients' syndicated feed data are compared for compatibility. When there is a match (i.e., a patient qualifies for enrollment in a study) an alert may be forwarded to an attending physician or other healthcare provider, along with information about the study, its purpose, and requirements of patients. Additionally, informed consent forms and other relevant enrollment materials may also be forward via syndication. Following enrollment, a duplicate "blinded" (i.e., no personal identifiers other than study ID) patient record may be forwarded by syndication to a separate clinical trial data repository.

In embodiments, syndication data streams of patient's data may be used to enroll patients in clinical trials by randomizing patients according to the analytic design of the clinical study. For example, clinical cohort studies may have a stratified design in which a predetermined number of patients from different age strata are sought for enrollment. By analyzing the demographic data included in the patient feeds, it may be possible to more efficiently stratify enrollment, while still maintaining randomization. Similarly, stratification could be carried out based upon clinical criteria, such as disease status/severity. Case-control studies, observational study, and/or trend analyses may be conducted in a similar manner.

In embodiments, syndicated data feeds may be used by patients to communicate health status data to their health care providers from home. Using a device capable of capturing and syndicating data, patients may record their symptoms in real-time, along with relevant health indicators (e.g., glucose levels, respiratory volume, etc.) and make the data available to their physician through an associated feed. Similarly, patients could record information relating to the timing of taking medications, their functional status, and so forth. Temporal comparisons may be made to determine the presence of any clinically relevant changes in a patient's health status. Clinically relevant changes in a patient's health status may be used to automatically generate an email to a healthcare provider alerting them to the change. If appropriate, an appointment may be scheduled.

In embodiments, a syndication feed may be used to alert patients to an upcoming appointment with a healthcare provider.

In embodiments, syndication feeds may be used to push medical content and information to patients based upon their medical condition(s). For example, a healthcare provider may be able to initiate an RSS feed for patients based upon clinical information, such as a patient's ICD-10 code. This may be used as a filter to screen information repositories (e.g., medical journal databases such as Medline) for information that is relevant to a patient. Similarly, breaking news from news wire services, such as Reuters, may also be screened for its relevance to a patient's health condition(s). Once aggregated, this information may be presented through a feed for review by patients.

In embodiments, syndication feeds may be based upon data collected from environmental toxin sensors. For example, public health departments may employ a variety of environmental sensors to monitor water, air, and soil pollutants, as well as toxic spills or other sudden changes in environmental status. This data may be stored in syndicated data pools 1010 and retrieved in real-time via syndication feeds for continuous monitoring. The data may be analyzed for trends and changes over time. The data may be merged with other community data (e.g., citizens' health status, location data, GPS data, etc.) to determine causal patterns and/or disease clustering. Similarly, environmental monitoring could be carried out within a single home and used to monitor radon levels, mildew/mold, lead dust, soil toxins, water toxins, etc. This information may be communicated through syndication to a homeowner's computer, PDA, or any other device capable of receiving such feeds.

While the invention has been disclosed in connection with certain preferred embodiments, other embodiments will be recognized by those of ordinary skill in the art, and all such variations, modifications, and substitutions are intended to fall within the scope of this disclosure. Thus, the inventions disclosed herein are to be understood with respect to the following claims, which should be interpreted in the broadest sense allowable by law.

What is claimed is:

1. A computer implemented method comprising:
generating a data pool to receive and publish data that includes ultrasound echo data, wherein generating the data pool is performed by a microprocessor of the computer executing instructions stored in a non-transitory computer memory and comprises:

receiving ultrasound echo data from one or more medical devices;

securing the ultrasound echo data with a conditional access mechanism to provide a secure item;

adding metadata to the secure item that includes metadata identifying characteristics of a patient;

publishing the secure item and the metadata in a syndicated data feed using the microprocessor of a computer executing instructions stored in a non-transitory computer memory;

subscribing to the syndicated data feed;

storing the syndicated data feed in the data pool, wherein the format of the syndicated data feed is selected from the group consisting of: Really Simple Syndication, Resource Description Framework Site Summary, Rich Site Summary and Outline Processor Markup Language;

extracting data related to an abnormality of the ultrasound echo data from the syndicated data feed;

comparing the extracted data related to the abnormality with comparable ultrasound echo data from a normal specimen;

extracting data related to adverse patient outcomes from the syndicated data feed; and correlating adverse patient outcomes with the abnormality of the ultrasound echo data.

2. The computer implemented method of claim 1 further comprising accessing the data pool to obtain data for authorizing a medical procedure.

3. The computer implemented method of claim 1 further comprising accessing the data pool to obtain data for authorizing payment for a medical procedure.

4. The computer implemented method of claim 1 further comprising limiting access to the secure item based upon a privacy rule.

5. The computer implemented method of claim 1 further comprising limiting access to the secure item based upon an identity of a requester of the secure item.

6. The computer implemented method of claim 1, further comprising adding metadata to the secure item that includes at least one item of metadata selected from the group consisting of metadata identifying the medical device, metadata identifying a time of creation of the ultrasound echo data, metadata identifying a physician who requested the ultrasound echo data, metadata identifying the patient, metadata identifying an intended recipient of the ultrasound echo data, and metadata identifying a laboratory where the medical device is located.

7. The computer implemented method of claim 1 wherein the metadata identifies the medical device.

8. The computer implemented method of claim 1 wherein the metadata identifies a time of creation of the ultrasound echo data.

9. The computer implemented method of claim 1 wherein the metadata identifies a physician who requested the ultrasound echo data.

10. A computer implemented method comprising:

generating a data pool to receive and publish data that includes ultrasound echo data, wherein generating the data pool is performed by a microprocessor of the computer executing instructions stored in a non-transitory computer memory and comprises:

receiving ultrasound echo data from a plurality of medical devices;

securing the ultrasound echo data with a conditional access mechanism to provide a secure item;

adding metadata to the secure item that includes metadata identifying characteristics of a patient;

publishing the secure item and the metadata in syndicated data feeds using the microprocessor of the computer executing instructions stored in a non-transitory computer memory;

subscribing to the syndicated data feeds;

storing the syndicated data feeds in the data pool, wherein the format of the syndicated data feeds is selected from the group consisting of: Really Simple Syndication, Resource Description Framework Site Summary, Rich Site Summary and Outline Processor Markup Language;

extracting information relating to an abnormality in the ultrasound echo data from the syndicated data feeds;

comparing the extracted data related to the abnormality in the ultrasound echo data with comparable ultrasound echo data from a normal specimen;

extracting information relating to a treatment of the patient and characteristics of the patient from the syndicated data feeds; and correlating the information relating to the normality of the ultrasound echo data with the information related to the treatment data.

11. The computer implemented method of claim 1 wherein the metadata identifies an intended recipient of the ultrasound echo data.

12. The computer implemented method of claim 1 wherein the metadata identifies a laboratory where the medical device is located.

13. The computer implemented method of claim 1 further comprising manually entering the metadata.

14. The computer implemented method of claim 1 wherein the medical device adds the metadata.

15. The computer implemented method of claim 1 wherein a physician adds the metadata.

16. The computer implemented method of claim 1 further comprising encrypting the secure item to prevent unauthorized access.

17. The computer implemented method of claim 1 wherein publishing the syndicated data feed includes publishing the syndicated data feed to a publicly-accessible network.

18. A computer implemented method, comprising:

generating a syndicated data feed using a microprocessor of the computer executing instructions stored in a non-transitory computer memory that includes aggregated ultrasound echo data from a plurality of medical devices secured using a conditional access mechanism, the syndicated data feed using a format selected from the group consisting of: Really Simple Syndication, Resource Description Framework Site Summary, Rich Site Summary and Outline Processor Markup Language;

publishing the syndicated data feed to a publicly-accessible network using the microprocessor of the computer executing instructions stored in a non-transitory computer memory;

extracting information relating to an abnormality in the ultrasound echo data from the syndicated data feed;

extracting information relating to patient treatment data and patient characteristics from the syndicated data feed;

searching for abnormalities in the ultrasound echo data;

comparing the extracted data related to the abnormality in the ultrasound data with comparable ultrasound echo data from a normal specimen; and correlating the abnormalities in the ultrasound echo data with the patient treatment data.

19. The computer implemented method of claim 18 further comprising extracting information from the syndicated data feed, the information selected from the group consisting of a virus, a virus parameter and an indication of a virus; and
    filtering the syndicated data feed based on the extracted information.

20. The computer implemented method of claim 18 further comprising:
    subscribing to the syndicated data feed; and storing the syndicated data feed in a data pool.

21. The computer implemented method of claim 20 further comprising accessing the data pool to obtain data for one or more of authorizing a medical procedure or authorizing payment for a medical procedure.

22. The computer implemented method of claim 18, further comprising adding metadata to the ultrasound echo data in the syndicated data feed.

23. The computer implemented method of claim 22 wherein the metadata comprises metadata selected from the group consisting of metadata identifying the medical device, metadata identifying a time of creation of the ultrasound echo data, metadata identifying a physician who requested the ultrasound echo data, metadata identifying a patient, metadata identifying an intended recipient of the ultrasound echo data, and metadata identifying a laboratory where the plurality of medical devices are located.

24. The computer implemented method of claim 10, further comprising adding metadata to the secure item that includes at least one item of metadata selected from the group consisting of metadata identifying the medical device, metadata identifying a time of creation of the ultrasound echo data, metadata identifying a physician who requested the ultrasound echo data, metadata identifying the patient, metadata identifying an intended recipient of the ultrasound echo data, and metadata identifying a laboratory where the medical device is located.

\* \* \* \* \*